US008475801B2

(12) United States Patent
Brown et al.

(10) Patent No.: US 8,475,801 B2
(45) Date of Patent: *Jul. 2, 2013

(54) IGE CH3 PEPTIDE VACCINE

(75) Inventors: Alan Daniel Brown, Sandwich (GB);
Brian Robert Champion, Sandwich (GB); Clare Christy, Sandwich (GB);
David Paul Gervais, Sandwich (GB);
Lyn Howard Jones, Sandwich (GB);
Anne Maria Kristina Kjerrstrom, Sandwich (GB); David Cameron Pryde, Sandwich (GB); Lee Richard Roberts, Sandwich (GB); David Michael Wyatt, Sandwich (GB)

(73) Assignee: Pfizer Vaccines, LCC, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/564,103

(22) Filed: Aug. 1, 2012

(65) Prior Publication Data

US 2012/0294848 A1 Nov. 22, 2012

Related U.S. Application Data

(62) Division of application No. 12/634,336, filed on Dec. 9, 2009, now Pat. No. 8,298,547.

(60) Provisional application No. 61/120,989, filed on Dec. 9, 2008.

(51) Int. Cl.
*A61K 39/00* (2006.01)

(52) U.S. Cl.
USPC .................. 424/185.1; 424/192.1; 424/194.1; 424/805; 424/810; 530/326; 530/806; 530/862; 530/868

(58) Field of Classification Search
None
See application file for complete search history.

(56) References Cited

U.S. PATENT DOCUMENTS

| | | | |
|---|---|---|---|
| 4,469,863 A | 9/1984 | Ts'o et al. | |
| 4,722,840 A | 2/1988 | Valenzuela et al. | |
| 5,023,243 A | 6/1991 | Tullis | |
| 5,071,651 A | 12/1991 | Sabara et al. | |
| 5,374,426 A | 12/1994 | Sabara et al. | |
| 5,658,738 A | 8/1997 | Nadeau et al. | |
| 5,668,265 A | 9/1997 | Nadeau et al. | |
| 5,792,463 A | 8/1998 | Valenzuela et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,231,864 B1 | 5/2001 | Birkett | |
| 6,239,116 B1 | 5/2001 | Krieg et al. | |
| 6,339,068 B1 | 1/2002 | Krieg et al. | |
| 2002/0064525 A1 | 5/2002 | Morsey et al. | |
| 2003/0170229 A1* | 9/2003 | Friede et al. | 424/130.1 |
| 2004/0146504 A1 | 7/2004 | Morsey et al. | |
| 2004/0176283 A1 | 9/2004 | Robinson et al. | |
| 2006/0062782 A1 | 3/2006 | Morsey et al. | |

FOREIGN PATENT DOCUMENTS

| | | |
|---|---|---|
| EP | 0 421 635 | 9/1990 |
| EP | 0 761 231 | 6/1993 |
| EP | 1 736 538 | 6/2005 |
| EP | 1 572 074 | 1/2012 |
| GB | 2 2220 221 | 6/1989 |
| WO | WO90/03184 | 4/1990 |
| WO | WO90/14837 | 12/1990 |
| WO | WO91/18926 | 12/1991 |
| WO | WO 92/11291 | 7/1992 |
| WO | WO93/05810 | 4/1993 |
| WO | WO95/17210 | 6/1993 |
| WO | WO94/21292 | 9/1994 |
| WO | WO95/01363 | 1/1995 |
| WO | WO96/02555 | 2/1996 |
| WO | WO96/11711 | 4/1996 |
| WO | WO96/30523 | 10/1996 |
| WO | WO97/01640 | 1/1997 |
| WO | WO97/31948 | 9/1997 |
| WO | WO98/07705 | 2/1998 |
| WO | WO98/15631 | 4/1998 |
| WO | WO98/16247 | 4/1998 |
| WO | WO98/18810 | 5/1998 |
| WO | WO98/36772 | 8/1998 |
| WO | WO98/37919 | 9/1998 |
| WO | WO98/40100 | 9/1998 |
| WO | WO98/52581 | 11/1998 |
| WO | WO98/55495 | 12/1998 |
| WO | WO98/57659 | 12/1998 |
| WO | WO99/10375 | 3/1999 |
| WO | WO99/11241 | 3/1999 |
| WO | WO99/44636 | 9/1999 |
| WO | WO99/52549 | 10/1999 |

(Continued)

OTHER PUBLICATIONS

Ballas, Z., et al, "Induction of NK Activity in Murine and Human Cells by CpG Motifs in Oligodeoxynucleotides and Bacterial DNA," *The Journal of Immunology*, 1996, vol. 157, 1840-1845.
Chen, S., et al., "Protection of IgE-mediated Allergic Sensitization by Active Immunization With IgE Loops Constrained in GFP Protein Scaffold," *Journal of Immunological Methods*, 2008, vol. 333, 10-23.
Chu, R., et al., "CpG Oligodeoxynucleotides Act As Adjuvants That Switch on T Helper 1 (Th1) Immunity," *Journal of Experimental Medicine*, 1997, vol. 186, No. 10, 1623-1631.
Cowdery, J., et al., "Bacterial DNA Induces NK Cells to Produce IFN-y In Vivo Land Increases the Toxicity of Lipopolysaccharides," *The Journal of Immunology*, 1996, vol. 156, 4570-4575.

(Continued)

*Primary Examiner* — Michael Szperka
(74) *Attorney, Agent, or Firm* — Austin W. Zhang

(57) ABSTRACT

The present invention relates to the provision of novel immunogens comprising an antigenic IgE peptide preferably linked to an immunogenic carrier for the prevention, treatment or alleviation of IgE-mediated disorders. The invention further relates to methods for production of these medicaments, immunogenic compositions and pharmaceutical compositing thereof and their use in medicine.

17 Claims, 2 Drawing Sheets

FOREIGN PATENT DOCUMENTS

| | | |
|---|---|---|
| WO | WO99/67293 | 12/1999 |
| WO | WO00/07621 | 2/2000 |
| WO | WO00/23105 | 4/2000 |
| WO | WO00/23955 | 4/2000 |
| WO | WO00/25722 | 5/2000 |
| WO | WO00/26385 | 5/2000 |
| WO | WO00/32227 | 6/2000 |
| WO | WO00/41720 | 7/2000 |
| WO | WO00/48630 | 8/2000 |
| WO | WO00/50461 | 8/2000 |
| WO | WO00/56358 | 9/2000 |
| WO | WO00/62800 | 10/2000 |
| WO | WO01/21152 | 3/2001 |
| WO | WO01/21207 | 3/2001 |
| WO | WO01/22990 | 4/2001 |
| WO | WO01/77158 | 10/2001 |
| WO | WO01/85208 | 11/2001 |
| WO | WO01/98333 | 12/2001 |
| WO | WO02/10416 | 2/2002 |
| WO | WO02/14478 | 2/2002 |
| WO | WO02/34288 | 5/2002 |
| WO | WO02/056905 | 7/2002 |
| WO | WO03/024480 | 3/2003 |
| WO | WO03/024481 | 3/2003 |
| WO | WO03/068169 | 8/2003 |
| WO | WO03/092714 | 11/2003 |
| WO | WO03/102165 | 12/2003 |
| WO | WO2004/007538 | 1/2004 |
| WO | WO2004/053091 | 6/2004 |
| WO | WO2004/058799 | 7/2004 |
| WO | WO2005/075504 | 8/2005 |
| WO | WO2006/134423 | 12/2006 |
| WO | WO2007/026190 | 3/2007 |
| WO | WO2007/095316 | 8/2007 |
| WO | WO2008/020331 | 2/2008 |
| WO | WO2008/123999 | 10/2008 |

OTHER PUBLICATIONS

Coyle, A., et al., "Central Role of Immunoglobulin (Ig) E in the Induction of Lung Eosinophil Infiltration and T Helper 2 Cell Cytokine Production: Inhibition by a Non-anaphylactogenic Anti-IgE Antibody," *Journal of Experimental Medicine*, 1996, vol. 183, 1303-1310.

Crooke, S., et al., "Progress in Antisense Oligonucleotide Therapeutics," *Annual Review of Pharmacology and Toxicology*, 1996, vol. 36, 107-129.

Davis, H., et al., "CpG DNA Is a Potent Enhancer of Specific Immunity in Mice Immunized With Recombinant Hepatitis B Surface Antigen," *The Journal of Immunology*, 1998, vol. 160, 870-876.

Froehler, B., et al., "Triple-helix Formation by Oligodeoxynucleotides Containing the Carbocyclic Analogs of Thymidine and 5-Methyl-2'-deoxycytidine," *Journal of the American Chemical Society*, 1992, vol. 114, 8320-8322.

Garman, S., et al., "Structure of the Fc Fragment of Human IgE Bound to Its High-affinity Receptor FcεRIα," *Nature*, 2000, vol. 406, No. 6793, 259-266.

Golmohammadi, R., et al., "The Crystal Structure of Bacteriophage Qβ at 3.5 Å Resolution," *Structure*, 1996, vol. 4, 543-554.

Goodchild, J., "Conjugates of Iligonucleotides and Modified Oligonucleotides: A review of their Synthesis and Properties," *Bioconjugate Chemistry*, 1990, vol. 1, No. 3, 165-187.

Halpern, M., et al., "Bacterial DNA Induces Murine Interferon-γ Production by Stimulation of Interleukin-12 and Tumor Necrosis Factor-α," *Cellular Immunology*, 1996, vol. 167, 72-78.

Hartmann, G. et al., "Mechanism and Function of a Newly Identified CpG DNA Motif in Human Primary B Cells," *The Journal of Immunology*, 2000, vol. 164, 944-953.

Hartmann, G., et al., "Delineation of a CpG Phosphorothioate Oligodeoxynucleotide for Activating Primate Immune Responses In Vitro and In Vivo," *The Journal of Immunology*, 2000, vol. 164, 1617-1624.

Hellman, L., "Therapeutic Vaccines Against IgE-mediated Allergies," *Expert Reviews Vaccines*, 2008, vol. 7, No. 2, 193-208.

Hunziker, J., et al "Nucleic Acid Analogues: Synthesis and Properties," *Modern Synthesis Methods*, 1995, vol. 7, 331-417.

Jiang, X., et al., "Norwalk Virus Genome Cloning and Characterization," *Science*, 1990, vol. 250, 1580-1583.

Jiang, Z., et al., "Pseudo-Cyclic Oligonucleotides: In Vitro and In Vivo Properties," *Bioorganic & Medicinal Chemistry*, 1999, vol. 7, No. 12, 2727-2735.

Jones, L., et al., "Active Immunization With a Glycolipid Transition State Analogue Protects Against Endotoxic Shock," *Angew. Chem. Int. Ed.*, 2002, vol. 41, No. 22, 4241-4244.

Kanzler, H., et al., "Therapeutic Targeting of Innate Immunity With Toll-like Receptor Agonists and Antagonists," *Nature Medicine*, 2007, vol. 13, No. 5, 552-559.

Kelso, M., et al., "A Cyclic Metallopeptide Induces α Helicity in Short Peptide Fragments of Thermolysin," *Angew. Chem. Int. Ed.*, 2003, vol. 42, No. 4, 421-424.

Klinman, D., et al., "CpG Motifs Present in Bacterial DNA Rapidly Induce Lymphocytes to Secrete Interleukin 6, Interleukin 12, and Interferon γ," *Proceedings of the National Academy of Science*, 1996, vol. 93, 2879-2883.

Klinman, D., et al., "Hierarchical Recognnition of CpG Motifs Expressed by Immunostimulatory Oligodeoxynucelotides," *Clinical Exp. Immunology*, 2003, vol. 133, 227-232.

Kolb, H., et al., "The Growing Impact of Click Chemistry on Drug Discovery," *Drug Discovery Today*, 2003, vol. 8, No. 24, 1128-1137.

Kozlovska, T., et al., "Recombinant RNA Phage Qβ Capsid Particles Synthesized and Self-assembled in Escherichia coli," *Gene*, 1993, vol. 137, No. 1, 133-137.

Kozlovska, T., et al., "RNA Phage Qβ Coat Protein as a Carrier for Foreign Epitopes," *Intervirology*, 1996, vol. 39, 9-15.

Krieg, A., "Immune Effects and Mechanisms of Action of CpG Motifs," *Vaccine*, 2000, vol. 19, 618-622.

Krieg, A., et al., "CpG Motifs in Bacterial DNA Trigger Direct B-cell Activation," Nature, 1995, vol. 374, 546-549.

Krieg, A., et al., "Enhancing Vaccines With Immune Stimulatory CpG DNA," *Current Opinion in Molecular Therapeutics*, 2001, vol. 3, No. 1, 15-24.

Krieg, A., et al., "Sequence Motifs in Adenoviral DNA Block Immune Activation by Stimulatory CpG Motifs," Proceedings of the National Academy of Science, 1998, vol. 95, 12631-12636.

Lipford, G., et al., "CpG-containing Synthetic Oligonucleotides Promote B and Cytotoxic T Cell Responses to Protein Antigen: A New Class of Vaccine Adjuvants," *European Journal of Immunology*, 1997, vol. 27, 2340-2344.

Litovchick, A., et al., "Selection of Cyclic Peptide Aptamers to HCV IRES RNA Using mRNA Display," *Proceedings of the National Academy of Science*, 2008, vol. 105, No. 40, 15293-15298.

Lloyd, C., et al., "Resolution of Bronchial Hyperresponsiveness and Pulmonary Inflammation Is Associated With IL-3 and Tissue Leukocyte Apoptosis," *The Journal of Immunology*, 2001, vol. 166, 2033-2040.

Matsui, S., et al., "The Isolation and Characterization of a Norwalk Virus-specific cDNA," *The American Journal of Clinical Investigation*, 1991, vol. 87, 1456-1461.

May, J., et al., "Intraannular Savige-Fontana Reaction: One-step Conversion of One Class of Monocyclic Peptides Into Another Class of Bicyclic Peptides," *Chemistry A European Journal*, 2008, vol. 14, 3404-3409.

Messina, J., et al., "Stimulation of In Vetro Murine Lymphocyte Proliferation by Bacterial DNA," *The Journal of Immunology*, 1991, vol. 147, 1759-1764.

Moldoveanu, Z., et al., "CpG DNA, A Novel Immune Enhancer for systemic and Mucosal Immunization With Influenza Virus," *Vaccine*, 1998, vol. 16, No. 11/12, 1216-1224.

Neirynck, S., et al., "A Universal Influenza A Vaccine Based on the Extracellular Domain of the M2 Protein," *Nature Medicine*, 1999, vol. 5, No. 10, 1157-1163.

Nielsen, P., et al., "Peptide Nucleic Acid (PNA). A DNA Mimic With A Peptide Backbone," *Bioconjugate Chemistry*, 1994, vol. 5, 3-7.

Ott, G., et al., "MF59, Design and Evaluation of a Safe and Potent Adjuvant for Human Vaccines," *Vaccine Design: The Subunit and Adjuvant Approach*, 1995, Chapter 10, 277-296, ed. Michael F. Powell & Mark J. Newman, Plenum Press, New York.

Pfeifer, M., et al., "Stabilisation of β-hairpin Conformations in a Protein Surface Mimetic Using a Bicyclic Template Derived From (2S,3R,4R)-diaminoprline," *Chemistry Communications*, 1998, 1977-1978.

Presta, L., et al., "Humanization of an Antibody Directed Against IgE," *The Journal of Immunology*, 1993, vol. 151, No. 5, 2623-2632.

Pumpens, P., et al., "HBV Core Particles as a Carrier for B Cell/T Cell Epitopes," *Intervirology*, 2001, vol. 44, 98-114.

Rodziewicz-Motowidlo, S., et al., "Conformation-activity Relationships of *Cyclo*-constrained μ/δOpioid agonists Derived From the N-Terminal Tetrapeptide Segment of Dermorhin/deltorphin," *Journal of Peptide Science* 2008 vol. 14 898-902.

Roman, M., et al., "Immunostimulatory DNA Seuences Function as T Helper-1-promoting Adjuvants," *Nature Medicine*, 1997, vol. 3, No. 6, 849-854.

Sasnauskas, K., et al. Generation of Recombinant Virus-Like Particles of Human and Non-Human Polyomaviruses in Yeast *Saccharomyces cerevisiae, Intervirology*, 2002, vol. 45, 308-317.

Sasnauskas, K., et al., "Yeast Cells Allow High-level Expression and Formation of Polyomavirus-like Particles," Biol. Chem., 1999, vol. 380, 381-386.

Schafmeister, C., et al., "An All-hydrocarbon Cross-linking System for Enhancing the Helicity and Metabolic Stability of Peptides," *Journal of the American Chemical Society*, 2000, vol. 122, 5891-5892.

Seliger, H., et al., "Oligonucleotide Analogues With Terminal 3' -3'- and 5' -5'—internucleotidic Linkages as Antisense Inhibitors of Viral Gene Expression," *Nucleosides & Nucleotides*, 1991, vol. 10 Nos. 1-3, 469-477.

Sjölander, A., et al., "ISCOMs: An Adjuvant with Multiple Functions," *Journal of Leukocyte Biology*, 1998, vol. 64, 713-723.

Smiley, B., et al., "Enhanced Readthrough of Opal (UGA) Stop Codons and Production of *Mycoplasma pneumoniae* P1 Epitopes in *Escherichia coli,*" *Gene*, 1993, vol. 134, No. 1, 33-40.

Späth, J., et al., "Stabilization of a β-Hairpin Conformation in a Cyclic Peptide Using The Templating Effect of a Heterochiral Diproline Unit," *Helvetica Chimica Acta*, 1998, vol. 81, 1726-1738.

Stacey, K., et al., "Macrophages Ingest and Are Activated by Bacterial DNA," *The Journal of Immunology*, 1996, vol. 157, 2116-2122.

Stirchak, E., et al., "Uncharged Stereoregular Nucleic Acid analogs: 2. Morpholino Nucleoside Oligomers With Carbonate Internucleoside Linkages," *Nucleic Acids Research*, 1989, vol. 17, No. 15, 6129-6141.

Tarköy, M., et al., "Nuccleic-acid Analogues With Constraint Conformational Flexibility in the Sugar-phosphate Backbone (Bicyclo-DNA)," *Helvetica Chimica Acta*, 1993, vol. 76, 481-510.

Timmerman, P., et al., "Rapid and Quantitative Cyclization of Multiple Peptide Loops Onto Synthetic Scaffolds for Structural Mimicry of Protein Surfaces," *ChemBioChem*, 2005, vol. 6, 821-824.

Twomey, T., et al., "Structure and Immunogenicity of Experimental Foot-and-mouth Disease and Poliomyelitis Vaccines," *Vaccine*, 1995, vol. 13, No. 16, 1603-1610.

Uhlmann, E., et al., "Antisense Oligonucleotides: A New Therapeutic Principle," *Chemical Reviews*, 1990, vol. 90, No. 4, 543-584.

Ulrich, R., et al., "Core Particles of Hepatitis B Virus as Carrier for Foreign Epitopes," *Advances in Virus Research*, 1998. vol. 50, 141-182.

Vandendriessche, F., et al., "Acyclic Oligonucleotides: Possibilities and Limitations," *Tetrahedron*, 1993, vol. 49, No. 33, 7223-7238.

Wagner, R., et al., "Potent and Selective Inhibition of Gene Expression by an Antisense Heptanucleotide," *Nature Biotechnology*, 1996, vol. 14, 840-844.

Warnes, A., "Expression of the Measles Virus Nucleoprotein Gene in *Escherichia coli* and Assembly of Nucleocapsid-like Structures," *Gene*, 1995, vol. 160, 173-178.

Weiner, G., et al., "Immunostimulatory Oligodeoxynucleotides Containing the CpG Motif Are Effective as Immune Adjuvants in Tumor Antigen Immunization," *Proceedings of the National Academy of Science USA*, 1997, vol. 94, 10833-10837.

Wurzburg, B., et al., "Structure of the Human IgE-Fc Cε3-Cε4 Reveals Conformational Flexibility in the Antibody Effector Domains," *Immunity*, 2000, vol. 13, 375-385.

Yamamoto, S., et al., "In Vitro Augmentation of Natural Killer Cell Activity and Production of Interferon- α/β and -γ With Deoxyribonucleic Acid Fraction From *Mycobacterium bovis* BCG," Japanese Journal of Cancer Research, 1988, vol. 79, 866-873.

Yamamoto, S., et al., "Unique Palindromic Sequences in Synthetic Oligonucleotides Are Required to Induce INF and Augment INF-Mediated Natural Killer Activity," *The Journal of Immunology*, 1992, vol. 148, No. 12, 4072-4076.

Yi, A., et al., "CpG DNA Rescue of Murine B Lymphoma Cells From Anti-IgM-Induced Growth Arrest and Programmed Cell Death Is Associated With Increased Expression of c-*myc* and *bcl*-$x_L$," *The Journal of Immunology*, 1996, vol. 157, 4918-4925.

Yi, A., et al., "CpG Motifs in Bacterial DNA Activate Leukocytes Through the pH-Dependent Generation of Reactive Oxygen Species," *The Journal of Immunology*, 1998, vol. 160, 4755-4761.

Yi, A., et al., "CpG Oligodeoxyribonucleotides Rescue Mature Spleen B Cells From Spontaneous Apoptosis and Promote Cell Cycle Entry," *The Journal of Immunology*, 1998, vol. 160, 5898-5906.

Yi, A., et al., "Rapid Immune Activation by CpG Motifs in Bacterial DNA," *The Journal of Immunology*, 1996, vol. 157, 5394-5402.

Yuan, T., et al., "Subtype-Independent Immature Secretion and Subtype-Dependent Replication Deficiency of a Highly Frequent, Naturally Occurring Mutaiton of Human Hepatititis B Virus Core Antigen," *Journal of Virology*, 1999, vol. 73, No. 12, 10122-10128.

Zhang, W., et al., "Novel Cyclic Analogs of Angiotension II With Cyclization Between Positions 5 and 7: Conformational and Biological Implications," *Journal of Medicinal Chemistry*, 1996, vol. 39, 2738-2744.

\* cited by examiner ated Jul. 11, 2012, which is 114 KB in size. The information in the electronic format of the Sequence Listing is incorporated herein by reference in its entirety.

SEQUENCE LISTING

<160> NUMBER OF SEQ ID NOS: 610

<210> SEQ ID NO 1
<211> LENGTH: 20
<212> TYPE: PRT
<213> ORGANISM: Artificial
<220> FEATURE:
<223> OTHER INFORMATION: Synthetic

<400> SEQUENCE: 1

Ser Thr Arg Lys Glu Glu Lys Gln Arg Asn Gly Thr Leu Thr Val Thr
1               5                   10                  15

Ser Thr Leu Pro
            20

```
<210> SEQ ID NO 2
<211> LENGTH: 19
<212> TYPE: PRT
<213> ORGANISM: Artificial
<220> FEATURE:
<223> OTHER INFORMATION: Synthetic

<400> SEQUENCE: 2

Thr Arg Lys Glu Glu Lys Gln Arg Asn Gly Thr Leu Thr Val Thr Ser
1               5                   10                  15

Thr Leu Pro

<210> SEQ ID NO 3
<211> LENGTH: 18
<212> TYPE: PRT
<213> ORGANISM: Artificial
<220> FEATURE:
<223> OTHER INFORMATION: Synthetic

<400> SEQUENCE: 3

Arg Lys Glu Glu Lys Gln Arg Asn Gly Thr Leu Thr Val Thr Ser Thr
1               5                   10                  15

Leu Pro

<210> SEQ ID NO 4
<211> LENGTH: 17
<212> TYPE: PRT
<213> ORGANISM: Artificial
<220> FEATURE:
<223> OTHER INFORMATION: Synthetic

<400> SEQUENCE: 4

Lys Glu Glu Lys Gln Arg Asn Gly Thr Leu Thr Val Thr Ser Thr Leu
1               5                   10                  15

Pro

<210> SEQ ID NO 5
<211> LENGTH: 16
<212> TYPE: PRT
<213> ORGANISM: Artificial
<220> FEATURE:
<223> OTHER INFORMATION: Synthetic

<400> SEQUENCE: 5

Glu Glu Lys Gln Arg Asn Gly Thr Leu Thr Val Thr Ser Thr Leu Pro
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic

<400> SEQUENCE: 6

Glu Lys Gln Arg Asn Gly Thr Leu Thr Val Thr Ser Thr Leu Pro
1               5                   10                  15

<210> SEQ ID NO 7
<211> LENGTH: 14
<212> TYPE: PRT
<213> ORGANISM: Artificial
<220> FEATURE:
<223> OTHER INFORMATION: Synthetic
```

```
<400> SEQUENCE: 7

Lys Gln Arg Asn Gly Thr Leu Thr Val Thr Ser Thr Leu Pro
1               5                   10

<210> SEQ ID NO 8
<211> LENGTH: 13
<212> TYPE: PRT
<213> ORGANISM: Artificial
<220> FEATURE:
<223> OTHER INFORMATION: Synthetic

<400> SEQUENCE: 8

Gln Arg Asn Gly Thr Leu Thr Val Thr Ser Thr Leu Pro
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic

<400> SEQUENCE: 9

Arg Asn Gly Thr Leu Thr Val Thr Ser Thr Leu Pro
1               5                   10

<210> SEQ ID NO 10
<211> LENGTH: 11
<212> TYPE: PRT
<213> ORGANISM: Artificial
<220> FEATURE:
<223> OTHER INFORMATION: Synthetic

<400> SEQUENCE: 10

Asn Gly Thr Leu Thr Val Thr Ser Thr Leu Pro
1               5                   10

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

Gly Thr Leu Thr Val Thr Ser Thr Leu Pro
1               5                   10

<210> SEQ ID NO 12
<211> LENGTH: 9
<212> TYPE: PRT
<213> ORGANISM: Artificial
<220> FEATURE:
<223> OTHER INFORMATION: Synthetic

<400> SEQUENCE: 12

Thr Leu Thr Val Thr Ser Thr Leu Pro
1               5

<210> SEQ ID NO 13
<211> LENGTH: 8
<212> TYPE: PRT
<213> ORGANISM: Artificial
<220> FEATURE:
<223> OTHER INFORMATION: Synthetic

<400> SEQUENCE: 13
```

```
Leu Thr Val Thr Ser Thr Leu Pro
1               5

<210> SEQ ID NO 14
<211> LENGTH: 7
<212> TYPE: PRT
<213> ORGANISM: Artificial
<220> FEATURE:
<223> OTHER INFORMATION: Synthetic

<400> SEQUENCE: 14

Thr Val Thr Ser Thr Leu Pro
1               5

<210> SEQ ID NO 15
<211> LENGTH: 6
<212> TYPE: PRT
<213> ORGANISM: Artificial
<220> FEATURE:
<223> OTHER INFORMATION: Synthetic

<400> SEQUENCE: 15

Val Thr Ser Thr Leu Pro
1               5

<210> SEQ ID NO 16
<211> LENGTH: 5
<212> TYPE: PRT
<213> ORGANISM: Artificial
<220> FEATURE:
<223> OTHER INFORMATION: Synthetic

<400> SEQUENCE: 16

Thr Ser Thr Leu Pro
1               5

<210> SEQ ID NO 17
<211> LENGTH: 4
<212> TYPE: PRT
<213> ORGANISM: Artificial
<220> FEATURE:
<223> OTHER INFORMATION: Synthetic

<400> SEQUENCE: 17

Ser Thr Leu Pro
1

<210> SEQ ID NO 18
<211> LENGTH: 19
<212> TYPE: PRT
<213> ORGANISM: Artificial
<220> FEATURE:
<223> OTHER INFORMATION: Synthetic

<400> SEQUENCE: 18

Ser Thr Arg Lys Glu Glu Lys Gln Arg Asn Gly Thr Leu Thr Val Thr
1               5                   10                  15

Ser Thr Leu

<210> SEQ ID NO 19
<211> LENGTH: 18
<212> TYPE: PRT
<213> ORGANISM: Artificial
<220> FEATURE:
<223> OTHER INFORMATION: Synthetic

<400> SEQUENCE: 19
```

Thr Arg Lys Glu Glu Lys Gln Arg Asn Gly Thr Leu Thr Val Thr Ser
1               5                   10                  15
Thr Leu

<210> SEQ ID NO 20
<211> LENGTH: 17
<212> TYPE: PRT
<213> ORGANISM: Artificial
<220> FEATURE:
<223> OTHER INFORMATION: Synthetic

<400> SEQUENCE: 20

Arg Lys Glu Glu Lys Gln Arg Asn Gly Thr Leu Thr Val Thr Ser Thr
1               5                   10                  15
Leu

<210> SEQ ID NO 21
<211> LENGTH: 16
<212> TYPE: PRT
<213> ORGANISM: Artificial
<220> FEATURE:
<223> OTHER INFORMATION: Synthetic

<400> SEQUENCE: 21

Lys Glu Glu Lys Gln Arg Asn Gly Thr Leu Thr Val Thr Ser Thr Leu
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthetic

<400> SEQUENCE: 22

Glu Glu Lys Gln Arg Asn Gly Thr Leu Thr Val Thr Ser Thr Leu
1               5                   10                  15

<210> SEQ ID NO 23
<211> LENGTH: 14
<212> TYPE: PRT
<213> ORGANISM: Artificial
<220> FEATURE:
<223> OTHER INFORMATION: Synthetic

<400> SEQUENCE: 23

Glu Lys Gln Arg Asn Gly Thr Leu Thr Val Thr Ser Thr Leu
1               5                   10

<210> SEQ ID NO 24
<211> LENGTH: 13
<212> TYPE: PRT
<213> ORGANISM: Artificial
<220> FEATURE:
<223> OTHER INFORMATION: Synthetic

<400> SEQUENCE: 24

Lys Gln Arg Asn Gly Thr Leu Thr Val Thr Ser Thr Leu
1               5                   10

<210> SEQ ID NO 25
<211> LENGTH: 12
<212> TYPE: PRT
<213> ORGANISM: Artificial
<220> FEATURE:
<223> OTHER INFORMATION: Synthetic

```
<400> SEQUENCE: 25

Gln Arg Asn Gly Thr Leu Thr Val Thr Ser Thr Leu
 1               5                  10

<210> SEQ ID NO 26
<211> LENGTH: 11
<212> TYPE: PRT
<213> ORGANISM: Artificial
<220> FEATURE:
<223> OTHER INFORMATION: Synthetic

<400> SEQUENCE: 26

Arg Asn Gly Thr Leu Thr Val Thr Ser Thr Leu
 1               5                  10

<210> SEQ ID NO 27
<211> LENGTH: 10
<212> TYPE: PRT
<213> ORGANISM: Artificial
<220> FEATURE:
<223> OTHER INFORMATION: Synthetic

<400> SEQUENCE: 27

Asn Gly Thr Leu Thr Val Thr Ser Thr Leu
 1               5                  10

<210> SEQ ID NO 28
<211> LENGTH: 9
<212> TYPE: PRT
<213> ORGANISM: Artificial
<220> FEATURE:
<223> OTHER INFORMATION: Synthetic

<400> SEQUENCE: 28

Gly Thr Leu Thr Val Thr Ser Thr Leu
 1               5

<210> SEQ ID NO 29
<211> LENGTH: 8
<212> TYPE: PRT
<213> ORGANISM: Artificial
<220> FEATURE:
<223> OTHER INFORMATION: Synthetic

<400> SEQUENCE: 29

Thr Leu Thr Val Thr Ser Thr Leu
 1               5

<210> SEQ ID NO 30
<211> LENGTH: 7
<212> TYPE: PRT
<213> ORGANISM: Artificial
<220> FEATURE:
<223> OTHER INFORMATION: Synthetic

<400> SEQUENCE: 30

Leu Thr Val Thr Ser Thr Leu
 1               5

<210> SEQ ID NO 31
<211> LENGTH: 6
<212> TYPE: PRT
<213> ORGANISM: Artificial
<220> FEATURE:
<223> OTHER INFORMATION: Synthetic

<400> SEQUENCE: 31
```

```
Thr Val Thr Ser Thr Leu
1               5

<210> SEQ ID NO 32
<211> LENGTH: 5
<212> TYPE: PRT
<213> ORGANISM: Artificial
<220> FEATURE:
<223> OTHER INFORMATION: Synthetic

<400> SEQUENCE: 32

Val Thr Ser Thr Leu
1               5

<210> SEQ ID NO 33
<211> LENGTH: 4
<212> TYPE: PRT
<213> ORGANISM: Artificial
<220> FEATURE:
<223> OTHER INFORMATION: Synthetic

<400> SEQUENCE: 33

Thr Ser Thr Leu
1

<210> SEQ ID NO 34
<211> LENGTH: 18
<212> TYPE: PRT
<213> ORGANISM: Artificial
<220> FEATURE:
<223> OTHER INFORMATION: Synthetic

<400> SEQUENCE: 34

Ser Thr Arg Lys Glu Glu Lys Gln Arg Asn Gly Thr Leu Thr Val Thr
1               5                   10                  15

Ser Thr

<210> SEQ ID NO 35
<211> LENGTH: 17
<212> TYPE: PRT
<213> ORGANISM: Artificial
<220> FEATURE:
<223> OTHER INFORMATION: Synthetic

<400> SEQUENCE: 35

Thr Arg Lys Glu Glu Lys Gln Arg Asn Gly Thr Leu Thr Val Thr Ser
1               5                   10                  15

Thr

<210> SEQ ID NO 36
<211> LENGTH: 16
<212> TYPE: PRT
<213> ORGANISM: Artificial
<220> FEATURE:
<223> OTHER INFORMATION: Synthetic

<400> SEQUENCE: 36

Arg Lys Glu Glu Lys Gln Arg Asn Gly Thr Leu Thr Val Thr Ser Thr
1               5                   10                  15

<210> SEQ ID NO 37
<211> LENGTH: 15
<212> TYPE: PRT
<213> ORGANISM: Artificial
<220> FEATURE:
<223> OTHER INFORMATION: Synthetic
```

```
<400> SEQUENCE: 37

Lys Glu Glu Lys Gln Arg Asn Gly Thr Leu Thr Val Thr Ser Thr
1               5                   10                  15

<210> SEQ ID NO 38
<211> LENGTH: 14
<212> TYPE: PRT
<213> ORGANISM: Artificial
<220> FEATURE:
<223> OTHER INFORMATION: Synthetic

<400> SEQUENCE: 38

Glu Glu Lys Gln Arg Asn Gly Thr Leu Thr Val Thr Ser Thr
1               5                   10

<210> SEQ ID NO 39
<211> LENGTH: 13
<212> TYPE: PRT
<213> ORGANISM: Artificial
<220> FEATURE:
<223> OTHER INFORMATION: Synthetic

<400> SEQUENCE: 39

Glu Lys Gln Arg Asn Gly Thr Leu Thr Val Thr Ser Thr
1               5                   10

<210> SEQ ID NO 40
<211> LENGTH: 12
<212> TYPE: PRT
<213> ORGANISM: Artificial
<220> FEATURE:
<223> OTHER INFORMATION: Synthetic

<400> SEQUENCE: 40

Lys Gln Arg Asn Gly Thr Leu Thr Val Thr Ser Thr
1               5                   10

<210> SEQ ID NO 41
<211> LENGTH: 11
<212> TYPE: PRT
<213> ORGANISM: Artificial
<220> FEATURE:
<223> OTHER INFORMATION: Synthetic

<400> SEQUENCE: 41

Gln Arg Asn Gly Thr Leu Thr Val Thr Ser Thr
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic

<400> SEQUENCE: 42

Arg Asn Gly Thr Leu Thr Val Thr Ser Thr
1               5                   10

<210> SEQ ID NO 43
<211> LENGTH: 9
<212> TYPE: PRT
<213> ORGANISM: Artificial
<220> FEATURE:
<223> OTHER INFORMATION: Synthetic

<400> SEQUENCE: 43
```

```
Asn Gly Thr Leu Thr Val Thr Ser Thr
1               5
```

<210> SEQ ID NO 44
<211> LENGTH: 8
<212> TYPE: PRT
<213> ORGANISM: Artificial
<220> FEATURE:
<223> OTHER INFORMATION: Synthetic

<400> SEQUENCE: 44

```
Gly Thr Leu Thr Val Thr Ser Thr
1               5
```

<210> SEQ ID NO 45
<211> LENGTH: 7
<212> TYPE: PRT
<213> ORGANISM: Artificial
<220> FEATURE:
<223> OTHER INFORMATION: Synthetic

<400> SEQUENCE: 45

```
Thr Leu Thr Val Thr Ser Thr
1               5
```

<210> SEQ ID NO 46
<211> LENGTH: 6
<212> TYPE: PRT
<213> ORGANISM: Artificial
<220> FEATURE:
<223> OTHER INFORMATION: Synthetic

<400> SEQUENCE: 46

```
Leu Thr Val Thr Ser Thr
1               5
```

<210> SEQ ID NO 47
<211> LENGTH: 5
<212> TYPE: PRT
<213> ORGANISM: Artificial
<220> FEATURE:
<223> OTHER INFORMATION: Synthetic

<400> SEQUENCE: 47

```
Thr Val Thr Ser Thr
1               5
```

<210> SEQ ID NO 48
<211> LENGTH: 4
<212> TYPE: PRT
<213> ORGANISM: Artificial
<220> FEATURE:
<223> OTHER INFORMATION: Synthetic

<400> SEQUENCE: 48

```
Val Thr Ser Thr
1
```

<210> SEQ ID NO 49
<211> LENGTH: 17
<212> TYPE: PRT
<213> ORGANISM: Artificial
<220> FEATURE:
<223> OTHER INFORMATION: Synthetic

<400> SEQUENCE: 49

```
Ser Thr Arg Lys Glu Glu Lys Gln Arg Asn Gly Thr Leu Thr Val Thr
1               5                   10                  15
```

Ser

<210> SEQ ID NO 50
<211> LENGTH: 16
<212> TYPE: PRT
<213> ORGANISM: Artificial
<220> FEATURE:
<223> OTHER INFORMATION: Synthetic

<400> SEQUENCE: 50

Thr Arg Lys Glu Glu Lys Gln Arg Asn Gly Thr Leu Thr Val Thr Ser
1               5                   10                  15

<210> SEQ ID NO 51
<211> LENGTH: 15
<212> TYPE: PRT
<213> ORGANISM: Artificial
<220> FEATURE:
<223> OTHER INFORMATION: Synthetic

<400> SEQUENCE: 51

Arg Lys Glu Glu Lys Gln Arg Asn Gly Thr Leu Thr Val Thr Ser
1               5                   10                  15

<210> SEQ ID NO 52
<211> LENGTH: 14
<212> TYPE: PRT
<213> ORGANISM: Artificial
<220> FEATURE:
<223> OTHER INFORMATION: Synthetic

<400> SEQUENCE: 52

Lys Glu Glu Lys Gln Arg Asn Gly Thr Leu Thr Val Thr Ser
1               5                   10

<210> SEQ ID NO 53
<211> LENGTH: 13
<212> TYPE: PRT
<213> ORGANISM: Artificial
<220> FEATURE:
<223> OTHER INFORMATION: Synthetic

<400> SEQUENCE: 53

Glu Glu Lys Gln Arg Asn Gly Thr Leu Thr Val Thr Ser
1               5                   10

<210> SEQ ID NO 54
<211> LENGTH: 12
<212> TYPE: PRT
<213> ORGANISM: Artificial
<220> FEATURE:
<223> OTHER INFORMATION: Synthetic

<400> SEQUENCE: 54

Glu Lys Gln Arg Asn Gly Thr Leu Thr Val Thr Ser
1               5                   10

<210> SEQ ID NO 55
<211> LENGTH: 11
<212> TYPE: PRT
<213> ORGANISM: Artificial
<220> FEATURE:
<223> OTHER INFORMATION: Synthetic

<400> SEQUENCE: 55

Lys Gln Arg Asn Gly Thr Leu Thr Val Thr Ser
1               5                   10

<210> SEQ ID NO 56
<211> LENGTH: 10
<212> TYPE: PRT
<213> ORGANISM: Artificial
<220> FEATURE:
<223> OTHER INFORMATION: Synthetic

<400> SEQUENCE: 56

Gln Arg Asn Gly Thr Leu Thr Val Thr Ser
1               5                   10

<210> SEQ ID NO 57
<211> LENGTH: 9
<212> TYPE: PRT
<213> ORGANISM: Artificial
<220> FEATURE:
<223> OTHER INFORMATION: Synthetic

<400> SEQUENCE: 57

Arg Asn Gly Thr Leu Thr Val Thr Ser
1               5

<210> SEQ ID NO 58
<211> LENGTH: 8
<212> TYPE: PRT
<213> ORGANISM: Artificial
<220> FEATURE:
<223> OTHER INFORMATION: Synthetic

<400> SEQUENCE: 58

Asn Gly Thr Leu Thr Val Thr Ser
1               5

<210> SEQ ID NO 59
<211> LENGTH: 7
<212> TYPE: PRT
<213> ORGANISM: Artificial
<220> FEATURE:
<223> OTHER INFORMATION: Synthetic

<400> SEQUENCE: 59

Gly Thr Leu Thr Val Thr Ser
1               5

<210> SEQ ID NO 60
<211> LENGTH: 6
<212> TYPE: PRT
<213> ORGANISM: Artificial
<220> FEATURE:
<223> OTHER INFORMATION: Synthetic

<400> SEQUENCE: 60

Thr Leu Thr Val Thr Ser
1               5

<210> SEQ ID NO 61
<211> LENGTH: 5
<212> TYPE: PRT
<213> ORGANISM: Artificial
<220> FEATURE:
<223> OTHER INFORMATION: Synthetic

<400> SEQUENCE: 61

Leu Thr Val Thr Ser
1               5

```
<210> SEQ ID NO 62
<211> LENGTH: 4
<212> TYPE: PRT
<213> ORGANISM: Artificial
<220> FEATURE:
<223> OTHER INFORMATION: Synthetic

<400> SEQUENCE: 62

Thr Val Thr Ser
1

<210> SEQ ID NO 63
<211> LENGTH: 16
<212> TYPE: PRT
<213> ORGANISM: Artificial
<220> FEATURE:
<223> OTHER INFORMATION: Synthetic

<400> SEQUENCE: 63

Ser Thr Arg Lys Glu Glu Lys Gln Arg Asn Gly Thr Leu Thr Val Thr
1               5                   10                  15

<210> SEQ ID NO 64
<211> LENGTH: 15
<212> TYPE: PRT
<213> ORGANISM: Artificial
<220> FEATURE:
<223> OTHER INFORMATION: Synthetic

<400> SEQUENCE: 64

Thr Arg Lys Glu Glu Lys Gln Arg Asn Gly Thr Leu Thr Val Thr
1               5                   10                  15

<210> SEQ ID NO 65
<211> LENGTH: 14
<212> TYPE: PRT
<213> ORGANISM: Artificial
<220> FEATURE:
<223> OTHER INFORMATION: Synthetic

<400> SEQUENCE: 65

Arg Lys Glu Glu Lys Gln Arg Asn Gly Thr Leu Thr Val Thr
1               5                   10

<210> SEQ ID NO 66
<211> LENGTH: 13
<212> TYPE: PRT
<213> ORGANISM: Artificial
<220> FEATURE:
<223> OTHER INFORMATION: Synthetic

<400> SEQUENCE: 66

Lys Glu Glu Lys Gln Arg Asn Gly Thr Leu Thr Val Thr
1               5                   10

<210> SEQ ID NO 67
<211> LENGTH: 12
<212> TYPE: PRT
<213> ORGANISM: Artificial
<220> FEATURE:
<223> OTHER INFORMATION: Synthetic

<400> SEQUENCE: 67

Glu Glu Lys Gln Arg Asn Gly Thr Leu Thr Val Thr
1               5                   10

<210> SEQ ID NO 68
<211> LENGTH: 11
```

```
<212> TYPE: PRT
<213> ORGANISM: Artificial
<220> FEATURE:
<223> OTHER INFORMATION: Synthetic

<400> SEQUENCE: 68

Glu Lys Gln Arg Asn Gly Thr Leu Thr Val Thr
1               5                   10

<210> SEQ ID NO 69
<211> LENGTH: 10
<212> TYPE: PRT
<213> ORGANISM: Artificial
<220> FEATURE:
<223> OTHER INFORMATION: Synthetic

<400> SEQUENCE: 69

Lys Gln Arg Asn Gly Thr Leu Thr Val Thr
1               5                   10

<210> SEQ ID NO 70
<211> LENGTH: 9
<212> TYPE: PRT
<213> ORGANISM: Artificial
<220> FEATURE:
<223> OTHER INFORMATION: Synthetic

<400> SEQUENCE: 70

Gln Arg Asn Gly Thr Leu Thr Val Thr
1               5

<210> SEQ ID NO 71
<211> LENGTH: 8
<212> TYPE: PRT
<213> ORGANISM: Artificial
<220> FEATURE:
<223> OTHER INFORMATION: Synthetic

<400> SEQUENCE: 71

Arg Asn Gly Thr Leu Thr Val Thr
1               5

<210> SEQ ID NO 72
<211> LENGTH: 7
<212> TYPE: PRT
<213> ORGANISM: Artificial
<220> FEATURE:
<223> OTHER INFORMATION: Synthetic

<400> SEQUENCE: 72

Asn Gly Thr Leu Thr Val Thr
1               5

<210> SEQ ID NO 73
<211> LENGTH: 6
<212> TYPE: PRT
<213> ORGANISM: Artificial
<220> FEATURE:
<223> OTHER INFORMATION: Synthetic

<400> SEQUENCE: 73

Gly Thr Leu Thr Val Thr
1               5

<210> SEQ ID NO 74
<211> LENGTH: 5
<212> TYPE: PRT
<213> ORGANISM: Artificial
```

```
<220> FEATURE:
<223> OTHER INFORMATION: Synthetic

<400> SEQUENCE: 74

Thr Leu Thr Val Thr
1               5

<210> SEQ ID NO 75
<211> LENGTH: 4
<212> TYPE: PRT
<213> ORGANISM: Artificial
<220> FEATURE:
<223> OTHER INFORMATION: Synthetic

<400> SEQUENCE: 75

Leu Thr Val Thr
1

<210> SEQ ID NO 76
<211> LENGTH: 15
<212> TYPE: PRT
<213> ORGANISM: Artificial
<220> FEATURE:
<223> OTHER INFORMATION: Synthetic

<400> SEQUENCE: 76

Ser Thr Arg Lys Glu Glu Lys Gln Arg Asn Gly Thr Leu Thr Val
1               5                   10                  15

<210> SEQ ID NO 77
<211> LENGTH: 14
<212> TYPE: PRT
<213> ORGANISM: Artificial
<220> FEATURE:
<223> OTHER INFORMATION: Synthetic

<400> SEQUENCE: 77

Thr Arg Lys Glu Glu Lys Gln Arg Asn Gly Thr Leu Thr Val
1               5                   10

<210> SEQ ID NO 78
<211> LENGTH: 13
<212> TYPE: PRT
<213> ORGANISM: Artificial
<220> FEATURE:
<223> OTHER INFORMATION: Synthetic

<400> SEQUENCE: 78

Arg Lys Glu Glu Lys Gln Arg Asn Gly Thr Leu Thr Val
1               5                   10

<210> SEQ ID NO 79
<211> LENGTH: 12
<212> TYPE: PRT
<213> ORGANISM: Artificial
<220> FEATURE:
<223> OTHER INFORMATION: Synthetic

<400> SEQUENCE: 79

Lys Glu Glu Lys Gln Arg Asn Gly Thr Leu Thr Val
1               5                   10

<210> SEQ ID NO 80
<211> LENGTH: 11
<212> TYPE: PRT
<213> ORGANISM: Artificial
<220> FEATURE:
<223> OTHER INFORMATION: Synthetic
```

<400> SEQUENCE: 80

Glu Glu Lys Gln Arg Asn Gly Thr Leu Thr Val
1               5                   10

<210> SEQ ID NO 81
<211> LENGTH: 10
<212> TYPE: PRT
<213> ORGANISM: Artificial
<220> FEATURE:
<223> OTHER INFORMATION: Synthetic

<400> SEQUENCE: 81

Glu Lys Gln Arg Asn Gly Thr Leu Thr Val
1               5                   10

<210> SEQ ID NO 82
<211> LENGTH: 9
<212> TYPE: PRT
<213> ORGANISM: Artificial
<220> FEATURE:
<223> OTHER INFORMATION: Synthetic

<400> SEQUENCE: 82

Lys Gln Arg Asn Gly Thr Leu Thr Val
1               5

<210> SEQ ID NO 83
<211> LENGTH: 8
<212> TYPE: PRT
<213> ORGANISM: Artificial
<220> FEATURE:
<223> OTHER INFORMATION: Synthetic

<400> SEQUENCE: 83

Gln Arg Asn Gly Thr Leu Thr Val
1               5

<210> SEQ ID NO 84
<211> LENGTH: 7
<212> TYPE: PRT
<213> ORGANISM: Artificial
<220> FEATURE:
<223> OTHER INFORMATION: Synthetic

<400> SEQUENCE: 84

Arg Asn Gly Thr Leu Thr Val
1               5

<210> SEQ ID NO 85
<211> LENGTH: 6
<212> TYPE: PRT
<213> ORGANISM: Artificial
<220> FEATURE:
<223> OTHER INFORMATION: Synthetic

<400> SEQUENCE: 85

Asn Gly Thr Leu Thr Val
1               5

<210> SEQ ID NO 86
<211> LENGTH: 5
<212> TYPE: PRT
<213> ORGANISM: Artificial
<220> FEATURE:
<223> OTHER INFORMATION: Synthetic

<400> SEQUENCE: 86

```
Gly Thr Leu Thr Val
1               5

<210> SEQ ID NO 87
<211> LENGTH: 4
<212> TYPE: PRT
<213> ORGANISM: Artificial
<220> FEATURE:
<223> OTHER INFORMATION: Synthetic

<400> SEQUENCE: 87

Thr Leu Thr Val
1

<210> SEQ ID NO 88
<211> LENGTH: 14
<212> TYPE: PRT
<213> ORGANISM: Artificial
<220> FEATURE:
<223> OTHER INFORMATION: Synthetic

<400> SEQUENCE: 88

Ser Thr Arg Lys Glu Glu Lys Gln Arg Asn Gly Thr Leu Thr
1               5                   10

<210> SEQ ID NO 89
<211> LENGTH: 13
<212> TYPE: PRT
<213> ORGANISM: Artificial
<220> FEATURE:
<223> OTHER INFORMATION: Synthetic

<400> SEQUENCE: 89

Thr Arg Lys Glu Glu Lys Gln Arg Asn Gly Thr Leu Thr
1               5                   10

<210> SEQ ID NO 90
<211> LENGTH: 12
<212> TYPE: PRT
<213> ORGANISM: Artificial
<220> FEATURE:
<223> OTHER INFORMATION: Synthetic

<400> SEQUENCE: 90

Arg Lys Glu Glu Lys Gln Arg Asn Gly Thr Leu Thr
1               5                   10

<210> SEQ ID NO 91
<211> LENGTH: 11
<212> TYPE: PRT
<213> ORGANISM: Artificial
<220> FEATURE:
<223> OTHER INFORMATION: Synthetic

<400> SEQUENCE: 91

Lys Glu Glu Lys Gln Arg Asn Gly Thr Leu Thr
1               5                   10

<210> SEQ ID NO 92
<211> LENGTH: 10
<212> TYPE: PRT
<213> ORGANISM: Artificial
<220> FEATURE:
<223> OTHER INFORMATION: Synthetic

<400> SEQUENCE: 92

Glu Glu Lys Gln Arg Asn Gly Thr Leu Thr
```

<210> SEQ ID NO 93
<211> LENGTH: 9
<212> TYPE: PRT
<213> ORGANISM: Artificial
<220> FEATURE:
<223> OTHER INFORMATION: Synthetic

<400> SEQUENCE: 93

Glu Lys Gln Arg Asn Gly Thr Leu Thr
1               5

<210> SEQ ID NO 94
<211> LENGTH: 8
<212> TYPE: PRT
<213> ORGANISM: Artificial
<220> FEATURE:
<223> OTHER INFORMATION: Synthetic

<400> SEQUENCE: 94

Lys Gln Arg Asn Gly Thr Leu Thr
1               5

<210> SEQ ID NO 95
<211> LENGTH: 7
<212> TYPE: PRT
<213> ORGANISM: Artificial
<220> FEATURE:
<223> OTHER INFORMATION: Synthetic

<400> SEQUENCE: 95

Gln Arg Asn Gly Thr Leu Thr
1               5

<210> SEQ ID NO 96
<211> LENGTH: 6
<212> TYPE: PRT
<213> ORGANISM: Artificial
<220> FEATURE:
<223> OTHER INFORMATION: Synthetic

<400> SEQUENCE: 96

Arg Asn Gly Thr Leu Thr
1               5

<210> SEQ ID NO 97
<211> LENGTH: 5
<212> TYPE: PRT
<213> ORGANISM: Artificial
<220> FEATURE:
<223> OTHER INFORMATION: Synthetic

<400> SEQUENCE: 97

Asn Gly Thr Leu Thr
1               5

<210> SEQ ID NO 98
<211> LENGTH: 4
<212> TYPE: PRT
<213> ORGANISM: Artificial
<220> FEATURE:
<223> OTHER INFORMATION: Synthetic

<400> SEQUENCE: 98

Gly Thr Leu Thr
1

<210> SEQ ID NO 99
<211> LENGTH: 13
<212> TYPE: PRT
<213> ORGANISM: Artificial
<220> FEATURE:
<223> OTHER INFORMATION: Synthetic

<400> SEQUENCE: 99

Ser Thr Arg Lys Glu Glu Lys Gln Arg Asn Gly Thr Leu
1               5                   10

<210> SEQ ID NO 100
<211> LENGTH: 12
<212> TYPE: PRT
<213> ORGANISM: Artificial
<220> FEATURE:
<223> OTHER INFORMATION: Synthetic

<400> SEQUENCE: 100

Thr Arg Lys Glu Glu Lys Gln Arg Asn Gly Thr Leu
1               5                   10

<210> SEQ ID NO 101
<211> LENGTH: 11
<212> TYPE: PRT
<213> ORGANISM: Artificial
<220> FEATURE:
<223> OTHER INFORMATION: Synthetic

<400> SEQUENCE: 101

Arg Lys Glu Glu Lys Gln Arg Asn Gly Thr Leu
1               5                   10

<210> SEQ ID NO 102
<211> LENGTH: 10
<212> TYPE: PRT
<213> ORGANISM: Artificial
<220> FEATURE:
<223> OTHER INFORMATION: Synthetic

<400> SEQUENCE: 102

Lys Glu Glu Lys Gln Arg Asn Gly Thr Leu
1               5                   10

<210> SEQ ID NO 103
<211> LENGTH: 9
<212> TYPE: PRT
<213> ORGANISM: Artificial
<220> FEATURE:
<223> OTHER INFORMATION: Synthetic

<400> SEQUENCE: 103

Glu Glu Lys Gln Arg Asn Gly Thr Leu
1               5

<210> SEQ ID NO 104
<211> LENGTH: 8
<212> TYPE: PRT
<213> ORGANISM: Artificial
<220> FEATURE:
<223> OTHER INFORMATION: Synthetic

<400> SEQUENCE: 104

Glu Lys Gln Arg Asn Gly Thr Leu
1               5

<210> SEQ ID NO 105

```
<211> LENGTH: 7
<212> TYPE: PRT
<213> ORGANISM: Artificial
<220> FEATURE:
<223> OTHER INFORMATION: Synthetic

<400> SEQUENCE: 105

Lys Gln Arg Asn Gly Thr Leu
1               5

<210> SEQ ID NO 106
<211> LENGTH: 6
<212> TYPE: PRT
<213> ORGANISM: Artificial
<220> FEATURE:
<223> OTHER INFORMATION: Synthetic

<400> SEQUENCE: 106

Gln Arg Asn Gly Thr Leu
1               5

<210> SEQ ID NO 107
<211> LENGTH: 5
<212> TYPE: PRT
<213> ORGANISM: Artificial
<220> FEATURE:
<223> OTHER INFORMATION: Synthetic

<400> SEQUENCE: 107

Arg Asn Gly Thr Leu
1               5

<210> SEQ ID NO 108
<211> LENGTH: 4
<212> TYPE: PRT
<213> ORGANISM: Artificial
<220> FEATURE:
<223> OTHER INFORMATION: Synthetic

<400> SEQUENCE: 108

Asn Gly Thr Leu
1

<210> SEQ ID NO 109
<211> LENGTH: 12
<212> TYPE: PRT
<213> ORGANISM: Artificial
<220> FEATURE:
<223> OTHER INFORMATION: Synthetic

<400> SEQUENCE: 109

Ser Thr Arg Lys Glu Glu Lys Gln Arg Asn Gly Thr
1               5                   10

<210> SEQ ID NO 110
<211> LENGTH: 11
<212> TYPE: PRT
<213> ORGANISM: Artificial
<220> FEATURE:
<223> OTHER INFORMATION: Synthetic

<400> SEQUENCE: 110

Thr Arg Lys Glu Glu Lys Gln Arg Asn Gly Thr
1               5                   10

<210> SEQ ID NO 111
<211> LENGTH: 10
<212> TYPE: PRT
```

```
<213> ORGANISM: Artificial
<220> FEATURE:
<223> OTHER INFORMATION: Synthetic

<400> SEQUENCE: 111

Arg Lys Glu Glu Lys Gln Arg Asn Gly Thr
1               5                   10

<210> SEQ ID NO 112
<211> LENGTH: 9
<212> TYPE: PRT
<213> ORGANISM: Artificial
<220> FEATURE:
<223> OTHER INFORMATION: Synthetic

<400> SEQUENCE: 112

Lys Glu Glu Lys Gln Arg Asn Gly Thr
1               5

<210> SEQ ID NO 113
<211> LENGTH: 8
<212> TYPE: PRT
<213> ORGANISM: Artificial
<220> FEATURE:
<223> OTHER INFORMATION: Synthetic

<400> SEQUENCE: 113

Glu Glu Lys Gln Arg Asn Gly Thr
1               5

<210> SEQ ID NO 114
<211> LENGTH: 7
<212> TYPE: PRT
<213> ORGANISM: Artificial
<220> FEATURE:
<223> OTHER INFORMATION: Synthetic

<400> SEQUENCE: 114

Glu Lys Gln Arg Asn Gly Thr
1               5

<210> SEQ ID NO 115
<211> LENGTH: 6
<212> TYPE: PRT
<213> ORGANISM: Artificial
<220> FEATURE:
<223> OTHER INFORMATION: Synthetic

<400> SEQUENCE: 115

Lys Gln Arg Asn Gly Thr
1               5

<210> SEQ ID NO 116
<211> LENGTH: 5
<212> TYPE: PRT
<213> ORGANISM: Artificial
<220> FEATURE:
<223> OTHER INFORMATION: Synthetic

<400> SEQUENCE: 116

Gln Arg Asn Gly Thr
1               5

<210> SEQ ID NO 117
<211> LENGTH: 4
<212> TYPE: PRT
<213> ORGANISM: Artificial
<220> FEATURE:
```

<223> OTHER INFORMATION: Synthetic

<400> SEQUENCE: 117

Arg Asn Gly Thr
1

<210> SEQ ID NO 118
<211> LENGTH: 11
<212> TYPE: PRT
<213> ORGANISM: Artificial
<220> FEATURE:
<223> OTHER INFORMATION: Synthetic

<400> SEQUENCE: 118

Ser Thr Arg Lys Glu Glu Lys Gln Arg Asn Gly
1               5                   10

<210> SEQ ID NO 119
<211> LENGTH: 10
<212> TYPE: PRT
<213> ORGANISM: Artificial
<220> FEATURE:
<223> OTHER INFORMATION: Synthetic

<400> SEQUENCE: 119

Thr Arg Lys Glu Glu Lys Gln Arg Asn Gly
1               5                   10

<210> SEQ ID NO 120
<211> LENGTH: 9
<212> TYPE: PRT
<213> ORGANISM: Artificial
<220> FEATURE:
<223> OTHER INFORMATION: Synthetic

<400> SEQUENCE: 120

Arg Lys Glu Glu Lys Gln Arg Asn Gly
1               5

<210> SEQ ID NO 121
<211> LENGTH: 8
<212> TYPE: PRT
<213> ORGANISM: Artificial
<220> FEATURE:
<223> OTHER INFORMATION: Synthetic

<400> SEQUENCE: 121

Lys Glu Glu Lys Gln Arg Asn Gly
1               5

<210> SEQ ID NO 122
<211> LENGTH: 7
<212> TYPE: PRT
<213> ORGANISM: Artificial
<220> FEATURE:
<223> OTHER INFORMATION: Synthetic

<400> SEQUENCE: 122

Glu Glu Lys Gln Arg Asn Gly
1               5

<210> SEQ ID NO 123
<211> LENGTH: 6
<212> TYPE: PRT
<213> ORGANISM: Artificial
<220> FEATURE:
<223> OTHER INFORMATION: Synthetic

```
<400> SEQUENCE: 123

Glu Lys Gln Arg Asn Gly
1               5

<210> SEQ ID NO 124
<211> LENGTH: 5
<212> TYPE: PRT
<213> ORGANISM: Artificial
<220> FEATURE:
<223> OTHER INFORMATION: Synthetic

<400> SEQUENCE: 124

Lys Gln Arg Asn Gly
1               5

<210> SEQ ID NO 125
<211> LENGTH: 4
<212> TYPE: PRT
<213> ORGANISM: Artificial
<220> FEATURE:
<223> OTHER INFORMATION: Synthetic

<400> SEQUENCE: 125

Gln Arg Asn Gly
1

<210> SEQ ID NO 126
<211> LENGTH: 10
<212> TYPE: PRT
<213> ORGANISM: Artificial
<220> FEATURE:
<223> OTHER INFORMATION: Synthetic

<400> SEQUENCE: 126

Ser Thr Arg Lys Glu Glu Lys Gln Arg Asn
1               5                   10

<210> SEQ ID NO 127
<211> LENGTH: 9
<212> TYPE: PRT
<213> ORGANISM: Artificial
<220> FEATURE:
<223> OTHER INFORMATION: Synthetic

<400> SEQUENCE: 127

Thr Arg Lys Glu Glu Lys Gln Arg Asn
1               5

<210> SEQ ID NO 128
<211> LENGTH: 8
<212> TYPE: PRT
<213> ORGANISM: Artificial
<220> FEATURE:
<223> OTHER INFORMATION: Synthetic

<400> SEQUENCE: 128

Arg Lys Glu Glu Lys Gln Arg Asn
1               5

<210> SEQ ID NO 129
<211> LENGTH: 7
<212> TYPE: PRT
<213> ORGANISM: Artificial
<220> FEATURE:
<223> OTHER INFORMATION: Synthetic

<400> SEQUENCE: 129
```

```
Lys Glu Glu Lys Gln Arg Asn
1               5

<210> SEQ ID NO 130
<211> LENGTH: 6
<212> TYPE: PRT
<213> ORGANISM: Artificial
<220> FEATURE:
<223> OTHER INFORMATION: Synthetic

<400> SEQUENCE: 130

Glu Glu Lys Gln Arg Asn
1               5

<210> SEQ ID NO 131
<211> LENGTH: 5
<212> TYPE: PRT
<213> ORGANISM: Artificial
<220> FEATURE:
<223> OTHER INFORMATION: Synthetic

<400> SEQUENCE: 131

Glu Lys Gln Arg Asn
1               5

<210> SEQ ID NO 132
<211> LENGTH: 4
<212> TYPE: PRT
<213> ORGANISM: Artificial
<220> FEATURE:
<223> OTHER INFORMATION: Synthetic

<400> SEQUENCE: 132

Lys Gln Arg Asn
1

<210> SEQ ID NO 133
<211> LENGTH: 9
<212> TYPE: PRT
<213> ORGANISM: Artificial
<220> FEATURE:
<223> OTHER INFORMATION: Synthetic

<400> SEQUENCE: 133

Ser Thr Arg Lys Glu Glu Lys Gln Arg
1               5

<210> SEQ ID NO 134
<211> LENGTH: 8
<212> TYPE: PRT
<213> ORGANISM: Artificial
<220> FEATURE:
<223> OTHER INFORMATION: Synthetic

<400> SEQUENCE: 134

Thr Arg Lys Glu Glu Lys Gln Arg
1               5

<210> SEQ ID NO 135
<211> LENGTH: 7
<212> TYPE: PRT
<213> ORGANISM: Artificial
<220> FEATURE:
<223> OTHER INFORMATION: Synthetic

<400> SEQUENCE: 135

Arg Lys Glu Glu Lys Gln Arg
1               5
```

```
<210> SEQ ID NO 136
<211> LENGTH: 6
<212> TYPE: PRT
<213> ORGANISM: Artificial
<220> FEATURE:
<223> OTHER INFORMATION: Synthetic

<400> SEQUENCE: 136

Lys Glu Glu Lys Gln Arg
1               5

<210> SEQ ID NO 137
<211> LENGTH: 5
<212> TYPE: PRT
<213> ORGANISM: Artificial
<220> FEATURE:
<223> OTHER INFORMATION: Synthetic

<400> SEQUENCE: 137

Glu Glu Lys Gln Arg
1               5

<210> SEQ ID NO 138
<211> LENGTH: 4
<212> TYPE: PRT
<213> ORGANISM: Artificial
<220> FEATURE:
<223> OTHER INFORMATION: Synthetic

<400> SEQUENCE: 138

Glu Lys Gln Arg
1

<210> SEQ ID NO 139
<211> LENGTH: 8
<212> TYPE: PRT
<213> ORGANISM: Artificial
<220> FEATURE:
<223> OTHER INFORMATION: Synthetic

<400> SEQUENCE: 139

Ser Thr Arg Lys Glu Glu Lys Gln
1               5

<210> SEQ ID NO 140
<211> LENGTH: 7
<212> TYPE: PRT
<213> ORGANISM: Artificial
<220> FEATURE:
<223> OTHER INFORMATION: Synthetic

<400> SEQUENCE: 140

Thr Arg Lys Glu Glu Lys Gln
1               5

<210> SEQ ID NO 141
<211> LENGTH: 6
<212> TYPE: PRT
<213> ORGANISM: Artificial
<220> FEATURE:
<223> OTHER INFORMATION: Synthetic

<400> SEQUENCE: 141

Arg Lys Glu Glu Lys Gln
1               5
```

```
<210> SEQ ID NO 142
<211> LENGTH: 5
<212> TYPE: PRT
<213> ORGANISM: Artificial
<220> FEATURE:
<223> OTHER INFORMATION: Synthetic

<400> SEQUENCE: 142

Lys Glu Glu Lys Gln
1               5

<210> SEQ ID NO 143
<211> LENGTH: 4
<212> TYPE: PRT
<213> ORGANISM: Artificial
<220> FEATURE:
<223> OTHER INFORMATION: Synthetic

<400> SEQUENCE: 143

Glu Glu Lys Gln
1

<210> SEQ ID NO 144
<211> LENGTH: 7
<212> TYPE: PRT
<213> ORGANISM: Artificial
<220> FEATURE:
<223> OTHER INFORMATION: Synthetic

<400> SEQUENCE: 144

Ser Thr Arg Lys Glu Glu Lys
1               5

<210> SEQ ID NO 145
<211> LENGTH: 6
<212> TYPE: PRT
<213> ORGANISM: Artificial
<220> FEATURE:
<223> OTHER INFORMATION: Synthetic

<400> SEQUENCE: 145

Thr Arg Lys Glu Glu Lys
1               5

<210> SEQ ID NO 146
<211> LENGTH: 5
<212> TYPE: PRT
<213> ORGANISM: Artificial
<220> FEATURE:
<223> OTHER INFORMATION: Synthetic

<400> SEQUENCE: 146

Arg Lys Glu Glu Lys
1               5

<210> SEQ ID NO 147
<211> LENGTH: 4
<212> TYPE: PRT
<213> ORGANISM: Artificial
<220> FEATURE:
<223> OTHER INFORMATION: Synthetic

<400> SEQUENCE: 147

Lys Glu Glu Lys
1

<210> SEQ ID NO 148
<211> LENGTH: 6
```

```
<212> TYPE: PRT
<213> ORGANISM: Artificial
<220> FEATURE:
<223> OTHER INFORMATION: Synthetic

<400> SEQUENCE: 148

Ser Thr Arg Lys Glu Glu
1               5

<210> SEQ ID NO 149
<211> LENGTH: 5
<212> TYPE: PRT
<213> ORGANISM: Artificial
<220> FEATURE:
<223> OTHER INFORMATION: Synthetic

<400> SEQUENCE: 149

Thr Arg Lys Glu Glu
1               5

<210> SEQ ID NO 150
<211> LENGTH: 4
<212> TYPE: PRT
<213> ORGANISM: Artificial
<220> FEATURE:
<223> OTHER INFORMATION: Synthetic

<400> SEQUENCE: 150

Arg Lys Glu Glu
1

<210> SEQ ID NO 151
<211> LENGTH: 5
<212> TYPE: PRT
<213> ORGANISM: Artificial
<220> FEATURE:
<223> OTHER INFORMATION: Synthetic

<400> SEQUENCE: 151

Ser Thr Arg Lys Glu
1               5

<210> SEQ ID NO 152
<211> LENGTH: 4
<212> TYPE: PRT
<213> ORGANISM: Artificial
<220> FEATURE:
<223> OTHER INFORMATION: Synthetic

<400> SEQUENCE: 152

Thr Arg Lys Glu
1

<210> SEQ ID NO 153
<211> LENGTH: 4
<212> TYPE: PRT
<213> ORGANISM: Artificial
<220> FEATURE:
<223> OTHER INFORMATION: Synthetic

<400> SEQUENCE: 153

Ser Thr Arg Lys
1

<210> SEQ ID NO 154
<211> LENGTH: 14
<212> TYPE: PRT
<213> ORGANISM: Artificial
```

```
<220> FEATURE:
<223> OTHER INFORMATION: Synthetic

<400> SEQUENCE: 154

Cys Leu Val Val Asp Leu Ala Pro Ser Lys Gly Thr Val Asn
1               5                   10

<210> SEQ ID NO 155
<211> LENGTH: 13
<212> TYPE: PRT
<213> ORGANISM: Artificial
<220> FEATURE:
<223> OTHER INFORMATION: Synthetic

<400> SEQUENCE: 155

Cys Leu Val Val Asp Leu Ala Pro Ser Lys Gly Thr Val
1               5                   10

<210> SEQ ID NO 156
<211> LENGTH: 12
<212> TYPE: PRT
<213> ORGANISM: Artificial
<220> FEATURE:
<223> OTHER INFORMATION: Synthetic

<400> SEQUENCE: 156

Cys Leu Val Val Asp Leu Ala Pro Ser Lys Gly Thr
1               5                   10

<210> SEQ ID NO 157
<211> LENGTH: 11
<212> TYPE: PRT
<213> ORGANISM: Artificial
<220> FEATURE:
<223> OTHER INFORMATION: Synthetic

<400> SEQUENCE: 157

Cys Leu Val Val Asp Leu Ala Pro Ser Lys Gly
1               5                   10

<210> SEQ ID NO 158
<211> LENGTH: 10
<212> TYPE: PRT
<213> ORGANISM: Artificial
<220> FEATURE:
<223> OTHER INFORMATION: Synthetic

<400> SEQUENCE: 158

Cys Leu Val Val Asp Leu Ala Pro Ser Lys
1               5                   10

<210> SEQ ID NO 159
<211> LENGTH: 9
<212> TYPE: PRT
<213> ORGANISM: Artificial
<220> FEATURE:
<223> OTHER INFORMATION: Synthetic

<400> SEQUENCE: 159

Cys Leu Val Val Asp Leu Ala Pro Ser
1               5

<210> SEQ ID NO 160
<211> LENGTH: 8
<212> TYPE: PRT
<213> ORGANISM: Artificial
<220> FEATURE:
<223> OTHER INFORMATION: Synthetic
```

```
<400> SEQUENCE: 160

Cys Leu Val Val Asp Leu Ala Pro
1               5

<210> SEQ ID NO 161
<211> LENGTH: 7
<212> TYPE: PRT
<213> ORGANISM: Artificial
<220> FEATURE:
<223> OTHER INFORMATION: Synthetic

<400> SEQUENCE: 161

Cys Leu Val Val Asp Leu Ala
1               5

<210> SEQ ID NO 162
<211> LENGTH: 6
<212> TYPE: PRT
<213> ORGANISM: Artificial
<220> FEATURE:
<223> OTHER INFORMATION: Synthetic

<400> SEQUENCE: 162

Cys Leu Val Val Asp Leu
1               5

<210> SEQ ID NO 163
<211> LENGTH: 5
<212> TYPE: PRT
<213> ORGANISM: Artificial
<220> FEATURE:
<223> OTHER INFORMATION: Synthetic

<400> SEQUENCE: 163

Cys Leu Val Val Asp
1               5

<210> SEQ ID NO 164
<211> LENGTH: 4
<212> TYPE: PRT
<213> ORGANISM: Artificial
<220> FEATURE:
<223> OTHER INFORMATION: Synthetic

<400> SEQUENCE: 164

Cys Leu Val Val
1

<210> SEQ ID NO 165
<211> LENGTH: 13
<212> TYPE: PRT
<213> ORGANISM: Artificial
<220> FEATURE:
<223> OTHER INFORMATION: Synthetic

<400> SEQUENCE: 165

Leu Val Val Asp Leu Ala Pro Ser Lys Gly Thr Val Asn
1               5                   10

<210> SEQ ID NO 166
<211> LENGTH: 12
<212> TYPE: PRT
<213> ORGANISM: Artificial
<220> FEATURE:
<223> OTHER INFORMATION: Synthetic

<400> SEQUENCE: 166
```

Leu Val Val Asp Leu Ala Pro Ser Lys Gly Thr Val
1               5                   10

<210> SEQ ID NO 167
<211> LENGTH: 11
<212> TYPE: PRT
<213> ORGANISM: Artificial
<220> FEATURE:
<223> OTHER INFORMATION: Synthetic

<400> SEQUENCE: 167

Leu Val Val Asp Leu Ala Pro Ser Lys Gly Thr
1               5                   10

<210> SEQ ID NO 168
<211> LENGTH: 10
<212> TYPE: PRT
<213> ORGANISM: Artificial
<220> FEATURE:
<223> OTHER INFORMATION: Synthetic

<400> SEQUENCE: 168

Leu Val Val Asp Leu Ala Pro Ser Lys Gly
1               5                   10

<210> SEQ ID NO 169
<211> LENGTH: 9
<212> TYPE: PRT
<213> ORGANISM: Artificial
<220> FEATURE:
<223> OTHER INFORMATION: Synthetic

<400> SEQUENCE: 169

Leu Val Val Asp Leu Ala Pro Ser Lys
1               5

<210> SEQ ID NO 170
<211> LENGTH: 8
<212> TYPE: PRT
<213> ORGANISM: Artificial
<220> FEATURE:
<223> OTHER INFORMATION: Synthetic

<400> SEQUENCE: 170

Leu Val Val Asp Leu Ala Pro Ser
1               5

<210> SEQ ID NO 171
<211> LENGTH: 7
<212> TYPE: PRT
<213> ORGANISM: Artificial
<220> FEATURE:
<223> OTHER INFORMATION: Synthetic

<400> SEQUENCE: 171

Leu Val Val Asp Leu Ala Pro
1               5

<210> SEQ ID NO 172
<211> LENGTH: 6
<212> TYPE: PRT
<213> ORGANISM: Artificial
<220> FEATURE:
<223> OTHER INFORMATION: Synthetic

<400> SEQUENCE: 172

Leu Val Val Asp Leu Ala

```
1               5

<210> SEQ ID NO 173
<211> LENGTH: 5
<212> TYPE: PRT
<213> ORGANISM: Artificial
<220> FEATURE:
<223> OTHER INFORMATION: Synthetic

<400> SEQUENCE: 173

Leu Val Val Asp Leu
1               5

<210> SEQ ID NO 174
<211> LENGTH: 4
<212> TYPE: PRT
<213> ORGANISM: Artificial
<220> FEATURE:
<223> OTHER INFORMATION: Synthetic

<400> SEQUENCE: 174

Leu Val Val Asp
1

<210> SEQ ID NO 175
<211> LENGTH: 12
<212> TYPE: PRT
<213> ORGANISM: Artificial
<220> FEATURE:
<223> OTHER INFORMATION: Synthetic

<400> SEQUENCE: 175

Val Val Asp Leu Ala Pro Ser Lys Gly Thr Val Asn
1               5                   10

<210> SEQ ID NO 176
<211> LENGTH: 11
<212> TYPE: PRT
<213> ORGANISM: Artificial
<220> FEATURE:
<223> OTHER INFORMATION: Synthetic

<400> SEQUENCE: 176

Val Val Asp Leu Ala Pro Ser Lys Gly Thr Val
1               5                   10

<210> SEQ ID NO 177
<211> LENGTH: 10
<212> TYPE: PRT
<213> ORGANISM: Artificial
<220> FEATURE:
<223> OTHER INFORMATION: Synthetic

<400> SEQUENCE: 177

Val Val Asp Leu Ala Pro Ser Lys Gly Thr
1               5                   10

<210> SEQ ID NO 178
<211> LENGTH: 9
<212> TYPE: PRT
<213> ORGANISM: Artificial
<220> FEATURE:
<223> OTHER INFORMATION: Synthetic

<400> SEQUENCE: 178

Val Val Asp Leu Ala Pro Ser Lys Gly
1               5
```

```
<210> SEQ ID NO 179
<211> LENGTH: 8
<212> TYPE: PRT
<213> ORGANISM: Artificial
<220> FEATURE:
<223> OTHER INFORMATION: Synthetic

<400> SEQUENCE: 179

Val Val Asp Leu Ala Pro Ser Lys
1               5

<210> SEQ ID NO 180
<211> LENGTH: 7
<212> TYPE: PRT
<213> ORGANISM: Artificial
<220> FEATURE:
<223> OTHER INFORMATION: Synthetic

<400> SEQUENCE: 180

Val Val Asp Leu Ala Pro Ser
1               5

<210> SEQ ID NO 181
<211> LENGTH: 6
<212> TYPE: PRT
<213> ORGANISM: Artificial
<220> FEATURE:
<223> OTHER INFORMATION: Synthetic

<400> SEQUENCE: 181

Val Val Asp Leu Ala Pro
1               5

<210> SEQ ID NO 182
<211> LENGTH: 5
<212> TYPE: PRT
<213> ORGANISM: Artificial
<220> FEATURE:
<223> OTHER INFORMATION: Synthetic

<400> SEQUENCE: 182

Val Val Asp Leu Ala
1               5

<210> SEQ ID NO 183
<211> LENGTH: 4
<212> TYPE: PRT
<213> ORGANISM: Artificial
<220> FEATURE:
<223> OTHER INFORMATION: Synthetic

<400> SEQUENCE: 183

Val Val Asp Leu
1

<210> SEQ ID NO 184
<211> LENGTH: 11
<212> TYPE: PRT
<213> ORGANISM: Artificial
<220> FEATURE:
<223> OTHER INFORMATION: Synthetic

<400> SEQUENCE: 184

Val Asp Leu Ala Pro Ser Lys Gly Thr Val Asn
1               5                   10

<210> SEQ ID NO 185
```

```
<211> LENGTH: 10
<212> TYPE: PRT
<213> ORGANISM: Artificial
<220> FEATURE:
<223> OTHER INFORMATION: Synthetic

<400> SEQUENCE: 185

Val Asp Leu Ala Pro Ser Lys Gly Thr Val
1               5                   10

<210> SEQ ID NO 186
<211> LENGTH: 9
<212> TYPE: PRT
<213> ORGANISM: Artificial
<220> FEATURE:
<223> OTHER INFORMATION: Synthetic

<400> SEQUENCE: 186

Val Asp Leu Ala Pro Ser Lys Gly Thr
1               5

<210> SEQ ID NO 187
<211> LENGTH: 8
<212> TYPE: PRT
<213> ORGANISM: Artificial
<220> FEATURE:
<223> OTHER INFORMATION: Synthetic

<400> SEQUENCE: 187

Val Asp Leu Ala Pro Ser Lys Gly
1               5

<210> SEQ ID NO 188
<211> LENGTH: 7
<212> TYPE: PRT
<213> ORGANISM: Artificial
<220> FEATURE:
<223> OTHER INFORMATION: Synthetic

<400> SEQUENCE: 188

Val Asp Leu Ala Pro Ser Lys
1               5

<210> SEQ ID NO 189
<211> LENGTH: 6
<212> TYPE: PRT
<213> ORGANISM: Artificial
<220> FEATURE:
<223> OTHER INFORMATION: Synthetic

<400> SEQUENCE: 189

Val Asp Leu Ala Pro Ser
1               5

<210> SEQ ID NO 190
<211> LENGTH: 5
<212> TYPE: PRT
<213> ORGANISM: Artificial
<220> FEATURE:
<223> OTHER INFORMATION: Synthetic

<400> SEQUENCE: 190

Val Asp Leu Ala Pro
1               5

<210> SEQ ID NO 191
<211> LENGTH: 4
<212> TYPE: PRT
```

<213> ORGANISM: Artificial
<220> FEATURE:
<223> OTHER INFORMATION: Synthetic

<400> SEQUENCE: 191

Val Asp Leu Ala
1

<210> SEQ ID NO 192
<211> LENGTH: 10
<212> TYPE: PRT
<213> ORGANISM: Artificial
<220> FEATURE:
<223> OTHER INFORMATION: Synthetic

<400> SEQUENCE: 192

Asp Leu Ala Pro Ser Lys Gly Thr Val Asn
1               5                   10

<210> SEQ ID NO 193
<211> LENGTH: 9
<212> TYPE: PRT
<213> ORGANISM: Artificial
<220> FEATURE:
<223> OTHER INFORMATION: Synthetic

<400> SEQUENCE: 193

Asp Leu Ala Pro Ser Lys Gly Thr Val
1               5

<210> SEQ ID NO 194
<211> LENGTH: 8
<212> TYPE: PRT
<213> ORGANISM: Artificial
<220> FEATURE:
<223> OTHER INFORMATION: Synthetic

<400> SEQUENCE: 194

Asp Leu Ala Pro Ser Lys Gly Thr
1               5

<210> SEQ ID NO 195
<211> LENGTH: 7
<212> TYPE: PRT
<213> ORGANISM: Artificial
<220> FEATURE:
<223> OTHER INFORMATION: Synthetic

<400> SEQUENCE: 195

Asp Leu Ala Pro Ser Lys Gly
1               5

<210> SEQ ID NO 196
<211> LENGTH: 6
<212> TYPE: PRT
<213> ORGANISM: Artificial
<220> FEATURE:
<223> OTHER INFORMATION: Synthetic

<400> SEQUENCE: 196

Asp Leu Ala Pro Ser Lys
1               5

<210> SEQ ID NO 197
<211> LENGTH: 5
<212> TYPE: PRT
<213> ORGANISM: Artificial
<220> FEATURE:

<223> OTHER INFORMATION: Synthetic

<400> SEQUENCE: 197

Asp Leu Ala Pro Ser
1               5

<210> SEQ ID NO 198
<211> LENGTH: 4
<212> TYPE: PRT
<213> ORGANISM: Artificial
<220> FEATURE:
<223> OTHER INFORMATION: Synthetic

<400> SEQUENCE: 198

Asp Leu Ala Pro
1

<210> SEQ ID NO 199
<211> LENGTH: 9
<212> TYPE: PRT
<213> ORGANISM: Artificial
<220> FEATURE:
<223> OTHER INFORMATION: Synthetic

<400> SEQUENCE: 199

Leu Ala Pro Ser Lys Gly Thr Val Asn
1               5

<210> SEQ ID NO 200
<211> LENGTH: 8
<212> TYPE: PRT
<213> ORGANISM: Artificial
<220> FEATURE:
<223> OTHER INFORMATION: Synthetic

<400> SEQUENCE: 200

Leu Ala Pro Ser Lys Gly Thr Val
1               5

<210> SEQ ID NO 201
<211> LENGTH: 7
<212> TYPE: PRT
<213> ORGANISM: Artificial
<220> FEATURE:
<223> OTHER INFORMATION: Synthetic

<400> SEQUENCE: 201

Leu Ala Pro Ser Lys Gly Thr
1               5

<210> SEQ ID NO 202
<211> LENGTH: 6
<212> TYPE: PRT
<213> ORGANISM: Artificial
<220> FEATURE:
<223> OTHER INFORMATION: Synthetic

<400> SEQUENCE: 202

Leu Ala Pro Ser Lys Gly
1               5

<210> SEQ ID NO 203
<211> LENGTH: 5
<212> TYPE: PRT
<213> ORGANISM: Artificial
<220> FEATURE:
<223> OTHER INFORMATION: Synthetic

```
<400> SEQUENCE: 203

Leu Ala Pro Ser Lys
1               5

<210> SEQ ID NO 204
<211> LENGTH: 4
<212> TYPE: PRT
<213> ORGANISM: Artificial
<220> FEATURE:
<223> OTHER INFORMATION: Synthetic

<400> SEQUENCE: 204

Leu Ala Pro Ser
1

<210> SEQ ID NO 205
<211> LENGTH: 8
<212> TYPE: PRT
<213> ORGANISM: Artificial
<220> FEATURE:
<223> OTHER INFORMATION: Synthetic

<400> SEQUENCE: 205

Ala Pro Ser Lys Gly Thr Val Asn
1               5

<210> SEQ ID NO 206
<211> LENGTH: 7
<212> TYPE: PRT
<213> ORGANISM: Artificial
<220> FEATURE:
<223> OTHER INFORMATION: Synthetic

<400> SEQUENCE: 206

Ala Pro Ser Lys Gly Thr Val
1               5

<210> SEQ ID NO 207
<211> LENGTH: 6
<212> TYPE: PRT
<213> ORGANISM: Artificial
<220> FEATURE:
<223> OTHER INFORMATION: Synthetic

<400> SEQUENCE: 207

Ala Pro Ser Lys Gly Thr
1               5

<210> SEQ ID NO 208
<211> LENGTH: 5
<212> TYPE: PRT
<213> ORGANISM: Artificial
<220> FEATURE:
<223> OTHER INFORMATION: Synthetic

<400> SEQUENCE: 208

Ala Pro Ser Lys Gly
1               5

<210> SEQ ID NO 209
<211> LENGTH: 4
<212> TYPE: PRT
<213> ORGANISM: Artificial
<220> FEATURE:
<223> OTHER INFORMATION: Synthetic

<400> SEQUENCE: 209
```

```
Ala Pro Ser Lys
1

<210> SEQ ID NO 210
<211> LENGTH: 7
<212> TYPE: PRT
<213> ORGANISM: Artificial
<220> FEATURE:
<223> OTHER INFORMATION: Synthetic

<400> SEQUENCE: 210

Pro Ser Lys Gly Thr Val Asn
1               5

<210> SEQ ID NO 211
<211> LENGTH: 6
<212> TYPE: PRT
<213> ORGANISM: Artificial
<220> FEATURE:
<223> OTHER INFORMATION: Synthetic

<400> SEQUENCE: 211

Pro Ser Lys Gly Thr Val
1               5

<210> SEQ ID NO 212
<211> LENGTH: 5
<212> TYPE: PRT
<213> ORGANISM: Artificial
<220> FEATURE:
<223> OTHER INFORMATION: Synthetic

<400> SEQUENCE: 212

Pro Ser Lys Gly Thr
1               5

<210> SEQ ID NO 213
<211> LENGTH: 4
<212> TYPE: PRT
<213> ORGANISM: Artificial
<220> FEATURE:
<223> OTHER INFORMATION: Synthetic

<400> SEQUENCE: 213

Pro Ser Lys Gly
1

<210> SEQ ID NO 214
<211> LENGTH: 6
<212> TYPE: PRT
<213> ORGANISM: Artificial
<220> FEATURE:
<223> OTHER INFORMATION: Synthetic

<400> SEQUENCE: 214

Ser Lys Gly Thr Val Asn
1               5

<210> SEQ ID NO 215
<211> LENGTH: 5
<212> TYPE: PRT
<213> ORGANISM: Artificial
<220> FEATURE:
<223> OTHER INFORMATION: Synthetic

<400> SEQUENCE: 215

Ser Lys Gly Thr Val
1               5
```

```
<210> SEQ ID NO 216
<211> LENGTH: 4
<212> TYPE: PRT
<213> ORGANISM: Artificial
<220> FEATURE:
<223> OTHER INFORMATION: Synthetic

<400> SEQUENCE: 216

Ser Lys Gly Thr
1

<210> SEQ ID NO 217
<211> LENGTH: 5
<212> TYPE: PRT
<213> ORGANISM: Artificial
<220> FEATURE:
<223> OTHER INFORMATION: Synthetic

<400> SEQUENCE: 217

Lys Gly Thr Val Asn
1               5

<210> SEQ ID NO 218
<211> LENGTH: 4
<212> TYPE: PRT
<213> ORGANISM: Artificial
<220> FEATURE:
<223> OTHER INFORMATION: Synthetic

<400> SEQUENCE: 218

Lys Gly Thr Val
1

<210> SEQ ID NO 219
<211> LENGTH: 4
<212> TYPE: PRT
<213> ORGANISM: Artificial
<220> FEATURE:
<223> OTHER INFORMATION: Synthetic

<400> SEQUENCE: 219

Gly Thr Val Asn
1

<210> SEQ ID NO 220
<211> LENGTH: 16
<212> TYPE: PRT
<213> ORGANISM: Artificial
<220> FEATURE:
<223> OTHER INFORMATION: Synthetic

<400> SEQUENCE: 220

Gln Cys Arg Val Thr His Pro His Leu Pro Arg Ala Leu Met Arg Ser
1               5                   10                  15

<210> SEQ ID NO 221
<211> LENGTH: 15
<212> TYPE: PRT
<213> ORGANISM: Artificial
<220> FEATURE:
<223> OTHER INFORMATION: Synthetic

<400> SEQUENCE: 221

Cys Arg Val Thr His Pro His Leu Pro Arg Ala Leu Met Arg Ser
1               5                   10                  15
```

```
<210> SEQ ID NO 222
<211> LENGTH: 14
<212> TYPE: PRT
<213> ORGANISM: Artificial
<220> FEATURE:
<223> OTHER INFORMATION: Synthetic

<400> SEQUENCE: 222

Arg Val Thr His Pro His Leu Pro Arg Ala Leu Met Arg Ser
1               5                   10

<210> SEQ ID NO 223
<211> LENGTH: 13
<212> TYPE: PRT
<213> ORGANISM: Artificial
<220> FEATURE:
<223> OTHER INFORMATION: Synthetic

<400> SEQUENCE: 223

Val Thr His Pro His Leu Pro Arg Ala Leu Met Arg Ser
1               5                   10

<210> SEQ ID NO 224
<211> LENGTH: 12
<212> TYPE: PRT
<213> ORGANISM: Artificial
<220> FEATURE:
<223> OTHER INFORMATION: Synthetic

<400> SEQUENCE: 224

Thr His Pro His Leu Pro Arg Ala Leu Met Arg Ser
1               5                   10

<210> SEQ ID NO 225
<211> LENGTH: 11
<212> TYPE: PRT
<213> ORGANISM: Artificial
<220> FEATURE:
<223> OTHER INFORMATION: Synthetic

<400> SEQUENCE: 225

His Pro His Leu Pro Arg Ala Leu Met Arg Ser
1               5                   10

<210> SEQ ID NO 226
<211> LENGTH: 10
<212> TYPE: PRT
<213> ORGANISM: Artificial
<220> FEATURE:
<223> OTHER INFORMATION: Synthetic

<400> SEQUENCE: 226

Pro His Leu Pro Arg Ala Leu Met Arg Ser
1               5                   10

<210> SEQ ID NO 227
<211> LENGTH: 9
<212> TYPE: PRT
<213> ORGANISM: Artificial
<220> FEATURE:
<223> OTHER INFORMATION: Synthetic

<400> SEQUENCE: 227

His Leu Pro Arg Ala Leu Met Arg Ser
1               5

<210> SEQ ID NO 228
<211> LENGTH: 8
```

-continued

```
<212> TYPE: PRT
<213> ORGANISM: Artificial
<220> FEATURE:
<223> OTHER INFORMATION: Synthetic

<400> SEQUENCE: 228

Leu Pro Arg Ala Leu Met Arg Ser
1               5

<210> SEQ ID NO 229
<211> LENGTH: 7
<212> TYPE: PRT
<213> ORGANISM: Artificial
<220> FEATURE:
<223> OTHER INFORMATION: Synthetic

<400> SEQUENCE: 229

Pro Arg Ala Leu Met Arg Ser
1               5

<210> SEQ ID NO 230
<211> LENGTH: 6
<212> TYPE: PRT
<213> ORGANISM: Artificial
<220> FEATURE:
<223> OTHER INFORMATION: Synthetic

<400> SEQUENCE: 230

Arg Ala Leu Met Arg Ser
1               5

<210> SEQ ID NO 231
<211> LENGTH: 5
<212> TYPE: PRT
<213> ORGANISM: Artificial
<220> FEATURE:
<223> OTHER INFORMATION: Synthetic

<400> SEQUENCE: 231

Ala Leu Met Arg Ser
1               5

<210> SEQ ID NO 232
<211> LENGTH: 4
<212> TYPE: PRT
<213> ORGANISM: Artificial
<220> FEATURE:
<223> OTHER INFORMATION: Synthetic

<400> SEQUENCE: 232

Leu Met Arg Ser
1

<210> SEQ ID NO 233
<211> LENGTH: 15
<212> TYPE: PRT
<213> ORGANISM: Artificial
<220> FEATURE:
<223> OTHER INFORMATION: Synthetic

<400> SEQUENCE: 233

Gln Cys Arg Val Thr His Pro His Leu Pro Arg Ala Leu Met Arg
1               5                   10                  15

<210> SEQ ID NO 234
<211> LENGTH: 14
<212> TYPE: PRT
<213> ORGANISM: Artificial
```

<220> FEATURE:
<223> OTHER INFORMATION: Synthetic

<400> SEQUENCE: 234

Cys Arg Val Thr His Pro His Leu Pro Arg Ala Leu Met Arg
1               5                   10

<210> SEQ ID NO 235
<211> LENGTH: 13
<212> TYPE: PRT
<213> ORGANISM: Artificial
<220> FEATURE:
<223> OTHER INFORMATION: Synthetic

<400> SEQUENCE: 235

Arg Val Thr His Pro His Leu Pro Arg Ala Leu Met Arg
1               5                   10

<210> SEQ ID NO 236
<211> LENGTH: 12
<212> TYPE: PRT
<213> ORGANISM: Artificial
<220> FEATURE:
<223> OTHER INFORMATION: Synthetic

<400> SEQUENCE: 236

Val Thr His Pro His Leu Pro Arg Ala Leu Met Arg
1               5                   10

<210> SEQ ID NO 237
<211> LENGTH: 11
<212> TYPE: PRT
<213> ORGANISM: Artificial
<220> FEATURE:
<223> OTHER INFORMATION: Synthetic

<400> SEQUENCE: 237

Thr His Pro His Leu Pro Arg Ala Leu Met Arg
1               5                   10

<210> SEQ ID NO 238
<211> LENGTH: 10
<212> TYPE: PRT
<213> ORGANISM: Artificial
<220> FEATURE:
<223> OTHER INFORMATION: Synthetic

<400> SEQUENCE: 238

His Pro His Leu Pro Arg Ala Leu Met Arg
1               5                   10

<210> SEQ ID NO 239
<211> LENGTH: 9
<212> TYPE: PRT
<213> ORGANISM: Artificial
<220> FEATURE:
<223> OTHER INFORMATION: Synthetic

<400> SEQUENCE: 239

Pro His Leu Pro Arg Ala Leu Met Arg
1               5

<210> SEQ ID NO 240
<211> LENGTH: 8
<212> TYPE: PRT
<213> ORGANISM: Artificial
<220> FEATURE:
<223> OTHER INFORMATION: Synthetic

```
<400> SEQUENCE: 240

His Leu Pro Arg Ala Leu Met Arg
1               5

<210> SEQ ID NO 241
<211> LENGTH: 7
<212> TYPE: PRT
<213> ORGANISM: Artificial
<220> FEATURE:
<223> OTHER INFORMATION: Synthetic

<400> SEQUENCE: 241

Leu Pro Arg Ala Leu Met Arg
1               5

<210> SEQ ID NO 242
<211> LENGTH: 6
<212> TYPE: PRT
<213> ORGANISM: Artificial
<220> FEATURE:
<223> OTHER INFORMATION: Synthetic

<400> SEQUENCE: 242

Pro Arg Ala Leu Met Arg
1               5

<210> SEQ ID NO 243
<211> LENGTH: 5
<212> TYPE: PRT
<213> ORGANISM: Artificial
<220> FEATURE:
<223> OTHER INFORMATION: Synthetic

<400> SEQUENCE: 243

Arg Ala Leu Met Arg
1               5

<210> SEQ ID NO 244
<211> LENGTH: 4
<212> TYPE: PRT
<213> ORGANISM: Artificial
<220> FEATURE:
<223> OTHER INFORMATION: Synthetic

<400> SEQUENCE: 244

Ala Leu Met Arg
1

<210> SEQ ID NO 245
<211> LENGTH: 14
<212> TYPE: PRT
<213> ORGANISM: Artificial
<220> FEATURE:
<223> OTHER INFORMATION: Synthetic

<400> SEQUENCE: 245

Gln Cys Arg Val Thr His Pro His Leu Pro Arg Ala Leu Met
1               5                   10

<210> SEQ ID NO 246
<211> LENGTH: 13
<212> TYPE: PRT
<213> ORGANISM: Artificial
<220> FEATURE:
<223> OTHER INFORMATION: Synthetic

<400> SEQUENCE: 246
```

Cys Arg Val Thr His Pro His Leu Pro Arg Ala Leu Met
1               5                   10

<210> SEQ ID NO 247
<211> LENGTH: 12
<212> TYPE: PRT
<213> ORGANISM: Artificial
<220> FEATURE:
<223> OTHER INFORMATION: Synthetic

<400> SEQUENCE: 247

Arg Val Thr His Pro His Leu Pro Arg Ala Leu Met
1               5                   10

<210> SEQ ID NO 248
<211> LENGTH: 11
<212> TYPE: PRT
<213> ORGANISM: Artificial
<220> FEATURE:
<223> OTHER INFORMATION: Synthetic

<400> SEQUENCE: 248

Val Thr His Pro His Leu Pro Arg Ala Leu Met
1               5                   10

<210> SEQ ID NO 249
<211> LENGTH: 10
<212> TYPE: PRT
<213> ORGANISM: Artificial
<220> FEATURE:
<223> OTHER INFORMATION: Synthetic

<400> SEQUENCE: 249

Thr His Pro His Leu Pro Arg Ala Leu Met
1               5                   10

<210> SEQ ID NO 250
<211> LENGTH: 9
<212> TYPE: PRT
<213> ORGANISM: Artificial
<220> FEATURE:
<223> OTHER INFORMATION: Synthetic

<400> SEQUENCE: 250

His Pro His Leu Pro Arg Ala Leu Met
1               5

<210> SEQ ID NO 251
<211> LENGTH: 8
<212> TYPE: PRT
<213> ORGANISM: Artificial
<220> FEATURE:
<223> OTHER INFORMATION: Synthetic

<400> SEQUENCE: 251

Pro His Leu Pro Arg Ala Leu Met
1               5

<210> SEQ ID NO 252
<211> LENGTH: 7
<212> TYPE: PRT
<213> ORGANISM: Artificial
<220> FEATURE:
<223> OTHER INFORMATION: Synthetic

<400> SEQUENCE: 252

His Leu Pro Arg Ala Leu Met

```
1               5

<210> SEQ ID NO 253
<211> LENGTH: 6
<212> TYPE: PRT
<213> ORGANISM: Artificial
<220> FEATURE:
<223> OTHER INFORMATION: Synthetic

<400> SEQUENCE: 253

Leu Pro Arg Ala Leu Met
1               5

<210> SEQ ID NO 254
<211> LENGTH: 5
<212> TYPE: PRT
<213> ORGANISM: Artificial
<220> FEATURE:
<223> OTHER INFORMATION: Synthetic

<400> SEQUENCE: 254

Pro Arg Ala Leu Met
1               5

<210> SEQ ID NO 255
<211> LENGTH: 4
<212> TYPE: PRT
<213> ORGANISM: Artificial
<220> FEATURE:
<223> OTHER INFORMATION: Synthetic

<400> SEQUENCE: 255

Arg Ala Leu Met
1

<210> SEQ ID NO 256
<211> LENGTH: 13
<212> TYPE: PRT
<213> ORGANISM: Artificial
<220> FEATURE:
<223> OTHER INFORMATION: Synthetic

<400> SEQUENCE: 256

Gln Cys Arg Val Thr His Pro His Leu Pro Arg Ala Leu
1               5                   10

<210> SEQ ID NO 257
<211> LENGTH: 12
<212> TYPE: PRT
<213> ORGANISM: Artificial
<220> FEATURE:
<223> OTHER INFORMATION: Synthetic

<400> SEQUENCE: 257

Cys Arg Val Thr His Pro His Leu Pro Arg Ala Leu
1               5                   10

<210> SEQ ID NO 258
<211> LENGTH: 11
<212> TYPE: PRT
<213> ORGANISM: Artificial
<220> FEATURE:
<223> OTHER INFORMATION: Synthetic

<400> SEQUENCE: 258

Arg Val Thr His Pro His Leu Pro Arg Ala Leu
1               5                   10
```

```
<210> SEQ ID NO 259
<211> LENGTH: 10
<212> TYPE: PRT
<213> ORGANISM: Artificial
<220> FEATURE:
<223> OTHER INFORMATION: Synthetic

<400> SEQUENCE: 259

Val Thr His Pro His Leu Pro Arg Ala Leu
1               5                   10

<210> SEQ ID NO 260
<211> LENGTH: 9
<212> TYPE: PRT
<213> ORGANISM: Artificial
<220> FEATURE:
<223> OTHER INFORMATION: Synthetic

<400> SEQUENCE: 260

Thr His Pro His Leu Pro Arg Ala Leu
1               5

<210> SEQ ID NO 261
<211> LENGTH: 8
<212> TYPE: PRT
<213> ORGANISM: Artificial
<220> FEATURE:
<223> OTHER INFORMATION: Synthetic

<400> SEQUENCE: 261

His Pro His Leu Pro Arg Ala Leu
1               5

<210> SEQ ID NO 262
<211> LENGTH: 7
<212> TYPE: PRT
<213> ORGANISM: Artificial
<220> FEATURE:
<223> OTHER INFORMATION: Synthetic

<400> SEQUENCE: 262

Pro His Leu Pro Arg Ala Leu
1               5

<210> SEQ ID NO 263
<211> LENGTH: 6
<212> TYPE: PRT
<213> ORGANISM: Artificial
<220> FEATURE:
<223> OTHER INFORMATION: Synthetic

<400> SEQUENCE: 263

His Leu Pro Arg Ala Leu
1               5

<210> SEQ ID NO 264
<211> LENGTH: 5
<212> TYPE: PRT
<213> ORGANISM: Artificial
<220> FEATURE:
<223> OTHER INFORMATION: Synthetic

<400> SEQUENCE: 264

Leu Pro Arg Ala Leu
1               5

<210> SEQ ID NO 265
```

```
<211> LENGTH: 4
<212> TYPE: PRT
<213> ORGANISM: Artificial
<220> FEATURE:
<223> OTHER INFORMATION: Synthetic

<400> SEQUENCE: 265

Pro Arg Ala Leu
1

<210> SEQ ID NO 266
<211> LENGTH: 12
<212> TYPE: PRT
<213> ORGANISM: Artificial
<220> FEATURE:
<223> OTHER INFORMATION: Synthetic

<400> SEQUENCE: 266

Gln Cys Arg Val Thr His Pro His Leu Pro Arg Ala
1               5                   10

<210> SEQ ID NO 267
<211> LENGTH: 11
<212> TYPE: PRT
<213> ORGANISM: Artificial
<220> FEATURE:
<223> OTHER INFORMATION: Synthetic

<400> SEQUENCE: 267

Cys Arg Val Thr His Pro His Leu Pro Arg Ala
1               5                   10

<210> SEQ ID NO 268
<211> LENGTH: 10
<212> TYPE: PRT
<213> ORGANISM: Artificial
<220> FEATURE:
<223> OTHER INFORMATION: Synthetic

<400> SEQUENCE: 268

Arg Val Thr His Pro His Leu Pro Arg Ala
1               5                   10

<210> SEQ ID NO 269
<211> LENGTH: 9
<212> TYPE: PRT
<213> ORGANISM: Artificial
<220> FEATURE:
<223> OTHER INFORMATION: Synthetic

<400> SEQUENCE: 269

Val Thr His Pro His Leu Pro Arg Ala
1               5

<210> SEQ ID NO 270
<211> LENGTH: 8
<212> TYPE: PRT
<213> ORGANISM: Artificial
<220> FEATURE:
<223> OTHER INFORMATION: Synthetic

<400> SEQUENCE: 270

Thr His Pro His Leu Pro Arg Ala
1               5

<210> SEQ ID NO 271
<211> LENGTH: 7
<212> TYPE: PRT
```

```
<213> ORGANISM: Artificial
<220> FEATURE:
<223> OTHER INFORMATION: Synthetic

<400> SEQUENCE: 271

His Pro His Leu Pro Arg Ala
1               5

<210> SEQ ID NO 272
<211> LENGTH: 6
<212> TYPE: PRT
<213> ORGANISM: Artificial
<220> FEATURE:
<223> OTHER INFORMATION: Synthetic

<400> SEQUENCE: 272

Pro His Leu Pro Arg Ala
1               5

<210> SEQ ID NO 273
<211> LENGTH: 5
<212> TYPE: PRT
<213> ORGANISM: Artificial
<220> FEATURE:
<223> OTHER INFORMATION: Synthetic

<400> SEQUENCE: 273

His Leu Pro Arg Ala
1               5

<210> SEQ ID NO 274
<211> LENGTH: 4
<212> TYPE: PRT
<213> ORGANISM: Artificial
<220> FEATURE:
<223> OTHER INFORMATION: Synthetic

<400> SEQUENCE: 274

Leu Pro Arg Ala
1

<210> SEQ ID NO 275
<211> LENGTH: 11
<212> TYPE: PRT
<213> ORGANISM: Artificial
<220> FEATURE:
<223> OTHER INFORMATION: Synthetic

<400> SEQUENCE: 275

Gln Cys Arg Val Thr His Pro His Leu Pro Arg
1               5                   10

<210> SEQ ID NO 276
<211> LENGTH: 10
<212> TYPE: PRT
<213> ORGANISM: Artificial
<220> FEATURE:
<223> OTHER INFORMATION: Synthetic

<400> SEQUENCE: 276

Cys Arg Val Thr His Pro His Leu Pro Arg
1               5                   10

<210> SEQ ID NO 277
<211> LENGTH: 9
<212> TYPE: PRT
<213> ORGANISM: Artificial
<220> FEATURE:
```

<223> OTHER INFORMATION: Synthetic

<400> SEQUENCE: 277

Arg Val Thr His Pro His Leu Pro Arg
1               5

<210> SEQ ID NO 278
<211> LENGTH: 8
<212> TYPE: PRT
<213> ORGANISM: Artificial
<220> FEATURE:
<223> OTHER INFORMATION: Synthetic

<400> SEQUENCE: 278

Val Thr His Pro His Leu Pro Arg
1               5

<210> SEQ ID NO 279
<211> LENGTH: 7
<212> TYPE: PRT
<213> ORGANISM: Artificial
<220> FEATURE:
<223> OTHER INFORMATION: Synthetic

<400> SEQUENCE: 279

Thr His Pro His Leu Pro Arg
1               5

<210> SEQ ID NO 280
<211> LENGTH: 6
<212> TYPE: PRT
<213> ORGANISM: Artificial
<220> FEATURE:
<223> OTHER INFORMATION: Synthetic

<400> SEQUENCE: 280

His Pro His Leu Pro Arg
1               5

<210> SEQ ID NO 281
<211> LENGTH: 5
<212> TYPE: PRT
<213> ORGANISM: Artificial
<220> FEATURE:
<223> OTHER INFORMATION: Synthetic

<400> SEQUENCE: 281

Pro His Leu Pro Arg
1               5

<210> SEQ ID NO 282
<211> LENGTH: 4
<212> TYPE: PRT
<213> ORGANISM: Artificial
<220> FEATURE:
<223> OTHER INFORMATION: Synthetic

<400> SEQUENCE: 282

His Leu Pro Arg
1

<210> SEQ ID NO 283
<211> LENGTH: 10
<212> TYPE: PRT
<213> ORGANISM: Artificial
<220> FEATURE:
<223> OTHER INFORMATION: Synthetic

```
<400> SEQUENCE: 283

Gln Cys Arg Val Thr His Pro His Leu Pro
1               5                   10

<210> SEQ ID NO 284
<211> LENGTH: 9
<212> TYPE: PRT
<213> ORGANISM: Artificial
<220> FEATURE:
<223> OTHER INFORMATION: Synthetic

<400> SEQUENCE: 284

Cys Arg Val Thr His Pro His Leu Pro
1               5

<210> SEQ ID NO 285
<211> LENGTH: 8
<212> TYPE: PRT
<213> ORGANISM: Artificial
<220> FEATURE:
<223> OTHER INFORMATION: Synthetic

<400> SEQUENCE: 285

Arg Val Thr His Pro His Leu Pro
1               5

<210> SEQ ID NO 286
<211> LENGTH: 7
<212> TYPE: PRT
<213> ORGANISM: Artificial
<220> FEATURE:
<223> OTHER INFORMATION: Synthetic

<400> SEQUENCE: 286

Val Thr His Pro His Leu Pro
1               5

<210> SEQ ID NO 287
<211> LENGTH: 6
<212> TYPE: PRT
<213> ORGANISM: Artificial
<220> FEATURE:
<223> OTHER INFORMATION: Synthetic

<400> SEQUENCE: 287

Thr His Pro His Leu Pro
1               5

<210> SEQ ID NO 288
<211> LENGTH: 5
<212> TYPE: PRT
<213> ORGANISM: Artificial
<220> FEATURE:
<223> OTHER INFORMATION: Synthetic

<400> SEQUENCE: 288

His Pro His Leu Pro
1               5

<210> SEQ ID NO 289
<211> LENGTH: 4
<212> TYPE: PRT
<213> ORGANISM: Artificial
<220> FEATURE:
<223> OTHER INFORMATION: Synthetic

<400> SEQUENCE: 289
```

```
Pro His Leu Pro
1

<210> SEQ ID NO 290
<211> LENGTH: 9
<212> TYPE: PRT
<213> ORGANISM: Artificial
<220> FEATURE:
<223> OTHER INFORMATION: Synthetic

<400> SEQUENCE: 290

Gln Cys Arg Val Thr His Pro His Leu
1               5

<210> SEQ ID NO 291
<211> LENGTH: 8
<212> TYPE: PRT
<213> ORGANISM: Artificial
<220> FEATURE:
<223> OTHER INFORMATION: Synthetic

<400> SEQUENCE: 291

Cys Arg Val Thr His Pro His Leu
1               5

<210> SEQ ID NO 292
<211> LENGTH: 7
<212> TYPE: PRT
<213> ORGANISM: Artificial
<220> FEATURE:
<223> OTHER INFORMATION: Synthetic

<400> SEQUENCE: 292

Arg Val Thr His Pro His Leu
1               5

<210> SEQ ID NO 293
<211> LENGTH: 6
<212> TYPE: PRT
<213> ORGANISM: Artificial
<220> FEATURE:
<223> OTHER INFORMATION: Synthetic

<400> SEQUENCE: 293

Val Thr His Pro His Leu
1               5

<210> SEQ ID NO 294
<211> LENGTH: 5
<212> TYPE: PRT
<213> ORGANISM: Artificial
<220> FEATURE:
<223> OTHER INFORMATION: Synthetic

<400> SEQUENCE: 294

Thr His Pro His Leu
1               5

<210> SEQ ID NO 295
<211> LENGTH: 4
<212> TYPE: PRT
<213> ORGANISM: Artificial
<220> FEATURE:
<223> OTHER INFORMATION: Synthetic

<400> SEQUENCE: 295

His Pro His Leu
1
```

```
<210> SEQ ID NO 296
<211> LENGTH: 8
<212> TYPE: PRT
<213> ORGANISM: Artificial
<220> FEATURE:
<223> OTHER INFORMATION: Synthetic

<400> SEQUENCE: 296

Gln Cys Arg Val Thr His Pro His
1               5

<210> SEQ ID NO 297
<211> LENGTH: 7
<212> TYPE: PRT
<213> ORGANISM: Artificial
<220> FEATURE:
<223> OTHER INFORMATION: Synthetic

<400> SEQUENCE: 297

Cys Arg Val Thr His Pro His
1               5

<210> SEQ ID NO 298
<211> LENGTH: 6
<212> TYPE: PRT
<213> ORGANISM: Artificial
<220> FEATURE:
<223> OTHER INFORMATION: Synthetic

<400> SEQUENCE: 298

Arg Val Thr His Pro His
1               5

<210> SEQ ID NO 299
<211> LENGTH: 5
<212> TYPE: PRT
<213> ORGANISM: Artificial
<220> FEATURE:
<223> OTHER INFORMATION: Synthetic

<400> SEQUENCE: 299

Val Thr His Pro His
1               5

<210> SEQ ID NO 300
<211> LENGTH: 4
<212> TYPE: PRT
<213> ORGANISM: Artificial
<220> FEATURE:
<223> OTHER INFORMATION: Synthetic

<400> SEQUENCE: 300

Thr His Pro His
1

<210> SEQ ID NO 301
<211> LENGTH: 7
<212> TYPE: PRT
<213> ORGANISM: Artificial
<220> FEATURE:
<223> OTHER INFORMATION: Synthetic

<400> SEQUENCE: 301

Gln Cys Arg Val Thr His Pro
1               5
```

```
<210> SEQ ID NO 302
<211> LENGTH: 6
<212> TYPE: PRT
<213> ORGANISM: Artificial
<220> FEATURE:
<223> OTHER INFORMATION: Synthetic

<400> SEQUENCE: 302

Cys Arg Val Thr His Pro
1               5

<210> SEQ ID NO 303
<211> LENGTH: 5
<212> TYPE: PRT
<213> ORGANISM: Artificial
<220> FEATURE:
<223> OTHER INFORMATION: Synthetic

<400> SEQUENCE: 303

Arg Val Thr His Pro
1               5

<210> SEQ ID NO 304
<211> LENGTH: 4
<212> TYPE: PRT
<213> ORGANISM: Artificial
<220> FEATURE:
<223> OTHER INFORMATION: Synthetic

<400> SEQUENCE: 304

Val Thr His Pro
1

<210> SEQ ID NO 305
<211> LENGTH: 6
<212> TYPE: PRT
<213> ORGANISM: Artificial
<220> FEATURE:
<223> OTHER INFORMATION: Synthetic

<400> SEQUENCE: 305

Gln Cys Arg Val Thr His
1               5

<210> SEQ ID NO 306
<211> LENGTH: 5
<212> TYPE: PRT
<213> ORGANISM: Artificial
<220> FEATURE:
<223> OTHER INFORMATION: Synthetic

<400> SEQUENCE: 306

Cys Arg Val Thr His
1               5

<210> SEQ ID NO 307
<211> LENGTH: 4
<212> TYPE: PRT
<213> ORGANISM: Artificial
<220> FEATURE:
<223> OTHER INFORMATION: Synthetic

<400> SEQUENCE: 307

Arg Val Thr His
1

<210> SEQ ID NO 308
<211> LENGTH: 5
```

```
<212> TYPE: PRT
<213> ORGANISM: Artificial
<220> FEATURE:
<223> OTHER INFORMATION: Synthetic

<400> SEQUENCE: 308

Gln Cys Arg Val Thr
1               5

<210> SEQ ID NO 309
<211> LENGTH: 4
<212> TYPE: PRT
<213> ORGANISM: Artificial
<220> FEATURE:
<223> OTHER INFORMATION: Synthetic

<400> SEQUENCE: 309

Cys Arg Val Thr
1

<210> SEQ ID NO 310
<211> LENGTH: 4
<212> TYPE: PRT
<213> ORGANISM: Artificial
<220> FEATURE:
<223> OTHER INFORMATION: Synthetic

<400> SEQUENCE: 310

Gln Cys Arg Val
1

<210> SEQ ID NO 311
<211> LENGTH: 18
<212> TYPE: PRT
<213> ORGANISM: Artificial
<220> FEATURE:
<223> OTHER INFORMATION: Synthetic

<400> SEQUENCE: 311

Cys Ala Asp Ser Asn Pro Arg Gly Val Ser Ala Tyr Leu Ser Arg Pro
1               5                   10                  15

Ser Pro

<210> SEQ ID NO 312
<211> LENGTH: 17
<212> TYPE: PRT
<213> ORGANISM: Artificial
<220> FEATURE:
<223> OTHER INFORMATION: Synthetic

<400> SEQUENCE: 312

Ala Asp Ser Asn Pro Arg Gly Val Ser Ala Tyr Leu Ser Arg Pro Ser
1               5                   10                  15

Pro

<210> SEQ ID NO 313
<211> LENGTH: 16
<212> TYPE: PRT
<213> ORGANISM: Artificial
<220> FEATURE:
<223> OTHER INFORMATION: Synthetic

<400> SEQUENCE: 313

Asp Ser Asn Pro Arg Gly Val Ser Ala Tyr Leu Ser Arg Pro Ser Pro
1               5                   10                  15
```

```
<210> SEQ ID NO 314
<211> LENGTH: 15
<212> TYPE: PRT
<213> ORGANISM: Artificial
<220> FEATURE:
<223> OTHER INFORMATION: Synthetic

<400> SEQUENCE: 314

Ser Asn Pro Arg Gly Val Ser Ala Tyr Leu Ser Arg Pro Ser Pro
1               5                   10                  15

<210> SEQ ID NO 315
<211> LENGTH: 14
<212> TYPE: PRT
<213> ORGANISM: Artificial
<220> FEATURE:
<223> OTHER INFORMATION: Synthetic

<400> SEQUENCE: 315

Asn Pro Arg Gly Val Ser Ala Tyr Leu Ser Arg Pro Ser Pro
1               5                   10

<210> SEQ ID NO 316
<211> LENGTH: 13
<212> TYPE: PRT
<213> ORGANISM: Artificial
<220> FEATURE:
<223> OTHER INFORMATION: Synthetic

<400> SEQUENCE: 316

Pro Arg Gly Val Ser Ala Tyr Leu Ser Arg Pro Ser Pro
1               5                   10

<210> SEQ ID NO 317
<211> LENGTH: 12
<212> TYPE: PRT
<213> ORGANISM: Artificial
<220> FEATURE:
<223> OTHER INFORMATION: Synthetic

<400> SEQUENCE: 317

Arg Gly Val Ser Ala Tyr Leu Ser Arg Pro Ser Pro
1               5                   10

<210> SEQ ID NO 318
<211> LENGTH: 11
<212> TYPE: PRT
<213> ORGANISM: Artificial
<220> FEATURE:
<223> OTHER INFORMATION: Synthetic

<400> SEQUENCE: 318

Gly Val Ser Ala Tyr Leu Ser Arg Pro Ser Pro
1               5                   10

<210> SEQ ID NO 319
<211> LENGTH: 10
<212> TYPE: PRT
<213> ORGANISM: Artificial
<220> FEATURE:
<223> OTHER INFORMATION: Synthetic

<400> SEQUENCE: 319

Val Ser Ala Tyr Leu Ser Arg Pro Ser Pro
1               5                   10

<210> SEQ ID NO 320
<211> LENGTH: 9
```

```
<212> TYPE: PRT
<213> ORGANISM: Artificial
<220> FEATURE:
<223> OTHER INFORMATION: Synthetic

<400> SEQUENCE: 320

Ser Ala Tyr Leu Ser Arg Pro Ser Pro
1               5

<210> SEQ ID NO 321
<211> LENGTH: 8
<212> TYPE: PRT
<213> ORGANISM: Artificial
<220> FEATURE:
<223> OTHER INFORMATION: Synthetic

<400> SEQUENCE: 321

Ala Tyr Leu Ser Arg Pro Ser Pro
1               5

<210> SEQ ID NO 322
<211> LENGTH: 7
<212> TYPE: PRT
<213> ORGANISM: Artificial
<220> FEATURE:
<223> OTHER INFORMATION: Synthetic

<400> SEQUENCE: 322

Tyr Leu Ser Arg Pro Ser Pro
1               5

<210> SEQ ID NO 323
<211> LENGTH: 6
<212> TYPE: PRT
<213> ORGANISM: Artificial
<220> FEATURE:
<223> OTHER INFORMATION: Synthetic

<400> SEQUENCE: 323

Leu Ser Arg Pro Ser Pro
1               5

<210> SEQ ID NO 324
<211> LENGTH: 5
<212> TYPE: PRT
<213> ORGANISM: Artificial
<220> FEATURE:
<223> OTHER INFORMATION: Synthetic

<400> SEQUENCE: 324

Ser Arg Pro Ser Pro
1               5

<210> SEQ ID NO 325
<211> LENGTH: 4
<212> TYPE: PRT
<213> ORGANISM: Artificial
<220> FEATURE:
<223> OTHER INFORMATION: Synthetic

<400> SEQUENCE: 325

Arg Pro Ser Pro
1

<210> SEQ ID NO 326
<211> LENGTH: 17
<212> TYPE: PRT
<213> ORGANISM: Artificial
```

<220> FEATURE:
<223> OTHER INFORMATION: Synthetic

<400> SEQUENCE: 326

Cys Ala Asp Ser Asn Pro Arg Gly Val Ser Ala Tyr Leu Ser Arg Pro
1               5                   10                  15

Ser

<210> SEQ ID NO 327
<211> LENGTH: 16
<212> TYPE: PRT
<213> ORGANISM: Artificial
<220> FEATURE:
<223> OTHER INFORMATION: Synthetic

<400> SEQUENCE: 327

Ala Asp Ser Asn Pro Arg Gly Val Ser Ala Tyr Leu Ser Arg Pro Ser
1               5                   10                  15

<210> SEQ ID NO 328
<211> LENGTH: 15
<212> TYPE: PRT
<213> ORGANISM: Artificial
<220> FEATURE:
<223> OTHER INFORMATION: Synthetic

<400> SEQUENCE: 328

Asp Ser Asn Pro Arg Gly Val Ser Ala Tyr Leu Ser Arg Pro Ser
1               5                   10                  15

<210> SEQ ID NO 329
<211> LENGTH: 14
<212> TYPE: PRT
<213> ORGANISM: Artificial
<220> FEATURE:
<223> OTHER INFORMATION: Synthetic

<400> SEQUENCE: 329

Ser Asn Pro Arg Gly Val Ser Ala Tyr Leu Ser Arg Pro Ser
1               5                   10

<210> SEQ ID NO 330
<211> LENGTH: 13
<212> TYPE: PRT
<213> ORGANISM: Artificial
<220> FEATURE:
<223> OTHER INFORMATION: Synthetic

<400> SEQUENCE: 330

Asn Pro Arg Gly Val Ser Ala Tyr Leu Ser Arg Pro Ser
1               5                   10

<210> SEQ ID NO 331
<211> LENGTH: 12
<212> TYPE: PRT
<213> ORGANISM: Artificial
<220> FEATURE:
<223> OTHER INFORMATION: Synthetic

<400> SEQUENCE: 331

Pro Arg Gly Val Ser Ala Tyr Leu Ser Arg Pro Ser
1               5                   10

<210> SEQ ID NO 332
<211> LENGTH: 11
<212> TYPE: PRT
<213> ORGANISM: Artificial

```
<220> FEATURE:
<223> OTHER INFORMATION: Synthetic

<400> SEQUENCE: 332

Arg Gly Val Ser Ala Tyr Leu Ser Arg Pro Ser
1               5                   10

<210> SEQ ID NO 333
<211> LENGTH: 10
<212> TYPE: PRT
<213> ORGANISM: Artificial
<220> FEATURE:
<223> OTHER INFORMATION: Synthetic

<400> SEQUENCE: 333

Gly Val Ser Ala Tyr Leu Ser Arg Pro Ser
1               5                   10

<210> SEQ ID NO 334
<211> LENGTH: 9
<212> TYPE: PRT
<213> ORGANISM: Artificial
<220> FEATURE:
<223> OTHER INFORMATION: Synthetic

<400> SEQUENCE: 334

Val Ser Ala Tyr Leu Ser Arg Pro Ser
1               5

<210> SEQ ID NO 335
<211> LENGTH: 8
<212> TYPE: PRT
<213> ORGANISM: Artificial
<220> FEATURE:
<223> OTHER INFORMATION: Synthetic

<400> SEQUENCE: 335

Ser Ala Tyr Leu Ser Arg Pro Ser
1               5

<210> SEQ ID NO 336
<211> LENGTH: 7
<212> TYPE: PRT
<213> ORGANISM: Artificial
<220> FEATURE:
<223> OTHER INFORMATION: Synthetic

<400> SEQUENCE: 336

Ala Tyr Leu Ser Arg Pro Ser
1               5

<210> SEQ ID NO 337
<211> LENGTH: 6
<212> TYPE: PRT
<213> ORGANISM: Artificial
<220> FEATURE:
<223> OTHER INFORMATION: Synthetic

<400> SEQUENCE: 337

Tyr Leu Ser Arg Pro Ser
1               5

<210> SEQ ID NO 338
<211> LENGTH: 5
<212> TYPE: PRT
<213> ORGANISM: Artificial
<220> FEATURE:
<223> OTHER INFORMATION: Synthetic
```

```
<400> SEQUENCE: 338

Leu Ser Arg Pro Ser
1               5

<210> SEQ ID NO 339
<211> LENGTH: 4
<212> TYPE: PRT
<213> ORGANISM: Artificial
<220> FEATURE:
<223> OTHER INFORMATION: Synthetic

<400> SEQUENCE: 339

Ser Arg Pro Ser
1

<210> SEQ ID NO 340
<211> LENGTH: 16
<212> TYPE: PRT
<213> ORGANISM: Artificial
<220> FEATURE:
<223> OTHER INFORMATION: Synthetic

<400> SEQUENCE: 340

Cys Ala Asp Ser Asn Pro Arg Gly Val Ser Ala Tyr Leu Ser Arg Pro
1               5                   10                  15

<210> SEQ ID NO 341
<211> LENGTH: 15
<212> TYPE: PRT
<213> ORGANISM: Artificial
<220> FEATURE:
<223> OTHER INFORMATION: Synthetic

<400> SEQUENCE: 341

Ala Asp Ser Asn Pro Arg Gly Val Ser Ala Tyr Leu Ser Arg Pro
1               5                   10                  15

<210> SEQ ID NO 342
<211> LENGTH: 14
<212> TYPE: PRT
<213> ORGANISM: Artificial
<220> FEATURE:
<223> OTHER INFORMATION: Synthetic

<400> SEQUENCE: 342

Asp Ser Asn Pro Arg Gly Val Ser Ala Tyr Leu Ser Arg Pro
1               5                   10

<210> SEQ ID NO 343
<211> LENGTH: 13
<212> TYPE: PRT
<213> ORGANISM: Artificial
<220> FEATURE:
<223> OTHER INFORMATION: Synthetic

<400> SEQUENCE: 343

Ser Asn Pro Arg Gly Val Ser Ala Tyr Leu Ser Arg Pro
1               5                   10

<210> SEQ ID NO 344
<211> LENGTH: 12
<212> TYPE: PRT
<213> ORGANISM: Artificial
<220> FEATURE:
<223> OTHER INFORMATION: Synthetic

<400> SEQUENCE: 344
```

Asn Pro Arg Gly Val Ser Ala Tyr Leu Ser Arg Pro
1               5                   10

<210> SEQ ID NO 345
<211> LENGTH: 11
<212> TYPE: PRT
<213> ORGANISM: Artificial
<220> FEATURE:
<223> OTHER INFORMATION: Synthetic

<400> SEQUENCE: 345

Pro Arg Gly Val Ser Ala Tyr Leu Ser Arg Pro
1               5                   10

<210> SEQ ID NO 346
<211> LENGTH: 10
<212> TYPE: PRT
<213> ORGANISM: Artificial
<220> FEATURE:
<223> OTHER INFORMATION: Synthetic

<400> SEQUENCE: 346

Arg Gly Val Ser Ala Tyr Leu Ser Arg Pro
1               5                   10

<210> SEQ ID NO 347
<211> LENGTH: 9
<212> TYPE: PRT
<213> ORGANISM: Artificial
<220> FEATURE:
<223> OTHER INFORMATION: Synthetic

<400> SEQUENCE: 347

Gly Val Ser Ala Tyr Leu Ser Arg Pro
1               5

<210> SEQ ID NO 348
<211> LENGTH: 8
<212> TYPE: PRT
<213> ORGANISM: Artificial
<220> FEATURE:
<223> OTHER INFORMATION: Synthetic

<400> SEQUENCE: 348

Val Ser Ala Tyr Leu Ser Arg Pro
1               5

<210> SEQ ID NO 349
<211> LENGTH: 7
<212> TYPE: PRT
<213> ORGANISM: Artificial
<220> FEATURE:
<223> OTHER INFORMATION: Synthetic

<400> SEQUENCE: 349

Ser Ala Tyr Leu Ser Arg Pro
1               5

<210> SEQ ID NO 350
<211> LENGTH: 6
<212> TYPE: PRT
<213> ORGANISM: Artificial
<220> FEATURE:
<223> OTHER INFORMATION: Synthetic

<400> SEQUENCE: 350

Ala Tyr Leu Ser Arg Pro

```
<210> SEQ ID NO 351
<211> LENGTH: 5
<212> TYPE: PRT
<213> ORGANISM: Artificial
<220> FEATURE:
<223> OTHER INFORMATION: Synthetic

<400> SEQUENCE: 351

Tyr Leu Ser Arg Pro
1               5

<210> SEQ ID NO 352
<211> LENGTH: 4
<212> TYPE: PRT
<213> ORGANISM: Artificial
<220> FEATURE:
<223> OTHER INFORMATION: Synthetic

<400> SEQUENCE: 352

Leu Ser Arg Pro
1

<210> SEQ ID NO 353
<211> LENGTH: 15
<212> TYPE: PRT
<213> ORGANISM: Artificial
<220> FEATURE:
<223> OTHER INFORMATION: Synthetic

<400> SEQUENCE: 353

Cys Ala Asp Ser Asn Pro Arg Gly Val Ser Ala Tyr Leu Ser Arg
1               5                   10                  15

<210> SEQ ID NO 354
<211> LENGTH: 14
<212> TYPE: PRT
<213> ORGANISM: Artificial
<220> FEATURE:
<223> OTHER INFORMATION: Synthetic

<400> SEQUENCE: 354

Ala Asp Ser Asn Pro Arg Gly Val Ser Ala Tyr Leu Ser Arg
1               5                   10

<210> SEQ ID NO 355
<211> LENGTH: 13
<212> TYPE: PRT
<213> ORGANISM: Artificial
<220> FEATURE:
<223> OTHER INFORMATION: Synthetic

<400> SEQUENCE: 355

Asp Ser Asn Pro Arg Gly Val Ser Ala Tyr Leu Ser Arg
1               5                   10

<210> SEQ ID NO 356
<211> LENGTH: 12
<212> TYPE: PRT
<213> ORGANISM: Artificial
<220> FEATURE:
<223> OTHER INFORMATION: Synthetic

<400> SEQUENCE: 356

Ser Asn Pro Arg Gly Val Ser Ala Tyr Leu Ser Arg
1               5                   10
```

```
<210> SEQ ID NO 357
<211> LENGTH: 11
<212> TYPE: PRT
<213> ORGANISM: Artificial
<220> FEATURE:
<223> OTHER INFORMATION: Synthetic

<400> SEQUENCE: 357

Asn Pro Arg Gly Val Ser Ala Tyr Leu Ser Arg
 1               5                  10

<210> SEQ ID NO 358
<211> LENGTH: 10
<212> TYPE: PRT
<213> ORGANISM: Artificial
<220> FEATURE:
<223> OTHER INFORMATION: Synthetic

<400> SEQUENCE: 358

Pro Arg Gly Val Ser Ala Tyr Leu Ser Arg
 1               5                  10

<210> SEQ ID NO 359
<211> LENGTH: 9
<212> TYPE: PRT
<213> ORGANISM: Artificial
<220> FEATURE:
<223> OTHER INFORMATION: Synthetic

<400> SEQUENCE: 359

Arg Gly Val Ser Ala Tyr Leu Ser Arg
 1               5

<210> SEQ ID NO 360
<211> LENGTH: 8
<212> TYPE: PRT
<213> ORGANISM: Artificial
<220> FEATURE:
<223> OTHER INFORMATION: Synthetic

<400> SEQUENCE: 360

Gly Val Ser Ala Tyr Leu Ser Arg
 1               5

<210> SEQ ID NO 361
<211> LENGTH: 7
<212> TYPE: PRT
<213> ORGANISM: Artificial
<220> FEATURE:
<223> OTHER INFORMATION: Synthetic

<400> SEQUENCE: 361

Val Ser Ala Tyr Leu Ser Arg
 1               5

<210> SEQ ID NO 362
<211> LENGTH: 6
<212> TYPE: PRT
<213> ORGANISM: Artificial
<220> FEATURE:
<223> OTHER INFORMATION: Synthetic

<400> SEQUENCE: 362

Ser Ala Tyr Leu Ser Arg
 1               5

<210> SEQ ID NO 363
```

```
<211> LENGTH: 5
<212> TYPE: PRT
<213> ORGANISM: Artificial
<220> FEATURE:
<223> OTHER INFORMATION: Synthetic

<400> SEQUENCE: 363

Ala Tyr Leu Ser Arg
1               5

<210> SEQ ID NO 364
<211> LENGTH: 4
<212> TYPE: PRT
<213> ORGANISM: Artificial
<220> FEATURE:
<223> OTHER INFORMATION: Synthetic

<400> SEQUENCE: 364

Tyr Leu Ser Arg
1

<210> SEQ ID NO 365
<211> LENGTH: 14
<212> TYPE: PRT
<213> ORGANISM: Artificial
<220> FEATURE:
<223> OTHER INFORMATION: Synthetic

<400> SEQUENCE: 365

Cys Ala Asp Ser Asn Pro Arg Gly Val Ser Ala Tyr Leu Ser
1               5                   10

<210> SEQ ID NO 366
<211> LENGTH: 13
<212> TYPE: PRT
<213> ORGANISM: Artificial
<220> FEATURE:
<223> OTHER INFORMATION: Synthetic

<400> SEQUENCE: 366

Ala Asp Ser Asn Pro Arg Gly Val Ser Ala Tyr Leu Ser
1               5                   10

<210> SEQ ID NO 367
<211> LENGTH: 12
<212> TYPE: PRT
<213> ORGANISM: Artificial
<220> FEATURE:
<223> OTHER INFORMATION: Synthetic

<400> SEQUENCE: 367

Asp Ser Asn Pro Arg Gly Val Ser Ala Tyr Leu Ser
1               5                   10

<210> SEQ ID NO 368
<211> LENGTH: 11
<212> TYPE: PRT
<213> ORGANISM: Artificial
<220> FEATURE:
<223> OTHER INFORMATION: Synthetic

<400> SEQUENCE: 368

Ser Asn Pro Arg Gly Val Ser Ala Tyr Leu Ser
1               5                   10

<210> SEQ ID NO 369
<211> LENGTH: 10
<212> TYPE: PRT
```

<213> ORGANISM: Artificial
<220> FEATURE:
<223> OTHER INFORMATION: Synthetic

<400> SEQUENCE: 369

Asn Pro Arg Gly Val Ser Ala Tyr Leu Ser
1               5                   10

<210> SEQ ID NO 370
<211> LENGTH: 9
<212> TYPE: PRT
<213> ORGANISM: Artificial
<220> FEATURE:
<223> OTHER INFORMATION: Synthetic

<400> SEQUENCE: 370

Pro Arg Gly Val Ser Ala Tyr Leu Ser
1               5

<210> SEQ ID NO 371
<211> LENGTH: 8
<212> TYPE: PRT
<213> ORGANISM: Artificial
<220> FEATURE:
<223> OTHER INFORMATION: Synthetic

<400> SEQUENCE: 371

Arg Gly Val Ser Ala Tyr Leu Ser
1               5

<210> SEQ ID NO 372
<211> LENGTH: 7
<212> TYPE: PRT
<213> ORGANISM: Artificial
<220> FEATURE:
<223> OTHER INFORMATION: Synthetic

<400> SEQUENCE: 372

Gly Val Ser Ala Tyr Leu Ser
1               5

<210> SEQ ID NO 373
<211> LENGTH: 6
<212> TYPE: PRT
<213> ORGANISM: Artificial
<220> FEATURE:
<223> OTHER INFORMATION: Synthetic

<400> SEQUENCE: 373

Val Ser Ala Tyr Leu Ser
1               5

<210> SEQ ID NO 374
<211> LENGTH: 5
<212> TYPE: PRT
<213> ORGANISM: Artificial
<220> FEATURE:
<223> OTHER INFORMATION: Synthetic

<400> SEQUENCE: 374

Ser Ala Tyr Leu Ser
1               5

<210> SEQ ID NO 375
<211> LENGTH: 4
<212> TYPE: PRT
<213> ORGANISM: Artificial
<220> FEATURE:

<223> OTHER INFORMATION: Synthetic

<400> SEQUENCE: 375

Ala Tyr Leu Ser
1

<210> SEQ ID NO 376
<211> LENGTH: 13
<212> TYPE: PRT
<213> ORGANISM: Artificial
<220> FEATURE:
<223> OTHER INFORMATION: Synthetic

<400> SEQUENCE: 376

Cys Ala Asp Ser Asn Pro Arg Gly Val Ser Ala Tyr Leu
1               5                   10

<210> SEQ ID NO 377
<211> LENGTH: 12
<212> TYPE: PRT
<213> ORGANISM: Artificial
<220> FEATURE:
<223> OTHER INFORMATION: Synthetic

<400> SEQUENCE: 377

Ala Asp Ser Asn Pro Arg Gly Val Ser Ala Tyr Leu
1               5                   10

<210> SEQ ID NO 378
<211> LENGTH: 11
<212> TYPE: PRT
<213> ORGANISM: Artificial
<220> FEATURE:
<223> OTHER INFORMATION: Synthetic

<400> SEQUENCE: 378

Asp Ser Asn Pro Arg Gly Val Ser Ala Tyr Leu
1               5                   10

<210> SEQ ID NO 379
<211> LENGTH: 10
<212> TYPE: PRT
<213> ORGANISM: Artificial
<220> FEATURE:
<223> OTHER INFORMATION: Synthetic

<400> SEQUENCE: 379

Ser Asn Pro Arg Gly Val Ser Ala Tyr Leu
1               5                   10

<210> SEQ ID NO 380
<211> LENGTH: 9
<212> TYPE: PRT
<213> ORGANISM: Artificial
<220> FEATURE:
<223> OTHER INFORMATION: Synthetic

<400> SEQUENCE: 380

Asn Pro Arg Gly Val Ser Ala Tyr Leu
1               5

<210> SEQ ID NO 381
<211> LENGTH: 8
<212> TYPE: PRT
<213> ORGANISM: Artificial
<220> FEATURE:
<223> OTHER INFORMATION: Synthetic

```
<400> SEQUENCE: 381

Pro Arg Gly Val Ser Ala Tyr Leu
1               5

<210> SEQ ID NO 382
<211> LENGTH: 7
<212> TYPE: PRT
<213> ORGANISM: Artificial
<220> FEATURE:
<223> OTHER INFORMATION: Synthetic

<400> SEQUENCE: 382

Arg Gly Val Ser Ala Tyr Leu
1               5

<210> SEQ ID NO 383
<211> LENGTH: 6
<212> TYPE: PRT
<213> ORGANISM: Artificial
<220> FEATURE:
<223> OTHER INFORMATION: Synthetic

<400> SEQUENCE: 383

Gly Val Ser Ala Tyr Leu
1               5

<210> SEQ ID NO 384
<211> LENGTH: 5
<212> TYPE: PRT
<213> ORGANISM: Artificial
<220> FEATURE:
<223> OTHER INFORMATION: Synthetic

<400> SEQUENCE: 384

Val Ser Ala Tyr Leu
1               5

<210> SEQ ID NO 385
<211> LENGTH: 4
<212> TYPE: PRT
<213> ORGANISM: Artificial
<220> FEATURE:
<223> OTHER INFORMATION: Synthetic

<400> SEQUENCE: 385

Ser Ala Tyr Leu
1

<210> SEQ ID NO 386
<211> LENGTH: 12
<212> TYPE: PRT
<213> ORGANISM: Artificial
<220> FEATURE:
<223> OTHER INFORMATION: Synthetic

<400> SEQUENCE: 386

Cys Ala Asp Ser Asn Pro Arg Gly Val Ser Ala Tyr
1               5                   10

<210> SEQ ID NO 387
<211> LENGTH: 11
<212> TYPE: PRT
<213> ORGANISM: Artificial
<220> FEATURE:
<223> OTHER INFORMATION: Synthetic

<400> SEQUENCE: 387
```

Ala Asp Ser Asn Pro Arg Gly Val Ser Ala Tyr
1               5                   10

<210> SEQ ID NO 388
<211> LENGTH: 10
<212> TYPE: PRT
<213> ORGANISM: Artificial
<220> FEATURE:
<223> OTHER INFORMATION: Synthetic

<400> SEQUENCE: 388

Asp Ser Asn Pro Arg Gly Val Ser Ala Tyr
1               5                   10

<210> SEQ ID NO 389
<211> LENGTH: 9
<212> TYPE: PRT
<213> ORGANISM: Artificial
<220> FEATURE:
<223> OTHER INFORMATION: Synthetic

<400> SEQUENCE: 389

Ser Asn Pro Arg Gly Val Ser Ala Tyr
1               5

<210> SEQ ID NO 390
<211> LENGTH: 8
<212> TYPE: PRT
<213> ORGANISM: Artificial
<220> FEATURE:
<223> OTHER INFORMATION: Synthetic

<400> SEQUENCE: 390

Asn Pro Arg Gly Val Ser Ala Tyr
1               5

<210> SEQ ID NO 391
<211> LENGTH: 7
<212> TYPE: PRT
<213> ORGANISM: Artificial
<220> FEATURE:
<223> OTHER INFORMATION: Synthetic

<400> SEQUENCE: 391

Pro Arg Gly Val Ser Ala Tyr
1               5

<210> SEQ ID NO 392
<211> LENGTH: 6
<212> TYPE: PRT
<213> ORGANISM: Artificial
<220> FEATURE:
<223> OTHER INFORMATION: Synthetic

<400> SEQUENCE: 392

Arg Gly Val Ser Ala Tyr
1               5

<210> SEQ ID NO 393
<211> LENGTH: 5
<212> TYPE: PRT
<213> ORGANISM: Artificial
<220> FEATURE:
<223> OTHER INFORMATION: Synthetic

<400> SEQUENCE: 393

Gly Val Ser Ala Tyr
1               5

<210> SEQ ID NO 394
<211> LENGTH: 4
<212> TYPE: PRT
<213> ORGANISM: Artificial
<220> FEATURE:
<223> OTHER INFORMATION: Synthetic

<400> SEQUENCE: 394

Val Ser Ala Tyr
1

<210> SEQ ID NO 395
<211> LENGTH: 11
<212> TYPE: PRT
<213> ORGANISM: Artificial
<220> FEATURE:
<223> OTHER INFORMATION: Synthetic

<400> SEQUENCE: 395

Cys Ala Asp Ser Asn Pro Arg Gly Val Ser Ala
1               5                   10

<210> SEQ ID NO 396
<211> LENGTH: 10
<212> TYPE: PRT
<213> ORGANISM: Artificial
<220> FEATURE:
<223> OTHER INFORMATION: Synthetic

<400> SEQUENCE: 396

Ala Asp Ser Asn Pro Arg Gly Val Ser Ala
1               5                   10

<210> SEQ ID NO 397
<211> LENGTH: 9
<212> TYPE: PRT
<213> ORGANISM: Artificial
<220> FEATURE:
<223> OTHER INFORMATION: Synthetic

<400> SEQUENCE: 397

Asp Ser Asn Pro Arg Gly Val Ser Ala
1               5

<210> SEQ ID NO 398
<211> LENGTH: 8
<212> TYPE: PRT
<213> ORGANISM: Artificial
<220> FEATURE:
<223> OTHER INFORMATION: Synthetic

<400> SEQUENCE: 398

Ser Asn Pro Arg Gly Val Ser Ala
1               5

<210> SEQ ID NO 399
<211> LENGTH: 7
<212> TYPE: PRT
<213> ORGANISM: Artificial
<220> FEATURE:
<223> OTHER INFORMATION: Synthetic

<400> SEQUENCE: 399

Asn Pro Arg Gly Val Ser Ala
1               5

```
<210> SEQ ID NO 400
<211> LENGTH: 6
<212> TYPE: PRT
<213> ORGANISM: Artificial
<220> FEATURE:
<223> OTHER INFORMATION: Synthetic

<400> SEQUENCE: 400

Pro Arg Gly Val Ser Ala
1               5

<210> SEQ ID NO 401
<211> LENGTH: 5
<212> TYPE: PRT
<213> ORGANISM: Artificial
<220> FEATURE:
<223> OTHER INFORMATION: Synthetic

<400> SEQUENCE: 401

Arg Gly Val Ser Ala
1               5

<210> SEQ ID NO 402
<211> LENGTH: 4
<212> TYPE: PRT
<213> ORGANISM: Artificial
<220> FEATURE:
<223> OTHER INFORMATION: Synthetic

<400> SEQUENCE: 402

Gly Val Ser Ala
1

<210> SEQ ID NO 403
<211> LENGTH: 10
<212> TYPE: PRT
<213> ORGANISM: Artificial
<220> FEATURE:
<223> OTHER INFORMATION: Synthetic

<400> SEQUENCE: 403

Cys Ala Asp Ser Asn Pro Arg Gly Val Ser
1               5                   10

<210> SEQ ID NO 404
<211> LENGTH: 9
<212> TYPE: PRT
<213> ORGANISM: Artificial
<220> FEATURE:
<223> OTHER INFORMATION: Synthetic

<400> SEQUENCE: 404

Ala Asp Ser Asn Pro Arg Gly Val Ser
1               5

<210> SEQ ID NO 405
<211> LENGTH: 8
<212> TYPE: PRT
<213> ORGANISM: Artificial
<220> FEATURE:
<223> OTHER INFORMATION: Synthetic

<400> SEQUENCE: 405

Asp Ser Asn Pro Arg Gly Val Ser
1               5

<210> SEQ ID NO 406
<211> LENGTH: 7
```

```
<212> TYPE: PRT
<213> ORGANISM: Artificial
<220> FEATURE:
<223> OTHER INFORMATION: Synthetic

<400> SEQUENCE: 406

Ser Asn Pro Arg Gly Val Ser
1               5

<210> SEQ ID NO 407
<211> LENGTH: 6
<212> TYPE: PRT
<213> ORGANISM: Artificial
<220> FEATURE:
<223> OTHER INFORMATION: Synthetic

<400> SEQUENCE: 407

Asn Pro Arg Gly Val Ser
1               5

<210> SEQ ID NO 408
<211> LENGTH: 5
<212> TYPE: PRT
<213> ORGANISM: Artificial
<220> FEATURE:
<223> OTHER INFORMATION: Synthetic

<400> SEQUENCE: 408

Pro Arg Gly Val Ser
1               5

<210> SEQ ID NO 409
<211> LENGTH: 4
<212> TYPE: PRT
<213> ORGANISM: Artificial
<220> FEATURE:
<223> OTHER INFORMATION: Synthetic

<400> SEQUENCE: 409

Arg Gly Val Ser
1

<210> SEQ ID NO 410
<211> LENGTH: 9
<212> TYPE: PRT
<213> ORGANISM: Artificial
<220> FEATURE:
<223> OTHER INFORMATION: Synthetic

<400> SEQUENCE: 410

Cys Ala Asp Ser Asn Pro Arg Gly Val
1               5

<210> SEQ ID NO 411
<211> LENGTH: 8
<212> TYPE: PRT
<213> ORGANISM: Artificial
<220> FEATURE:
<223> OTHER INFORMATION: Synthetic

<400> SEQUENCE: 411

Ala Asp Ser Asn Pro Arg Gly Val
1               5

<210> SEQ ID NO 412
<211> LENGTH: 7
<212> TYPE: PRT
<213> ORGANISM: Artificial
```

```
<220> FEATURE:
<223> OTHER INFORMATION: Synthetic

<400> SEQUENCE: 412

Asp Ser Asn Pro Arg Gly Val
1               5

<210> SEQ ID NO 413
<211> LENGTH: 6
<212> TYPE: PRT
<213> ORGANISM: Artificial
<220> FEATURE:
<223> OTHER INFORMATION: Synthetic

<400> SEQUENCE: 413

Ser Asn Pro Arg Gly Val
1               5

<210> SEQ ID NO 414
<211> LENGTH: 5
<212> TYPE: PRT
<213> ORGANISM: Artificial
<220> FEATURE:
<223> OTHER INFORMATION: Synthetic

<400> SEQUENCE: 414

Asn Pro Arg Gly Val
1               5

<210> SEQ ID NO 415
<211> LENGTH: 4
<212> TYPE: PRT
<213> ORGANISM: Artificial
<220> FEATURE:
<223> OTHER INFORMATION: Synthetic

<400> SEQUENCE: 415

Pro Arg Gly Val
1

<210> SEQ ID NO 416
<211> LENGTH: 8
<212> TYPE: PRT
<213> ORGANISM: Artificial
<220> FEATURE:
<223> OTHER INFORMATION: Synthetic

<400> SEQUENCE: 416

Cys Ala Asp Ser Asn Pro Arg Gly
1               5

<210> SEQ ID NO 417
<211> LENGTH: 7
<212> TYPE: PRT
<213> ORGANISM: Artificial
<220> FEATURE:
<223> OTHER INFORMATION: Synthetic

<400> SEQUENCE: 417

Ala Asp Ser Asn Pro Arg Gly
1               5

<210> SEQ ID NO 418
<211> LENGTH: 6
<212> TYPE: PRT
<213> ORGANISM: Artificial
<220> FEATURE:
<223> OTHER INFORMATION: Synthetic
```

<400> SEQUENCE: 418

Asp Ser Asn Pro Arg Gly
1               5

<210> SEQ ID NO 419
<211> LENGTH: 5
<212> TYPE: PRT
<213> ORGANISM: Artificial
<220> FEATURE:
<223> OTHER INFORMATION: Synthetic

<400> SEQUENCE: 419

Ser Asn Pro Arg Gly
1               5

<210> SEQ ID NO 420
<211> LENGTH: 4
<212> TYPE: PRT
<213> ORGANISM: Artificial
<220> FEATURE:
<223> OTHER INFORMATION: Synthetic

<400> SEQUENCE: 420

Asn Pro Arg Gly
1

<210> SEQ ID NO 421
<211> LENGTH: 7
<212> TYPE: PRT
<213> ORGANISM: Artificial
<220> FEATURE:
<223> OTHER INFORMATION: Synthetic

<400> SEQUENCE: 421

Cys Ala Asp Ser Asn Pro Arg
1               5

<210> SEQ ID NO 422
<211> LENGTH: 6
<212> TYPE: PRT
<213> ORGANISM: Artificial
<220> FEATURE:
<223> OTHER INFORMATION: Synthetic

<400> SEQUENCE: 422

Ala Asp Ser Asn Pro Arg
1               5

<210> SEQ ID NO 423
<211> LENGTH: 5
<212> TYPE: PRT
<213> ORGANISM: Artificial
<220> FEATURE:
<223> OTHER INFORMATION: Synthetic

<400> SEQUENCE: 423

Asp Ser Asn Pro Arg
1               5

<210> SEQ ID NO 424
<211> LENGTH: 4
<212> TYPE: PRT
<213> ORGANISM: Artificial
<220> FEATURE:
<223> OTHER INFORMATION: Synthetic

<400> SEQUENCE: 424

Ser Asn Pro Arg
1

<210> SEQ ID NO 425
<211> LENGTH: 6
<212> TYPE: PRT
<213> ORGANISM: Artificial
<220> FEATURE:
<223> OTHER INFORMATION: Synthetic

<400> SEQUENCE: 425

Cys Ala Asp Ser Asn Pro
1               5

<210> SEQ ID NO 426
<211> LENGTH: 5
<212> TYPE: PRT
<213> ORGANISM: Artificial
<220> FEATURE:
<223> OTHER INFORMATION: Synthetic

<400> SEQUENCE: 426

Ala Asp Ser Asn Pro
1               5

<210> SEQ ID NO 427
<211> LENGTH: 4
<212> TYPE: PRT
<213> ORGANISM: Artificial
<220> FEATURE:
<223> OTHER INFORMATION: Synthetic

<400> SEQUENCE: 427

Asp Ser Asn Pro
1

<210> SEQ ID NO 428
<211> LENGTH: 5
<212> TYPE: PRT
<213> ORGANISM: Artificial
<220> FEATURE:
<223> OTHER INFORMATION: Synthetic

<400> SEQUENCE: 428

Cys Ala Asp Ser Asn
1               5

<210> SEQ ID NO 429
<211> LENGTH: 4
<212> TYPE: PRT
<213> ORGANISM: Artificial
<220> FEATURE:
<223> OTHER INFORMATION: Synthetic

<400> SEQUENCE: 429

Ala Asp Ser Asn
1

<210> SEQ ID NO 430
<211> LENGTH: 4
<212> TYPE: PRT
<213> ORGANISM: Artificial
<220> FEATURE:
<223> OTHER INFORMATION: Synthetic

<400> SEQUENCE: 430

Cys Ala Asp Ser

```
<210> SEQ ID NO 431
<211> LENGTH: 21
<212> TYPE: DNA
<213> ORGANISM: Artificial
<220> FEATURE:
<223> OTHER INFORMATION: Synthetic

<400> SEQUENCE: 431
tcgtcgtttt tcggtgcttt t                                              21

<210> SEQ ID NO 432
<211> LENGTH: 21
<212> TYPE: DNA
<213> ORGANISM: Artificial
<220> FEATURE:
<223> OTHER INFORMATION: Synthetic

<400> SEQUENCE: 432
tcgtcgtttt tcggtcgttt t                                              21

<210> SEQ ID NO 433
<211> LENGTH: 24
<212> TYPE: DNA
<213> ORGANISM: Artificial
<220> FEATURE:
<223> OTHER INFORMATION: Synthetic

<400> SEQUENCE: 433
tcgtcgtttt gtcgttttgt cgtt                                           24

<210> SEQ ID NO 434
<211> LENGTH: 18
<212> TYPE: PRT
<213> ORGANISM: Artificial
<220> FEATURE:
<223> OTHER INFORMATION: Synthetic

<400> SEQUENCE: 434

Ala Asp Ser Asn Pro Arg Gly Val Ser Ala Tyr Leu Ser Arg Pro Ser
1               5                   10                  15

Pro Cys

<210> SEQ ID NO 435
<211> LENGTH: 133
<212> TYPE: PRT
<213> ORGANISM: Artificial
<220> FEATURE:
<223> OTHER INFORMATION: Synthetic

<400> SEQUENCE: 435

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95
```

```
Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr
    130

<210> SEQ ID NO 436
<211> LENGTH: 21
<212> TYPE: PRT
<213> ORGANISM: Artificial
<220> FEATURE:
<223> OTHER INFORMATION: Synthetic

<400> SEQUENCE: 436

Ser Thr Arg Lys Glu Glu Lys Gln Arg Asn Gly Thr Leu Thr Val Thr
1               5                   10                  15

Ser Thr Leu Pro Cys
            20

<210> SEQ ID NO 437
<211> LENGTH: 14
<212> TYPE: PRT
<213> ORGANISM: Artificial
<220> FEATURE:
<223> OTHER INFORMATION: Synthetic

<400> SEQUENCE: 437

Leu Val Val Asp Leu Ala Pro Ser Lys Gly Thr Val Asn Cys
1               5                   10

<210> SEQ ID NO 438
<211> LENGTH: 20
<212> TYPE: PRT
<213> ORGANISM: Artificial
<220> FEATURE:
<223> OTHER INFORMATION: Synthetic

<400> SEQUENCE: 438

Cys Leu Val Val Asp Leu Ala Pro Ser Lys Gly Thr Val Asn Gly Gly
1               5                   10                  15

Gly Gly Gly Cys
            20

<210> SEQ ID NO 439
<211> LENGTH: 19
<212> TYPE: PRT
<213> ORGANISM: Artificial
<220> FEATURE:
<223> OTHER INFORMATION: Synthetic

<400> SEQUENCE: 439

Cys Ala Asp Ser Asn Pro Arg Gly Val Ser Ala Tyr Leu Ser Arg Pro
1               5                   10                  15

Ser Pro Cys

<210> SEQ ID NO 440
<211> LENGTH: 21
<212> TYPE: DNA
<213> ORGANISM: Artificial
<220> FEATURE:
<223> OTHER INFORMATION: Synthetic

<400> SEQUENCE: 440
```
ggggacgacg tcgtgggggg g                                              21

<210> SEQ ID NO 441
<211> LENGTH: 24
<212> TYPE: DNA
<213> ORGANISM: Artificial
<220> FEATURE:
<223> OTHER INFORMATION: Synthetic

<400> SEQUENCE: 441
tcgtcgtttc gtcgttttgt cgtt                                           24

<210> SEQ ID NO 442
<211> LENGTH: 24
<212> TYPE: DNA
<213> ORGANISM: Artificial
<220> FEATURE:
<223> OTHER INFORMATION: Synthetic

<400> SEQUENCE: 442
tcgtcgtttt gtcgtttttt tcga                                           24

<210> SEQ ID NO 443
<211> LENGTH: 22
<212> TYPE: DNA
<213> ORGANISM: Artificial
<220> FEATURE:
<223> OTHER INFORMATION: Synthetic

<400> SEQUENCE: 443
tcgcgtcgtt cggcgcgcgc cg                                             22

<210> SEQ ID NO 444
<211> LENGTH: 23
<212> TYPE: DNA
<213> ORGANISM: Artificial
<220> FEATURE:
<223> OTHER INFORMATION: Synthetic

<400> SEQUENCE: 444
tcgtcgacgt tcggcgcgcg ccg                                            23

<210> SEQ ID NO 445
<211> LENGTH: 21
<212> TYPE: DNA
<213> ORGANISM: Artificial
<220> FEATURE:
<223> OTHER INFORMATION: Synthetic

<400> SEQUENCE: 445
tcggacgttc ggcgcgcgcc g                                              21

<210> SEQ ID NO 446
<211> LENGTH: 19
<212> TYPE: DNA
<213> ORGANISM: Artificial
<220> FEATURE:
<223> OTHER INFORMATION: Synthetic

<400> SEQUENCE: 446
tcggacgttc ggcgcgccg                                                 19

<210> SEQ ID NO 447
<211> LENGTH: 20
<212> TYPE: DNA
<213> ORGANISM: Artificial
<220> FEATURE:

<223> OTHER INFORMATION: Synthetic

<400> SEQUENCE: 447
tcgcgtcgtt cggcgcgccg          20

<210> SEQ ID NO 448
<211> LENGTH: 20
<212> TYPE: DNA
<213> ORGANISM: Artificial
<220> FEATURE:
<223> OTHER INFORMATION: Synthetic

<400> SEQUENCE: 448
tcgacgttcg gcgcgcgccg          20

<210> SEQ ID NO 449
<211> LENGTH: 18
<212> TYPE: DNA
<213> ORGANISM: Artificial
<220> FEATURE:
<223> OTHER INFORMATION: Synthetic

<400> SEQUENCE: 449
tcgacgttcg gcgcgccg          18

<210> SEQ ID NO 450
<211> LENGTH: 18
<212> TYPE: DNA
<213> ORGANISM: Artificial
<220> FEATURE:
<223> OTHER INFORMATION: Synthetic

<400> SEQUENCE: 450
tcgcgtcgtt cggcgccg          18

<210> SEQ ID NO 451
<211> LENGTH: 22
<212> TYPE: DNA
<213> ORGANISM: Artificial
<220> FEATURE:
<223> OTHER INFORMATION: Synthetic

<400> SEQUENCE: 451
tcgcgacgtt cggcgcgcgc cg          22

<210> SEQ ID NO 452
<211> LENGTH: 22
<212> TYPE: DNA
<213> ORGANISM: Artificial
<220> FEATURE:
<223> OTHER INFORMATION: Synthetic

<400> SEQUENCE: 452
tcgtcgtttt cggcgcgcgc cg          22

<210> SEQ ID NO 453
<211> LENGTH: 22
<212> TYPE: DNA
<213> ORGANISM: Artificial
<220> FEATURE:
<223> OTHER INFORMATION: Synthetic

<400> SEQUENCE: 453
tcgtcgtttt cggcggccgc cg          22

<210> SEQ ID NO 454

-continued

<211> LENGTH: 24
<212> TYPE: DNA
<213> ORGANISM: Artificial
<220> FEATURE:
<223> OTHER INFORMATION: Synthetic

<400> SEQUENCE: 454
tcgtcgtttt acggcgccgt gccg                                          24

<210> SEQ ID NO 455
<211> LENGTH: 23
<212> TYPE: DNA
<213> ORGANISM: Artificial
<220> FEATURE:
<223> OTHER INFORMATION: Synthetic

<400> SEQUENCE: 455
tcgtcgtttt cggcgcgcgc cgt                                           23

<210> SEQ ID NO 456
<211> LENGTH: 23
<212> TYPE: DNA
<213> ORGANISM: Artificial
<220> FEATURE:
<223> OTHER INFORMATION: Synthetic

<400> SEQUENCE: 456
tcgtcgacga tcggcgcgcg ccg                                           23

<210> SEQ ID NO 457
<211> LENGTH: 20
<212> TYPE: PRT
<213> ORGANISM: Artificial
<220> FEATURE:
<223> OTHER INFORMATION: Synthetic

<400> SEQUENCE: 457

Ala Asp Ser Asn Pro Arg Gly Val Ser Ala Tyr Leu Ser Arg Pro Ser
1               5                   10                  15

Pro Gly Gly Cys
            20

<210> SEQ ID NO 458
<211> LENGTH: 16
<212> TYPE: PRT
<213> ORGANISM: Artificial
<220> FEATURE:
<223> OTHER INFORMATION: Synthetic

<400> SEQUENCE: 458

Gln Cys Ile Val Asp His Pro Asp Phe Pro Lys Pro Ile Val Arg Ser
1               5                   10                  15

<210> SEQ ID NO 459
<211> LENGTH: 18
<212> TYPE: PRT
<213> ORGANISM: Artificial
<220> FEATURE:
<223> OTHER INFORMATION: Synthetic

<400> SEQUENCE: 459

Pro Asp His Glu Pro Arg Gly Val Ile Thr Tyr Leu Ile Pro Pro Ser
1               5                   10                  15

Pro Cys

<210> SEQ ID NO 460

```
<211> LENGTH: 6
<212> TYPE: PRT
<213> ORGANISM: Artificial
<220> FEATURE:
<223> OTHER INFORMATION: Synthetic Construct

<400> SEQUENCE: 460

Gly Gly Gly Gly Gly Cys
1               5

<210> SEQ ID NO 461
<211> LENGTH: 5
<212> TYPE: PRT
<213> ORGANISM: Artificial
<220> FEATURE:
<223> OTHER INFORMATION: Synthetic Construct

<400> SEQUENCE: 461

Gly Gly Gly Gly Cys
1               5

<210> SEQ ID NO 462
<211> LENGTH: 4
<212> TYPE: PRT
<213> ORGANISM: Artificial
<220> FEATURE:
<223> OTHER INFORMATION: Synthetic Construct

<400> SEQUENCE: 462

Gly Gly Gly Cys
1

<210> SEQ ID NO 463
<211> LENGTH: 6
<212> TYPE: PRT
<213> ORGANISM: Artificial
<220> FEATURE:
<223> OTHER INFORMATION: Synthetic Construct

<400> SEQUENCE: 463

Gly Gly Gly Gly Gly Lys
1               5

<210> SEQ ID NO 464
<211> LENGTH: 5
<212> TYPE: PRT
<213> ORGANISM: Artificial
<220> FEATURE:
<223> OTHER INFORMATION: Synthetic Construct

<400> SEQUENCE: 464

Gly Gly Gly Gly Lys
1               5

<210> SEQ ID NO 465
<211> LENGTH: 4
<212> TYPE: PRT
<213> ORGANISM: Artificial
<220> FEATURE:
<223> OTHER INFORMATION: Synthetic Construct

<400> SEQUENCE: 465

Gly Gly Gly Lys
1

<210> SEQ ID NO 466
<211> LENGTH: 6
<212> TYPE: PRT
```

<213> ORGANISM: Artificial
<220> FEATURE:
<223> OTHER INFORMATION: Synthetic Construct

<400> SEQUENCE: 466

Gly Gly Gly Gly Ser Cys
1               5

<210> SEQ ID NO 467
<211> LENGTH: 5
<212> TYPE: PRT
<213> ORGANISM: Artificial
<220> FEATURE:
<223> OTHER INFORMATION: Synthetic Construct

<400> SEQUENCE: 467

Gly Gly Gly Ser Cys
1               5

<210> SEQ ID NO 468
<211> LENGTH: 4
<212> TYPE: PRT
<213> ORGANISM: Artificial
<220> FEATURE:
<223> OTHER INFORMATION: Synthetic Construct

<400> SEQUENCE: 468

Gly Gly Ser Cys
1

<210> SEQ ID NO 469
<211> LENGTH: 6
<212> TYPE: PRT
<213> ORGANISM: Artificial
<220> FEATURE:
<223> OTHER INFORMATION: Synthetic Construct

<400> SEQUENCE: 469

Cys Ser Gly Gly Gly Gly
1               5

<210> SEQ ID NO 470
<211> LENGTH: 5
<212> TYPE: PRT
<213> ORGANISM: Artificial
<220> FEATURE:
<223> OTHER INFORMATION: Synthetic Construct

<400> SEQUENCE: 470

Cys Ser Gly Gly Gly
1               5

<210> SEQ ID NO 471
<211> LENGTH: 4
<212> TYPE: PRT
<213> ORGANISM: Artificial
<220> FEATURE:
<223> OTHER INFORMATION: Synthetic Construct

<400> SEQUENCE: 471

Cys Ser Gly Gly
1

<210> SEQ ID NO 472
<211> LENGTH: 6
<212> TYPE: PRT
<213> ORGANISM: Artificial
<220> FEATURE:

-continued

<223> OTHER INFORMATION: Synthetic Construct

<400> SEQUENCE: 472

Cys Gly Gly Gly Gly Gly
1               5

<210> SEQ ID NO 473
<211> LENGTH: 5
<212> TYPE: PRT
<213> ORGANISM: Artificial
<220> FEATURE:
<223> OTHER INFORMATION: Synthetic Construct

<400> SEQUENCE: 473

Cys Gly Gly Gly Gly
1               5

<210> SEQ ID NO 474
<211> LENGTH: 4
<212> TYPE: PRT
<213> ORGANISM: Artificial
<220> FEATURE:
<223> OTHER INFORMATION: Synthetic Construct

<400> SEQUENCE: 474

Cys Gly Gly Gly
1

<210> SEQ ID NO 475
<211> LENGTH: 5
<212> TYPE: PRT
<213> ORGANISM: Artificial
<220> FEATURE:
<223> OTHER INFORMATION: Synthetic Construct

<400> SEQUENCE: 475

Gly Gly Gly Gly Ser
1               5

<210> SEQ ID NO 476
<211> LENGTH: 10
<212> TYPE: PRT
<213> ORGANISM: Artificial
<220> FEATURE:
<223> OTHER INFORMATION: Synthetic Construct

<400> SEQUENCE: 476

Cys Gly Asp Lys Thr His Thr Ser Pro Pro
1               5                   10

<210> SEQ ID NO 477
<211> LENGTH: 10
<212> TYPE: PRT
<213> ORGANISM: Artificial
<220> FEATURE:
<223> OTHER INFORMATION: Synthetic Construct

<400> SEQUENCE: 477

Asp Lys Thr His Thr Ser Pro Pro Cys Gly
1               5                   10

<210> SEQ ID NO 478
<211> LENGTH: 17
<212> TYPE: PRT
<213> ORGANISM: Artificial
<220> FEATURE:
<223> OTHER INFORMATION: Synthetic Construct

```
<400> SEQUENCE: 478

Cys Gly Gly Pro Lys Pro Ser Thr Pro Pro Gly Ser Ser Gly Gly Ala
1               5                   10                  15

Pro

<210> SEQ ID NO 479
<211> LENGTH: 18
<212> TYPE: PRT
<213> ORGANISM: Artificial
<220> FEATURE:
<223> OTHER INFORMATION: Synthetic Construct

<400> SEQUENCE: 479

Pro Lys Pro Ser Thr Pro Pro Gly Ser Ser Gly Gly Ala Pro Gly Gly
1               5                   10                  15

Cys Gly

<210> SEQ ID NO 480
<211> LENGTH: 6
<212> TYPE: PRT
<213> ORGANISM: Artificial
<220> FEATURE:
<223> OTHER INFORMATION: Synthetic Construct

<400> SEQUENCE: 480

Gly Cys Gly Gly Gly Gly
1               5

<210> SEQ ID NO 481
<211> LENGTH: 6
<212> TYPE: PRT
<213> ORGANISM: Artificial
<220> FEATURE:
<223> OTHER INFORMATION: Synthetic Construct

<400> SEQUENCE: 481

Gly Gly Gly Gly Cys Gly
1               5

<210> SEQ ID NO 482
<211> LENGTH: 6
<212> TYPE: PRT
<213> ORGANISM: Artificial
<220> FEATURE:
<223> OTHER INFORMATION: Synthetic Construct

<400> SEQUENCE: 482

Cys Gly Lys Lys Gly Gly
1               5

<210> SEQ ID NO 483
<211> LENGTH: 6
<212> TYPE: PRT
<213> ORGANISM: Artificial
<220> FEATURE:
<223> OTHER INFORMATION: Synthetic Construct

<400> SEQUENCE: 483

Cys Gly Asp Glu Gly Gly
1               5

<210> SEQ ID NO 484
<211> LENGTH: 6
<212> TYPE: PRT
<213> ORGANISM: Artificial
<220> FEATURE:
```

```
<223> OTHER INFORMATION: Synthetic Construct

<400> SEQUENCE: 484

Gly Gly Lys Lys Gly Cys
1               5

<210> SEQ ID NO 485
<211> LENGTH: 6
<212> TYPE: PRT
<213> ORGANISM: Artificial
<220> FEATURE:
<223> OTHER INFORMATION: Synthetic Construct

<400> SEQUENCE: 485

Gly Gly Glu Asp Gly Cys
1               5

<210> SEQ ID NO 486
<211> LENGTH: 4
<212> TYPE: PRT
<213> ORGANISM: Artificial
<220> FEATURE:
<223> OTHER INFORMATION: Synthetic Construct

<400> SEQUENCE: 486

Gly Gly Cys Gly
1

<210> SEQ ID NO 487
<211> LENGTH: 12
<212> TYPE: DNA
<213> ORGANISM: Artificial
<220> FEATURE:
<223> OTHER INFORMATION: Synthetic Construct

<400> SEQUENCE: 487
cgacgttcgt cg                                                         12

<210> SEQ ID NO 488
<211> LENGTH: 13
<212> TYPE: DNA
<213> ORGANISM: Artificial
<220> FEATURE:
<223> OTHER INFORMATION: Synthetic Construct

<400> SEQUENCE: 488
cggcgccgtg ccg                                                        13

<210> SEQ ID NO 489
<211> LENGTH: 12
<212> TYPE: DNA
<213> ORGANISM: Artificial
<220> FEATURE:
<223> OTHER INFORMATION: Synthetic Construct

<400> SEQUENCE: 489
cccccagggg gg                                                         12

<210> SEQ ID NO 490
<211> LENGTH: 12
<212> TYPE: DNA
<213> ORGANISM: Artificial
<220> FEATURE:
<223> OTHER INFORMATION: Synthetic Construct

<400> SEQUENCE: 490 gggggggcccc cc                                                        12
```

<210> SEQ ID NO 491
<211> LENGTH: 10
<212> TYPE: DNA
<213> ORGANISM: Artificial
<220> FEATURE:
<223> OTHER INFORMATION: Synthetic Construct

<400> SEQUENCE: 491
cccccggggg                                                          10

<210> SEQ ID NO 492
<211> LENGTH: 10
<212> TYPE: DNA
<213> ORGANISM: Artificial
<220> FEATURE:
<223> OTHER INFORMATION: Synthetic Construct

<400> SEQUENCE: 492
gggggccccc                                                          10

<210> SEQ ID NO 493
<211> LENGTH: 18
<212> TYPE: PRT
<213> ORGANISM: Artificial
<220> FEATURE:
<223> OTHER INFORMATION: Synthetic Construct

<400> SEQUENCE: 493

Ala Asp Ser Asn Pro Arg Gly Val Ser Ala Tyr Leu Ser Arg Pro Ser
1               5                   10                  15

Pro Cys

<210> SEQ ID NO 494
<211> LENGTH: 20
<212> TYPE: PRT
<213> ORGANISM: Artificial
<220> FEATURE:
<223> OTHER INFORMATION: Synthetic Construct

<400> SEQUENCE: 494

Ala Asp Ser Asn Pro Arg Gly Val Ser Ala Tyr Leu Ser Arg Pro Ser
1               5                   10                  15

Pro Gly Gly Cys
            20

<210> SEQ ID NO 495
<211> LENGTH: 20
<212> TYPE: PRT
<213> ORGANISM: Artificial
<220> FEATURE:
<223> OTHER INFORMATION: Synthetic Construct

<400> SEQUENCE: 495

Cys Gly Gly Ala Asp Ser Asn Pro Arg Gly Val Ser Ala Tyr Leu Ser
1               5                   10                  15

Arg Pro Ser Pro
            20

<210> SEQ ID NO 496
<211> LENGTH: 11
<212> TYPE: PRT
<213> ORGANISM: Artificial
<220> FEATURE:
<223> OTHER INFORMATION: Synthetic Construct -continued

```
<400> SEQUENCE: 496

Ala Asp Ser Asn Pro Arg Gly Val Gly Gly Cys
1               5                   10

<210> SEQ ID NO 497
<211> LENGTH: 20
<212> TYPE: PRT
<213> ORGANISM: Artificial
<220> FEATURE:
<223> OTHER INFORMATION: Synthetic Construct

<400> SEQUENCE: 497

Ala Asp Ser Asn Pro Arg Gly Val Ser Ala Tyr Leu Ser Arg Pro Ser
1               5                   10                  15

Pro Gly Gly Cys
            20

<210> SEQ ID NO 498
<211> LENGTH: 19
<212> TYPE: PRT
<213> ORGANISM: Artificial
<220> FEATURE:
<223> OTHER INFORMATION: Synthetic Construct

<400> SEQUENCE: 498

Ala Asp Ser Asn Pro Arg Gly Val Ser Ala Tyr Leu Ser Arg Pro Ser
1               5                   10                  15

Gly Gly Cys

<210> SEQ ID NO 499
<211> LENGTH: 18
<212> TYPE: PRT
<213> ORGANISM: Artificial
<220> FEATURE:
<223> OTHER INFORMATION: Synthetic Construct

<400> SEQUENCE: 499

Ala Asp Ser Asn Pro Arg Gly Val Ser Ala Tyr Leu Ser Arg Pro Gly
1               5                   10                  15

Gly Cys

<210> SEQ ID NO 500
<211> LENGTH: 17
<212> TYPE: PRT
<213> ORGANISM: Artificial
<220> FEATURE:
<223> OTHER INFORMATION: Synthetic Construct

<400> SEQUENCE: 500

Ala Asp Ser Asn Pro Arg Gly Val Ser Ala Tyr Leu Ser Arg Gly Gly
1               5                   10                  15

Cys

<210> SEQ ID NO 501
<211> LENGTH: 16
<212> TYPE: PRT
<213> ORGANISM: Artificial
<220> FEATURE:
<223> OTHER INFORMATION: Synthetic Construct

<400> SEQUENCE: 501

Ala Asp Ser Asn Pro Arg Gly Val Ser Ala Tyr Leu Ser Gly Gly Cys
1               5                   10                  15
```

-continued

```
<210> SEQ ID NO 502
<211> LENGTH: 15
<212> TYPE: PRT
<213> ORGANISM: Artificial
<220> FEATURE:
<223> OTHER INFORMATION: Synthetic Construct

<400> SEQUENCE: 502

Ala Asp Ser Asn Pro Arg Gly Val Ser Ala Tyr Leu Gly Gly Cys
1               5                   10                  15

<210> SEQ ID NO 503
<211> LENGTH: 14
<212> TYPE: PRT
<213> ORGANISM: Artificial
<220> FEATURE:
<223> OTHER INFORMATION: Synthetic Construct

<400> SEQUENCE: 503

Ala Asp Ser Asn Pro Arg Gly Val Ser Ala Tyr Gly Gly Cys
1               5                   10

<210> SEQ ID NO 504
<211> LENGTH: 13
<212> TYPE: PRT
<213> ORGANISM: Artificial
<220> FEATURE:
<223> OTHER INFORMATION: Synthetic Construct

<400> SEQUENCE: 504

Ala Asp Ser Asn Pro Arg Gly Val Ser Ala Gly Gly Cys
1               5                   10

<210> SEQ ID NO 505
<211> LENGTH: 12
<212> TYPE: PRT
<213> ORGANISM: Artificial
<220> FEATURE:
<223> OTHER INFORMATION: Synthetic Construct

<400> SEQUENCE: 505

Ala Asp Ser Asn Pro Arg Gly Val Ser Gly Gly Cys
1               5                   10

<210> SEQ ID NO 506
<211> LENGTH: 11
<212> TYPE: PRT
<213> ORGANISM: Artificial
<220> FEATURE:
<223> OTHER INFORMATION: Synthetic Construct

<400> SEQUENCE: 506

Ala Asp Ser Asn Pro Arg Gly Val Gly Gly Cys
1               5                   10

<210> SEQ ID NO 507
<211> LENGTH: 10
<212> TYPE: PRT
<213> ORGANISM: Artificial
<220> FEATURE:
<223> OTHER INFORMATION: Synthetic Construct

<400> SEQUENCE: 507

Ala Asp Ser Asn Pro Arg Gly Gly Gly Cys
1               5                   10

<210> SEQ ID NO 508
<211> LENGTH: 9
```

```
<212> TYPE: PRT
<213> ORGANISM: Artificial
<220> FEATURE:
<223> OTHER INFORMATION: Synthetic Construct

<400> SEQUENCE: 508

Ala Asp Ser Asn Pro Arg Gly Gly Cys
1               5

<210> SEQ ID NO 509
<211> LENGTH: 8
<212> TYPE: PRT
<213> ORGANISM: Artificial
<220> FEATURE:
<223> OTHER INFORMATION: Synthetic Construct

<400> SEQUENCE: 509

Ala Asp Ser Asn Pro Gly Gly Cys
1               5

<210> SEQ ID NO 510
<211> LENGTH: 19
<212> TYPE: PRT
<213> ORGANISM: Artificial
<220> FEATURE:
<223> OTHER INFORMATION: Synthetic Construct

<400> SEQUENCE: 510

Asp Ser Asn Pro Arg Gly Val Ser Ala Tyr Leu Ser Arg Pro Ser Pro
1               5                   10                  15

Gly Gly Cys

<210> SEQ ID NO 511
<211> LENGTH: 18
<212> TYPE: PRT
<213> ORGANISM: Artificial
<220> FEATURE:
<223> OTHER INFORMATION: Synthetic Construct

<400> SEQUENCE: 511

Ser Asn Pro Arg Gly Val Ser Ala Tyr Leu Ser Arg Pro Ser Pro Gly
1               5                   10                  15

Gly Cys

<210> SEQ ID NO 512
<211> LENGTH: 17
<212> TYPE: PRT
<213> ORGANISM: Artificial
<220> FEATURE:
<223> OTHER INFORMATION: Synthetic Construct

<400> SEQUENCE: 512

Asn Pro Arg Gly Val Ser Ala Tyr Leu Ser Arg Pro Ser Pro Gly Gly
1               5                   10                  15

Cys

<210> SEQ ID NO 513
<211> LENGTH: 16
<212> TYPE: PRT
<213> ORGANISM: Artificial
<220> FEATURE:
<223> OTHER INFORMATION: Synthetic Construct

<400> SEQUENCE: 513

Pro Arg Gly Val Ser Ala Tyr Leu Ser Arg Pro Ser Pro Gly Gly Cys
1               5                   10                  15
```

```
<210> SEQ ID NO 514
<211> LENGTH: 15
<212> TYPE: PRT
<213> ORGANISM: Artificial
<220> FEATURE:
<223> OTHER INFORMATION: Synthetic Construct

<400> SEQUENCE: 514

Arg Gly Val Ser Ala Tyr Leu Ser Arg Pro Ser Pro Gly Gly Cys
1               5                   10                  15

<210> SEQ ID NO 515
<211> LENGTH: 14
<212> TYPE: PRT
<213> ORGANISM: Artificial
<220> FEATURE:
<223> OTHER INFORMATION: Synthetic Construct

<400> SEQUENCE: 515

Gly Val Ser Ala Tyr Leu Ser Arg Pro Ser Pro Gly Gly Cys
1               5                   10

<210> SEQ ID NO 516
<211> LENGTH: 13
<212> TYPE: PRT
<213> ORGANISM: Artificial
<220> FEATURE:
<223> OTHER INFORMATION: Synthetic Construct

<400> SEQUENCE: 516

Val Ser Ala Tyr Leu Ser Arg Pro Ser Pro Gly Gly Cys
1               5                   10

<210> SEQ ID NO 517
<211> LENGTH: 12
<212> TYPE: PRT
<213> ORGANISM: Artificial
<220> FEATURE:
<223> OTHER INFORMATION: Synthetic Construct

<400> SEQUENCE: 517

Ser Ala Tyr Leu Ser Arg Pro Ser Pro Gly Gly Cys
1               5                   10

<210> SEQ ID NO 518
<211> LENGTH: 11
<212> TYPE: PRT
<213> ORGANISM: Artificial
<220> FEATURE:
<223> OTHER INFORMATION: Synthetic Construct

<400> SEQUENCE: 518

Ala Tyr Leu Ser Arg Pro Ser Pro Gly Gly Cys
1               5                   10

<210> SEQ ID NO 519
<211> LENGTH: 10
<212> TYPE: PRT
<213> ORGANISM: Artificial
<220> FEATURE:
<223> OTHER INFORMATION: Synthetic Construct

<400> SEQUENCE: 519

Tyr Leu Ser Arg Pro Ser Pro Gly Gly Cys
1               5                   10
```

```
<210> SEQ ID NO 520
<211> LENGTH: 19
<212> TYPE: PRT
<213> ORGANISM: Artificial
<220> FEATURE:
<223> OTHER INFORMATION: Synthetic Construct

<400> SEQUENCE: 520

Cys Gly Gly Asp Ser Asn Pro Arg Gly Val Ser Ala Tyr Leu Ser Arg
1               5                   10                  15

Pro Ser Pro

<210> SEQ ID NO 521
<211> LENGTH: 18
<212> TYPE: PRT
<213> ORGANISM: Artificial
<220> FEATURE:
<223> OTHER INFORMATION: Synthetic Construct

<400> SEQUENCE: 521

Cys Gly Gly Ser Asn Pro Arg Gly Val Ser Ala Tyr Leu Ser Arg Pro
1               5                   10                  15

Ser Pro

<210> SEQ ID NO 522
<211> LENGTH: 17
<212> TYPE: PRT
<213> ORGANISM: Artificial
<220> FEATURE:
<223> OTHER INFORMATION: Synthetic Construct

<400> SEQUENCE: 522

Cys Gly Gly Asn Pro Arg Gly Val Ser Ala Tyr Leu Ser Arg Pro Ser
1               5                   10                  15

Pro

<210> SEQ ID NO 523
<211> LENGTH: 16
<212> TYPE: PRT
<213> ORGANISM: Artificial
<220> FEATURE:
<223> OTHER INFORMATION: Synthetic Construct

<400> SEQUENCE: 523

Cys Gly Gly Pro Arg Gly Val Ser Ala Tyr Leu Ser Arg Pro Ser Pro
1               5                   10                  15

<210> SEQ ID NO 524
<211> LENGTH: 15
<212> TYPE: PRT
<213> ORGANISM: Artificial
<220> FEATURE:
<223> OTHER INFORMATION: Synthetic Construct

<400> SEQUENCE: 524

Cys Gly Gly Arg Gly Val Ser Ala Tyr Leu Ser Arg Pro Ser Pro
1               5                   10                  15

<210> SEQ ID NO 525
<211> LENGTH: 14
<212> TYPE: PRT
<213> ORGANISM: Artificial
<220> FEATURE:
<223> OTHER INFORMATION: Synthetic Construct

<400> SEQUENCE: 525
```

```
Cys Gly Gly Gly Val Ser Ala Tyr Leu Ser Arg Pro Ser Pro
1               5                   10
```

<210> SEQ ID NO 526
<211> LENGTH: 12
<212> TYPE: PRT
<213> ORGANISM: Artificial
<220> FEATURE:
<223> OTHER INFORMATION: Synthetic Construct

<400> SEQUENCE: 526

```
Cys Gly Gly Val Ser Ala Tyr Leu Ser Arg Pro Ser
1               5                   10
```

<210> SEQ ID NO 527
<211> LENGTH: 13
<212> TYPE: PRT
<213> ORGANISM: Artificial
<220> FEATURE:
<223> OTHER INFORMATION: Synthetic Construct

<400> SEQUENCE: 527

```
Cys Gly Gly Val Ser Ala Tyr Leu Ser Arg Pro Ser Pro
1               5                   10
```

<210> SEQ ID NO 528
<211> LENGTH: 12
<212> TYPE: PRT
<213> ORGANISM: Artificial
<220> FEATURE:
<223> OTHER INFORMATION: Synthetic Construct

<400> SEQUENCE: 528

```
Cys Gly Gly Ser Ala Tyr Leu Ser Arg Pro Ser Pro
1               5                   10
```

<210> SEQ ID NO 529
<211> LENGTH: 11
<212> TYPE: PRT
<213> ORGANISM: Artificial
<220> FEATURE:
<223> OTHER INFORMATION: Synthetic Construct

<400> SEQUENCE: 529

```
Cys Gly Gly Ala Tyr Leu Ser Arg Pro Ser Pro
1               5                   10
```

<210> SEQ ID NO 530
<211> LENGTH: 10
<212> TYPE: PRT
<213> ORGANISM: Artificial
<220> FEATURE:
<223> OTHER INFORMATION: Synthetic Construct

<400> SEQUENCE: 530

```
Cys Gly Gly Tyr Leu Ser Arg Pro Ser Pro
1               5                   10
```

<210> SEQ ID NO 531
<211> LENGTH: 19
<212> TYPE: PRT
<213> ORGANISM: Artificial
<220> FEATURE:
<223> OTHER INFORMATION: Synthetic Construct

<400> SEQUENCE: 531

```
Cys Gly Gly Ala Asp Ser Asn Pro Arg Gly Val Ser Ala Tyr Leu Ser
1               5                   10                  15
```

Arg Pro Ser

<210> SEQ ID NO 532
<211> LENGTH: 18
<212> TYPE: PRT
<213> ORGANISM: Artificial
<220> FEATURE:
<223> OTHER INFORMATION: Synthetic Construct

<400> SEQUENCE: 532

Cys Gly Gly Ala Asp Ser Asn Pro Arg Gly Val Ser Ala Tyr Leu Ser
1               5                   10                  15

Arg Pro

<210> SEQ ID NO 533
<211> LENGTH: 17
<212> TYPE: PRT
<213> ORGANISM: Artificial
<220> FEATURE:
<223> OTHER INFORMATION: Synthetic Construct

<400> SEQUENCE: 533

Cys Gly Gly Ala Asp Ser Asn Pro Arg Gly Val Ser Ala Tyr Leu Ser
1               5                   10                  15

Arg

<210> SEQ ID NO 534
<211> LENGTH: 16
<212> TYPE: PRT
<213> ORGANISM: Artificial
<220> FEATURE:
<223> OTHER INFORMATION: Synthetic Construct

<400> SEQUENCE: 534

Cys Gly Gly Ala Asp Ser Asn Pro Arg Gly Val Ser Ala Tyr Leu Ser
1               5                   10                  15

<210> SEQ ID NO 535
<211> LENGTH: 15
<212> TYPE: PRT
<213> ORGANISM: Artificial
<220> FEATURE:
<223> OTHER INFORMATION: Synthetic Construct

<400> SEQUENCE: 535

Cys Gly Gly Ala Asp Ser Asn Pro Arg Gly Val Ser Ala Tyr Leu
1               5                   10                  15

<210> SEQ ID NO 536
<211> LENGTH: 14
<212> TYPE: PRT
<213> ORGANISM: Artificial
<220> FEATURE:
<223> OTHER INFORMATION: Synthetic Construct

<400> SEQUENCE: 536

Cys Gly Gly Ala Asp Ser Asn Pro Arg Gly Val Ser Ala Tyr
1               5                   10

<210> SEQ ID NO 537
<211> LENGTH: 13
<212> TYPE: PRT
<213> ORGANISM: Artificial
<220> FEATURE:
<223> OTHER INFORMATION: Synthetic Construct

```
<400> SEQUENCE: 537

Cys Gly Gly Ala Asp Ser Asn Pro Arg Gly Val Ser Ala
1               5                   10

<210> SEQ ID NO 538
<211> LENGTH: 12
<212> TYPE: PRT
<213> ORGANISM: Artificial
<220> FEATURE:
<223> OTHER INFORMATION: Synthetic Construct

<400> SEQUENCE: 538

Cys Gly Gly Ala Asp Ser Asn Pro Arg Gly Val Ser
1               5                   10

<210> SEQ ID NO 539
<211> LENGTH: 11
<212> TYPE: PRT
<213> ORGANISM: Artificial
<220> FEATURE:
<223> OTHER INFORMATION: Synthetic Construct

<400> SEQUENCE: 539

Cys Gly Gly Ala Asp Ser Asn Pro Arg Gly Val
1               5                   10

<210> SEQ ID NO 540
<211> LENGTH: 19
<212> TYPE: PRT
<213> ORGANISM: Artificial
<220> FEATURE:
<223> OTHER INFORMATION: Synthetic Construct

<400> SEQUENCE: 540

Cys Gly Gly Ala Tyr Leu Ser Arg Pro Ser Pro Phe Asp Leu Phe Ile
1               5                   10                  15

Arg Lys Ser

<210> SEQ ID NO 541
<211> LENGTH: 15
<212> TYPE: PRT
<213> ORGANISM: Artificial
<220> FEATURE:
<223> OTHER INFORMATION: Synthetic Construct

<400> SEQUENCE: 541

Cys Gly Gly Ala Tyr Leu Ser Arg Pro Ser Pro Phe Asp Leu Phe
1               5                   10                  15

<210> SEQ ID NO 542
<211> LENGTH: 16
<212> TYPE: PRT
<213> ORGANISM: Artificial
<220> FEATURE:
<223> OTHER INFORMATION: Synthetic Construct

<400> SEQUENCE: 542

Gln Cys Arg Val Thr His Pro His Leu Pro Arg Ala Leu Met Arg Ser
1               5                   10                  15

<210> SEQ ID NO 543
<211> LENGTH: 17
<212> TYPE: PRT
<213> ORGANISM: Artificial
<220> FEATURE:
<223> OTHER INFORMATION: Synthetic Construct
```

<400> SEQUENCE: 543

Arg Val Thr His Pro His Leu Pro Arg Ala Leu Met Arg Ser Gly Gly
1               5                   10                  15

Cys

<210> SEQ ID NO 544
<211> LENGTH: 17
<212> TYPE: PRT
<213> ORGANISM: Artificial
<220> FEATURE:
<223> OTHER INFORMATION: Synthetic Construct

<400> SEQUENCE: 544

Cys Gly Gly Arg Val Thr His Pro His Leu Pro Arg Ala Leu Met Arg
1               5                   10                  15

Ser

<210> SEQ ID NO 545
<211> LENGTH: 16
<212> TYPE: PRT
<213> ORGANISM: Artificial
<220> FEATURE:
<223> OTHER INFORMATION: Synthetic Construct

<400> SEQUENCE: 545

Arg Val Thr His Pro His Leu Pro Arg Ala Leu Met Arg Gly Gly Cys
1               5                   10                  15

<210> SEQ ID NO 546
<211> LENGTH: 15
<212> TYPE: PRT
<213> ORGANISM: Artificial
<220> FEATURE:
<223> OTHER INFORMATION: Synthetic Construct

<400> SEQUENCE: 546

Arg Val Thr His Pro His Leu Pro Arg Ala Leu Met Gly Gly Cys
1               5                   10                  15

<210> SEQ ID NO 547
<211> LENGTH: 14
<212> TYPE: PRT
<213> ORGANISM: Artificial
<220> FEATURE:
<223> OTHER INFORMATION: Synthetic Construct

<400> SEQUENCE: 547

Arg Val Thr His Pro His Leu Pro Arg Ala Leu Gly Gly Cys
1               5                   10

<210> SEQ ID NO 548
<211> LENGTH: 13
<212> TYPE: PRT
<213> ORGANISM: Artificial
<220> FEATURE:
<223> OTHER INFORMATION: Synthetic Construct

<400> SEQUENCE: 548

Arg Val Thr His Pro His Leu Pro Arg Ala Gly Gly Cys
1               5                   10

<210> SEQ ID NO 549
<211> LENGTH: 16
<212> TYPE: PRT
<213> ORGANISM: Artificial
<220> FEATURE:

<223> OTHER INFORMATION: Synthetic Construct

<400> SEQUENCE: 549

Cys Gly Gly Arg Val Thr His Pro His Leu Pro Arg Ala Leu Met Arg
1               5                   10                  15

<210> SEQ ID NO 550
<211> LENGTH: 15
<212> TYPE: PRT
<213> ORGANISM: Artificial
<220> FEATURE:
<223> OTHER INFORMATION: Synthetic Construct

<400> SEQUENCE: 550

Cys Gly Gly Arg Val Thr His Pro His Leu Pro Arg Ala Leu Met
1               5                   10                  15

<210> SEQ ID NO 551
<211> LENGTH: 14
<212> TYPE: PRT
<213> ORGANISM: Artificial
<220> FEATURE:
<223> OTHER INFORMATION: Synthetic Construct

<400> SEQUENCE: 551

Cys Gly Gly Arg Val Thr His Pro His Leu Pro Arg Ala Leu
1               5                   10

<210> SEQ ID NO 552
<211> LENGTH: 13
<212> TYPE: PRT
<213> ORGANISM: Artificial
<220> FEATURE:
<223> OTHER INFORMATION: Synthetic Construct

<400> SEQUENCE: 552

Cys Gly Gly Arg Val Thr His Pro His Leu Pro Arg Ala
1               5                   10

<210> SEQ ID NO 553
<211> LENGTH: 17
<212> TYPE: PRT
<213> ORGANISM: Artificial
<220> FEATURE:
<223> OTHER INFORMATION: Synthetic Construct

<400> SEQUENCE: 553

Arg Val Thr His Pro His Leu Pro Arg Ala Leu Met Arg Ser Gly Gly
1               5                   10                  15

Cys

<210> SEQ ID NO 554
<211> LENGTH: 16
<212> TYPE: PRT
<213> ORGANISM: Artificial
<220> FEATURE:
<223> OTHER INFORMATION: Synthetic Construct

<400> SEQUENCE: 554

Val Thr His Pro His Leu Pro Arg Ala Leu Met Arg Ser Gly Gly Cys
1               5                   10                  15

<210> SEQ ID NO 555
<211> LENGTH: 15
<212> TYPE: PRT
<213> ORGANISM: Artificial
<220> FEATURE:

<223> OTHER INFORMATION: Synthetic Construct

<400> SEQUENCE: 555

Thr His Pro His Leu Pro Arg Ala Leu Met Arg Ser Gly Gly Cys
1               5                   10                  15

<210> SEQ ID NO 556
<211> LENGTH: 17
<212> TYPE: PRT
<213> ORGANISM: Artificial
<220> FEATURE:
<223> OTHER INFORMATION: Synthetic Construct

<400> SEQUENCE: 556

Cys Gly Gly Arg Val Thr His Pro His Leu Pro Arg Ala Leu Met Arg
1               5                   10                  15

Ser

<210> SEQ ID NO 557
<211> LENGTH: 16
<212> TYPE: PRT
<213> ORGANISM: Artificial
<220> FEATURE:
<223> OTHER INFORMATION: Synthetic Construct

<400> SEQUENCE: 557

Cys Gly Gly Val Thr His Pro His Leu Pro Arg Ala Leu Met Arg Ser
1               5                   10                  15

<210> SEQ ID NO 558
<211> LENGTH: 15
<212> TYPE: PRT
<213> ORGANISM: Artificial
<220> FEATURE:
<223> OTHER INFORMATION: Synthetic Construct

<400> SEQUENCE: 558

Cys Gly Gly Thr His Pro His Leu Pro Arg Ala Leu Met Arg Ser
1               5                   10                  15

<210> SEQ ID NO 559
<211> LENGTH: 13
<212> TYPE: PRT
<213> ORGANISM: Artificial
<220> FEATURE:
<223> OTHER INFORMATION: Synthetic Construct

<400> SEQUENCE: 559

Val Thr His Pro His Leu Pro Arg Ala Leu Gly Gly Cys
1               5                   10

<210> SEQ ID NO 560
<211> LENGTH: 11
<212> TYPE: PRT
<213> ORGANISM: Artificial
<220> FEATURE:
<223> OTHER INFORMATION: Synthetic Construct

<400> SEQUENCE: 560

Thr His Pro His Leu Pro Arg Ala Gly Gly Cys
1               5                   10

<210> SEQ ID NO 561
<211> LENGTH: 13
<212> TYPE: PRT
<213> ORGANISM: Artificial
<220> FEATURE:

<223> OTHER INFORMATION: Synthetic Construct

<400> SEQUENCE: 561

Cys Gly Gly Val Thr His Pro His Leu Pro Arg Ala Leu
1               5                   10

<210> SEQ ID NO 562
<211> LENGTH: 12
<212> TYPE: PRT
<213> ORGANISM: Artificial
<220> FEATURE:
<223> OTHER INFORMATION: Synthetic Construct

<400> SEQUENCE: 562

Cys Gly Gly Val Thr His Pro His Leu Pro Arg Ala
1               5                   10

<210> SEQ ID NO 563
<211> LENGTH: 16
<212> TYPE: PRT
<213> ORGANISM: Artificial
<220> FEATURE:
<223> OTHER INFORMATION: Synthetic Construct

<400> SEQUENCE: 563

Gln Cys Arg Val Thr His Pro His Leu Pro Ser Ala Leu Met Ser Ser
1               5                   10                  15

<210> SEQ ID NO 564
<211> LENGTH: 16
<212> TYPE: PRT
<213> ORGANISM: Artificial
<220> FEATURE:
<223> OTHER INFORMATION: Synthetic Construct

<400> SEQUENCE: 564

Gln Cys Arg Val Thr His Pro His Leu Pro Arg Ala Leu Met Ser Ser
1               5                   10                  15

<210> SEQ ID NO 565
<211> LENGTH: 16
<212> TYPE: PRT
<213> ORGANISM: Artificial
<220> FEATURE:
<223> OTHER INFORMATION: Synthetic Construct

<400> SEQUENCE: 565

Gln Cys Arg Val Thr His Pro His Leu Pro Ser Ala Leu Met Arg Ser
1               5                   10                  15

<210> SEQ ID NO 566
<211> LENGTH: 20
<212> TYPE: PRT
<213> ORGANISM: Artificial
<220> FEATURE:
<223> OTHER INFORMATION: Synthetic Construct

<400> SEQUENCE: 566

Gln Cys Arg Val Thr His Pro His Leu Pro Cys Ile Thr Ala Leu Met
1               5                   10                  15

Cys Ile Thr Ser
            20

<210> SEQ ID NO 567
<211> LENGTH: 18
<212> TYPE: PRT
<213> ORGANISM: Artificial

<220> FEATURE:
<223> OTHER INFORMATION: Synthetic Construct

<400> SEQUENCE: 567

Gln Cys Arg Val Thr His Pro His Leu Pro Arg Ala Leu Met Cys Ile
1               5                   10                  15
Thr Ser

<210> SEQ ID NO 568
<211> LENGTH: 18
<212> TYPE: PRT
<213> ORGANISM: Artificial
<220> FEATURE:
<223> OTHER INFORMATION: Synthetic Construct

<400> SEQUENCE: 568

Gln Cys Arg Val Thr His Pro His Leu Pro Cys Ile Thr Ala Leu Met
1               5                   10                  15
Arg Ser

<210> SEQ ID NO 569
<211> LENGTH: 19
<212> TYPE: PRT
<213> ORGANISM: Artificial
<220> FEATURE:
<223> OTHER INFORMATION: Synthetic Construct

<400> SEQUENCE: 569

Cys Asp Asp Asp Asp Arg Val Thr His Pro His Leu Pro Arg Ala Leu
1               5                   10                  15
Met Arg Ser

<210> SEQ ID NO 570
<211> LENGTH: 17
<212> TYPE: PRT
<213> ORGANISM: Artificial
<220> FEATURE:
<223> OTHER INFORMATION: Synthetic Construct

<400> SEQUENCE: 570

Cys Asp Asp Asp Asp Arg Val Thr His Pro His Leu Pro Arg Ala Leu
1               5                   10                  15
Met

<210> SEQ ID NO 571
<211> LENGTH: 18
<212> TYPE: PRT
<213> ORGANISM: Artificial
<220> FEATURE:
<223> OTHER INFORMATION: Synthetic Construct

<400> SEQUENCE: 571

Cys Asp Asp Asp Asp Val Thr His Pro His Leu Pro Arg Ala Leu Met
1               5                   10                  15
Arg Ser

<210> SEQ ID NO 572
<211> LENGTH: 16
<212> TYPE: PRT
<213> ORGANISM: Artificial
<220> FEATURE:
<223> OTHER INFORMATION: Synthetic Construct

<400> SEQUENCE: 572

Cys Asp Asp Asp Val Thr His Pro His Leu Pro Arg Ala Leu Met
1               5                   10                  15

<210> SEQ ID NO 573
<211> LENGTH: 21
<212> TYPE: PRT
<213> ORGANISM: Artificial
<220> FEATURE:
<223> OTHER INFORMATION: Synthetic Construct

<400> SEQUENCE: 573

Ser Thr Arg Lys Glu Glu Lys Gln Arg Asn Gly Thr Leu Thr Val Thr
1               5                   10                  15

Ser Thr Leu Pro Cys
            20

<210> SEQ ID NO 574
<211> LENGTH: 23
<212> TYPE: PRT
<213> ORGANISM: Artificial
<220> FEATURE:
<223> OTHER INFORMATION: Synthetic Construct

<400> SEQUENCE: 574

Ser Thr Arg Lys Glu Glu Lys Gln Arg Asn Gly Thr Leu Thr Val Thr
1               5                   10                  15

Ser Thr Leu Pro Gly Gly Cys
            20

<210> SEQ ID NO 575
<211> LENGTH: 23
<212> TYPE: PRT
<213> ORGANISM: Artificial
<220> FEATURE:
<223> OTHER INFORMATION: Synthetic Construct

<400> SEQUENCE: 575

Cys Gly Gly Ser Thr Arg Lys Glu Glu Lys Gln Arg Asn Gly Thr Leu
1               5                   10                  15

Thr Val Thr Ser Thr Leu Pro
            20

<210> SEQ ID NO 576
<211> LENGTH: 10
<212> TYPE: PRT
<213> ORGANISM: Artificial
<220> FEATURE:
<223> OTHER INFORMATION: Synthetic Construct

<400> SEQUENCE: 576

Lys Gly Gly Cys Gln Arg Asn Gly Thr Cys
1               5                   10

<210> SEQ ID NO 577
<211> LENGTH: 21
<212> TYPE: PRT
<213> ORGANISM: Artificial
<220> FEATURE:
<223> OTHER INFORMATION: Synthetic Construct

<400> SEQUENCE: 577

Ser Thr Arg Lys Glu Glu Lys Gln Arg Asn Gly Thr Leu Thr Val Thr
1               5                   10                  15

Ser Thr Gly Gly Cys
            20

<210> SEQ ID NO 578
<211> LENGTH: 20
<212> TYPE: PRT
<213> ORGANISM: Artificial
<220> FEATURE:
<223> OTHER INFORMATION: Synthetic Construct

<400> SEQUENCE: 578

Ser Thr Arg Lys Glu Glu Lys Gln Arg Asn Gly Thr Leu Thr Val Thr
1               5                   10                  15

Ser Gly Gly Cys
            20

<210> SEQ ID NO 579
<211> LENGTH: 19
<212> TYPE: PRT
<213> ORGANISM: Artificial
<220> FEATURE:
<223> OTHER INFORMATION: Synthetic Construct

<400> SEQUENCE: 579

Ser Thr Arg Lys Glu Glu Lys Gln Arg Asn Gly Thr Leu Thr Val Thr
1               5                   10                  15

Gly Gly Cys

<210> SEQ ID NO 580
<211> LENGTH: 18
<212> TYPE: PRT
<213> ORGANISM: Artificial
<220> FEATURE:
<223> OTHER INFORMATION: Synthetic Construct

<400> SEQUENCE: 580

Ser Thr Arg Lys Glu Glu Lys Gln Arg Asn Gly Thr Leu Thr Val Gly
1               5                   10                  15

Gly Cys

<210> SEQ ID NO 581
<211> LENGTH: 17
<212> TYPE: PRT
<213> ORGANISM: Artificial
<220> FEATURE:
<223> OTHER INFORMATION: Synthetic Construct

<400> SEQUENCE: 581

Ser Thr Arg Lys Glu Glu Lys Gln Arg Asn Gly Thr Leu Thr Gly Gly
1               5                   10                  15

Cys

<210> SEQ ID NO 582
<211> LENGTH: 16
<212> TYPE: PRT
<213> ORGANISM: Artificial
<220> FEATURE:
<223> OTHER INFORMATION: Synthetic Construct

<400> SEQUENCE: 582

Ser Thr Arg Lys Glu Glu Lys Gln Arg Asn Gly Thr Leu Gly Gly Cys
1               5                   10                  15

<210> SEQ ID NO 583
<211> LENGTH: 21
<212> TYPE: PRT
<213> ORGANISM: Artificial
<220> FEATURE:
<223> OTHER INFORMATION: Synthetic Construct

```
<400> SEQUENCE: 583

Cys Gly Gly Ser Thr Arg Lys Glu Glu Lys Gln Arg Asn Gly Thr Leu
1               5                   10                  15

Thr Val Thr Ser Thr
            20

<210> SEQ ID NO 584
<211> LENGTH: 20
<212> TYPE: PRT
<213> ORGANISM: Artificial
<220> FEATURE:
<223> OTHER INFORMATION: Synthetic Construct

<400> SEQUENCE: 584

Cys Gly Gly Ser Thr Arg Lys Glu Glu Lys Gln Arg Asn Gly Thr Leu
1               5                   10                  15

Thr Val Thr Ser
            20

<210> SEQ ID NO 585
<211> LENGTH: 19
<212> TYPE: PRT
<213> ORGANISM: Artificial
<220> FEATURE:
<223> OTHER INFORMATION: Synthetic Construct

<400> SEQUENCE: 585

Cys Gly Gly Ser Thr Arg Lys Glu Glu Lys Gln Arg Asn Gly Thr Leu
1               5                   10                  15

Thr Val Thr

<210> SEQ ID NO 586
<211> LENGTH: 18
<212> TYPE: PRT
<213> ORGANISM: Artificial
<220> FEATURE:
<223> OTHER INFORMATION: Synthetic Construct

<400> SEQUENCE: 586

Cys Gly Gly Ser Thr Arg Lys Glu Glu Lys Gln Arg Asn Gly Thr Leu
1               5                   10                  15

Thr Val

<210> SEQ ID NO 587
<211> LENGTH: 17
<212> TYPE: PRT
<213> ORGANISM: Artificial
<220> FEATURE:
<223> OTHER INFORMATION: Synthetic Construct

<400> SEQUENCE: 587

Cys Gly Gly Ser Thr Arg Lys Glu Glu Lys Gln Arg Asn Gly Thr Leu
1               5                   10                  15

Thr

<210> SEQ ID NO 588
<211> LENGTH: 16
<212> TYPE: PRT
<213> ORGANISM: Artificial
<220> FEATURE:
<223> OTHER INFORMATION: Synthetic Construct
```

```
<400> SEQUENCE: 588

Cys Gly Gly Ser Thr Arg Lys Glu Glu Lys Gln Arg Asn Gly Thr Leu
1               5                   10                  15

<210> SEQ ID NO 589
<211> LENGTH: 20
<212> TYPE: PRT
<213> ORGANISM: Artificial
<220> FEATURE:
<223> OTHER INFORMATION: Synthetic Construct

<400> SEQUENCE: 589

Thr Arg Lys Glu Glu Lys Gln Arg Asn Gly Thr Leu Thr Val Thr Ser
1               5                   10                  15

Thr Gly Gly Cys
            20

<210> SEQ ID NO 590
<211> LENGTH: 19
<212> TYPE: PRT
<213> ORGANISM: Artificial
<220> FEATURE:
<223> OTHER INFORMATION: Synthetic Construct

<400> SEQUENCE: 590

Arg Lys Glu Glu Lys Gln Arg Asn Gly Thr Leu Thr Val Thr Ser Thr
1               5                   10                  15

Gly Gly Cys

<210> SEQ ID NO 591
<211> LENGTH: 18
<212> TYPE: PRT
<213> ORGANISM: Artificial
<220> FEATURE:
<223> OTHER INFORMATION: Synthetic Construct

<400> SEQUENCE: 591

Lys Glu Glu Lys Gln Arg Asn Gly Thr Leu Thr Val Thr Ser Thr Gly
1               5                   10                  15

Gly Cys

<210> SEQ ID NO 592
<211> LENGTH: 17
<212> TYPE: PRT
<213> ORGANISM: Artificial
<220> FEATURE:
<223> OTHER INFORMATION: Synthetic Construct

<400> SEQUENCE: 592

Glu Glu Lys Gln Arg Asn Gly Thr Leu Thr Val Thr Ser Thr Gly Gly
1               5                   10                  15

Cys

<210> SEQ ID NO 593
<211> LENGTH: 16
<212> TYPE: PRT
<213> ORGANISM: Artificial
<220> FEATURE:
<223> OTHER INFORMATION: Synthetic Construct

<400> SEQUENCE: 593

Glu Lys Gln Arg Asn Gly Thr Leu Thr Val Thr Ser Thr Gly Gly Cys
1               5                   10                  15
```

```
<210> SEQ ID NO 594
<211> LENGTH: 20
<212> TYPE: PRT
<213> ORGANISM: Artificial
<220> FEATURE:
<223> OTHER INFORMATION: Synthetic Construct

<400> SEQUENCE: 594

Cys Gly Gly Thr Arg Lys Glu Glu Lys Gln Arg Asn Gly Thr Leu Thr
1               5                   10                  15

Val Thr Ser Thr
            20

<210> SEQ ID NO 595
<211> LENGTH: 19
<212> TYPE: PRT
<213> ORGANISM: Artificial
<220> FEATURE:
<223> OTHER INFORMATION: Synthetic Construct

<400> SEQUENCE: 595

Cys Gly Gly Arg Lys Glu Glu Lys Gln Arg Asn Gly Thr Leu Thr Val
1               5                   10                  15

Thr Ser Thr

<210> SEQ ID NO 596
<211> LENGTH: 18
<212> TYPE: PRT
<213> ORGANISM: Artificial
<220> FEATURE:
<223> OTHER INFORMATION: Synthetic Construct

<400> SEQUENCE: 596

Cys Gly Gly Lys Glu Glu Lys Gln Arg Asn Gly Thr Leu Thr Val Thr
1               5                   10                  15

Ser Thr

<210> SEQ ID NO 597
<211> LENGTH: 17
<212> TYPE: PRT
<213> ORGANISM: Artificial
<220> FEATURE:
<223> OTHER INFORMATION: Synthetic Construct

<400> SEQUENCE: 597

Cys Gly Gly Glu Glu Lys Gln Arg Asn Gly Thr Leu Thr Val Thr Ser
1               5                   10                  15

Thr

<210> SEQ ID NO 598
<211> LENGTH: 16
<212> TYPE: PRT
<213> ORGANISM: Artificial
<220> FEATURE:
<223> OTHER INFORMATION: Synthetic Construct

<400> SEQUENCE: 598

Cys Gly Gly Glu Lys Gln Arg Asn Gly Thr Leu Thr Val Thr Ser Thr
1               5                   10                  15

<210> SEQ ID NO 599
<211> LENGTH: 19
<212> TYPE: PRT
<213> ORGANISM: Artificial
<220> FEATURE:
<223> OTHER INFORMATION: Synthetic Construct
```

```
<400> SEQUENCE: 599

Thr Arg Lys Glu Glu Lys Gln Arg Asn Gly Thr Leu Thr Val Thr Ser
1               5                   10                  15

Gly Gly Cys

<210> SEQ ID NO 600
<211> LENGTH: 17
<212> TYPE: PRT
<213> ORGANISM: Artificial
<220> FEATURE:
<223> OTHER INFORMATION: Synthetic Construct

<400> SEQUENCE: 600

Arg Lys Glu Glu Lys Gln Arg Asn Gly Thr Leu Thr Val Thr Gly Gly
1               5                   10                  15

Cys

<210> SEQ ID NO 601
<211> LENGTH: 15
<212> TYPE: PRT
<213> ORGANISM: Artificial
<220> FEATURE:
<223> OTHER INFORMATION: Synthetic Construct

<400> SEQUENCE: 601

Lys Glu Glu Lys Gln Arg Asn Gly Thr Leu Thr Val Gly Gly Cys
1               5                   10                  15

<210> SEQ ID NO 602
<211> LENGTH: 13
<212> TYPE: PRT
<213> ORGANISM: Artificial
<220> FEATURE:
<223> OTHER INFORMATION: Synthetic Construct

<400> SEQUENCE: 602

Glu Glu Lys Gln Arg Asn Gly Thr Leu Thr Gly Gly Cys
1               5                   10

<210> SEQ ID NO 603
<211> LENGTH: 11
<212> TYPE: PRT
<213> ORGANISM: Artificial
<220> FEATURE:
<223> OTHER INFORMATION: Synthetic Construct

<400> SEQUENCE: 603

Glu Lys Gln Arg Asn Gly Thr Leu Gly Gly Cys
1               5                   10

<210> SEQ ID NO 604
<211> LENGTH: 19
<212> TYPE: PRT
<213> ORGANISM: Artificial
<220> FEATURE:
<223> OTHER INFORMATION: Synthetic Construct

<400> SEQUENCE: 604

Cys Gly Gly Thr Arg Lys Glu Glu Lys Gln Arg Asn Gly Thr Leu Thr
1               5                   10                  15

Val Thr Ser
```

<210> SEQ ID NO 605
<211> LENGTH: 17
<212> TYPE: PRT
<213> ORGANISM: Artificial
<220> FEATURE:
<223> OTHER INFORMATION: Synthetic Construct

<400> SEQUENCE: 605

Cys Gly Gly Arg Lys Glu Glu Lys Gln Arg Asn Gly Thr Leu Thr Val
1               5                   10                  15

Thr

<210> SEQ ID NO 606
<211> LENGTH: 15
<212> TYPE: PRT
<213> ORGANISM: Artificial
<220> FEATURE:
<223> OTHER INFORMATION: Synthetic Construct

<400> SEQUENCE: 606

Cys Gly Gly Lys Glu Glu Lys Gln Arg Asn Gly Thr Leu Thr Val
1               5                   10                  15

<210> SEQ ID NO 607
<211> LENGTH: 13
<212> TYPE: PRT
<213> ORGANISM: Artificial
<220> FEATURE:
<223> OTHER INFORMATION: Synthetic Construct

<400> SEQUENCE: 607

Cys Gly Gly Glu Glu Lys Gln Arg Asn Gly Thr Leu Thr
1               5                   10

<210> SEQ ID NO 608
<211> LENGTH: 16
<212> TYPE: PRT
<213> ORGANISM: Artificial
<220> FEATURE:
<223> OTHER INFORMATION: Synthetic Construct

<400> SEQUENCE: 608

Leu Val Val Asp Leu Ala Pro Ser Lys Gly Thr Val Asn Gly Gly Cys
1               5                   10                  15

<210> SEQ ID NO 609
<211> LENGTH: 16
<212> TYPE: PRT
<213> ORGANISM: Artificial
<220> FEATURE:
<223> OTHER INFORMATION: Synthetic Construct

<400> SEQUENCE: 609

Cys Gly Gly Leu Val Val Asp Leu Ala Pro Ser Lys Gly Thr Val Asn
1               5                   10                  15

<210> SEQ ID NO 610
<211> LENGTH: 21
<212> TYPE: PRT
<213> ORGANISM: Artificial
<220> FEATURE:
<223> OTHER INFORMATION: Synthetic Construct

```
<400> SEQUENCE: 610

Cys Gly Gly Gly Gly Ser Asp Leu Ala Pro Ser Lys Gly Thr Val Ser
1               5                   10                  15

Gly Gly Gly Gly Cys
            20
```

IGE CH3 PEPTIDE VACCINE

CROSS-REFERENCE TO RELATED APPLICATIONS

This application is a division of U.S. patent application Ser. No. 12/634,336, filed Dec. 9, 2009, now allowed, which claims priority to U.S. Provisional Application No. 61/120,989 filed on Dec. 9, 2008. The disclosure of each of U.S. patent application Ser. No. 12/634,336 and U.S. Provisional Application No. 61/120,989 is incorporated herein by reference in its entirety.

FIELD OF THE INVENTION

The present invention relates to the provision of novel immunogens comprising an antigenic IgE peptide preferably linked to an immunogenic carrier for the prevention, treatment or alleviation of IgE-mediated disorders. The invention further relates to methods for production of these medicaments, immunogenic compositions and pharmaceutical composition thereof and their use in medicine.

REFERENCE TO SEQUENCE LISTING

The present application is being filed along with a Sequence Listing in electronic format. The Sequence Listing is provided as a file entitled PC33841BSeqListingST25.txt, created Jul. 11, 2012, which is 114 KB in size. The information in the electronic format of the Sequence Listing is incorporated herein by reference in its entirety.

BACKGROUND

During the past few decades, allergic diseases have increased to almost epidemic proportions and estimates suggest that 20-30% of the total population in many Western countries is affected. The key role played by IgE in initiating the allergic responses is well documented. Upon release from B lymphocytes, IgE binds to the high affinity IgE receptor (FceRl) present on mast cells and basophils. The subsequent cross-linkage of adjacent IgE molecules on these cells by specific allergens then results in their activation, leading to the release of a number of pro-inflammatory mediators (e.g. histamine, leukotrinenes, prostaglandins), as well as key cytokines and chemokines. Consequently, acute local responses are followed by recruitment and activation of other inflammatory cells (e.g. eosinophils, T lymphocytes), thereby amplifying the allergic cascade. Dendritic cells, for example those present at sites of allergic inflammation (e.g. the lung) may also express FceR1 and can use this receptor to selectively and efficiently take up allergens present in immune complexes with IgE and process these allergens selectively for presentation to allergen-specific T-cells, thus providing a mechanism for persistent T-cell activation and pathologic inflammatory responses.

Most current treatment regimens aim at relieving symptoms rather than treating the cause of the disease and are based primarily on the use of antihistamines, antileukotrienes, cromoglycates, beta-agonists and on general anti-inflammatory compounds such as corticosteroids. Although some of the affected patients have their disease under relatively good control with these drugs, their frequency of administration (often daily or even several times a day) often leads to poor patient compliance and subsequent deterioration of the disease. In addition, in some cases such as severe asthma and severe atopic dermatitis, existing therapies are insufficient to control the disease.

Very recently, a monoclonal antibody (omalizumab, also termed E25, marketed under the trade name Xolair®; Presta et al. *J. Immunol.* 1993 Sep. 1; 151(5):2623-32.) gained approval from several agencies around the world, primarily for treatment of severe asthma and rhinitis. Despite showing efficacy against severe asthma, this antibody still has some drawbacks. Firstly this is a humanized murine monoclonal antibody, and as such, does not entirely preclude immunological reactions in human patients, thus possibly raising some safety concerns. Secondly, the dose of omalizumab used in treating severe asthma is based on both body weight and the level of circulating free IgE. Patients whose body weight and circulating free IgE that deviate from a specified range are recommended not to use this treatment. Those patients that can be treated may require to receive up to three subcutaneous injections once every two weeks. This heavily impacts on the costs of treatment (estimated to range at US $15,000-44,000 annually per patient), as well as on the quality of life of the patients, making it difficult to use as a general strategy for treatment of allergies.

To overcome the problems of high cost and frequent administrations, an alternative is to trigger our own immune system to produce the therapeutic antibodies by vaccination. In the course of their investigations, previous workers in the allergy field have encountered a number of considerations, and problems, which have to be taken into account when designing new anti-allergy therapies. One of the most dangerous problems revolves around the involvement of IgE cross-linking in the histamine release signal. It is most often the case that the generation of anti-IgE antibodies during active vaccination, are capable of triggering histamine release per se, by the cross-linking of neighbouring IgE-receptor complexes in the absence of allergen. This phenomenon is termed anaphylactogenicity. Indeed many commercially available anti-IgE monoclonal antibodies which are normally used for IgE detection assays, are anaphylactogenic, and consequently useless and potentially dangerous if administered to a patient. Therefore, in order to be safe and effective, the passively administered, or vaccine induced, antibodies must bind in a region of IgE which is capable of, inhibiting IgE activities without being anaphylactic per se.

The structure of the constant domains CH3-CH4 from human IgE interacting with the IgE high affinity receptor FceRl alpha subunit has been solved (Wurzburg B A et al. (2000) *Immunity* 13 (3) 375-85; Garman S C et al., (2000) *Nature* 20; 406 (6793):259-66). Previous work had also identified a number of IgE peptides or derived peptides or mimotopes deemed to be useful for inducing non anaphylactogenic anti-IgE antibodies (WO 1993/005810; WO99/67293; WO2004/058799, WO97/31948, WO2000/25722, WO05/075504, US2002/0645525, US2004/146504 and US2006/062782; WO00/050461, WO02/34288 and WO2003/092714; Chen et al. (2008) *J. Immunologic. Meth.* 333:10-23; Hellman *Expert Rev. Vaccines* 7(2):193-208 (2008)). Such IgE domains or peptides are usually linked to carriers to increase their immunogenicity in order to break self-tolerance to IgE in an individual.

It is therefore desirable to provide a composition, such as an antigenic IgE peptide or the combination of several thereof coupled to an immunogenic carrier, and optionally administered with one or more adjuvants, able to induce potent non anaphylactogenic anti-IgE antibodies in an individual capable of significantly reducing levels of circulating free IgE. Increased potency would typically result in the following benefits: lower doses required to achieve clinical benefits, lower volume of injection required e.g. for subcutaneous or intramuscular administration (compared to monoclonal antibody therapies, for example), lower cost of treatment, increased chances of treatment success, decreased frequency of administration in the treatment regimen, thus providing access to treatment to a wider population of patients, including patients with higher body weight and/or high levels of circulating IgE, and improving patients' quality of life.

SUMMARY OF THE INVENTION

The present invention relates to an immunogen comprising an antigenic IgE peptide preferably linked to an immunogenic carrier. Said IgE antigenic peptide comprises an amino acid sequence selected from the group consisting of SEQ ID Nos: 1 to 430, preferably from the group consisting of SEQ ID NOs: 1 to 153 and 220 to 430, even more preferably from the group consisting of SEQ ID NOs: 220 to 430. Said antigenic IgE peptide might be modified for conjugation purposes, preferably by the addition of cysteine or lysine residues and/or the addition of linkers such as GC/GGC linkers. In preferred embodiments, said antigenic IgE peptide is conformationally constrained, preferably simply constrained. Said immunogenic carrier is an heterologous protein, preferably a virus-like particle (VLP), more preferably a HBcAg, HBsAg or Qbeta VLP. The invention also relates to methods for producing such antigenic IgE peptide preferably linked to an immunogenic carrier The invention also relates to immunogenic compositions comprising such antigenic IgE peptide preferably linked to an immunogenic carrier, preferably to immunogenic compositions, optionally comprising an adjuvant preferably selected from the group consisting of alum; CpG-containing oligonucleotides, preferably CpG7909 and CpG24555; and saponin-based adjuvants, preferably Iscomatrix. Preferably, said CpG-containing nucleic acid comprises one or more modified linkages, preferably one or more phosphorothioate linkages, even more preferably all internucleotide linkages of the oligonucleotide are phosphorothioate linkages.

Another aspect of the invention relates to pharmaceutical compositions comprising an antigenic IgE peptide according to the invention, or an immunogenic composition thereof, as well as to medical uses of such compositions.

In particular, the invention relates to an antigenic IgE peptide of the invention, or an immunogenic or pharmaceutical composition thereof, for use as a medicament, preferably in treatment, alleviation or prophylaxis of IgE-mediated disorders. The invention also relates to methods of inducing an immune response in an individual to self-IgE and to methods for treating, alleviating or preventing IgE-mediated disorders comprising administering an effective amount of said antigenic IgE peptide or immunogenic or pharmaceutical composition thereof.

DETAILED DESCRIPTION OF THE INVENTION

Definitions and General Techniques

Figure 1:
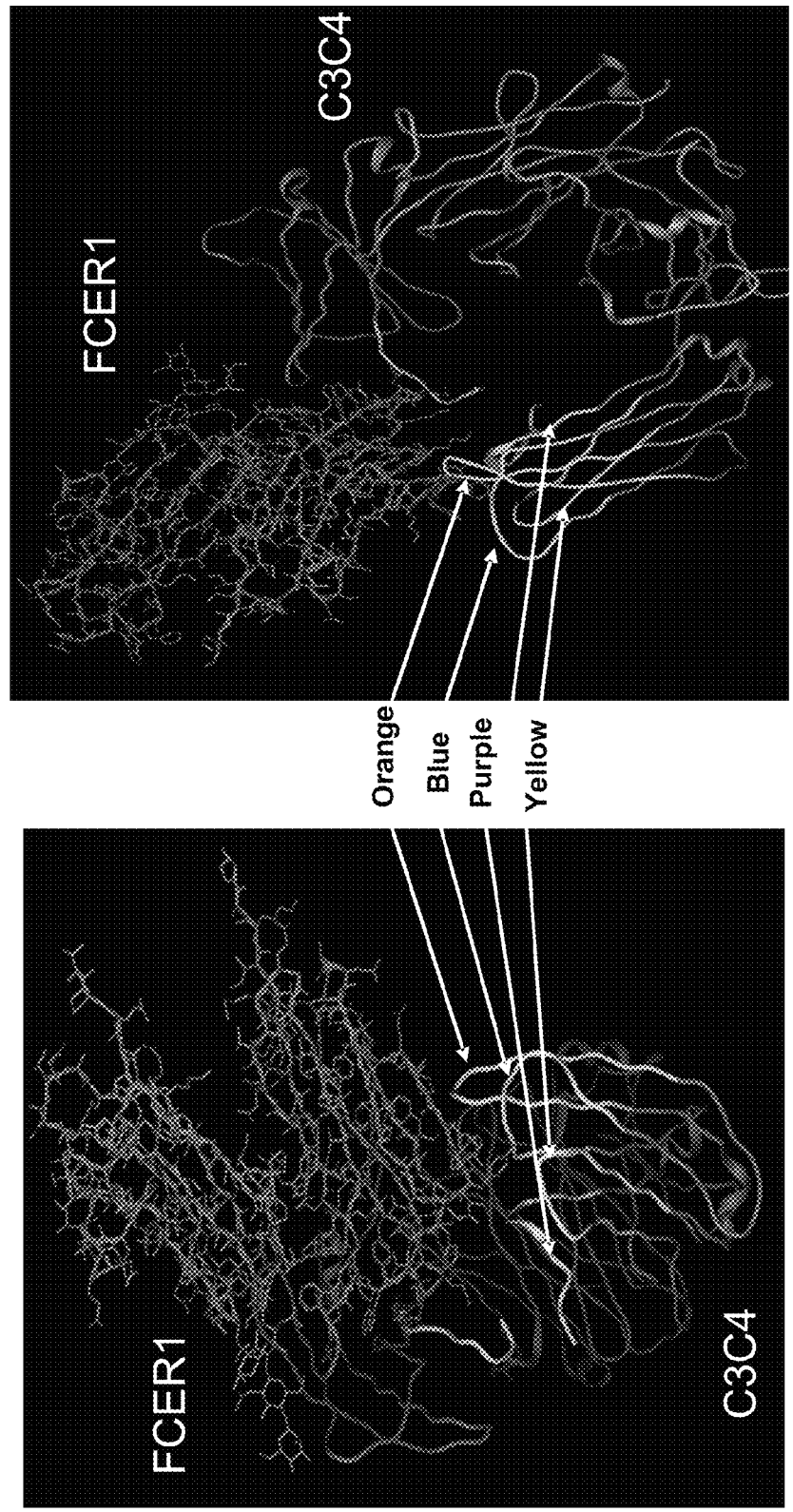
FIG. 1: Structural display of the interaction between the CH3-CH4 region of human IgE with its high affinity receptor FceRI. Displayed are 4 loops (blue, purple, orange and yellow) corresponding to the 4 peptides of SEQ ID Nos: 165, 312, 1 and 220 respectively.

Unless otherwise defined herein, scientific and technical terms used in connection with the present invention shall have the meanings that are commonly understood by those of ordinary skill in the art. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). Enzymatic reactions and purification techniques are performed according to manufacturer's specifications, as commonly accomplished in the art or as described herein.

The nomenclature used in connection with, and the laboratory procedures and techniques of, analytical chemistry, synthetic organic chemistry, and medicinal and pharmaceutical chemistry described herein are those well known and commonly used in the art.

Throughout this specification and claims, the word "comprise," or variations such as "comprises" or "comprising," will be understood to imply the inclusion of a stated integer or group of integers but not the exclusion of any other integer or group of integers. The terms "comprising", "consisting of" and "consisting essentially of" are meant to be interchangeable. When the terms "one," "a," or "an" are used in this disclosure, they mean "at least one" or "one or more,", unless otherwise indicated. Further, unless otherwise required by context, singular terms shall include pluralities and plural terms shall include the singular unless the content clearly dictates otherwise.

All publications, patents and patent applications cited herein, whether supra or infra, are hereby incorporated by reference in their entirety.

General Definitions:

The term "peptide" or "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "isolated protein", "isolated polypeptide" or "isolated peptide" is a protein, polypeptide or peptide that by virtue of its origin or source of derivation (1) is not associated with naturally associated components that accompany it in its native state, (2) is free of other proteins from the same species, (3) is expressed by a cell from a different species, or (4) does not occur in nature. Thus, a peptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

As used herein, when the term "purified" is used in reference to a molecule (e.g., a peptide, polypeptide or protein), it means that the concentration of the molecule being purified has been increased relative to molecules associated with it in its natural environment, or environment in which it was produced, found or synthesized. Naturally associated molecules include proteins, nucleic acids, lipids and sugars but generally do not include water, buffers, and reagents added to maintain the integrity or facilitate the purification of the molecule being purified.

In some embodiments, a compound is substantially pure or purified when it is at least 20%, at least 30%, at least 40%, at least 50%, or at least 60%, by weight, free from organic molecules with which it is naturally associated or with which it is associated during manufacture. In some embodiments, the preparation is at least 70%, at least 75%, at least 90%, at least 95%, or at least 99%, by weight, of the compound of interest relative to its contaminants.

A substantially pure or purified compound can be obtained, for example, by extraction from a natural source (e.g., bacteria), by chemically synthesizing a compound, or by a combination of purification and chemical modification. A substantially pure or purified compound can also be obtained by, for example, enriching a sample having a compound that binds an antibody of interest. Purity can be measured by any appropriate method, e.g., chromatography, mass spectroscopy, high performance liquid chromatography analysis, etc.

The term "heterologous," as used herein in the context of an IgE peptide or polypeptide, where a IgE polypeptide fusion protein comprises an IgE peptide or polypeptide and a "heterologous" polypeptide, refers to a polypeptide that is other than an IgE peptide or polypeptide, e.g., a polypeptide that is not normally associated in nature with an IgE peptide or polypeptide. For example, a heterologous polypeptide bears no significant amino acid sequence identity to the IgE peptide or polypeptide, e.g., the heterologous polypeptide has less than about 50%, less than about 40%, less than about 30%, or less than about 20% amino acid sequence identity to the IgE peptide or polypeptide.

As used herein, the term "IgE-mediated disorder" or "IgE-related disorder" means a condition or disease which is characterized by the overproduction and/or hypersensitivity to the immunoglobulin IgE. Specifically it would be construed to include conditions associated with anaphylactic hypersensitivity and atopic allergies, including for example: asthma, allergic asthma, allergic rhinitis and conjunctivitis (hay fever), eczema, urticaria, atopic dermatitis, and food allergies including peanut allergy. The serious physiological condition of anaphylactic shock caused by, e.g., bee stings, snake bites, food or medication, is also encompassed under the scope of this term. Other IgE-mediated disorders include anaphylaxis, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, ulcerative colitis, indeterminate colitis and infectious colitis), urticaria, and psoriasis.

Antigenic IgE Peptide of the Invention

The present invention relates to IgE peptides, and peptides derived thereof, which have been identified as portions of the IgE CH3 domain able to form loops participating in the interaction of CH3-CH4 region with its high affinity receptor FceRl (cf FIG. 1). Such IgE peptides were shown to be immunogenic and non-anaphylactogenic.

Such antigenic IgE peptides may be used alone or in combination, preferably when conjugated to an immunogenic carrier, to induce auto anti-IgE antibodies in a subject in order to treat, prevent or ameliorate IgE-related disorders.

In particular, the present invention relates to an immunogen consisting of, consisting essentially of, or comprising an antigenic IgE peptide preferably linked to an immunogenic carrier.

In one embodiment, the antigenic IgE peptide of the invention consists of, consists essentially of, or comprises an amino acid sequence selected from the group consisting of SEQ ID Nos: 1 to 430 and functionally active variants thereof, preferably selected from the group consisting of SEQ ID Nos: 1 to 430. In another embodiment, said antigenic IgE peptide consists of, consists essentially of, or comprises an amino acid sequence selected from the group consisting of SEQ ID Nos: 1 to 153 and functionally active variants thereof, preferably selected from the group consisting of SEQ ID Nos:1 to 153. In another embodiment, said antigenic IgE peptide consists of, consists essentially of, or comprises an amino acid sequence selected from the group consisting of SEQ ID Nos: 154 to 219 and functionally active variants thereof, preferably selected from the group consisting of SEQ ID Nos: 154 to 219. In still another embodiment, said antigenic IgE peptide consists of, consists essentially of, or comprises an amino acid sequence selected from the group consisting of SEQ ID Nos: 220 to 310 and functionally active variants thereof, preferably selected from the group consisting of SEQ ID Nos: 220 to 310. In still another embodiment, said antigenic IgE peptide consists of, consists essentially of, or comprises an amino acid sequence selected from the group consisting of SEQ ID Nos: 311 to 430 and functionally active variants thereof, preferably selected from the group consisting of SEQ ID Nos: 311 to 430.

The term "antigenic IgE peptide", within the meaning of the present invention includes all IgE CH3-derived peptides, preferably from mammalian species, more preferably human, as well as their variants, analogs, orthologs, homologs and derivatives, and fragments thereof that exhibit an "antigenic IgE peptide biological activity". Preferably, the term "antigenic IgE peptide" refers to peptides comprising, consisting of or consisting essentially of an amino acid sequence selected from the group consisting of SEQ ID Nos: 1 to 430, as well as to their variants, homologs and derivatives exhibiting essentially the same biological activity. More preferably, the term "antigenic IgE peptide" refers to peptides comprising, consisting of or consisting essentially of an amino acid sequence selected from the group consisting of SEQ ID 1 to 430, more preferably to peptides comprising, consisting of or consisting essentially of an amino acid sequence selected from the group consisting of SEQ ID Nos: 1 to 153 and 220 to 430, even more preferably, to peptides comprising, consisting of or consisting essentially of an amino acid sequence selected from the group consisting of SEQ ID Nos: 220 to 430.

In an embodiment, the antigenic IgE peptide of the invention consists of, or consists essentially of, an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, , 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430.

In another embodiment, the antigenic IgE peptide of the invention consists of, or consists essentially of, an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, and 153. Preferably, said antigenic IgE peptide consists of, or consists essentially of, an amino acid sequence selected from the group consisting of SEQ ID Nos: 1, 2, 3, 4, 5, 6, 7, 8, 9, 10, 11, 12, 13, 14, 15, 18, 19, 20, 21, 22, 23, 24, 25, 26, 27, 28, 29, 30, 31, 34, 35, 36, 37, 38, 39, 40, 41, 42, 43, 44, 45, 46, 49, 50, 51, 52, 53, 54, 55, 56, 57, 58, 59, 60, 63, 64, 65, 66, 67, 68, 69, 70, 71, 72, 73, 76, 77, 78, 79, 80, 81, 82, 83, 84, 85, 88, 89, 90, 91, 92, 93, 94, 95, 96, 99, 100, 101, 102, 103, 104, 105, 106, 109, 110, 111, 112, 113, 114, 115, 118, 119, 120, 121, 122, 123, 126, 127, 128, 129, 130, 133, 134, 135, 136, 139, 140, 141, 144, 145 and 148. More preferably, said antigenic IgE peptide consists of, or consists essentially of, an amino acid sequence selected from the group consisting of SEQ ID Nos: 1, 2, 3, 4, 5, 6, 7, 8, 9, 10, 11, 12, 18, 19, 20, 21, 22, 23, 24, 25, 26, 27, 28, 34, 35, 36, 37, 38, 39, 40, 41, 42, 43, 49, 50, 51, 52, 53, 54, 55, 56, 57, 63, 64, 65, 66, 67, 68, 69, 70, 76, 77, 78, 79, 80, 81, 82, 88, 89, 90, 91, 92, 93, 99, 100, 101, 102, 103, 109, 110, 111, 112, 118, 119, 120, 126, 127, 133, and 139. Even more preferably, said antigenic IgE peptide consists of, or consists essentially of, an amino acid sequence selected from the group consisting of SEQ ID Nos: 1, 2, 3, 4, 5, 6, 7, 8, 9, 18, 19, 20, 21, 22, 23, 24, 25, 34, 35, 36, 37, 38, 39, 40, 49, 50, 51, 52, 53, 54, 63, 64, 65, 66, 67, 76, 77, 78, 79, 88, 89, 90, 99, 100, 101 and 109. Even more preferably, said antigenic IgE peptide consists of, or consists essentially of, an amino acid sequence selected from the group consisting of SEQ ID Nos: 1, 2, 3, 4, 5, 6, 18, 19, 20, 21, 22, 34, 35, 36, 37, 49, 50, 51, 63, 64 and 76. Even more preferably, said antigenic IgE peptide consists of, or consists essentially of, an amino acid sequence selected from the group consisting of SEQ ID Nos: 1, 2, 3, 18, 19 and 34. Most preferably, said antigenic IgE peptide consists of, or consists essentially of, an amino acid sequence of SEQ ID Nos: 1 or 18.

In another embodiment, the antigenic IgE peptide of the invention consists of, or consists essentially of, an amino acid sequence selected from the group consisting of SEQ ID Nos: 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, and 219. Preferably, said antigenic IgE peptide consists of, or consists essentially of, an amino acid sequence selected from the group consisting of SEQ ID Nos: 154, 155, 156, 157, 158, 159, 160, 161, 162, 165, 166, 167, 168, 169, 170, 171, 172, 175, 176, 177, 178, 179, 180, 181, 184, 185, 186, 187, 188, 189, 192, 193, 194, 195, 196, 199, 200, 201, 202, 205, 206, 207, 210, 211, 214 and 217. More preferably, said antigenic IgE peptide consists of, or consists essentially of, an amino acid sequence selected from the group consisting of SEQ ID Nos: 154, 155, 156, 157, 158, 159, 165, 166, 167, 168, 169, 175, 176, 177, 178, 184, 185, 186, 192, 193, 199 and 200. Even more preferably, said antigenic IgE peptide consists of, or consists essentially of, an amino acid sequence selected from the group consisting of SEQ ID Nos: 154, 155, 156, 165, 166 and 175. Most preferably, said antigenic IgE peptide consists of, or consists essentially of, an amino acid sequence of SEQ ID Nos: 154 or 165.

In another embodiment, the antigenic IgE peptide of the invention consists of, or consists essentially of, an amino acid sequence selected from the group consisting of SEQ ID Nos: 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, and 310. Preferably, said antigenic IgE peptide consists of, or consists essentially of, an amino acid sequence selected from the group consisting of SEQ ID Nos: 220, 221, 222, 223, 224, 225, 226, 227, 228, 229, 230, 233, 234, 235, 236, 237, 238, 239, 240, 241, 242, 245, 246, 247, 248, 249, 250, 251, 252, 253, 256, 257, 258, 259, 260, 261, 262, 263, 266, 267, 268, 269, 270, 271, 272, 275, 276, 277, 278, 279, 280, 283, 284, 285, 286, 287, 290, 291, 292, 293, 296, 297, 298, 301, 302 and 305. More preferably, said antigenic IgE peptide consists of, or consists essentially of, an amino acid sequence selected from the group consisting of SEQ ID Nos: 220, 221, 222, 223, 224, 225, 226, 227, 233, 234, 235, 236, 237, 238, 239, 245, 246, 247, 248, 249, 250, 256, 257, 258, 259, 260, 266, 267, 268, 269, 275, 276, 277, 283, 284 and 290. Even more preferably, said antigenic IgE peptide consists of, or consists essentially of, an amino acid sequence selected from the group consisting of SEQ ID Nos: 220, 221, 222, 223, 224, 233, 234, 235, 236, 245, 246, 247, 256, 257 and 266. Even more preferably, said antigenic IgE peptide consists of, or consists essentially of, an amino acid sequence selected from the group consisting of SEQ ID Nos: 220, 221, 222, 233, 234 and 245. Most preferably, said antigenic IgE peptide consists of, or consists essentially of, an amino acid sequence of SEQ ID Nos: 220 or 233.

In yet another embodiment, the antigenic IgE peptide of the invention consists of, or consists essentially of, an amino acid sequence selected from the group consisting of SEQ ID Nos: 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430. Preferably, said antigenic IgE peptide consists of, or consists essentially of, an amino acid sequence selected from the group consisting of SEQ ID Nos:311, 312, 313, 314, 315, 316, 317, 318, 319, 320, 321, 322, 323, 326, 327, 328, 329, 330, 331, 332, 333, 334, 335, 336, 337, 340, 341, 342, 343, 344, 345, 346, 347, 348, 349, 350, 353, 354, 355, 356, 357, 358, 359, 360, 361, 362, 365, 366, 367, 368, 369, 370, 371, 372, 373, 376, 377, 378, 379, 380, 381, 382, 383, 386, 387, 388, 389, 390, 391, 392, 395, 396, 397, 398, 399, 400, 403, 404, 405, 406, 407, 410, 411, 412, 413, 416, 417, 418, 421, 422 and 425. More preferably, said antigenic IgE peptide consists of, or consists essentially of, an amino acid sequence selected from the group consisting of SEQ ID Nos: 311, 312, 313, 314, 315, 316, 317, 318, 319, 320, 326, 327, 328, 329, 330, 331, 332, 333, 334, 340, 341, 342, 343, 344, 345, 346, 347, 353, 354, 355, 356, 357, 358, 359, 365, 366, 367, 368, 369, 370, 376, 377, 378, 379, 380, 386, 387, 388, 389, 395, 396, 397, 403, 404 and 410. Even more preferably, said antigenic IgE peptide consists of, or consists essentially of, an amino acid sequence selected from the group consisting of SEQ ID Nos: 311, 312, 313, 314, 315, 316, 317, 326, 327, 328, 329, 330, 331, 340, 341, 342, 343, 344, 353, 354, 355, 356, 365, 366, 367, 376, 377 and 386. Even more preferably, said antigenic IgE peptide consists of, or consists essentially of, an amino acid sequence selected from the group consisting of SEQ ID Nos: 311, 312, 313, 314, 326, 327, 328, 340, 341 and 353. Even more preferably, said antigenic IgE peptide consists of, or consists essentially of, an amino acid sequence selected from the group consisting of SEQ ID Nos: 311, 312 and 326. Most preferably, said antigenic IgE peptide consists of, or consists essentially of, an amino acid sequence of SEQ ID Nos:311 or 312.

The term "antigenic IgE peptide biological activity", when used herein, refers to the ability of the antigenic IgE peptides of the invention to induce auto anti-IgE antibodies in a patient, with an antagonistic profile, such auto-antibodies being able to decrease the level of circulating free IgE while not causing any significant IgE-mediated release of inflammatory mediators and while being substantially unable to bind to IgE bound to its high affinity receptor. It will be apparent to the man skilled in the art which techniques may be used to confirm whether a specific construct falls within the scope of the present invention. Such techniques include, but are not restricted to, the techniques described in the Example section of the present application, and also to the following. The putative peptide can be assayed to ascertain the immunogenicity of the construct, in that antisera raised by the putative peptide cross-react with the native IgE molecule, and are also functional in blocking allergic mediator release from allergic effector cells.

The specificity of these responses can be confirmed by functional assays where pulldown of IgE can be quantified and/or by inhibition of degranulation of cells expressing the IgE receptor, or by competition experiments by blocking the activity of the antiserum with the peptide itself or the native IgE, and/or specific monoclonal antibodies that are known to bind the epitope within IgE. Techniques to ascertain binding to IgE-FcRl are also well known to those skilled in the art.

In an embodiment the antigenic IgE peptides of the present invention are of a size such that they mimic a region selected from the whole IgE domain in which the native epitope is found. In a particular embodiment, the antigenic IgE peptides of the invention, are less than 100 amino acids in length, preferably shorter than 75 amino acids, more preferably less than 50 amino acids, even more preferably less than 40 amino acids. The antigenic IgE peptides of the invention are typically 4, 5, 6, 7, 8, 9, 10, 11, 12, 13, 14, 15, 16, 17, 18, 19, 20, 21, 22, 23, 24, 25, 26, 27, 28, 29 or 30 amino acids in length, preferably from 4 to 20 amino acids, for example 6 to 12, or 6 to 9 amino acids.

Specific examples of antigenic IgE peptides of the invention are provided in the sequence listing and include peptides ranging from 4 to 20 amino acids in length. The antigenic peptides of the invention include an amino acid sequence derived from a portion of human IgE CH3, such derived portion of human CH3 either corresponding to the amino acid sequence of naturally occurring IgE or corresponding to variant IgE, i.e. the amino acid sequence of naturally occurring IgE in which a small number of amino acids have been substituted, added or deleted but which retains essentially the same immunological properties. In addition, such derived IgE CH3 portion can be further modified by amino acids, especially at the N- and C-terminal ends to allow the antigenic IgE peptide to be conformationally constrained and/or to allow coupling of the antigenic IgE peptide to an immunogenic carrier after appropriate chemistry has been carried out. The antigenic IgE peptides of the present invention encompass functionally active variant peptides derived from the amino acid sequence of IgE CH3 in which amino acids have been deleted, inserted or substituted without essentially detracting from the immunological properties thereof, i.e. such functionally active variant peptides retain a substantial antigenic IgE peptide biological activity. Typically, such functionally variant peptides have an amino acid sequence homologous, preferably highly homologous, to an amino acid sequence selected from the group consisting of SEQ ID Nos: 1 to 430, more preferably to an amino acid sequence selected from the group consisting of SEQ ID Nos: 1 to 153 and 220 to 430, even more preferably to an amino acid sequence selected from the group consisting of SEQ ID Nos: 220 to 430.

In one embodiment, such functionally active variant peptides exhibit at least 60%, 65%, 70%, 75%, 80%, 85%, 90% or 95% identity to an amino acid sequence selected from the group consisting of SEQ ID Nos: 1 to 430, more preferably to an amino acid sequence selected from the group consisting of SEQ ID Nos: 1 to 153 and 220 to 430, even more preferably to an amino acid sequence selected from the group consisting of SEQ ID Nos: 220 to 430.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, *Methods Enzymol.* 183:63-98 (1990); Pearson, *Methods Mol. Biol.* 132:185-219 (2000)). An alternative algorithm when comparing a sequence of the invention to a database containing a large number of sequences from different organisms is the computer program BLAST, especially blastp or tblastn, using default parameters. See, e.g., Altschul et al., *J. Mol. Biol.* 215:403-410 (1990); Altschul et al., *Nucleic Acids Res.* 25:3389-402 (1997).

Functionally active variants comprise naturally occurring functionally active variants such as allelic variants and species variants and non-naturally occurring functionally active variants that can be produced by, for example, mutagenesis techniques or by direct synthesis.

A functionally active variant differs by about, for example, 1, 2, 3, 4, 5, 6, 7, 8, 9, or 10 amino acid residues from any of the peptide shown at SEQ ID Nos: 1 to 430, more preferably at SEQ ID Nos: 1 to 153 and 220 to 430, even more preferably at SEQ ID Nos: 220 to 430, and yet retain an antigenic IgE biological activity. Where this comparison requires alignment the sequences are aligned for maximum homology. The site of variation can occur anywhere in the peptide, as long as the biological activity is substantially similar to a peptide shown in SEQ ID Nos: 1 to 430, more preferably substantially similar to a peptide shown in SEQ ID Nos: 1 to 153 and 220 to 430, even more preferably substantially similar to a peptide shown in SEQ ID Nos: 220 to 430. Guidance concerning how to make phenotypically silent amino acid substitutions is provided in Bowie et al., Science, 247: 1306-1310 (1990), which teaches that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific immunogenic activity of the modified peptide.

The second strategy uses genetic engineering to introduce amino acid changes at specific positions of a cloned gene to identify regions critical for protein function. For example, site-directed mutagenesis or alanine-scanning mutagenesis can be used (Cunningham et al., Science, 244: 1081-1085 (1989)). The resulting variant peptides can then be tested for specific antigenic IgE biological activity.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein is well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)). Mutations can also be introduced using commercially available kits such as "QuikChange™ Site-Directed Mutagenesis Kit" (Stratagene) or directly by peptide synthesis. The generation of a functionally active variant to an antigenic IgE peptide by replacing an amino acid which does not significantly influence the function of said antigenic IgE peptide can be accomplished by one skilled in the art.

A type of amino acid substitution that may be made in one of the peptides according to the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g. Pearson, *Methods Mol. Biol.* 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science* 256:1443-45 (1992). A "moderately conservative" replacement is any change having a nonnegative value in the PAM250 log-likelihood matrix.

A functionally active variant peptide can also be isolated using a hybridization technique. Briefly, DNA having a high homology to the whole or part of a nucleic acid sequence encoding the peptide, polypeptide or protein of interest, e.g. SEQ ID Nos: 1 to 430 is used to prepare a functionally active peptide. Therefore, an antigenic IgE peptide of the invention also includes peptides which are functionally equivalent to one or more of the peptide of SEQ ID Nos: 1 to 430 and which are encoded by a nucleic acid molecule which hybridizes with a nucleic acid encoding any one of SEQ ID Nos: 1 to 430 or a complement thereof. One of skill in the art can easily determine nucleic acid sequences that encode peptides of the invention using readily available codon tables. As such, these nucleic acid sequences are not presented herein.

The stringency of hybridization for a nucleic acid encoding a peptide, polypeptide or protein that is a functionally active variant is, for example, 10% formamide, 5×SSPE, 1× Denhart's solution, and 1× salmon sperm DNA (low stringency conditions). More preferable conditions are, 25% formamide, 5×SSPE, 1× Denhart's solution, and 1× salmon sperm DNA (moderate stringency conditions), and even more preferable conditions are, 50% formamide, 5×SSPE, 1× Denhart's solution, and 1× salmon sperm DNA (high stringency conditions). However, several factors influence the stringency of hybridization other than the above-described formamide concentration, and one skilled in the art can suitably select these factors to accomplish a similar stringency.

Nucleic acid molecules encoding a functionally active variant can also be isolated by a gene amplification method such as PCR using a portion of a nucleic acid molecule DNA encoding a peptide, polypeptide or protein of interest, e.g. any one of the peptides shown SEQ ID Nos: 1 to 430, as the probe.

For the purpose of the present invention, it should be considered that several antigenic IgE peptides of the invention may be used in combination. All types of possible combinations can be envisioned. For example, a polypeptide comprising more than one antigenic IgE peptide, preferably selected from SEQ ID Nos: 1 to 430, more preferably from SEQ ID Nos: 1 to 153 and 220 to 430, even more preferably from SEQ ID Nos: 220 to 430, could be used, wherein the same antigenic IgE peptide is used in several copies on the same polypeptide molecule, or wherein antigenic IgE peptides of different amino acid sequences are used on the same polypeptide molecule; the different antigenic IgE peptides or copies being directly fused to each other or spaced by appropriate linkers. As used herein the term "multimerized antigenic IgE (poly)peptide" refers to both types of combination wherein antigenic IgE peptides of either different or the same amino acid sequence are present on a single polypeptide molecule. From 2 to about 20 identical and/or different antigenic IgE peptides, preferably 2, 3, 4, 5, 6, or 7 antigenic IgE peptides, can be thus present on a single multimerized antigenic IgE polypeptide molecule.

In one aspect of the invention, the immunogen consists of, consists essentially of, or comprises a multimerized antigenic IgE peptide consisting of, consisting essentially of, or comprising at least one amino acid sequence selected from the group consisting of SEQ ID Nos: 1 to 430 and functionally active variants thereof, preferably selected from the group consisting of SEQ ID Nos: 1 to 430. In one embodiment, said multimerized IgE peptide comprises a first antigenic IgE peptide comprising an amino acid sequence selected from the group consisting of SEQ ID No: 1 to 153 and a second antigenic IgE peptide comprising an amino acid sequence selected from the group consisting of SEQ ID No: 154 to 219 or SEQ ID No: 220 to 310 or SEQ ID No: 311 to 430. In another embodiment, said multimerized IgE peptide comprises a first antigenic IgE peptide comprising an amino acid sequence selected from the group consisting of SEQ ID No: 154 to 219 and a second antigenic IgE peptide comprising an amino acid sequence selected from the group consisting of SEQ ID No: 1 to 153 or SEQ ID No: 220 to 310 or SEQ ID No: 311 to 430. In still another embodiment, said multimerized IgE peptide comprises a first antigenic IgE peptide comprising an amino acid sequence selected from the group consisting of SEQ ID No: 220 to 310 and a second antigenic IgE peptide comprising an amino acid sequence selected from the group consisting of SEQ ID No: 1 to 153 or SEQ ID No: 154 to 219 or SEQ ID No: 311 to 430. In still another embodiment, said multimerized IgE peptide comprises a first antigenic IgE peptide comprising an amino acid sequence selected from the group consisting of SEQ ID No: 311 to 430 and a second antigenic IgE peptide comprising an amino acid sequence selected from the group consisting of SEQ ID No: 1 to 153 or SEQ ID No: 154 to 219 or SEQ ID No: 220 to 310. In still another embodiment, said multimerized IgE peptide comprises a first antigenic IgE peptide comprising an amino acid sequence selected from the group consisting of SEQ ID No: 311 to 430, a second antigenic IgE peptide comprising an amino acid sequence selected from the group consisting of SEQ ID No: 220 to 310 and a third antigenic IgE peptide comprising an amino acid sequence selected from the group consisting of SEQ ID No: 154 to 219 or SEQ ID NO: 1 to 153.

In one embodiment of the invention, a peptide, polypeptide or protein of the invention is derived from a natural source and isolated from a mammal, such as a human, a primate, a cat, a dog, a horse, a mouse, or a rat, preferably from a human source. A peptide, polypeptide or protein of the invention can thus be isolated from cells or tissue sources using standard protein purification techniques.

Alternatively, peptides, polypeptides and proteins of the invention can be synthesized chemically or produced using recombinant DNA techniques.

For example, a peptide, polypeptide or protein of the invention can be synthesized by solid phase procedures well known in the art. Suitable syntheses may be performed by utilising "T-boc" or "F-moc" procedures. Cyclic peptides can be synthesised by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in 'Solid Phase Peptide Synthesis: A Practical Approach' by E. Atherton and R. C. Sheppard, published by IRL at Oxford University Press (1989) and 'Methods in Molecular Biology, Vol. 35: Peptide Synthesis Protocols (ed. M. W. Pennington and B. M. Dunn), chapter 7, pp 91-171 by D. Andreau et al.

Alternatively, a polynucleotide encoding a peptide, polypeptide or protein of the invention can be introduced into an expression vector that can be expressed in a suitable expression system using techniques well known in the art, followed by isolation or purification of the expressed peptide, polypeptide, or protein of interest. A variety of bacterial, yeast, plant, mammalian, and insect expression systems are available in the art and any such expression system can be used. Optionally, a polynucleotide encoding a peptide, polypeptide or protein of the invention can be translated in a cell-free translation system.

Antigenic IgE peptides of the invention can also comprise those that arise as a result of the existence of multiple genes, alternative transcription events, alternative RNA splicing events, and alternative translational and postranslational events. A peptide can be expressed in systems, e.g. cultured cells, which result in substantially the same postranslational modifications present as when the peptide is expressed in a native cell, or in systems that result in the alteration or omission of postranslational modifications, e.g. glycosylation or cleavage, present when expressed in a native cell.

A peptide, polypeptide or protein of the invention, such as an antigenic IgE peptide, can be produced as a fusion protein that contains other non-IgE or non-IgE-derived amino acid sequences, such as amino acid linkers or signal sequences or immunogenic carriers as defined herein, as well as ligands useful in protein purification, such as glutathione-S-transferase, histidine tag, and staphylococcal protein A. More than one antigenic IgE peptide of the invention can be present in a fusion protein. The heterologous polypeptide can be fused, for example, to the N-terminus or C-terminus of the peptide, polypeptide or protein of the invention. A peptide, polypeptide or protein of the invention can also be produced as fusion proteins comprising homologous amino acid sequences, i.e., other IgE or IgE-derived sequences.

The antigenic IgE peptides of the invention might be linear or conformationally constrained. In preferred embodiments of the invention, the antigenic IgE peptide is conformationally constrained. As used herein in reference to a molecule, the term "conformationally constrained" means a molecule, such as a peptide, polypeptide or protein, in which the three-dimensional structure is maintained substantially in one spatial arrangement over time. Conformationally constrained molecules can have improved properties such as increased affinity, metabolic stability, membrane permeability or solubility.

In addition, such conformationally constrained molecules are expected to present the antigenic IgE epitope in a conformation similar to their native loop conformation, thereby inducing anti-IgE antibodies more susceptible to recognize intact, native self IgE molecules or with an increased affinity to recognize self IgE molecules. Methods of conformational constraint are well known in the art and include, without limitation, bridging and cyclization.

There are several approaches known in the prior art to introduce conformational constraints into a linear peptide or polypeptide chain. For example, bridging between two neighbouring amino acids in a peptide leads to a local conformational modification, the flexibility of which is limited in comparison with that of regular peptides. Some possibilities for forming such bridges include incorporation of lactams and piperazinones (for review see Giannis and. Kolter, Angew. Chem. Int. Ed., 1993, 32: 1244).

As used herein in reference to a peptide, the term "cyclic" refers to a structure including an intramolecular bond between two non-adjacent amino acids or amino acid analogs. The cyclization can be effected through a covalent or non-covalent bond. Intramolecular bonds include, but are not limited to, backbone to backbone, side-chain to backbone, side-chain to side-chain, side chain to end-group, end-to-end bonds. Methods of cyclization include, without limitation, formation of a disulfide bond between the side-chains of non-adjacent amino acids or amino acid analogs; formaion of an amide bond between the side-chains of Lys and Asp/Glu residues; formation of an ester bond between serine residues and Asp/Glu residues; formation of a lactam bond, for example, between a side-chain group of one amino acid or analog thereof to the N-terminal amine of the amino-terminal residue; and formation of lysinonorleucine and dityrosine bonds. Carbon versions of a disulfide linkage, for example an ethenyl or ethyl linkage, could also be used (*J. Peptide Sc.,* 2008, 14, 898-902) as well as alkylation reactions with an appropriately polysubstituted electrophilic reagent such as a di-, tri- or tetrahaloalkane (*PNAS,* 2008, 105(40), 15293-15298; *ChemBioChem,* 2005, 6, 821-824). Various modified proline analogs can also be used to incorporate conformational constraints into peptides (Zhang et al., J. Med. Chem., 1996, 39: 2738-2744; Pfeifer and Robinson, Chem. Comm., 1998, 1977-1978). Chemistries that may be used to cyclise peptides of the invention result in peptides cyclised with a bond including, but not limiting to the following: lactam, hydrazone, oxime, thiazolidine, thioether or sulfonium bonds.

Yet another approach in the design of conformationally constrained peptides, which is described in U.S. Ser. No. 10/114, 918, is to attach a short amino acid sequence of interest to a template, to generate a cyclic constrained peptide. Such cyclic peptides are not only structurally stabilized by their templates, and thereby offer three-dimensional conformations that may imitate conformational epitopes on native proteins such as on viruses and parasites or on self proteins (autologous mammalian proteins such as IgE), but they are also more resistant than linear peptides to proteolytic degradation in serum. U.S. Ser. No. 10/114,918 further discloses the synthesis of conformationally constrained cross-linked peptides by preparation of synthetic amino acids for backbone coupling to appropriately positioned amino acids in order to stabilize the supersecondary structure of peptides. Cross-linking can be achieved by amide coupling of the primary amino group of an orthogonally protected (2S, 3R)-3-aminoproline residue to a suitably positioned side chain carboxyl group of glutamate. This approach has been followed in the preparation of conformationally constrained tetrapeptide repeats of the CS protein wherein at least one proline has been replaced by 2S, 3R)-3-aminoproline and, in order to introduce a side chain carboxyl group, glutamate has been incorporated as a replacement for alanine.

Cross-linking strategies also include the application of the Grubbs ring-closing metathesis reaction to form 'stapled' peptides designed to mimic alpha-helical conformations (*Angew. Int. Ed. Engl.,* 1998, 37, 3281; *JACS,* 2000, 122, 5891); use of poly-functionalised saccharides; use of a tryptathionine linkage (*Chemistry Eu. J.,* 2008, 24, 3404-3409); use of 'click' reaction of azides and alkynes which could be incorporated as either a side chain amino acid residues or located within the backbone of the peptide sequence (*Drug Disc. Today,* 2003, 8(24), 1128-1137). It is also known in the literature that metal ions can stabilise constrained conformations of linear peptides through sequestering specific residues e.g. histidine, which co-ordinate to metal cations (*Angew. Int. Ed. Engl.,* 2003, 42, 421). Similarly, functionalising a linear peptide sequence with non-natural acid and amine functionality, or polyamine and polyacid functionality can be used to allow access to cyclised structures following activation and amide bond formation.

Figure 2:
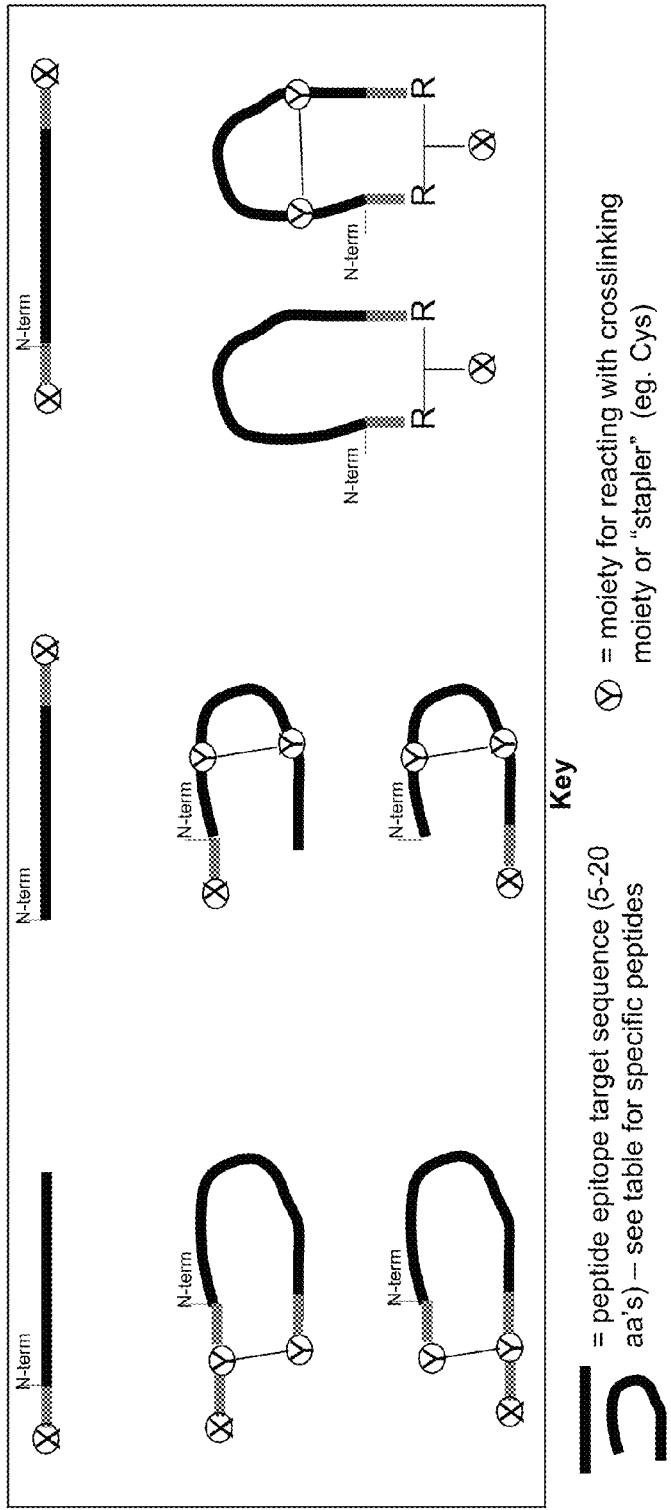
FIG. 2. Graphic depictions of peptide formats for inducing antibody responses to structurally defined epitopes of human IgE.

According to one embodiment, the antigenic IgE peptide is conformationally constrained by intramolecular covalent bonding of two non-adjacent amino acids of the antigenic IgE peptide to each other, e.g. the N- and C-terminal amino acids. According to another embodiment, the antigenic IgE peptide of the invention is conformationally constrained by covalent binding to a scaffold molecule. According to a further embodiment, the antigenic IgE peptide is simply constrained, i.e. coupled either at one end, (C or N terminus) or through another amino acid not located at either end, to the scaffold molecule. According to another embodiment, the antigenic IgE peptide is doubly constrained, i.e. coupled at both C and N termini to the scaffold molecule. According to another embodiment, the antigenic peptide is constrained by cyclising via the templating effect of a heterochiral Diproline unit (D-Pro-L-Pro) (Spath et al, 1998, Helvetica Chimica Acta 81, p1726-1738). Illustrating but not limiting examples of conformationally constrained peptides according to the invention are graphically depicted in FIG. 2. The scaffold (also called 'platform') can be any molecule which is capable of reducing, through covalent bonding, the number of conformations which the antigenic IgE peptide can assume. Examples of conformation-constraining scaffolds include proteins and peptides, for example lipocalin-related molecules such as beta-barrel containing thioredoxin and thioredoxin-like proteins, nucleases (e.g. RNaseA), proteases (e.g. trypsin), protease inhibitors (e.g. eglin C), antibodies or structurally-rigid fragments thereof, fluorescent proteins such as GFP or YFP, conotoxins, loop regions of fibronectin type III domain, CTL-A4, and virus-like particles (VLPs).

Other suitable platform molecules include carbohydrates such as sepharose. The platform may be a linear or circular molecule, for example, closed to form a loop. The platform is generally heterologous with respect to the antigenic IgE peptide. Such conformationally constrained peptides linked to a platform are thought to be more resistant to proteolytic degradation than linear peptide.

According to a preferred embodiment, the scaffold is an immunogenic carrier as defined in the present application, preferably an heterologous carrier protein or a VLP. In a further embodiment, the antigenic IgE peptide is simply constrained onto the immunogenic carrier. In another further embodiment, the antigenic IgE peptide is doubly constrained onto the immunogenic carrier. In this manner, the antigenic IgE peptide forms a conformationally constrained loop structure which has proven to be a particularly suitable structure as an intracellular recognition molecule.

The antigenic IgE peptides of the invention may be modified for the ease of conjugation to a platform, for example by the addition of a terminal cysteine at one or both ends and/or by the addition of a linker sequence, such a double glycine head or tail, a linker terminating with a lysine residue or any other linker known to those skilled in the art to perform such function. Bioorthogonal chemistry (such as the click reaction described above) to couple the full peptide sequence to the carrier, thus avoiding any regiochemical and chemoselectivity issues, might also be used. Rigidified linkers such as the one described in Jones et al. Angew. Chem. Int. Ed. 2002, 41:4241-4244 are known to elicit an improved immunological response and might also be used.

In a further embodiment, the antigenic IgE peptide is attached to a multivalent template, which itself is coupled to the carrier, thus increasing the density of the antigen (see below). The multivalent template could be an appropriately functionalised polymer or oligomer such as (but not limited to) oligoglutamate or oligochitosan.

Said linker might be located at the N-terminus of the peptide, or at the C-terminus of the peptide, or both ends of the peptide. Said linker might be from 0 to 10 amino acid long, preferably from 0 to 6 amino acid long, even more preferably 2-3 amino acids long. Alternatively, the addition or substitution of a D-stereoisomer form of one or more of the amino acids may be performed to create a beneficial derivative, for example to enhance stability of the peptide.

Exemplary combinations of conjugations, all within the scope of the present invention and constituting various embodiments, using various linkers are provided below:

```
                                        (SEQ ID NO: 460)
    Peptide - GGGGGC - scaffold (SEQ ID NO: 461)
    Peptide - GGGGC - scaffold (SEQ ID NO: 462)
    Peptide - GGGC - scaffold Peptide - GGC - scaffold Peptide - GC - scaffold Peptide - C - scaffold (SEQ ID NO: 463)
    Peptide - GGGGGK
```

```
Peptide - GGGGK                    (SEQ ID NO: 464)

Peptide - GGGK                     (SEQ ID NO: 465)

Peptide - GGK

Peptide - GK

Peptide - K

Peptide - GGGGSC                   (SEQ ID NO: 466)

Peptide - GGGSC                    (SEQ ID NO: 467)

Peptide - GGSC                     (SEQ ID NO: 468)

Peptide - GSC

Peptide - SC

CSGGGG - Peptide                   (SEQ ID NO: 469)

CSGGG - Peptide                    (SEQ ID NO: 470)

CSGG - Peptide                     (SEQ ID NO: 471)

CSG - Peptide

CS - Peptide
```

In an embodiment, the peptide consists of any of the antigenic IgE peptide disclosed herein and the scaffold consists of any of the immunogenic carrier disclosed herein, preferably a VLP.

Exemplary combinations of conjugations using various linkers and doubly constrained peptides are provided below, where the carrier can be the identical monomer of a carrier or a differential monomer of a carrier. (In the example below, the GC linker can be substituted by any of the GK linker or GSC linker exemplified above or any other known to those skilled in the art):

```
Carrier - CGGGGG -                 (SEQ ID NO: 472)

Peptide - GGGGGC - carrier         (SEQ ID NO: 460)

Carrier - CGGGG -                  (SEQ ID NO: 473)

Peptide - GGGGC - carrier          (SEQ ID NO: 461)

Carrier - CGGGG -                  (SEQ ID NO: 473)

Peptide - GGGGC - carrier          (SEQ ID NO: 461)

Carrier - CGGG -                   (SEQ ID NO: 474)

Peptide - GGGC - carrier           (SEQ ID NO: 462)

Carrier - CG - Peptide - GC - carrier

Carrier - C - Peptide - C - carrier
```

In an embodiment, the peptide consists of any of the antigenic IgE peptide disclosed herein and the carrier consists of any of the immunogenic carrier disclosed herein, preferably a VLP.

In one embodiment, a terminal cysteine residue, if not already present in the amino acid sequence of the antigenic IgE peptide, is added to one or both ends of any of the antigenic IgE peptide of SEQ ID Nos: 1 to 430 to generate a conformationally constrained peptide. In a preferred embodiment, the conformationally constrained antigenic IgE peptide of the invention is selected from the group consisting of SEQ ID Nos: 1 to 430 and functionally active variants thereof, preferably from the group consisting of SEQ ID Nos: 1 to 430, more preferably from the group consisting of SEQ ID Nos: 1 to 153 and 220 to 430, even more preferably from the group consisting of SEQ ID Nos: 220 to 430. In an embodiment, said terminal cysteine residue is added at the C-terminus of said antigenic IgE peptide. In another ambodiment said terminal cysteine residue is added at the N-terminus of said antigenic IgE peptide. In another embodiment a terminal cysteine residue is added at both the C-terminus and N-terminus of said antigenic IgE peptide.

In another embodiment, a GC linker comprising a variable number of glycine residues and one terminal cysteine residue is added to one or both ends of any of the antigenic IgE peptide of SEQ ID Nos: 1 to 430 to generate a conformationally constrained peptide. Preferably, the GC linker comprises from 1 to 10 glycine residues, more preferably 1, 2, 3, 4 or 5 glycine residues. In a further preferred embodiment, the conformationally constrained antigenic IgE peptide of the invention is selected from the group consisting of SEQ ID Nos: 1 to 430, and functionally active variants thereof, preferably from the group consisting of SEQ ID Nos: 1 to 430, more preferably from the group consisting of SEQ ID Nos: 1 to 153 and 220 to 430, even more preferably from the group consisting of SEQ ID Nos: 220 to 430. In an embodiment, said GC linker is added at the C-terminus of said antigenic IgE peptide. In another ambodiment said GC linker is added at the N-terminus of said antigenic IgE peptide. In another embodiment a said GC linker is added at both the C-terminus and N-terminus of said antigenic IgE peptide.

In yet another embodiment, a GC linker comprising a variable number of glycine residues and one terminal cysteine residue is added to one end of the antigenic IgE peptide of SEQ ID Nos: 1 to 430 and a terminal cysteine residue, if not already present to the other end of the antigenic IgE peptide, is added to the other end of the antigenic peptide. Preferably, the GC linker comprises from 1 to 10 glycine residues, more preferably 1, 2, 3, 4, or 5 glycine residues. In a further preferred embodiment, the conformationally constrained antigenic IgE peptide of the invention is selected from the group consisting of SEQ ID Nos: 1 to 430, and functionally active variants thereof, preferably from the group consisting of SEQ ID Nos: 1 to 430, more preferably from the group consisting of SEQ ID Nos: 1 to 153 and 220 to 430, even more preferably from the group consisting of SEQ ID Nos: 220 to 430. In an embodiment, said GC linker is added at the C-terminus of said antigenic IgE peptide and said terminal cysteine residue is added at the N-terminus of said antigenic IgE peptide. In another ambodiment said GC linker is added at the N-terminus of said antigenic IgE peptide and said terminal cysteine residue is added at the C-terminus of said antigenic IgE peptide.

In a further preferred embodiment, the GC linker is modified, preferably by the addition of a lysine residue, in order to allow conjugation of said linker coupled to said antigenic IgE peptide to a scaffold molecule. In an even further preferred embodiment, the conformationally constrained antigenic IgE peptide of the invention is selected from the group consisting of from the group consisting of SEQ ID Nos: 1 to 430, and functionally active variants thereof, preferably from the group consisting of SEQ ID Nos: 1 to 430, more preferably from the group consisting of SEQ ID Nos: 1 to 153 and 220 to 430, even more preferably from the group consisting of SEQ ID Nos: 220 to 430. In an embodiment, said modified GC linker is added at the C-terminus of said antigenic IgE peptide. In another ambodiment said modified GC linker is added at the N-terminus of said antigenic IgE peptide.

In an embodiment, the conformationally constrained antigenic IgE peptide of the invention is any of the peptide disclosed at table 9.

Immunogenic Carrier of the Invention

In an embodiment of the present invention, the antigenic IgE peptide or polypeptide of the invention is linked to an immunogenic carrier molecule to form immunogens for vaccination protocols, preferably wherein the carrier molecule is not related to the native IgE molecule.

The term "immunogenic carrier" herein includes those materials which have the property of independently eliciting an immunogenic response in a host animal and which can be covalently coupled to a peptide, polypeptide or protein either directly via formation of peptide or ester bonds between free carboxyl, amino or hydroxyl groups in the peptide, polypeptide or protein and corresponding groups on the immunogenic carrier material, or alternatively by bonding through a conventional bifunctional linking group, or as a fusion protein.

The types of carriers used in the immunogens of the present invention will be readily known to the person skilled in the art. Examples of such immunogenic carriers are: serum albumins such as bovine serum albumin (BSA); globulins; thyroglobulins; hemoglobins; hemocyanins (particularly Keyhole Limpet Hemocyanin [KLH]); proteins extracted from *ascaris*, inactivated bacterial toxins or toxoids such as tetanus or diptheria toxins (TT and DT) or CRM197, the purified protein derivative of tuberculin (PPD); or Protein D from *Haemophilus influenzae* (WO 91/18926) or recombinant fragments thereof (for example, Domain 1 of Fragment C of TT, or the translocation domain of DT or Protein D ⅓rd comprising the N-terminal 100-110 amino acids of *Haemophilus influenzae* protein D (GB 9717953. 5); polylysin; polyglutamic acid; lysine-glutamic acid copolymers; copolymers containing lysine or ornithine; liposome carriers, etc.

In an embodiment, the immunogic carrier is KLH. In another embodiment, the immunogenic carrier is a virus-like particle (VLPs), preferably a recombinant virus-like particle.

As used herein, the term "virus-like particle" refers to a structure resembling a virus particle but which has been demonstrated to be non pathogenic. In general, virus-like particles lack at least part of the viral genome. Also, virus-like particles can often be produced in large quantities by heterologous expression and can be easily purified. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage.

As used herein, the term "virus-like particle of a bacteriophage" refers to a virus-like particle resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage. The capsid structure formed from the self-assembly of 180 subunits of RNA phage coat protein and optionally containing host RNA is herein referred to as a "VLP of RNA phage coat protein". A specific example is the VLP of Qbeta coat protein. In this particular case, the VLP of Qbeta coat protein may either be assembled exclusively from Qbeta CP subunits (generated by expression of a Qbeta CP gene containing, for example, a TAA stop codon precluding any expression of the longer A1 protein through suppression, see Kozlovska, T. M., et al., Intervirology 39: 9-15 (1996)), or additionally contain A1 protein subunits in the capsid assembly. Generally, the percentage of Qbeta A1 protein relative to Qbeta CP in the capsid assembly will be limited, in order to ensure capsid formation.

Examples of VLPs suitable as immunogenic carriers in the context of the present invention include, but are not limited to, the capsid proteins of Hepatitis B virus (Ulrich, et al., Virus Res. 50: 141-182 (1998)), measles virus (Warnes, et al., Gene 160: 173-178 (1995)), Sindbis virus, rotavirus (U.S. Pat. Nos. 5, 071, 651 and 5, 374, 426), foot-and-mouth-disease virus (Twomey, et al., Vaccine 13: 1603-1610, (1995)), Norwalk virus (Jiang, X., et al., Science 250: 1580-1583 (1990); Matsui, S. M., et al., J. Clin. Invest. 87: 1456-1461 (1991)), the retroviral GAG protein (PCT Patent Appl. No. WO 96/30523), the retrotransposon Ty protein pl, the surface protein of Hepatitis B virus (WO 92/11291), human papilloma virus (WO 98/15631), human polyoma virus (Sasnauskas K., et al., Biol. Chem. 380 (3): 381-386 (1999); Sasnauskas K., et al., Generation of recombinant virus-like particles of different polyomaviruses in yeast. 3rd Interational Workshop"Virus-like particles as vaccines." Berlin, September 26-29 (2001)), RNA phages, Ty, frphage, GA-phage, AP 205-phage and, in particular, Qbeta-phage, Cowpea chlorotic mottle virus, human papilloma viruses (HPV), bovine papilloma viruses, porcine parvovirus, parvovirus, caliciviruses (e.g. Norwalk virus), rabbit hemorrhagic disease virus, animal hepadnavirus core Antigen VLPs.

As will be readily apparent to those skilled in the art, the VLP to be used as an immunogenic carrier of the invention is not limited to any specific form. The particle can be synthesized chemically or through a biological process, which can be natural or normatural. By way of example, this type of embodiment includes a virus-like particle or a recombinant form thereof. In a more specific embodiment, the VLP can comprise, or alternatively consist of, recombinant polypeptides of any of the virus known to form a VLP. The virus-like particle can further comprise, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts. Variant VLPs suitable for use in the present invention can be derived from any organism so long as they are able to form a "virus-like particle" and can be used as an "immunogenic carrier" as defined herein.

Preferred VLPs according to the invention include the capsid protein or surface antigen of HBV (HBcAg and HBsAg respectively) or recombinant proteins or fragments thereof, and the coat proteins of RNA-phages or recombinant proteins or fragments thereof, more preferably the coat protein of Qbeta or recombinant proteins or fragments thereof. In one embodiment, the immunogic carrier used in combination with an antigenic IgE peptide or polypeptide of the invention is an HBcAg protein. Examples of HBcAg proteins that could be used can be used in the context of the present invention can be readily determined by one skilled in the art. Examples include, but are limited to, HBV core proteins described in Yuan et al., (J. Virol. 73: 10122-10128 (1999)), and in WO00/198333, WO 00/177158, WO 00/214478, WO WO00/32227, WO01/85208, WO02/056905, WO03/024480, and WO03/024481. HBcAgs suitable for use in the present invention can be derived from any organism so long as they are able to form a "virus-like particle" and can be used as an "immunogenic carrier" as defined herein. HBcAg variants of particular interest that could be used in the context of the present invention are those variants in which one or more naturally resident cysteine residues have been either deleted or substituted. It is well known in the art that free cysteine residues can be involved in a number of chemical side reactions including disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together. In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether. In addition, the processed form of HBcAg lacking the N-terminal leader sequence of the Hepatitis B core antigen precursor protein can also be used in the context of the invention, especially when HBcAg is produced under conditions where processing will not occur (e.g. expression in bacterial systems).

Other HBcAg variants according to the invention include i) polypeptide sequence having at least 80%, 85%, 90%, 95%, 97% or 99% identical to one of the wild-type HBcAg amino acid sequences, or a subportion thereof, using conventionally using known computer programs, ii) C-terminal truncation mutants including mutants where 1, 5, 10, 15, 20, 25, 30, 34 or 35, amino acids have been removed from the C-terminus, ii) N-terminal truncation mutants including mutants where 1, 2, 5, 7, 9, 10, 12, 14, 15, or 17 amino acids have been removed from the N-terminus, iii) mutants truncated in both N-terminal and C-terminal include HBcAgs where 1, 2, 5, 7, 9, 10, 12, 14, 15 or 17 amino acids have been removed from the N-terminus and 1, 5, 10, 15, 20, 25, 30, 34 or 35 amino acids have been removed from the C-terminus.

Still other HBcAg variant proteins within the scope of the invention are those variants modified in order to enhance immunogenic presentation of a foreign epitope wherein one or more of the four arginine repeats has been deleted, but in which the C-terminal cysteine is retained (see e.g. WO01/98333), and chimeric C-terminally truncated HBcAg such as those described in WO02/14478, WO03/102165 and WO04/053091.

In another embodiment, the immunogic carrier used in combination with an antigenic IgE peptide or poypeptide of the invention is an HBsAg protein. HBsAg proteins that could be used in the context of the present invention can be readily determined by one skilled in the art. Examples include, but are limited to, HBV surface proteins described in U.S. Pat. No. 5,792,463, WO02/10416, and WO08/020331. HBsAgs suitable for use in the present invention can be derived from any organism so long as they are able to form a "virus-like particle" and can be used as an "immunogenic carrier" as defined herein. For example, subtype adw (see example part of the present document).

In still another embodiment, the immunogic carrier used in combination with an antigenic IgE peptide or polypeptide of the invention is a Qbeta coat protein.

Qbeta coat protein was found to self-assemble into capsids when expressed in E. coli (Kozlovska T M. et al., GENE 137: 133-137 (1993)). The obtained capsids or virus-like particles showed an icosahedral phage-like capsid structure with a diameter of 25 nm and T=3 quasi symmetry. Further, the crystal structure of phage Qss has been solved. The capsid contains 180 copies of the coat protein, which are linked in covalent pentamers and hexamers by disulfide bridges (Golmohammadi, R. et al., Structure 4: 5435554 (1996)) leading to a remarkable stability of the capsid of Qbeta coat protein. Qbeta capsid protein also shows unusual resistance to organic solvents and denaturing agents. The high stability of the capsid of Qbeta coat protein is an advantageous feature, in particular, for its use in immunization and vaccination of mammals and humans in accordance of the present invention.

Examples of Qbeta coat proteins that can be used in the context of the present invention can be readily determined by one skilled in the art. Examples have been extensively described in WO02/056905, WO03/024480, WO03/024481 (incorporated by reference in their entirety) and include, but are not limited to, amino acid sequences disclosed in PIR database, accession No. VCBPQbeta referring to Qbeta CP; Accession No. AAA16663 referring to Qbeta A1 protein; and variants thereof including variants proteins in which the N-terminal methionine is cleaved; C-terminal truncated forms of Qbeta A1 missing as much as 100, 150 or 180 amino acids; variant proteins which have been modified by the removal of a lysine residue by deletion or substitution or by the addition of a lysine residue by substitution or insertion (see for example Qbeta-240, Qbeta-243, Qbeta-250, Qbeta-251 and Qbeta-259 disclosed in WO03/024481, incorporated by reference in its entirety), and variants exhibiting at least 80%, 85%, 90%, 95%, 97%, or 99% identity to any of the Qbeta core proteins described above. Variant Qbeta coat proteins suitable for use in the present invention can be derived from any organism so long as they are able to form a "virus-like particle" and can be used as "immunogenic carriers" as defined herein.

The antigenic IgE peptides of the invention may be coupled to immunogenic carriers via chemical conjugation or by expression of genetically engineered fusion partners. The coupling does not necessarily need to be direct, but can occur through linker sequences. More generally, in the case that antigenic peptides either fused, conjugated or otherwise attached to an immunogenic carrier, spacer or linker sequences are typically added at one or both ends of the antigenic peptides. Such linker sequences generally comprise sequences recognized by the proteasome, proteases of the endosomes or other vesicular compartment of the cell.

In one embodiment, the peptides of the present invention are expressed as fusion proteins with the immunogenic carrier. Fusion of the peptide can be effected by insertion into the immunogenic carrier primary sequence, or by fusion to either the N- or C-terminus of the immunogenic carrier. Hereinafter, when referring to fusion proteins of a peptide to an immunogenic carrier, the fusion to either ends of the subunit sequence or internal insertion of the peptide within the carrier sequence are encompassed. Fusion, as referred to hereinafter, may be effected by insertion of the antigenic peptide into the sequence of carrier, by substitution of part of the sequence of the carrier with the antigenic peptide, or by a combination of deletion, substitution or insertions.

When the immunogenic carrier is a VLP, the chimeric antigenic peptide-VLP subunit will be in general capable of self-assembly into a VLP. VLP displaying epitopes fused to their subunits are also herein referred to as chimeric VLPs. For example, EP 0 421 635 B describes the use of chimaeric hepadnavirus core antigen particles to present foreign peptide sequences in a virus-like particle.

Flanking amino acid residues may be added to either end of the sequence of the antigenic peptide to be fused to either end of the sequence of the subunit of a VLP, or for internal insertion of such peptidic sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In a specific embodiment of the invention, the immunogenic carrier is a HBcAg VLP. Fusion proteins of the antigenic peptide to either the N-terminus of a HBcAg (Neyrinck, S. et al., Nature Med. 5: 11571163 (1999)) or insertions in the so called major immunodominant region (MIR) have been described (Pumpens, P. and Grens, E., Intervirology 44: 98114 (2001)), WO 01/98333, and are specific embodiments of the invention. Naturally occurring variants of HBcAg with deletions in the MIR have also been described (Pumpens, P. and Grens, E., Intervirology 44: 98-114 (2001)), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., Intervirology 44: 98-114 (2001)). One skilled in the art will easily find guidance on how to construct fusion proteins using classical molecular biology techniques. Vectors and plasmids encoding HBcAg and HBcAg fusion proteins and useful for the expression of a HBcAg and HBcAg fusion proteins have been described (Pumpens, P. and #38; Grens, E. Intervirology 44: 98-114 (2001), Neyrinck, S. et al., Nature Med. 5: 1157-1163 (1999)) and can be used in the practice of the invention. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., Intervirology 44: 98-114 (2001); EP 0 421 635; U.S. Pat. No. 6,231,864) upon insertion, or in other words, which amino acids form HBcAg are to be substituted with the new epitope. For example, substitution of HBcAg amino acids 76-80, 79-81, 79-80, 75-85 or 80-81 with foreign epitopes has been described (Pumpens, P. and Grens, E., Intervirology 44: 98-114 (2001); EP0421635; U.S. Pat. No. 6, 231, 864, WO00/26385). HBcAg contains a long arginine tail (Pumpens, P. and Grens, E., Intervirology 44: 98-114 (2001)) which is dispensable for capsid assembly and capable of binding nucleic acids (Pumpens, P. and Grens, E., Intervirology 44: 98-114 (2001)). HBcAg either comprising or lacking this arginine tail are both embodiments of the invention.

In another specific embodiment of the invention, the immunogenic carrier is a VLP of a RNA phage, preferably Qbeta. The major coat proteins of RNA phages spontaneously assemble into VLPs upon expression in bacteria, and in particular in $E.\ coli$. Fusion protein constructs wherein antigenic peptides have been fused to the C-terminus of a truncated form of the A1 protein of Qbeta, or inserted within the A1 protein have been described (Kozlovska, T. M., et al., Intervirology, 39: 9-15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qbeta CP gene) usually takes place in $E.\ coli$, and such is the case for N-termini of the Qbeta coat proteins. The part of the A1 gene, 3' of the UGA amber codon encodes the CP extension, which has a length of 195 amino acids. Insertion of the antigenic peptide between position 72 and 73 of the CP extension leads to further embodiments of the invention (Kozlovska, T. M., et al., Intervirology 39: 9-15 (1996)). Fusion of an antigenic peptide at the C-terminus of a C-terminally truncated Qbeta A1 protein leads to further preferred embodiments of the invention. For example, Kozlovska et al., (Intervirology, 39: 9-15 (1996)) describe Qbeta A1 protein fusions where the epitope is fused at the C-terminus of the Qbeta CP extension truncated at position 19.

As described by Kozlovska et al. (Intervirology, 39: 9-15 (1996)), assembly of the particles displaying the fused epitopes typically requires the presence of both the AI protein-antigen fusion and the wt CP to form a mosaic particle. However, embodiments comprising virus-like particles, and hereby in particular the VLPs of the RNA phage Qbeta coat protein, which are exclusively composed of VLP subunits having an antigenic peptide fused thereto, are also within the scope of the present invention.

The production of mosaic particles may be effected in a number of ways. Kozlovska et al., Intervirology, 39: 9-15 (1996), describe three methods, which all can be used in the practice of the invention. In the first approach, efficient display of the fused epitope on the VLPs is mediated by the expression of the plasmid encoding the Qbeta A1I protein fusion having a UGA stop codon between CP and CP extension in a $E.\ coli$ strain harboring a plasmid encoding a cloned UGA suppressor tRNA which leads to translation of the UGA codon into Trp (pISM3001 plasmid (Smiley B. K., et al., Gene 134: 33-40 (1993))). In another approach, the CP gene stop codon is modified into UAA, and a second plasmid expressing the A1 protein-antigen fusion is cotransformed. The second plasmid encodes a different antibiotic resistance and the origin of replication is compatible with the first plasmid. In a third approach, CP and the A1 protein-antigen fusion are encoded in a bicistronic manner, operatively linked to a promoter such as the Trp promoter, as described in FIG. 1 of Kozlovska et al., Intervirology, 39: 9-15 (1996).

Further VLPs suitable for fusion of antigens or antigenic determinants are described in WO03/024481 and include bacteriophage fr, RNA phage MS-2, capsid proteine of papillomavirus, retrotransposon Ty, yeast and also Retrovirus-like-particles, HIV2 Gag, Cowpea Mosaic Virus, parvovirus VP2 VLP, HBsAg (U.S. Pat. No. 4, 722, 840, EP0020416B1). Examples of chimeric VLPs suitable for the practice of the invention are also those described in Intervirology 39: 1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus.

For any recombinantly expressed peptide or protein which forms part of the present invention, including an antigenic IgE peptide according to the invention coupled or not to an immunogenic carrier, the nucleic acid which encodes said peptide or protein also forms an aspect of the present invention, as does an expression vector comprising the nucleic acid, and a host cell containing the expression vector (autonomously or chromosomally inserted). A method of recombinantly producing the peptide or protein by expressing it in the above host cell and isolating the immunogen therefrom is a further aspect of the invention. The full-length native IgE molecule or the full-length native DNA sequence encoding it are not covered by the present invention.

In another embodiment, the peptide of the invention is chemically coupled to an immunogenic carrier, using techniques well known in the art. Conjugation can occur to allow free movement of peptides via single point conjugation (e.g. either N-terminal or C-terminal point) or as locked down structure where both ends of peptides are conjugated to either a immunogenic carrier protein or to a scaffold structure such as a VLP. Where conjugation occurs via conjugation chemistry known to those skilled in the art such as via cysteine residues, lysine residues or other carboxy moiety's commonly known as conjugation points such as glutamic acid or aspartic acid. Thus, for example, for direct covalent coupling it is possible to utilise a carbodiimide, glutaraldehyde or (N-[γ-malcimidobutyryloxy] succinimide ester, utilising common commercially available heterobifunctional linkers such as CDAP and SPDP (using manufacturers instructions). Examples of conjugation of peptides, particularly cyclised peptides, to a protein carrier via acylhydrazine peptide derivatives are described in WO03/092714. After the coupling reaction, the immunogen can easily be isolated and purified by means of a dialysis method, a gel filtration method, a fractionation method etc. Peptides terminating with a cysteine residue (preferably with a linker outside the cyclised region) may be conveniently conjugated to a carrier protein via maleimide chemistry.

When the immunogenic carrier is a VLP, several antigenic peptide, either having an identical amino acid sequence or a different amino acid sequence, may be coupled to a single VLP molecule, leading preferably to a repetitive and ordered structure presenting several antigenic determinants in an oriented manner as described in WO00/32227, WO03/024481, WO02/056905 and WO04/007538.

In one aspect of the invention, the antigenic peptide is bound to the VLP by way of chemical cross-linking, typically and preferably by using a heterobifunctional cross-linker. Several hetero-bifunctional cross-linkers are known to the art. In some embodiments, the hetero-bifunctional crosslinker contains a functional group which can react with first attachment sites, i.e. with the side-chain amino group of lysine residues of the VLP or VLP subunit, and a further functional group which can react with a preferred second attachment site, i.e. a cysteine residue fused to the antigenic peptide and optionally also made available for reaction by reduction. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigenic peptide is reacted with the activated VLP, and this step is typically called the coupling step. Unreacted antigenic peptide may be optionally removed in a fourth step, for example by dialysis. Several hetero-bifunctional crosslinkers are known to the art. These include the preferred cross-linkers SMPH (Succinimidyl-6-[β-maleimidopropionamido]hexanoate), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thio-ether linkage.

Another class of cross-linkers suitable in the practice of the invention is characterized by the introduction of a disulfide linkage between the antigenic peptide and the VLP upon coupling. Preferred cross-linkers belonging to this class include for example SPDP and Sulfo-LC-SPDP (Pierce). The extent of derivatization of the VLP with cross-linker can be influenced by varying experimental conditions such as the concentration of each of the reaction partners, the excess of one reagent over the other, the pH, the temperature and the ionic strength. The degree of coupling, i.e. the amount of antigenic peptide per subunits of the VLP can be adjusted by varying the experimental conditions described above to match the requirements of the vaccine.

Another method of binding of antigenic peptides to the VLP, is the linking of a lysine residue on the surface of the VLP with a cysteine residue on the antigenic peptide In some embodiments, fusion of an amino acid linker containing a cysteine residue, as a second attachment site or as a part thereof, to the antigenic peptide for coupling to the VLP may be required. In general, flexible amino acid linkers are favored. Examples of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) (G) kC (G) n with n=0-12 and k=0-5; (g) N-terminal glycine-serine linkers; (h) (G) kC (G) m (S) i (GGGGS SEQ ID NO: 475) n with n=0-3, k=0-5, m=0-10, i=0-2; (i) GGC; (k) GGC-NH2; (l) C-terminal gamma 1-linker; (m) C-terminal gamma 3-linker; (n) C-terminal glycine linkers; (O) (G) nC (G) k with n=0-12 and k=0-5; (p) C-terminal glycine-serine linkers; (q) (G) m (S) t (GGGGS (SEQ ID NO: 475) n (G) oC (G) k with n=0-3, k=0-5, m=0-10, 1=0-2, and o=0-8. Further examples of amino acid linkers are the hinge region of immunoglobulins, glycine serine linkers (GGGGS (SEQ ID NO: 475) n, and glycine linkers (G) n all further containing a cysteine residue as second attachment site and optionally further glycine residues. Typically preferred examples of said amino acid linkers are N-terminal gamma 1: CGDKTHTSPP (SEQ ID NO: 476); C-terminal gamma 1: DKTHTSPPCG (SEQ ID NO: 477); N-terminal gamma 3: CGGPKPSTPPGSSGGAP (SEQ ID NO: 478); C-terminal gamma 3: PKPSTPPGSSGGAPG-GCG (SEQ ID NO: 479); N-terminal glycine linker: GCGGG (SEQ ID NO: 480) and C-terminal glycine linker: GGGGCG (SEQ ID NO: 481).

Other amino acid linkers particularly suitable in the practice of the invention, when a hydrophobic antigenic peptide is bound to a VLP, are CGKKGG (SEQ ID NO: 482), or CGDEGG (SEQ ID NO: 483) for N-terminal linkers, or GGKKGC (SEQ ID NO: 484) and GGEDGC (SEQ ID NO: 485), for the C-terminal linkers. For the C-terminal linkers, the terminal cysteine is optionally C-terminally amidated.

In some embodiments of the present invention, GGCG (SEQ ID NO: 486), GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction. In a further embodiment of the invention, the amino acid linker GGC-NH2 is fused to the C-terminus of the antigenic peptide.

The cysteine residue present on the antigenic peptide has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or p-mercaptoethanol is required. Low concentrations of reducing agent are compatible with coupling as described in WO02/05690, higher concentrations inhibit the coupling reaction, as a skilled artisan would know, in which case the reductand has to be removed or its concentration decreased prior to coupling, e.g. by dialysis, gel filtration or reverse phase HPLC.

Binding of the antigenic peptide to the VLP by using a hetero-bifunctional cross-linker according to the methods described above, allows coupling of the antigenic peptide to the VLP in an oriented fashion. Other methods of binding the antigenic peptide to the VLP include methods wherein the antigenic peptide is cross-linked to the VLP using the carbodiimide EDC, and NHS.

In other methods, the antigenic peptide is attached to the VLP using a homo-bifunctional cross-linker such as glutaraldehyde, DSGBM [PEO] 4, BS3, (Pierce Chemical Company, Rockford, Ill., USA) or other known homo-bifunctional cross-linkers with functional groups reactive towards amine groups or carboxyl groups of the VLP. Other methods of binding the VLP to an antigenic peptide include methods where the VLP is biotinylated, and the antigenic peptide expressed as a streptavidin-fusion protein, or methods wherein both the antigenic peptide and the VLP are biotinylated, for example as described in WO 00/23955. In this case, the antigenic peptide may be first bound to streptavidin or avidin by adjusting the ratio of antigenic peptide to streptavidin such that free binding sites are still available for binding of the VLP, which is added in the next step. Alternatively, all components may be mixed in a "one pot" reaction. Other ligand-receptor pairs, where a soluble form of the receptor and of the ligand is available, and are capable of being cross-linked to the VLP or the antigenic peptide, may be used as binding agents for binding antigenic peptide to the VLP. Alternatively, either the ligand or the receptor may be fused to the antigenic peptide, and so mediate binding to the VLP chemically bound or fused either to the receptor, or the ligand respectively. Fusion may also be effected by insertion or substitution.

One or several antigen molecules can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the QP coat protein VLP is thus the possibility to couple several antigens per subunit. This allows for the generation of a dense antigen array.

In one embodiment of the invention, the binding and attachment, respectively, of the at least one antigen or antigenic determinant to the virus-like particle is by way of interaction and association, respectively, between at least one first attachment site of the virus-like particle and at least one second attachment of the antigenic peptide. VLPs or capsids of Q coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In a further embodiment of the present invention, the first attachment site is a lysine residue and/or the second attachment comprises sulfhydryl group or a cysteine residue. In an even further embodiment of the present invention, the first attachment site is a lysine residue and the second attachment is a cysteine residue. In further embodiments of the invention, the antigen or antigenic determinant is bound via a cysteine residue, to lysine residues of the VLP of RNA phage coat protein, and in particular to the VLP of Qbeta coat protein.

Another advantage of the VLPs derived from RNA phages is their high expression yield in bacteria that allows production of large quantities of material at affordable cost. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qbeta coat protein allows to achieve very high epitope density.

In some embodiments of the invention, immunogenic compositions of the invention may comprise mixtures of immunogenic conjugates, i.e. immunogenic carriers coupled to one or several antigenic IgE peptides of the invention. Thus, these immunogenic compositions may be composed of immunogenic carriers which differ in amino acid sequence. For example, vaccine compositions could be prepared comprising a "wild-type" VLP and a modified VLP protein in which one or more amino acid residues have been altered (e.g., deleted, inserted or substituted). Alternatively, the same immunogenic carrier might be used but coupled to antigenic IgE peptides of different amino acid sequences.

The invention therefore also relates to method for producing an immunogen according to the invention comprising i) providing an antigenic IgE peptide according to the invention, ii) providing an immunogenic carrier according to the invention, preferably a VLP, and iii) combining said antigenic IgE peptide and said immunogenic carrier. In one embodiment, said combining step occurs through chemical cross-linking, preferably through an heterobifunctional cross-linker.

In an embodiment, the antigenic IgE peptide of the invention consists of, or consists essentially of, an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430.

In another embodiment, the antigenic IgE peptide of the invention consists of, or consists essentially of, an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, and 153. Preferably, said antigenic IgE peptide consists of, or consists essentially of, an amino acid sequence selected from the group consisting of SEQ ID Nos: 1, 2, 3, 4, 5, 6, 7, 8, 9, 10, 11, 12, 13, 14, 15, 18, 19, 20, 21, 22, 23, 24, 25, 26, 27, 28, 29, 30, 31, 34, 35, 36, 37, 38, 39, 40, 41, 42, 43, 44, 45, 46, 49, 50, 51, 52, 53, 54, 55, 56, 57, 58, 59, 60, 63, 64, 65, 66, 67, 68, 69, 70, 71, 72, 73, 76, 77, 78, 79, 80, 81, 82, 83, 84, 85, 88, 89, 90, 91, 92, 93, 94, 95, 96, 99, 100, 101, 102, 103, 104, 105, 106, 109, 110, 111, 112, 113, 114, 115, 118, 119, 120, 121, 122, 123, 126, 127, 128, 129, 130, 133, 134, 135, 136, 139, 140, 141, 144, 145 and 148. More preferably, said antigenic IgE peptide consists of, or consists essentially of, an amino acid sequence selected from the group consisting of SEQ ID Nos: 1, 2, 3, 4, 5, 6, 7, 8, 9, 10, 11, 12, 18, 19, 20, 21, 22, 23, 24, 25, 26, 27, 28, 34, 35, 36, 37, 38, 39, 40, 41, 42, 43, 49, 50, 51, 52, 53, 54, 55, 56, 57, 63, 64, 65, 66, 67, 68, 69, 70, 76, 77, 78, 79, 80, 81, 82, 88, 89, 90, 91, 92, 93, 99, 100, 101, 102, 103, 109, 110, 111, 112, 118, 119, 120, 126, 127, 133, and 139. Even more preferably, said antigenic IgE peptide consists of, or consists essentially of, an amino acid sequence selected from the group consisting of SEQ ID Nos: 1, 2, 3, 4, 5, 6, 7, 8, 9, 18, 19, 20, 21, 22, 23, 24, 25, 34, 35, 36, 37, 38, 39, 40, 49, 50, 51, 52, 53, 54, 63, 64, 65, 66, 67, 76, 77, 78, 79, 88, 89, 90, 99, 100, 101 and 109. Even more preferably, said antigenic IgE peptide consists of, or consists essentially of, an amino acid sequence selected from the group consisting of SEQ ID Nos: 1, 2, 3, 4, 5, 6, 18, 19, 20, 21, 22, 34, 35, 36, 37, 49, 50, 51, 63, 64 and 76. Even more preferably, said antigenic IgE peptide consists of, or consists essentially of, an amino acid sequence selected from the group consisting of SEQ ID Nos: 1, 2, 3, 18, 19 and 34. Most preferably, said antigenic IgE peptide consists of, or consists essentially of, an amino acid sequence of SEQ ID Nos: 1 or 18.

In another embodiment, the antigenic IgE peptide of the invention consists of, or consists essentially of, an amino acid sequence selected from the group consisting of SEQ ID Nos: 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, and 219. Preferably, said antigenic IgE peptide consists of, or consists essentially of, an amino acid sequence selected from the group consisting of SEQ ID Nos: 154, 155, 156, 157, 158, 159, 160, 161, 162, 165, 166, 167, 168, 169, 170, 171, 172, 175, 176, 177, 178, 179, 180, 181, 184, 185, 186, 187, 188, 189, 192, 193, 194, 195, 196, 199, 200, 201, 202, 205, 206, 207, 210, 211, 214 and 217. More preferably, said antigenic IgE peptide consists of, or consists essentially of, an amino acid sequence selected from the group consisting of SEQ ID Nos: 154, 155, 156, 157, 158, 159, 165, 166, 167, 168, 169, 175, 176, 177, 178, 184, 185, 186, 192, 193, 199 and 200. Even more preferably, said antigenic IgE peptide consists of, or consists essentially of, an amino acid sequence selected from the group consisting of SEQ ID Nos: 154, 155, 156, 165, 166 and 175. Most preferably, said antigenic IgE peptide consists of, or consists essentially of, an amino acid sequence of SEQ ID Nos: 154 or 165.

In another embodiment, the antigenic IgE peptide of the invention consists of, or consists essentially of, an amino acid sequence selected from the group consisting of SEQ ID Nos: 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, and 310. Preferably, said antigenic IgE peptide consists of, or consists essentially of, an amino acid sequence selected from the group consisting of SEQ ID Nos: 220, 221, 222, 223, 224, 225, 226, 227, 228, 229, 230, 233, 234, 235, 236, 237, 238, 239, 240, 241, 242, 245, 246, 247, 248, 249, 250, 251, 252, 253, 256, 257, 258, 259, 260, 261, 262, 263, 266, 267, 268, 269, 270, 271, 272, 275, 276, 277, 278, 279, 280, 283, 284, 285, 286, 287, 290, 291, 292, 293, 296, 297, 298, 301, 302 and 305.

More preferably, said antigenic IgE peptide consists of, or consists essentially of, an amino acid sequence selected from the group consisting of SEQ ID Nos: 220, 221, 222, 223, 224, 225, 226, 227, 233, 234, 235, 236, 237, 238, 239, 245, 246, 247, 248, 249, 250, 256, 257, 258, 259, 260, 266, 267, 268, 269, 275, 276, 277, 283, 284 and 290. Even more preferably, said antigenic IgE peptide consists of, or consists essentially of, an amino acid sequence selected from the group consisting of SEQ ID Nos: 220, 221, 222, 223, 224, 233, 234, 235, 236, 245, 246, 247, 256, 257 and 266. Even more preferably, said antigenic IgE peptide consists of, or consists essentially of, an amino acid sequence selected from the group consisting of SEQ ID Nos:220, 221, 222, 233, 234 and 245. Most preferably, said antigenic IgE peptide consists of, or consists essentially of, an amino acid sequence of SEQ ID Nos: 220 or 233.

In yet another embodiment, the antigenic IgE peptide of the invention consists of, or consists essentially of, an amino acid sequence selected from the group consisting of SEQ ID Nos: 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430. Preferably, said antigenic IgE peptide consists of, or consists essentially of, an amino acid sequence selected from the group consisting of SEQ ID Nos:311, 312, 313, 314, 315, 316, 317, 318, 319, 320, 321, 322, 323, 326, 327, 328, 329, 330, 331, 332, 333, 334, 335, 336, 337, 340, 341, 342, 343, 344, 345, 346, 347, 348, 349, 350, 353, 354, 355, 356, 357, 358, 359, 360, 361, 362, 365, 366, 367, 368, 369, 370, 371, 372, 373, 376, 377, 378, 379, 380, 381, 382, 383, 386, 387, 388, 389, 390, 391, 392, 395, 396, 397, 398, 399, 400, 403, 404, 405, 406, 407, 410, 411, 412, 413, 416, 417, 418, 421, 422 and 425. More preferably, said antigenic IgE peptide consists of, or consists essentially of, an amino acid sequence selected from the group consisting of SEQ ID Nos: 311, 312, 313, 314, 315, 316, 317, 318, 319, 320, 326, 327, 328, 329, 330, 331, 332, 333, 334, 340, 341, 342, 343, 344, 345, 346, 347, 353, 354, 355, 356, 357, 358, 359, 365, 366, 367, 368, 369, 370, 376, 377, 378, 379, 380, 386, 387, 388, 389, 395, 396, 397, 403, 404 and 410. Even more preferably, said antigenic IgE peptide consists of, or consists essentially of, an amino acid sequence selected from the group consisting of SEQ ID Nos: 311, 312, 313, 314, 315, 316, 317, 326, 327, 328, 329, 330, 331, 340, 341, 342, 343, 344, 353, 354, 355, 356, 365, 366, 367, 376, 377 and 386. Even more preferably, said antigenic IgE peptide consists of, or consists essentially of, an amino acid sequence selected from the group consisting of SEQ ID Nos: 311, 312, 313, 314, 326, 327, 328, 340, 341 and 353. Even more preferably, said antigenic IgE peptide consists of, or consists essentially of, an amino acid sequence selected from the group consisting of SEQ ID Nos: 311, 312 and 326. Most preferably, said antigenic IgE peptide consists of, or consists essentially of, an amino acid sequence of SEQ ID Nos:311 or 312.

In an embodiment of the present invention, the antigenic IgE peptide disclosed herein is linked to an immunogenic carrier molecule. In an embodiment said immunogenic carrier is selected from the group consisting of any of the immunogenic carrier described herein. In another embodiment said immunogenic carrier is selected from the group consisting of: serum albumins such as bovine serum albumin (BSA); globulins; thyroglobulins; hemoglobins; hemocyanins (particularly Keyhole Limpet Hemocyanin [KLH]) and virus-like particle (VLPs). In a preferred embodiment said immunogenic carrier is Keyhole Limpet Hemocyanin or virus-like particle (VLPs). In an even preferred embodiment, said immunogenic carrier is a VLP selected from the group consisting of HBcAg VLP, HBsAg VLP, Qbeta VLP or any variant disclosed herein. In an even preferred embodiment, said immunogenic carrier is a Qbeta VLP selected from the group consisting of Qbeta CP; Qbeta A1, Qbeta-240, Qbeta-243, Qbeta-250, Qbeta-251 and Qbeta-259 (disclosed in WO03/024481).

In an embodiment, said immunogenic carrier is covalently linked to the antigenic IgE peptide disclosed herein either directly or via a linker. In an embodiment, said immunogenic carrier is linked to the antigenic IgE peptide disclosed herein by expression of a fusion protein as described herein. In another embodiment, the antigenic IgE peptide disclosed herein is linked to the immunogenic carrier, preferably a VLP, by way of chemical cross-linking as described herein and preferably by using a heterobifunctional cross-linker. Several hetero-bifunctional cross-linkers are known to the art. In some embodiments, the hetero-bifunctional crosslinker contains a functional group which can react with first attachment sites, i.e. with the side-chain amino group of lysine residues of the VLP or VLP subunit, and a further functional group which can react with a preferred second attachment site, i.e. a cysteine residue fused to the antigenic peptide made available for reaction by reduction.

Therefore in an embodiment of the present invention the antigenic IgE peptide disclosed herein further comprise either at its N-terminus, or at its C-terminus or at both the N-terminus and C-terminus a linker which is able to react with an attachment site of the immunogenic carrier in a chemical cross-linking reaction. In an embodiment, the antigenic IgE peptide disclosed herein further comprise at its C-terminus a linker having the formula $(G)_n C$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0 said formula represents a cysteine). Preferably the antigenic IgE peptide disclosed herein further comprise at its C-terminus a linker having the formula GGGC (SEQ ID NO: 462), GGC, GC or C.

In another embodiment of the present invention the antigenic IgE peptide disclosed herein further comprise at its N-terminus a linker having the formula $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine). Preferably the antigenic IgE peptide disclosed herein further comprise at its N-terminus a linker having the formula CGGG (SEQ ID NO: 475), CGG, CG or C.

In another embodiment the antigenic IgE peptide disclosed herein further comprise at its N-terminus a linker having the formula GGGC (SEQ ID NO: 462), GGC, GC or C.

In another embodiment the antigenic IgE peptide disclosed herein further comprise at its C-terminus a linker having the formula $(G)_n C$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n 0 or 1 (where n is equal to 0 said formula represents a cysteine) and at its N-terminus a linker having the formula $C(G)_n$ wherein n is an integer chosen in the group consisting of 0, 1, 2, 3, 4, 5, 6, 7, 8, 9 and 10, preferably in the group consisting of 0, 1, 2, 3, 4 and 5, more preferably in the groups consisting of 0, 1, 2 and 3, most preferably n is 0 or 1 (where n is equal to 0, the formula represents a cysteine). Preferably the antigenic IgE peptide disclosed herein further comprise at its N-terminus a linker having the formula GGGC, GGC, GC or C and at its C-terminus a linker having the formula GGGC, GGC, GC or C. More preferably the antigenic IgE peptide disclosed herein further comprise at its N-terminus a cysteine and at its C-terminus a cysteine.

Representative of said antigenic IgE peptides further comprising such a linker are disclosed at SEQ ID NO: 434, 436, 437, 438 and 439. In an embodiment of the invention, the antigenic IgE peptide comprising a linker is any of the peptide disclosed at table 9.

The cysteine residue added at the N-terminus and/or C-terminus of the IgE antigenic peptide is available for reaction by reduction (chemical cross-linking) typically and preferably by using a heterobifunctional cross-linker. Several heterobifunctional cross-linkers are known to the art. In some embodiments, the IgE antigenic peptide which further comprise a linker described herein are cross-linked with the side-chain amino group of lysine residues of a VLP.

Therefore in an embodiment, the IgE antigenic peptide which further comprise a linker described above are corsslinked to the immunogenic carrier (in particular to a VLP, preferably HBcAg VLP, HBsAg VLP or Qbeta VLP. The first step of the procedure, typically called the derivatization, is the reaction of the VLP with the cross-linker. The product of this reaction is an activated VLP, also called activated carrier. In the second step, unreacted cross-linker is removed using usual methods such as gel filtration or dialysis. In the third step, the antigenic peptide is reacted with the activated VLP, and this step is typically called the coupling step. Unreacted antigenic peptide may be optionally removed in a fourth step, for example by dialysis. Several heterobifunctional crosslinkers are known to the art. These include the preferred cross-linkers SMPH (Succinimidyl-6-[β-maleimidopropionamido]hexanoate), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage.

In an embodiment, the invention relates to immunogen comprising an antigenic IgE consisting of, or consisting essentially of, an amino acid sequence of SEQ ID Nos: 1, 2, 3, 18, 19 or 34, most preferably, of SEQ ID Nos: 1 or 18, wherein said antigenic IgE further comprises at its C-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 1, 2, 3, 18, 19 or 34, most preferably, of SEQ ID Nos: 1 or 18, wherein said antigenic IgE further comprises at its N-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 154, 155, 156, 165, 166 and 175, most preferably, of SEQ ID Nos: 154 or 165, wherein said antigenic IgE further comprises at its C-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 154, 155, 156, 165, 166 and 175, most preferably, of SEQ ID Nos: 154 or 165, wherein said antigenic IgE further comprises at its N-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 220, 221, 222, 233, 234 and 245, most preferably, of SEQ ID Nos: 220 or 233, wherein said antigenic IgE further comprises at its C-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 220, 221, 222, 233, 234 and 245, most preferably, of SEQ ID Nos: 220 or 233, wherein said antigenic IgE further comprises at its N-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 311, 312 and 326, most preferably, of SEQ ID Nos: 311 or 312, wherein said antigenic IgE further comprises at its C-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 311, 312 and 326, most preferably, of SEQ ID Nos: 311 or 312, wherein said antigenic IgE further comprises at its N-terminus a cysteine which is chemically cross linked to a virus-like particle via a thioether linkage. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 311, 312 and 326, most preferably, of SEQ ID Nos: 311 or 312. Preferably, said antigenic IgE further comprises at its C-terminus a GC linker, preferably a linker having the formula GGC (preferably said antigenic IgE peptide which comprises at its C-terminus a GC linker consists of, or consists essentially of amino acid sequence of SEQ ID No: 457) which is chemically cross linked to a virus-like particle via a thioether linkage using SMPH (Succinimidyl-6-[β-maleimidopropionamido]hexanoate) as cross linker, said linkage being between a lysine residues of the VLP and the cysteine residue of said C-terminus linker. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of, an amino acid sequence of SEQ ID Nos: 220, 221, 233, 234, 244 and 246, most preferably, of SEQ ID Nos: 220 or 233, which is chemically cross linked to a virus-like particle via a thioether linkage, said linkage being between a lysine residues of the VLP and the cysteine residue of said antigenic IgE peptide. In said embodiment, the antigenic IgE peptide disclosed herein is linked to the immunogenic carrier, preferably a VLP, by way of chemical cross-linking as described herein and preferably by using a heterobifunctional cross-linker. Several hetero-bifunctional cross-linkers are known to the art. In some embodiments, the hetero-bifunctional crosslinker contains a functional group which can react with first attachment sites, i.e. with the side-chain amino group of lysine residues of the VLP or VLP subunit, and a further functional group which can react with a preferred second attachment site, i.e. the cysteine residue of the antigenic peptide made available for reaction by reduction. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to immunogen comprising an antigenic IgE consisting of, or consisting essentially of an amino acid sequence of SEQ ID No: 220 which is chemically cross linked to a virus-like particle via a thioether linkage using SMPH (Succinimidyl-6-[β-maleimidopropionamido]hexanoate) as cross linker, said linkage being between a lysine residues of the VLP and the cysteine residue of said antigenic IgE peptide. In a preferred embodiment, said VLP is selected from the group consisting of HBcAg, HBsAg and Qbeta. Preferably said VLP is Qbeta, even more preferably Qbeta of SEQ ID NO: 435.

In a particular embodiment, when the sequence of the antigenic IgE peptide disclosed herein comprises a cysteine, said antigenic IgE peptide is covalently linked to the immunogenic carrier directly via said cysteine. In said embodiment, the antigenic IgE peptide disclosed herein is linked to the immunogenic carrier, preferably a VLP, by way of chemical cross-linking as described herein and preferably by using a heterobifunctional cross-linker. Several hetero-bifunctional cross-linkers are known to the art. In some embodiments, the hetero-bifunctional crosslinker contains a functional group which can react with first attachment sites, i.e. with the side-chain amino group of lysine residues of the VLP or VLP subunit, and a further functional group which can react with a preferred second attachment site, i.e. a cysteine residue fused to the antigenic peptide made available for reaction by reduction. Therefore in some embodiment, when the sequence of the antigenic IgE peptide disclosed herein comprises a cysteine, said antigenic IgE peptide is chemically cross linked to the immunogenic carrier via a thioether linkage, said linkage being between a lysine residues of the immunogenic carrier and the cysteine residue of said antigenic IgE. In a preferred embodiment, said immunogenic carrier is a VLP, preferably a Qbeta virus-like particle (even more preferably Qbeta of SEQ ID NO: 435).

In a further aspect the present invention relates to a composition comprising at least two immunogens described herein. In an embodiment, the present invention relates to a composition comprising at least two immunogen wherein each of these immunogen comprises an antigenic IgE peptide disclosed herein linked to an immunogenic carrier. In an embodiment said composition comprises two, three, four or five immunogens of the present invention wherein each of these immunogen comprises an antigenic IgE peptide disclosed herein linked to an immunogenic carrier.

Preferably, each antigenic IgE peptide is individually linked to different molecules of immunogenic carrier (each molecule of immunogenic carrier only having one type of antigenic IgE peptide conjugated to it). In said embodiment, the antigenic IgE peptide is said to be individually conjugated to the immunogenic carrier.

In an embodiment, the invention relates to a composition comprising or consisting of two immunogens each of these immunogen comprising an antigenic IgE peptide disclosed herein linked to an immunogenic carrier. Preferably, each antigenic IgE peptides are individually conjugated to the immunogenic carrier.

In an embodiment, the antigenic IgE peptide of the first immunogen consists of: an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, and 153, preferably from the group consisting of SEQ ID Nos: 1, 2, 3, 4, 5, 6, 7, 8, 9, 10, 11, 12, 13, 14, 15, 18, 19, 20, 21, 22, 23, 24, 25, 26, 27, 28, 29, 30, 31, 34, 35, 36, 37, 38, 39, 40, 41, 42, 43, 44, 45, 46, 49, 50, 51, 52, 53, 54, 55, 56, 57, 58, 59, 60, 63, 64, 65, 66, 67, 68, 69, 70, 71, 72, 73, 76, 77, 78, 79, 80, 81, 82, 83, 84, 85, 88, 89, 90, 91, 92, 93, 94, 95, 96, 99, 100, 101, 102, 103, 104, 105, 106, 109, 110, 111, 112, 113, 114, 115, 118, 119, 120, 121, 122, 123, 126, 127, 128, 129, 130, 133, 134, 135, 136, 139, 140, 141, 144, 145 and 148, more preferably from the group consisting of SEQ ID Nos: 1, 2, 3, 4, 5, 6, 7, 8, 9, 10, 11, 12, 18, 19, 20, 21, 22, 23, 24, 25, 26, 27, 28, 34, 35, 36, 37, 38, 39, 40, 41, 42, 43, 49, 50, 51, 52, 53, 54, 55, 56, 57, 63, 64, 65, 66, 67, 68, 69, 70, 76, 77, 78, 79, 80, 81, 82, 88, 89, 90, 91, 92, 93, 99, 100, 101, 102, 103, 109, 110, 111, 112, 118, 119, 120, 126, 127, 133, and 139, even more preferably, from the group consisting of SEQ ID Nos: 1, 2, 3, 4, 5, 6, 7, 8, 9, 18, 19, 20, 21, 22, 23, 24, 25, 34, 35, 36, 37, 38, 39, 40, 49, 50, 51, 52, 53, 54, 63, 64, 65, 66, 67, 76, 77, 78, 79, 88, 89, 90, 99, 100, 101 and 109, even more preferably, from the group consisting of SEQ ID Nos: 1, 2, 3, 4, 5, 6, 18, 19, 20, 21, 22, 34, 35, 36, 37, 49, 50, 51, 63, 64 and 76, even more preferably from the group consisting of SEQ ID Nos: 1, 2, 3, 18, 19 and 34, most preferably, said antigenic IgE peptide consists of an amino acid sequence of SEQ ID Nos: 1 or 18.

In an embodiment, the antigenic IgE peptide of the second immunogen consists of an amino acid sequence selected from the group consisting of SEQ ID Nos: 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, and 219, preferably from the group consisting of SEQ ID Nos: 154, 155, 156, 157, 158, 159, 160, 161, 162, 165, 166, 167, 168, 169, 170, 171, 172, 175, 176, 177, 178, 179, 180, 181, 184, 185, 186, 187, 188, 189, 192, 193, 194, 195, 196, 199, 200, 201, 202, 205, 206, 207, 210, 211, 214 and 217, more preferably from the group consisting of SEQ ID Nos: 154, 155, 156, 157, 158, 159, 165, 166, 167, 168, 169, 175, 176, 177, 178, 184, 185, 186, 192, 193, 199 and 200, even more preferably from the group consisting of SEQ ID Nos: 154, 155, 156, 165, 166 and 175, most preferably said antigenic IgE peptide consists of an amino acid sequence of SEQ ID Nos: 154 or 165.

In another embodiment, the antigenic IgE peptide of the second immunogen consists of an amino acid sequence selected from the group consisting of SEQ ID Nos:220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, and 310, preferably from the group consisting of SEQ ID Nos: 220, 221, 222, 223, 224, 225, 226, 227, 228, 229, 230, 233, 234, 235, 236, 237, 238, 239, 240, 241, 242, 245, 246, 247, 248, 249, 250, 251, 252, 253, 256, 257, 258, 259, 260, 261, 262, 263, 266, 267, 268, 269, 270, 271, 272, 275, 276, 277, 278, 279, 280, 283, 284, 285, 286, 287, 290, 291, 292, 293, 296, 297, 298, 301, 302 and 305, more preferably from the group consisting of SEQ ID Nos: 220, 221, 222, 223, 224, 225, 226, 227, 233, 234, 235, 236, 237, 238, 239, 245, 246, 247, 248, 249, 250, 256, 257, 258, 259, 260, 266, 267, 268, 269, 275, 276, 277, 283, 284 and 290, even more preferably from the group consisting of SEQ ID Nos: 220, 221, 222, 223, 224, 233, 234, 235, 236, 245, 246, 247, 256, 257 and 266, even more preferably from the group consisting of SEQ ID Nos:220, 221, 222, 233, 234 and 245, most preferably, said antigenic IgE peptide consists of an amino acid sequence of SEQ ID Nos: 220 or 233.

In yet another the antigenic IgE peptide of the second immunogen consists of an amino acid sequence selected from the group consisting of SEQ ID Nos:311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430, preferably from the group consisting of SEQ ID Nos:311, 312, 313, 314, 315, 316, 317, 318, 319, 320, 321, 322, 323, 326, 327, 328, 329, 330, 331, 332, 333, 334, 335, 336, 337, 340, 341, 342, 343, 344, 345, 346, 347, 348, 349, 350, 353, 354, 355, 356, 357, 358, 359, 360, 361, 362, 365, 366, 367, 368, 369, 370, 371, 372, 373, 376, 377, 378, 379, 380, 381, 382, 383, 386, 387, 388, 389, 390, 391, 392, 395, 396, 397, 398, 399, 400, 403, 404, 405, 406, 407, 410, 411, 412, 413, 416, 417, 418, 421, 422 and 425, more preferably from the group consisting of SEQ ID Nos: 311, 312, 313, 314, 315, 316, 317, 318, 319, 320, 326, 327, 328, 329, 330, 331, 332, 333, 334, 340, 341, 342, 343, 344, 345, 346, 347, 353, 354, 355, 356, 357, 358, 359, 365, 366, 367, 368, 369, 370, 376, 377, 378, 379, 380, 386, 387, 388, 389, 395, 396, 397, 403, 404 and 410, even more preferably from the group consisting of SEQ ID Nos: 311, 312, 313, 314, 315, 316, 317, 326, 327, 328, 329, 330, 331, 340, 341, 342, 343, 344, 353, 354, 355, 356, 365, 366, 367, 376, 377 and 386, even more preferably from the group consisting of SEQ ID Nos: 311, 312, 313, 314, 326, 327, 328, 340, 341 and 353, even more preferably from the group consisting of SEQ ID Nos: 311, 312 and 326, most preferably, said antigenic IgE peptide consists of an amino acid sequence of SEQ ID Nos:311 or 312.

In an embodiment, the invention relates to a composition comprising or consisting of two immunogens each of these immunogen comprising an antigenic IgE peptide linked to an immunogenic carrier wherein, the antigenic IgE peptide of the first immunogen consists of an amino acid sequence of SEQ ID Nos: 1 and the antigenic IgE peptide of the second immunogen consists of 165. In another embodiment, the antigenic IgE peptide of the first immunogen consists of an amino acid sequence of SEQ ID Nos: 1 and the antigenic IgE peptide of the second immunogen consists of an amino acid sequence of SEQ ID Nos:220. In another embodiment, the antigenic IgE peptide of the first immunogen consists of an amino acid sequence of SEQ ID Nos: 1 and the antigenic IgE peptide of the second immunogen consists of an amino acid sequence of SEQ ID Nos: 312. Preferably, each antigenic IgE peptides are individually conjugated to the immunogenic carrier.

In an embodiment, the invention relates to a composition comprising or consisting of two immunogens each of these immunogen comprising an antigenic IgE peptide disclosed herein linked to an immunogenic carrier. Preferably, each antigenic IgE peptides are individually conjugated to the immunogenic carrier. In an embodiment, the antigenic IgE peptide of the first immunogen consists of: an amino acid sequence selected from the group consisting of SEQ ID Nos: 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, and 219, preferably from the group consisting of SEQ ID Nos: 154, 155, 156, 157, 158, 159, 160, 161, 162, 165, 166, 167, 168, 169, 170, 171, 172, 175, 176, 177, 178, 179, 180, 181, 184, 185, 186, 187, 188, 189, 192, 193, 194, 195, 196, 199, 200, 201, 202, 205, 206, 207, 210, 211, 214 and 217, more preferably from the group consisting of SEQ ID Nos: 154, 155, 156, 157, 158, 159, 165, 166, 167, 168, 169, 175, 176, 177, 178, 184, 185, 186, 192, 193, 199 and 200, even more preferably from the group consisting of SEQ ID Nos: 154, 155, 156, 165, 166 and 175, most preferably said antigenic IgE peptide consists of an amino acid sequence of SEQ ID Nos: 154 or 165.

In an embodiment, the antigenic IgE peptide of the second immunogen consists of an amino acid sequence selected from the group consisting of SEQ ID Nos:220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, and 310, preferably from the group consisting of SEQ ID Nos: 220, 221, 222, 223, 224, 225, 226, 227, 228, 229, 230, 233, 234, 235, 236, 237, 238, 239, 240, 241, 242, 245, 246, 247, 248, 249, 250, 251, 252, 253, 256, 257, 258, 259, 260, 261, 262, 263, 266, 267, 268, 269, 270, 271, 272, 275, 276, 277, 278, 279, 280, 283, 284, 285, 286, 287, 290, 291, 292, 293, 296, 297, 298, 301, 302 and 305, more preferably from the group consisting of SEQ ID Nos: 220, 221, 222, 223, 224, 225, 226, 227, 233, 234, 235, 236, 237, 238, 239, 245, 246, 247, 248, 249, 250, 256, 257, 258, 259, 260, 266, 267, 268, 269, 275, 276, 277, 283, 284 and 290, even more preferably from the group consisting of SEQ ID Nos: 220, 221, 222, 223, 224, 233, 234, 235, 236, 245, 246, 247, 256, 257 and 266, even more preferably from the group consisting of SEQ ID Nos:220, 221, 222, 233, 234 and 245, most preferably, said antigenic IgE peptide consists of an amino acid sequence of SEQ ID Nos: 220 or 233.

In another embodiment the antigenic IgE peptide of the second immunogen consists of an amino acid sequence selected from the group consisting of SEQ ID Nos:311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430, preferably from the group consisting of SEQ ID Nos:311, 312, 313, 314, 315, 316, 317, 318, 319, 320, 321, 322, 323, 326, 327, 328, 329, 330, 331, 332, 333, 334, 335, 336, 337, 340, 341, 342, 343, 344, 345, 346, 347, 348, 349, 350, 353, 354, 355, 356, 357, 358, 359, 360, 361, 362, 365, 366, 367, 368, 369, 370, 371, 372, 373, 376, 377, 378, 379, 380, 381, 382, 383, 386, 387, 388, 389, 390, 391, 392, 395, 396, 397, 398, 399, 400, 403, 404, 405, 406, 407, 410, 411, 412, 413, 416, 417, 418, 421, 422 and 425, more preferably from the group consisting of SEQ ID Nos: 311, 312, 313, 314, 315, 316, 317, 318, 319, 320, 326, 327, 328, 329, 330, 331, 332, 333, 334, 340, 341, 342, 343, 344, 345, 346, 347, 353, 354, 355, 356, 357, 358, 359, 365, 366, 367, 368, 369, 370, 376, 377, 378, 379, 380, 386, 387, 388, 389, 395, 396, 397, 403, 404 and 410, even more preferably from the group consisting of SEQ ID Nos: 311, 312, 313, 314, 315, 316, 317, 326, 327, 328, 329, 330, 331, 340, 341, 342, 343, 344, 353, 354, 355, 356, 365, 366, 367, 376, 377 and 386, even more preferably from the group consisting of SEQ ID Nos: 311, 312, 313, 314, 326, 327, 328, 340, 341 and 353, even more preferably from the group consisting of SEQ ID Nos: 311, 312 and 326, most preferably, said antigenic IgE peptide consists of an amino acid sequence of SEQ ID Nos:311 or 312.

In an embodiment, the invention relates to a composition comprising or consisting of two immunogens each of these immunogen comprising an antigenic IgE peptide linked to an immunogenic carrier wherein, the antigenic IgE peptide of the first immunogen consists of an amino acid sequence of SEQ ID Nos: 165 and the antigenic IgE peptide of the second immunogen consists of 220. In another embodiment, the antigenic IgE peptide of the first immunogen consists of an amino acid sequence of SEQ ID Nos: 165 and the antigenic IgE peptide of the second immunogen consists of an amino acid sequence of SEQ ID Nos:312. Preferably, each antigenic IgE peptides are individually conjugated to the immunogenic carrier.

In an embodiment, the invention relates to a composition comprising or consisting of two immunogens each of these immunogen comprising an antigenic IgE peptide disclosed herein linked to an immunogenic carrier. Preferably, each antigenic IgE peptides are individually conjugated to the immunogenic carrier. In an embodiment, the antigenic IgE peptide of the first immunogen consists of: an amino acid sequence selected from the group consisting of SEQ ID Nos: 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, and 310, preferably from the group consisting of SEQ ID Nos: 220, 221, 222, 223, 224, 225, 226, 227, 228, 229, 230, 233, 234, 235, 236, 237, 238, 239, 240, 241, 242, 245, 246, 247, 248, 249, 250, 251, 252, 253, 256, 257, 258, 259, 260, 261, 262, 263, 266, 267, 268, 269, 270, 271, 272, 275, 276, 277, 278, 279, 280, 283, 284, 285, 286, 287, 290, 291, 292, 293, 296, 297, 298, 301, 302 and 305, more preferably from the group consisting of SEQ ID Nos: 220, 221, 222, 223, 224, 225, 226, 227, 233, 234, 235, 236, 237, 238, 239, 245, 246, 247, 248, 249, 250, 256, 257, 258, 259, 260, 266, 267, 268, 269, 275, 276, 277, 283, 284 and 290, even more preferably from the group consisting of SEQ ID Nos: 220, 221, 222, 223, 224, 233, 234, 235, 236, 245, 246, 247, 256, 257 and 266, even more preferably from the group consisting of SEQ ID Nos:220, 221, 222, 233, 234 and 245, most preferably, said antigenic IgE peptide consists of an amino acid sequence of SEQ ID Nos: 220 or 233.

In an embodiment the antigenic IgE peptide of the second immunogen consists of an amino acid sequence selected from the group consisting of SEQ ID Nos:311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430, preferably from the group consisting of SEQ ID Nos:311, 312, 313, 314, 315, 316, 317, 318, 319, 320, 321, 322, 323, 326, 327, 328, 329, 330, 331, 332, 333, 334, 335, 336, 337, 340, 341, 342, 343, 344, 345, 346, 347, 348, 349, 350, 353, 354, 355, 356, 357, 358, 359, 360, 361, 362, 365, 366, 367, 368, 369, 370, 371, 372, 373, 376, 377, 378, 379, 380, 381, 382, 383, 386, 387, 388, 389, 390, 391, 392, 395, 396, 397, 398, 399, 400, 403, 404, 405, 406, 407, 410, 411, 412, 413, 416, 417, 418, 421, 422 and 425, more preferably from the group consisting of SEQ ID Nos: 311, 312, 313, 314, 315, 316, 317, 318, 319, 320, 326, 327, 328, 329, 330, 331, 332, 333, 334, 340, 341, 342, 343, 344, 345, 346, 347, 353, 354, 355, 356, 357, 358, 359, 365, 366, 367, 368, 369, 370, 376, 377, 378, 379, 380, 386, 387, 388, 389, 395, 396, 397, 403, 404 and 410, even more preferably from the group consisting of SEQ ID Nos: 311, 312, 313, 314, 315, 316, 317, 326, 327, 328, 329, 330, 331, 340, 341, 342, 343, 344, 353, 354, 355, 356, 365, 366, 367, 376, 377 and 386, even more preferably from the group consisting of SEQ ID Nos: 311, 312, 313, 314, 326, 327, 328, 340, 341 and 353, even more preferably from the group consisting of SEQ ID Nos: 311, 312 and 326, most preferably, said antigenic IgE peptide consists of an amino acid sequence of SEQ ID Nos:311 or 312.

In an embodiment, the invention relates to a composition comprising or consisting of two immunogens each of these immunogen comprising an antigenic IgE peptide linked to an immunogenic carrier wherein, the antigenic IgE peptide of the first immunogen consists of an amino acid sequence of SEQ ID Nos: 220 and the antigenic IgE peptide of the second immunogen consists of 312. Preferably, each antigenic IgE peptides are individually conjugated to the immunogenic carrier.

According to an embodiment of the present invention the immunogen of the composition disclosed here above are linked, preferably chemically cross linked, to an immunogenic carrier either directly or via a linker as disclosed herein. In an embodiment, the immunogenic carrier is Keyhole Limpet Hemocyanin [KLH]) or a virus-like particle (VLPs). In a preferred embodiment said immunogenic carrier is a VLP selected from the group consisting of HBcAg VLP, HBsAg VLP, Qbeta VLP or any variant disclosed herein. In an even preferred embodiment, said immunogenic carrier is a Qbeta VLP selected from the group consisting of Qbeta CP; Qbeta A1, Qbeta-240, Qbeta-243, Qbeta-250, Qbeta-251 and Qbeta-259.

In an embodiment, the invention relates to a composition comprising or consisting of two immunogens each of these immunogen comprising an antigenic IgE peptide disclosed herein linked to an immunogenic carrier. In an embodiment the first immunogen consists of an immunogen comprising an antigenic IgE consisting of, or consisting essentially of, an amino acid sequence of SEQ ID Nos: 220, 221, 233, 234, 244 and 246, most preferably, of SEQ ID Nos: 220 or 233, which is chemically cross linked to a Qbeta virus-like particle (more preferably Qbeta of SEQ ID NO: 435) via a thioether linkage, said linkage being between a lysine residues of the VLP and the cysteine residue of said antigenic IgE peptide, and the second immunogen consists of an immunogen comprising an antigenic IgE consisting of, or consisting essentially of, an amino acid sequence of SEQ ID Nos: 311, 312 and 326, most preferably of SEQ ID Nos: 311 or 312, wherein said antigenic IgE further comprises at its C-terminus a cysteine which is chemically cross linked to a Qbeta virus-like particle, more preferably Qbeta of SEQ ID NO: 435. Preferably, each antigenic IgE peptides are individually conjugated to the immunogenic carrier.

In an embodiment, the invention relates to a composition comprising or consisting of two immunogens each of these immunogen comprising an antigenic IgE peptide disclosed herein linked to an immunogenic carrier. In an embodiment the first immunogen consists of an immunogen comprising an antigenic IgE consisting of, or consisting essentially of, an amino acid sequence of SEQ ID Nos: 220, 221, 233, 234, 244 and 246, most preferably, of SEQ ID Nos: 220 or 233, which is chemically cross linked to a Qbeta virus-like particle (more preferably Qbeta of SEQ ID NO: 435) via a thioether linkage, said linkage being between a lysine residues of the VLP and the cysteine residue of said antigenic IgE peptide, the second immunogen consists of an immunogen comprising an antigenic IgE consisting of, or consisting essentially of, an amino acid sequence of SEQ ID Nos: 1, 2, 3, 18, 19 or 34, most preferably, of SEQ ID Nos: 1 or 18, wherein said antigenic IgE further comprises at its C-terminus a cysteine which is chemically cross linked to a Qbeta virus-like particle, more preferably Qbeta of SEQ ID NO: 435. Preferably, each antigenic IgE peptides are individually conjugated to the immunogenic carrier.

In an embodiment, the invention relates to a composition comprising or consisting of three immunogens each of these immunogen comprising an antigenic IgE peptide disclosed herein linked to an immunogenic carrier. In an embodiment the first immunogen consists of an immunogen comprising an antigenic IgE consisting of, or consisting essentially of, an amino acid sequence of SEQ ID Nos: 220, 221, 233, 234, 244 and 246, most preferably, of SEQ ID Nos: 220 or 233, which is chemically cross linked to a Qbeta virus-like particle (more preferably Qbeta of SEQ ID NO: 435) via a thioether linkage, said linkage being between a lysine residues of the VLP and the cysteine residue of said antigenic IgE peptide, the second immunogen consists of an immunogen comprising an antigenic IgE consisting of, or consisting essentially of, an amino acid sequence of SEQ ID Nos: 311, 312 and 326, most preferably of SEQ ID Nos: 311 or 312, wherein said antigenic IgE further comprises at its C-terminus a cysteine which is chemically cross linked to a Qbeta virus-like particle, more preferably Qbeta of SEQ ID NO: 435 and the third immunogen consists of an immunogen comprising an antigenic IgE consisting of, or consisting essentially of, an amino acid sequence of SEQ ID Nos: 1, 2, 3, 18, 19 or 34, most preferably, of SEQ ID Nos: 1 or 18, wherein said antigenic IgE further comprises at its C-terminus a cysteine which is chemically cross linked to a Qbeta virus-like particle, more preferably Qbeta of SEQ ID NO: 435. Preferably, each antigenic IgE peptides are individually conjugated to the immunogenic carrier.

In an embodiment, the invention relates to a composition comprising or consisting of two immunogens each of these immunogen comprising an antigenic IgE peptide disclosed herein individually conjugated to an immunogenic carrier. In an embodiment the first immunogen consists of an immunogen comprising an antigenic IgE peptide consisting of, or consisting essentially of, an amino acid sequence of SEQ ID Nos: 220, 221, 233, 234, 244 and 246, most preferably, of SEQ ID Nos: 220 or 233. Preferably said first antigenic IgE peptide is chemically cross linked to a Qbeta virus-like particle (more preferably Qbeta of SEQ ID NO: 435) via a thioether linkage using SMPH (Succinimidyl-6-[β-maleimidopropionamido]hexanoate) as cross linker, said linkage being between a lysine residues of the VLP and the cysteine residue of said antigenic IgE peptide. Preferably, the second immunogen consists of an immunogen comprising an antigenic IgE peptide consisting of, or consisting essentially of, an amino acid sequence of SEQ ID Nos: 311, 312 or 326, most preferably, of SEQ ID Nos: 311 or 312. Preferably, said second antigenic IgE peptide further comprises at its C-terminus a GC linker, preferably a linker having the formula GGC (preferably said second antigenic IgE peptide which comprises at its C-terminus a GC linker consists of, or consists essentially of amino acid sequence of SEQ ID No: 457) which is chemically cross linked to a virus-like particle via a thioether linkage using SMPH (Succinimidyl-6-[β-maleimidopropionamido]hexanoate) as cross linker, said linkage being between a lysine residues of the VLP and the cysteine residue of said C-terminus linker. In a preferred embodiment, said VLP is selected from the group consisting of HBcAg, HBsAg and Qbeta. Preferably said VLP is Qbeta, even more preferably Qbeta of SEQ ID NO: 435.

In an embodiment, the invention relates to a composition comprising, or consisting of, two, three, four or more immunogens wherein each of these immunogen comprise an antigenic IgE peptide linked to an immunogenic carrier and wherein, said antigenic IgE peptide consists of, or consists essentially of, an amino acid sequence selected from the group consisting of SEQ ID Nos: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430. In an embodiment, said antigenic IgE peptides are linked to the same immunogenic carrier. In another embodiment, said antigenic IgE peptides are linked to different immunogenic carrier and then mixed.

Method of Production of the Immunogen of the Invention

The invention further relates to a process for the production of the immunogen disclosed herein. In an embodiment said immunogen comprises at least one antigenic IgE peptide disclosed herein linked to an immunogenic carrier disclosed herein. Therefore the invention further relates to a process for the production of an immunogen comprising the step of linking at least one antigenic IgE peptide disclosed herein to an immunogenic carrier disclosed herein. In an embodiment said linkage is performed by chemical cross linkage, either directly or via a linker, in particular a GC linker (eg. a cysteine) as disclosed herein. In an embodiment, the invention relates to a process for the production of an immunogen comprising the step of linking at least one antigenic IgE peptide disclosed herein, optionally further comprising a linker as disclosed herein, to a VLP disclosed herein, said linkage being performed by chemical cross linkage, either directly or via a linker, in particular a GC linker (eg. a cysteine) as disclosed herein. In a particular embodiment, when the sequence of the antigenic IgE peptide disclosed herein comprises a cysteine, said antigenic IgE peptide is covalently linked to the VLP directly via said cysteine. In said embodiment, the process include a step of chemical cross-linking as described herein and preferably using a heterobifunctional cross-linker (e.g. N-gamma-maleimido-butyryloxy-succinimide ester (GMBS) or Succinimidyl-6-[β-maleimidopropionamido]hexanoate (SMPH)). Therefore in some embodiments, the chemical cross-linking step results in the VLP being cross linked via a thioether linkage, said linkage being between a lysine residues of the VLP and the cysteine residue of said antigenic IgE. In a preferred embodiment, said VLP is preferably a Qbeta virus-like particle (even more preferably Qbeta of SEQ ID NO: 435). A further embodiment of the present invention relates to an immunogen obtainable by the process disclosed herein.

Compositions Comprising an Antigenic IgE Peptide of the Invention

The present invention further relates to compositions, particularly immunogenic compositions also referred to as "subject immunogenic compositions", comprising an antigenic IgE peptide of the invention, preferably linked to an immunogenic carrier, more preferably a VLP, even more preferably a HBsAg, HbcAg or Qbeta VLP, and optionally at least one adjuvant. Such immunogenic compositions, particularly when formulated as pharmaceutical compositions, are deemed useful to prevent, treat or alleviate IgE-related disorders.

In some embodiments, a subject immunogenic composition according to the invention comprises an antigenic IgE peptide comprising an amino acid sequence selected from SEQ ID Nos: 1 to 430, and functionally active variants thereof, preferably from the group consisting of SEQ ID Nos: 1 to 430, more preferably from the group consisting of SEQ ID Nos: 1 to 153 and 220 to 430, even more preferably from the group consisting of SEQ ID Nos: 220 to 430. In some embodiment, said antigenic IgE peptide is linked to an immunogenic carrier, preferably a VLP, more preferably to a HBsAg, HbcAg or Qbeta VLP.

A subject immunogenic composition comprising an antigenic IgE peptide according to the invention can be formulated in a number of ways, as described in more detail below. In some embodiments, a subject immunogenic composition comprises single species of antigenic IgE peptide, e.g., the immunogenic composition comprises a population of antigenic IgE peptides, substantially all of which have the same amino acid sequence. In other embodiments, a subject immunogenic composition comprises two or more different antigenic IgE peptides, e.g., the immunogenic composition comprises a population of antigenic IgE peptides, the members of which population can differ in amino acid sequence. A subject immunogenic composition can comprise from two to about 20 different antigenic IgE peptides, e.g., a subject immunogenic composition can comprise 2, 3, 4, 5, 6, 7, 8, 9, 10, 11-15, or 15-20 different antigenic IgE peptides, each having an amino acid that differs from the amino acid sequences of the other antigenic IgE peptides.

For example, in some embodiments, a subject immunogenic composition comprises a first antigenic IgE peptide, preferably linked to an immunogenic carrier, more preferably to a VLP, even more preferably to a HBsAg, HbcAg or Qbeta VLP, and comprising a first amino acid sequence selected from the group consisting of SEQ ID Nos: SEQ ID Nos: 1 to 430, more preferably from the group consisting of SEQ ID Nos: 1 to 153 and 220 to 430, even more preferably from the group consisting of SEQ ID Nos: 220 to 430; and at least a second antigenic IgE peptide, preferably linked to an immunogenic carrier, more preferably to a VLP, even more preferably to a HBsAg, HbcAg or Qbeta VLP, and comprising a second amino acid sequence, preferably selected from the group consisting of SEQ ID Nos: 1 to 430, more preferably from the group consisting of SEQ ID Nos: 1 to 153 and 220 to 430, even more preferably from the group consisting of SEQ ID Nos: 220 to 430; where the second amino acid sequence differs from the first amino acid sequence by at least 1, 2, 3, 4, 5, 6 to 10, or 15 amino acids. In a further embodiment, the first antigenic IgE peptide comprises an amino acid sequence selected from the group consisting of SEQ ID NOs: 311 to 430 and said second antigenic IgE peptide comprises an amino acid sequence selected from the group consisting of SEQ ID NOs: 1 to 310, preferably from the group consisting of SEQ ID NOs: 220 to 310 or of SEQ ID NOs: 1 to 153, or of SEQ ID NOs: 154 to 219, more preferably from the group consisting of SEQ ID NOs: 220 to 310. In another further embodiment, the first antigenic IgE peptide comprises an amino acid sequence selected from the group consisting of SEQ ID NOs: 220 to 310 and said second antigenic IgE peptide comprises an amino acid sequence selected from the group consisting of SEQ ID NOs: 1 to 219 and 311 to 430, preferably from the group consisting of SEQ ID NOs: 311 to 430 or of SEQ ID NOs: 1 to 153, or of SEQ ID NOs: 154 to 219, more preferably from the group consisting of SEQ ID NOs: 311 to 430. In another further embodiment, the first antigenic IgE peptide comprises an amino acid sequence selected from the group consisting of SEQ ID NOs: 1 to 153 and said second antigenic IgE peptide comprises an amino acid sequence selected from the group consisting of SEQ ID NOs: 154 to 430, preferably from the group consisting of SEQ ID NOs: 220 to 310, of SEQ ID NOs: 311 to 430, or of SEQ ID NOs: 154 to 219. In another further embodiment, the first antigenic IgE peptide comprises an amino acid sequence selected from the group consisting of SEQ ID NOs: 154 to 219 and said second antigenic IgE peptide comprises an amino acid sequence selected from the group consisting of SEQ ID NOs: 1 to 153 and 220 to 430, preferably from the group consisting of SEQ ID NOs: 220 to 310, or of SEQ ID NOs: 1 to 153, or of SEQ ID NOs: 311 to 430.

As another example, a subject immunogenic composition comprises a first antigenic IgE peptide, preferably linked to an immunogenic carrier, more preferably to a VLP, even more preferably to a HBsAg, HbcAg or Qbeta VLP, and comprising a first amino acid sequence selected from the group consisting of SEQ ID Nos: 1 to 430; a second antigenic IgE peptide, preferably linked to an immunogenic carrier, more preferably to a VLP, even more preferably to a HBsAg, HbcAg or Qbeta VLP, and comprising a second amino acid sequence, preferably selected from the group consisting of SEQ ID Nos: 1 to 430 where the second amino acid sequence differs from the first amino acid sequence by at least 1, 2, 3, 4, 5, 6 to 10, or 15 amino acids; and at least a third antigenic IgE polypeptide, preferably linked to an immunogenic carrier, more preferably to a VLP, even more preferably to a HBsAg, HbcAg or Qbeta VLP, and comprising a third amino acid sequence, preferably selected from the group consisting of SEQ ID Nos: 1 to 430, where the third amino acid sequence differs from both the first and the second amino acid sequences by at least 1, 2, 3, 4, 5, 6 to 10, or 15 amino acids. In a further embodiment, the first antigenic IgE peptide comprises an amino acid sequence selected from the group consisting of SEQ ID NOs: 311 to 430; and said second and third antigenic IgE peptides comprise an amino acid sequence selected from the group consisting of SEQ ID NOs: 1 to 310, preferably from the group consisting of SEQ ID NOs: 220 to 310 or of SEQ ID NOs: 1 to 153 or of SEQ ID NOs: 154 to 219.

In another further embodiment, the first antigenic IgE peptide comprises an amino acid sequence selected from the group consisting of SEQ ID NOs: 220 to 310 and said second and third antigenic IgE peptides comprise an amino acid sequence selected from the group consisting of SEQ ID NOs: 1 to 219 and 311 to 430, preferably from the group consisting of SEQ ID NOs: 311 to 430 or of SEQ ID NOs: 1 to 153 or of SEQ ID NOs: 154 to 219.

In other embodiments, a subject immunogenic composition comprises a multimerized antigenic IgE polypeptide, as described above. As used herein, the terms "immunogenic composition comprising an antigenic IgE peptide" or "immunogenic composition of the invention" or "subject immunogenic composition" refers to an immunogenic composition comprising either single species (multimerized or not) or multiple species of antigenic IgE peptide(s) coupled or not to an immunogenic carrier. Where two or more peptides are used coupled to a carrier, the peptide may be coupled to the same carrier molecule or individually coupled to carrier molecules and then combined to produce an immunogenic composition.

Another aspect of the invention relates to methods for producing an immunogen according to the invention, said method comprising coupling an antigenic IgE peptide to an immunogenic carrier. In one embodiment, said coupling is chemical.

In some embodiments, a subject immunogenic composition comprises at least one adjuvant. Suitable adjuvants include those suitable for use in mammals, preferably in humans. Examples of known suitable adjuvants that can be used in humans include, but are not necessarily limited to, alum, aluminum phosphate, aluminum hydroxide, MF59 (4.3% w/v squalene, 0.5% w/v polysorbate 80 (Tween 80), 0.5% w/v sorbitan trioleate (Span 85)), CpG-containing nucleic acid (where the cytosine is unmethylated), QS21 (saponin adjuvant), MPL (Monophosphoryl Lipid A), 3DMPL (3-O-deacylated MPL), extracts from Aquilla, ISCOMS (see, e.g., Sjolander et al. (1998) *J. Leukocyte Biol.* 64:713; WO90/03184, WO96/11711, WO 00/48630, WO98/36772, WO00/41720, WO06/134423 and WO07/026, 190), LT/CT mutants, poly(D, L-lactide-co-glycolide) (PLG) microparticles, Quil A, interleukins, and the like. For veterinary applications including but not limited to animal experimentation, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+ TDM+CWS) in a 2% squalene/Tween 80 emulsion.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine design: the subunit and adjuvant approach*, eds. Powell & Newman, Plenum Press 1995), containing 5% Squalene, 0.5% Tween 80 (polyoxyethylene sorbitan mono-oleate), and 0.5% Span 85 (sorbitan trioleate) (optionally containing muramyl tri-peptide covalently linked to dipalmitoyl phosphatidylethanolamine (MTP-PE)) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+ CWS (DETOX™); (2) saponin adjuvants, such as QS21, STIMULON™ (Cambridge Bioscience, Worcester, Mass.), Abisco® (Isconova, Sweden), or Iscomatrix® (Commonwealth Serum Laboratories, Australia), may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg Vaccine 2000, 19, 618-622; Krieg *Curr opin Mol Ther* 2001 3:15-24; Roman et al., *Nat. Med.*, 1997, 3, 849-854; Weiner et al., *PNAS USA*, 1997, 94, 10833-10837; Davis et al, *J. Immunol*, 1998, 160, 870-876; Chu et al., *J. Exp. Med*, 1997, 186, 1623-1631; Lipford et al, *Ear. J. Immunol.*, 1997, 27, 2340-2344; Moldoveami e/al., *Vaccine*, 1988, 16, 1216-1224, Krieg et al., *Nature*, 1995, 374, 546-549; Klinman et al., *PNAS USA*, 1996, 93, 2879-2883; Ballas et al, *J. Immunol*, 1996, 157, 1840-1845; Cowdery et al, *J. Immunol*, 1996, 156, 4570-4575; Halpern et al, *Cell Immunol*, 1996, 167, 72-78; Yamamoto et al, *Jpn. J. Cancer Res.*, 1988, 79, 866-873; Stacey et al, *J. Immunol.*, 1996, 157, 2116-2122; Messina et al, *J. Immunol*, 1991, 147, 1759-1764; Yi et al, *J. Immunol*, 1996, 157, 4918-4925; Yi et al, *J. Immunol*, 1996, 157, 5394-5402; Yi et al, *J. Immunol*, 1998, 160, 4755-4761; and Yi et al, *J. Immunol*, 1998, 160, 5898-5906; International patent applications WO96/02555, WO98/16247, WO98/18810, WO98/40100, WO98/55495, WO98/37919 and WO98/52581] i.e. containing at least one CG dinucleotide, where the cytosine is unmethylated; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g. a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+ IM2 (optionally+a sterol) e.g. WO98/57659; (14) other substances that act as immunostimulating agents to enhance the efficacy of the composition, such as Muramyl peptides include N-acetyl-muramyl-L-threonyl-D-isoglutamine (thr- MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), (15) ligands for toll-like receptors (TLR), natural or synthesized (e.g. as described in Kanzler et al 2007, Nature Medicine 13, p1552-9), including TLR3 ligands such as polyI:C and similar compounds such as Hiltonol and Ampligen.

In an embodiment, the immunogenic composition of the present invention comprises at least one adjuvant. In a particular embodiment, said adjuvant is an immunostimulatory oligonucleotide and more preferably a CpG oligonucleotide. In an embodiment, the CpG oligonucleotide has the nucleic acid sequence 5' TCGTCGTTTTTCGGTGCTTTT 3' (ODN CpG 24555; SEQ ID NO: 431). The immunostimulatory oligonucleotide nucleic acid sequence of SEQ ID NO: 431 differs from a previously reported immunostimulatory oligonucleotide (ODN 10103) 5' TCGTCGTTTTTCGGTCGTTTT 3' (SEQ ID NO: 432) by the reversal of the 3' most CG dinucleotide. The similarities in activity between these two immunostimulatory oligonucleotides is surprising because it has been previously reported that immunostimulatory activity of CpG oligonucleotides is dependent on the number of CpG motifs, the sequences flanking the CG dinucleotide, the location of the CpG motif(s) and the spacing between the CpG motifs (Ballas et al., 1996, J. Immunol.; Hartmann et al., 2000, J. Immunol.; Klinman et al., 2003, Clin. Exp. Immunol.). The removal of the 3' most CG dinucleotide in immunostimulatory oligonucleotide CpG ODN 24555 (SEQ ID NO: 431) did not result in a negative impact on the ability of this immunostimulatory oligonucleotide to augment antigen-specific immune responses as would have been expected from previous disclosures. CpG ODN 24555 demonstrated similar and in some cases enhanced immunostimulatory activity when compared with CpG ODN 10103.

The immunostimulatory oligonucleotide can be double-stranded or single-stranded. Generally, double-stranded molecules are more stable in vivo, while single-stranded molecules have increased immune activity. Thus in some aspects of the invention it is preferred that the nucleic acid be single stranded and in other aspects it is preferred that the nucleic acid be double-stranded The terms "nucleic acid" and "oligonucleotide" are used interchangeably herein to mean multiple nucleotides (i.e. molecules comprising a sugar (e.g. ribose or deoxyribose) linked to a phosphate group and to an exchangeable organic base, which is either a substituted pyrimidine (e.g. cytosine (C), thymidine (T) or uracil (U)) or a substituted purine (e.g. adenine (A) or guanine (G)). As used herein, the terms refer to oligoribonucleotides (i.e. a polynucleotide minus the phosphate) and any other organic base containing polymer. Nucleic acid molecules can be obtained from existing nucleic acid sources (e.g. genominc or cDNA), but are preferably synthetic (e.g. produced by nucleic acid synthesis).

In an embodiment, the immunostimulatory oligonucleotides can encompass various chemical modifications and substitutions, in comparison to natural RNA and DNA, involving a phosphodiester internucleoside bridge, a β-D-ribose unit and/or a natural nucleoside base (adenine, guanine, cytosine, thymine, uracil). Examples of chemical modifications are known to the skilled person and are described, for example in Uhlmann E. et al. (1990), Chem. Rev. 90:543; "Protocols for Oligonucleotides and Analogs" Synthesis and Properties & Synthesis and Analytical Techniques, S. Agrawal, Ed., Humana Press, Totowa, USA 1993; Crooke, S. T. et al. (1996) Annu. Rev. Pharmacol. Toxicol. 36:107-129; and Hunziker J. et al., (1995), Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

For example, the oligonucleotides may comprise one or more modifications. Such modifications may be selected from: a) the replacement of a phosphodiester internucleoside bridge located at the 3' and/or the 5' end of a nucleoside by a modified internucleoside bridge, b) the replacement of phosphodiester bridge located at the 3' and/or the 5' end of a nucleoside by a dephospho bridge, c) the replacement of a sugar phosphate unit from the sugar phosphate backbone by another unit, d) the replacement of a β-D-ribose unit by a modified sugar unit, and e) the replacement of a natural nucleoside base.

Nucleic acids also include substituted purines and pyrimidines, such as C-5 propyne pyrimidine and 7-deaza-7-substituted purine modified bases (Wagner et al., 1996, Nat. Biotechnol. 14:840-4). Purines and pyrimidines include but are not limited to adenine, cytosine, guanine, thymidine, 5-methlycytosine, 2-aminopurine, 2-amino-6-chloropurine, 2, 6-diaminoputine, hypoxanthine, and other naturally and non-naturally occurring nucleobases, substituted and unsubstituted aromatic moieties. Other such modifications are well known to those of skill in the art.

A modified base is any base which is chemically distinct from the naturally occurring bases typically found in DNA and RNA, such as T, C, G, A, and U, but which share basic chemical structures with these naturally occurring bases. The modified nucleoside base may be, for example, selected from hypoxanthine, uracil, dihydrouracil pseudouracil, 2-thiouracil, 4-thiouracil, 5-aminouracil, 5-(C1-C6)-alkyluracil, 5-(C2-C6)-alkenyluracil, 5-(C2-C6)-alkylnyluracil, 5-(hydroxymethyl)uracil, 5-chlorouracil, 5-fluorouracil, 5-bromouracil, 5-hydroxycytosine, 5-(C1-C6)-alkylcytosine, 5-(C2-C6)-alkenylcytosine, 5-(C2-C6)-alkylnylcytosine, 5-chlorocytosine, 5-fluorocytosine, 5-bromocytosine, N2-dimethylguanine, 2, 4-dimaino-purine, 8-azapurine, a substituted 7-deazapurine, preferably 7-deaza-7-substituted and/or 7-deaza-8-substituted purine, 5-hydroxymethlycytosine, N4-alkylcytosine, e.g., N4-ethylcytosine, 5-hydroxydeoxycytidine, 5-hydroxymethyldeoxycytidine, N4-alkyldeoxycytidine, e.g. N4-ethyldeoxycytidine, 6-thiodeoxyguanosine, and deoxyribonucleosides of nitropyrrole, C5-propynylpyrimisine, and diaminopurine e.g., 2, 6-diaminopurine, inosine, 5-methylcytosine, 2-aminopurine, 2-amino-6-chloropurine, hypoxanthine or other modifications of a natural nucleoside base. This list is meant to be exemplary and is not to be interpreted to be limiting.

In some aspects of the invention, the CpG dinculeotide of the immunostimulatory oligonucleotides described herein are preferably unmethylated. An unmethylated CpG motif is an unmethylated cytosine-guanine dinucleotide sequence (i.e. an unmethylated 5' cytosine followed by 3' guanosine and linked by a phosphate bond). In other aspects, the CpG motifs are methylated. A methylated CpG motif is a methylated cytosine-guanine dinucleotide sequence (i.e. a methylated 5' cytosine followed by a 3' guanosine and linked by a phosphate bond).

In some aspects of the invention, an immunostimulatory oligonucleotide can contain a modified cytosine. A modified cytosine is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N, N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer).

In some aspects of the invention, an immunostimulatory oligonucleotide can contain a modified guanine. A modified guanine is a naturally occurring or non-naturally occurring purine base analog of guanine which can replace this base without impairing the immunostimulatory activity of the oligonucleotide. Modified guanines include but are not limited to 7-deeazaguanine, 7-deaza-7-substituted guanine, hypoxanthine, N2-substituted guanines (e.g. N2-methyl-guanine), 5-amino-3-methyl-3H, 6H-thiazolo[4, 5-d]pyrimidine-2, 7-dione, 2, 6-diaminopurine, 2-aminopurine, purine, indole, adenine, substituted adenines (e.g. N6-methyl-adenine, 8-oxo-adenine), 8-substituted guanine (e.g. 8-hydroxyguanine and 8-bromoguanine), and 6-thioguanine. In another embodiment of the invention, the guanine base is substituted by a universal base (e.g. 4-methyl-indole, 5-nitro-indole, and K-base), an aromatic ring system (e.g. benzimidazole or dichloro-benzimidazole, 1-methyl-1H-[1, 2, 4]triazole-3-carboxylic acid amide) or a hydrogen atom (dSpacer).

In certain aspects, the oligonucleotides may include modified internucleotide linkages. These modified linkages may be partially resistant to degradation (e.g. are stabilized). A "stabilized nucleic acid molecule" shall mean a nucleic acid molecule that is relatively resistant to in vivo degradation (e.g. via an exo- or endo-nuclease). Stabilization can be a function of length or secondary structure. Nucleic acids that are tens to hundreds of kilobases long are relatively resistant to in vivo degradation. For shorter nucleic acids, secondary structure can stabilize and increase their effect. The formation of a stem loop structure can stabilize a nucleic acid molecule. For example, if the 3' end of a nucleic acid has self-complementarity to an upstream region so that it can fold back and form a stem loop structure, then the nucleic acid can become stabilized and exhibit more activity.

Nucleic acid stabilization can also be accomplished via phosphate backbone modifications. Oligonucleotides having phosphorothioate linkages, in some embodiments, may provide maximal activity and protect the oligonucleotide from degradation by intracellular exo- and end-nucleases.

For use in vivo, nucleic acids are preferably relatively resistant to degradation (e.g. via endo- and exo-nucleases). It has been demonstrated that modification of the nucleic acid backbone provides enhanced activity of nucleic acids when administered in vivo. Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made e.g. as described in U.S. Pat. No. 4, 469, 863; and alkylphosphotriesters (in which the charged oxygen moiety is alkylated as described in U.S. Pat. No. 5, 023, 243 and European Patent No. 092, 574) can be prepared by automated solid phase synthesis using commercially available reagents. Methods for making other DNA backbone modifications and substitutions have been described (Uhlmann, E. and Peyman, A. (1990) Chem. Rev. 90:544; Goodchild, J. (1990) Bioconjugate Chem. 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C. Constructs having phosphorothioate linkages provide maximal activity and protect the nucleic acid from degradation by intracellular exo- and endo-nucleases. Other modified nucleic acids include phosphodiester modified nucleic acids, combinations of phosphodiester and phosphorothioate nucleic acid, methylphosphonate, methylphosphorothioate, phosphorordithioate, p-ethoxy, and combinations thereof. Each of these combinations and their particular effects on immune cells is discussed in more detail with respect to CpG nucleic acids in PCT Published Patent Applications PCT/US95/01570 (WO 96/02555) and PCT/US97/19791 (WO 98/18810) and in U.S. Pat. Nos. 6,194,388 B1 issued Feb. 27, 2001 and 6,239,116 B1 issued May 29, 2001, the entire contents of which are herein incorporated by reference. It is believed that these modified nucleic acids may show more stimulatory activity due to enhanced nuclease resistance, increased cellular uptake, increased protein binding, and/or altered intracellular localization.

For administration in vivo, nucleic acids may be associated with a molecule that results in higher affinity binding to target cell (e.g. dendritic cell, B-cell, monocytic cell and natural killer (NK) cell) surfaces and/or increased cellular uptake by target cells to form a "nucleic acid delivery complex". Nucleic acids can be ionically, or covalently associated with appropriate molecules using techniques which are well known in the art. A variety of coupling or crosslinking agents can be used e.g. protein A, carbodiimide, and N-succinimidyl-3-(2-pyridyldithio) propionate (SPDP). Nucleic acids can alternatively be encapsulated in liposomes or virosomes using well-known techniques.

Other stabilized nucleic acids include, but are not limited to, nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation. In some embodiments, an immunostimulatory oligonucleotide of the invention may include at least one lipophilic substituted nucleotide analog and/or a pyrimidine-purine dinucleotide.

The oligonucleotides may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'3'-linkage may be a phosphodiester, phosphorothioate or any other modified internucleoside bridge. Methods for accomplishing such linkages are known in the art. For instance, such linkages have been described in Seliger, H. et al., Oligonucleotide analogs with terminal 3'-3'- and 5'-5'-internucleotidic linkages as antisense inhibitors of viral gene expression, Nucleosides & Nucleotides (1991), 10(1-3), 469-77 and Jiang, et al., Pseudocyclic oligonucleotides: in vitro and in vivo properties, Bioorganic & Medicinal Chemistry (1999), 7(12), 2727-2735.

Additionally, 3'3'-linked ODNs where the linkage between the 3' terminal nucleosides is not a phosphodiester, phosphorothioate or other modified bridge, can be prepared using an additional spacer, such as tri- or tetra-ethylenglycol phosphate moiety (Durand, M. et al., Triple-helix formation by an oligonucleotide containing one (dA)12 and two (dT)12 sequences bridged by two hexaethylene glycol chains, Biochemistry (1992), 31(38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence et al., Sterical Recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, NR1R2-phosphoramidate, boranophosphate, α-hydroxybenzyl phosphonate, phosphate-(C1-C21)—O-alkyl ester, phosphate-[(C6-C12)aryl-(C1-C21)-O-alkyl]ester, (C1-C8)alkylphosphonate and/or (C6-C12)arylphosphonate bridges, (C7-C12)-α-hydroxymethyl-aryl (e.g. disclosed in WO 95/01363), wherein (C6-C12)aryl, (C6-C20)aryl and (C6-C14)aryl are optionally substituted by halogen, alkyl, alkoxy, nitro, cyano, and where R1 and R2 are, independently of each other, hydrogen, (C1-C18)-alkyl, (C6-C20)-aryl, (C6-C14)-aryl, (C1-C8)-alkyl, preferably hydrogen, (C1-C8)-alkyl, preferably (C1-C4)-alkyl and/or methoxyethyl, or R1 and R2 form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann E. and Peyman A. in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

The immunostimulatory oligonucleotides of the invention may optionally have chimeric backbones. A chimeric backbone is one that comprises more than one type of linkage. In one embodiment, the chimeric backbone can be represented by the formula: 5'Y1N1ZN2Y2 3'. Y1 and Y2 are nucleic acid molecules having between 1 and 10 nucleotides. Y1 and Y2 each include at least one modified internucleotide linkage. Since at least 2 nucleotides of the chimeric oligonucleotides include backbone modifications these nucleic acids are an example of one type of "stabilized immunostimulatory nucleic acids".

With respect to the chimeric oligonucleotides, Y1 and Y2 are considered independent of one another. This means that each of Y1 and Y2 may or may not have different sequences and different backbone linkages from one another in the same molecule. In some embodiments, Y1 and/or Y2 have between 3 and 8 nucleotides. N1 and N2 are nucleic acid molecules having between 0 and 5 nucleotides as long as N1ZN2 has at least 6 nucleotides in total. The nucleotides of N1ZN2 have a phosphodiester backbone and do not include nucleic acids having a modified backbone. Z is an immunostimulatory nucleic acid motif, preferably selected from those recited herein.

The center nucleotides (N1ZN2) of the formula Y1N1ZN2Y2 have phosphodiester internucleotide linkages and Y1 and Y2 have at least one, but may have more than one or even may have all modified internucleotide linkages. In preferred embodiments, Y1 and/or Y2 have at least two or between two and five modified internucleotide linkages or Y1 has five modified internucleotide linkages and Y2 has two modified internucleotide linkages. The modified internucleotide linkage, in some embodiments, is a phosphorothioate modified linkage, a phosphoroditioate linkage or a p-ethoxy modified linkage.

The nucleic acids also include nucleic acids having backbone sugars which are covalently attached to low molecular weight organic groups other than a hydroxyl group at the 2' position and other than a phosphate group at the 5' position. Thus, modified nucleic acids may include a 2'-O-alkylated ribose group. In addition, modified nucleic acids may include sugars such as arabinose or 2'-fluoroarabinsoe instead of ribose. Thus the nucleic acids may be heterogeneous in backbone composition thereby containing any possible combination of polymer units linked together such as peptide-nucleic acids (which have amino acid backbone with nucleic acid bases). In some embodiments, the nucleic acids are homogeneous in backbone composition.

A sugar phosphate unit (i.e. a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E. P. et al. (1989) Nucleic Acid Res. 17:6129-41), that is, e.g., the replacement by a morpholino-derivative; or to build up a polyamide nucleic acid ("PNA"; as described for example, in Nielsen P. E. et al. (1994) Bioconjug. Chem. 5:3-7), that is e.g., the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A β-ribose unit or a β-D-2' deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O—(C1-C6)alkyl-ribose, preferably 2'-O—(C1-C6) alkyl-ribose is 2'-O-methylribose, 2'-O—(C1-C6)alkenyl-ribose, 2'40-(C1-C6)alkyl-O—(C1-C6)alkylFribose, 2'—NH2-2'-deoxyribose, β-D-xylo-furanose, α-arabinofuranose, 2, 4-dideoxy-β-D-erythro-hexo-pyranose, and carbocyclic (described, for example, in Froehler J. (1992) Am. Chem. Soc. 114:8320) and/or open-chain sugar analogs (described, for example, in Vandendriessche et al. (1993) Tetrahedron 49:7223) and/or bicyclosugar analogs (described, for example, in Tarkov M. et al. (1993) Helv. Chim. Acta. 76:481.

In some embodiments, the sugar is 2'-O-methylribose, particularly for one or both nucleotides linked by a phosphodiester or phosphodiester-like internucleoside linkage. The oligonucleotides of the invention can be synthesized de novo using any of a number of procedures well known in the art. For example, the b-cyanoethyl phosphoramidite method (Beaucage, S. L., and Caruthers, M. H., (1981) Tet. Let. 22:1589); nucleoside H-phosphonate method (Garegg et al., (1986) Tet. Let. 27:4051-4054; Froehler et al., (1986) Nucl. Acid Res.14:5399-5407; Garegg et al., (1986) 27:4055-4058; Gaffney et al., (1988) Tet. Let. 29:2619-2622). These chemistries can be performed by a variety of automated nucleic acid synthesizers available in the market. These oligonucleotides are referred to as synthetic oligonucleotides. Alternatively, T-rich and/or TG dinucleotides can be produced on a large scale in plasmids, (see Sambrook T. et al., "Molecular Cloning: A Laboratory Manual", Cold Spring Harbor laboratory Press, New York, 1989) and separated into smaller pieces or administered whole. Nucleic acids can be prepared from existing nucleic acid sequences (e.g. genomic or cDNA) using known techniques, such as those employing restriction enzymes, exonucleases or endonucleases.

Modified backbones such as phosphorothioates may be synthesized using automated techniques employing either phosphoramidate or H-phosphonate chemistries. Aryl- and alkyl-phoshonates can be made, e.g. as described in U.S. Pat. No. 4, 469, 863, and alkylphosphotriesters (in which the charged oxygen moiety is alkylated as described in U.S. Pat. No. 5,023,243) can be prepared by automated solid phase synthesis using commercially available reagents. Methods for making other DNA backbone modifications and substitutions have been described (e.g. Uhlmann, E. and Peyman, A., Chem. Rev. 90:544, 1990; Goodchild, J., Bioconjugate Chem. 1:165, 1990).

Nucleic acids prepared in this manner are referred to as isolated nucleic acid. An "isolated nucleic acid" generally refers to a nucleic acid which is separated from components with which it is separated from a cell, from a nucleus, from mitochondria or from chromatin and any other components that may be considered as contaminants.

In an embodiment, the immunogenic composition of the present invention comprises at least one adjuvant which is a CpG Oligonucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

Different classes of CpG immunostimulatory oligonucleotides have been identified. These are referred to as A, B, C and P class, and are described in greater detail below. Methods and compositions of the invention embrace the use of these different classes of CpG immunostimulatory oligonucleotides.

Any of the classes may be subjugated to an E modification which enhances its potency. An E modification may be a halogen substitution for the 5' terminal nucleotide; examples of such substitutions include but are not limited to bromo-uridine or iodo-uridine substitutions. An E modification can also include an ethyl-uridine substitution for the 5' terminal nucleotide.

The "A class" CpG immunostimulatory oligonucleotides are characterized functionally by the ability to induce high levels of interferon-alpha (IFN-α) from plasmacytoid dendritic cells (pDC) and inducing NK cell activation while having minimal effects on B cell activation. Structurally, this class typically has stabilized poly-G sequences at 5' and 3' ends. It also has a palindromic phosphodiester CpG dinucleotide-containing sequence of at least 6 nucleotides, for example but not necessarily, it contains one of the following hexamer palindromes: GACGTC, AGCGCT, or AACGTT described by Yamamoto and colleagues. Yamamoto S et al. J. Immunol. 148:4072-6 (1992). A class CpG immunostimulatory oligonucleotides and exemplary sequences of this class have been described in U.S. Non-Provisional patent application Ser. No. 09/672, 126 and published PCT application PCT/US00/26527 (WO 01/22990), both filed on Sep. 27, 2000.

In an embodiment, the "A class" CpG oligonucleotide of the invention has the following nucleic acid sequence: 5' GGGGACGACGTCGTGGGGGGG 3' (SEQ ID NO: 440).

Some non-limiting examples of A-Class oligonucleotides include: 5' G*G*G_G_A_C_G_A_C_G_T_C_G_T_G_G* G*G*G*G*G 3' (SEQ ID NO: 440); wherein * refers to a phosphorothioate bond and _ refers to a phosphodiester bond.

The "B class" CpG immunostimulatory oligonucleotides are characterized functionally by the ability to activate B cells and pDC except are relatively weak in inducing IFN-α and NK cell activation. Structurally, this class typically may be fully stabilized with phosphorothioate linkages, but it may also have one or more phosphodiester linkages, preferably between the cytosine and guanine of the CpG motif(s), in which case the molecule is referred to as semi-soft. In one embodiment, the CpG Oligonucleotide of the present invention is a B class CpG oligonucleotide represented by at least the formula:

5' $X_1X_2CGX_3X_4$ 3', wherein X1, X2, X3, and $X_4$ are nucleotides. In one embodiment, $X_2$ is adenine, guanine, or thymine. In another embodiment, $X_3$ is cytosine, adenine, or thymine.

In another embodiment, the CpG Oligonucleotide of the present invention is a B class CpG oligonucleotide represented by at least the formula:
5' $N_1X_1X_2CGX_3X_4N_2$ 3', wherein $X_1$, $X_2$, $X_3$, and $X_4$ are nucleotides and N is any nucleotide and $N_1$ and $N_2$ are nucleic acid sequences composed of from about 0-25 N's each. In one embodiment, $X_1X_2$ is a dinucleotide selected from the group consisting of GpT, GpG, GpA, ApA, ApT, ApG, CpT, CpA, CpG, TpA, TpT and TpG; and $X_3X_4$ is a dinucleotide selected from the group consisting of TpT, ApT, TpG, ApG, CpG, TpC, ApC, CpC, TpA, ApA and CpA. Preferably $X_1X_2$ is GpA or GpT and X3X4 is TpT. In other embodiments, $X_1$ or $X_2$ or both are purines and $X_3$ or $X_4$ or both are pyrimidines or $X_1X_2$ is GpA and $X_3$ or $X_4$ or both are pyrimidines. In one preferred embodiment, $X_1X_2$ is a dinucleotide selected from the group consisting of TpA, ApA, ApC, ApG and GpG. In yet another embodiment, $X_3X_4$ is a dinucleotide selected from the group consisting of TpT, TpA, TpG, ApA, ApG, GpA and CpA. $X_1X_2$, in another embodiment, is a dinucleotide selected from the group consisting of TpT, TpG, ApT, GpC, CpC, CpT, TpC, GpT and CpG; $X_3$ is a nucleotide selected from the group consisting of A and T, and $X_4$ is a nucleotide, but when $X_1X_2$ is TpC, GpT or CpG, $X_3X_4$ is not TpC, ApT or ApC.

In another preferred embodiment, the CpG oligonucleotide has the sequence 5' TCN$_1$TX$_1$X$_2$CGX$_3$X$_4$ 3'. The CpG oligonucleotides of the invention, in some embodiments, include $X_1X_2$ selected from the group consisting of GpT, GpG, GpA and ApA and X3X4 selected from the group consisting of TpT, CpT and TpC.

The B class CpG oligonucleotide sequences of the invention are those broadly described above as well as disclosed in published PCT Patent Applications PCT/US95/01570 and PCT/US97/19791, and in U.S. Pat. Nos. 6,194,388, 6,207, 646, 6, 214,806, 6,218,371, 6,239,116 and 6,339,068. Exemplary sequences include but are not limited to those disclosed in these latter applications and patents.

In an embodiment, the "B class" CpG oligonucleotide of the invention has the following nucleic acid sequence:

```
                                           (SEQ ID NO: 431)
5' TCGTCGTTTTTCGGTGCTTTT 3',
or
                                           (SEQ ID NO: 432)
5' TCGTCGTTTTTCGGTCGTTTT 3',
or
                                           (SEQ ID NO: 433)
5' TCGTCGTTTGTCGTTTTGTCGTT 3',
or
                                           (SEQ ID NO: 441)
5' TCGTCGTTTCGTCGTTTTGTCGTT 3',
or
                                           (SEQ ID NO: 442)
5' TCGTCGTTTTGTCGTTTTTTTCGA 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

Some non-limiting examples of B-Class oligonucleotides include:

```
                                           (SEQ ID NO: 431)
5'T*C*G*T*C*G*T*T*T*T*T*C*G*G*T*G*C*T*T*T*T 3',
or
                                           (SEQ ID NO: 432)
5'T*C*G*T*C*G*T*T*T*T*T*C*G*G*T*C*G*T*T*T*T 3',
or
                                           (SEQ ID NO: 433)
5'T*C*G*T*C*G*T*T*T*T*G*T*C*G*T*T*T*T*G*T*C*G*T*T 3',
or
                                           (SEQ ID NO: 441)
5'T*C*G*T*C*G*T*T*T*C*G*T*C*G*T*T*T*T*G*T*C*G*T*T 3',
or
                                           (SEQ ID NO: 442)
5'T*C*G*T*C*G*T*T*T*T*G*T*C*G*T*T*T*T*T*T*T*C*G*A 3',
wherein * refers to a phosphorothioate bond.
```

The "C class" of CpG immunostimulatory oligonucleotides is characterized functionally by the ability to activate B cells and NK cells and induce IFN-α. Structurally, this class typically includes a region with one or more B class-type immunostimulatory CpG motifs, and a GC-rich palindrome or near-palindrome region that allows the molecules to form secondary (e.g., stem-loop) or tertiary (e.g., dimer) type structures. Some of these oligonucleotides have both a traditional "stimulatory" CpG sequence and a "GC-rich" or "B-cell neutralizing" motif. These combination motif oligonucleotides have immune stimulating effects that fall somewhere between the effects associated with traditional B class CpG oligonucleotides (i.e., strong induction of B cell activation and dendritic cell (DC) activation), and the effects associated with A class CpG ODN (i.e., strong induction of IFN-α and NK cell activation but relatively poor induction of B cell and DC activation). Krieg A M et al. (1995) Nature 374:546-9; Ballas Z K et al. (1996) J Immunol 157:1840-5; Yamamoto S et al. (1992) J Immunol 148:4072-6.

The C class of combination motif immune stimulatory oligonucleotides may have either completely stabilized, (e.g., all phosphorothioate), chimeric (phosphodiester central region), or semi-soft (e.g., phosphodiester within CpG motif) backbones. This class has been described in U.S. patent application U.S. Ser. No. 10/224,523 filed on Aug. 19, 2002. One stimulatory domain or motif of the C class CpG oligonucleotide is defined by the formula: 5' $X_1DCGHX_2$ 3'. D is a nucleotide other than C. C is cytosine. G is guanine. H is a nucleotide other than G. $X_1$ and $X_2$ are any nucleic acid sequence 0 to 10 nucleotides long. $X_1$ may include a CG, in which case there is preferably a T immediately preceding this CG. In some embodiments, DCG is TCG. $X_1$ is preferably from 0 to 6 nucleotides in length. In some embodiments, $X_2$ does not contain any poly G or poly A motifs. In other embodiments, the immunostimulatory oligonucleotide has a poly-T sequence at the 5' end or at the 3' end. As used herein, "poly-A" or "poly-T" shall refer to a stretch of four or more consecutive A's or T's respectively, e.g., 5' AAAA 3' or 5' TTTT 3'. As used herein, "poly-G end" shall refer to a stretch of four or more consecutive G's, e.g., 5' GGGG 3', occurring at the 5' end or the 3' end of a nucleic acid. As used herein, "poly-G oligonucleotide" shall refer to an oligonucleotide having the formula 5' $X_1X_2GGGX_3X_4$ 3' wherein $X_1$, $X_2$, $X_3$, and $X_4$ are nucleotides and preferably at least one of $X_3$ and $X_4$ is a G. Some preferred designs for the B cell stimulatory domain under this formula comprise TTTTTCG, TCG, TTCG, TTTCG, TTTTCG, TCGT, TTCGT, TTTCGT, TCGTCGT.

The second motif of the C class CpG oligonucleotide is referred to as either P or N and is positioned immediately 5' to $X_1$ or immediately 3' to $X_2$.

N is a B cell neutralizing sequence that begins with a CGG trinucleotide and is at least 10 nucleotides long. A B cell neutralizing motif includes at least one CpG sequence in which the CG is preceded by a C or followed by a G (Krieg A M et al. (1998) Proc Natl Acad Sd USA 95:12631-12636) or is a CG containing DNA sequence in which the C of the CG is methylated. Neutralizing motifs or sequences have some degree of immunostimulatory capability when present in an otherwise non-stimulatory motif, but when present in the context of other immunostimulatory motifs serve to reduce the immunostimulatory potential of the other motifs.

P is a GC-rich palindrome containing sequence at least 10 nucleotides long.

As used herein, "palindrome" and equivalently "palindromic sequence" shall refer to an inverted repeat, i.e., a sequence such as ABCDEE'D'C'B'A' in which A and A', B and B', etc., are bases capable of forming the usual Watson-Crick base pairs.

As used herein, "GC-rich palindrome" shall refer to a palindrome having a base composition of at least two-thirds G's and Cs. In some embodiments the GC-rich domain is preferably 3' to the "B cell stimulatory domain". In the case of a 10-base long GC-rich palindrome, the palindrome thus contains at least 8 G's and Cs. In the case of a 12-base long GC-rich palindrome, the palindrome also contains at least 8 G's and Cs. In the case of a 14-mer GC-rich palindrome, at least ten bases of the palindrome are G's and Cs. In some embodiments the GC-rich palindrome is made up exclusively of G's and Cs.

In some embodiments the GC-rich palindrome has a base composition of at least 81% G's and Cs. In the case of such a 10-base long GC-rich palindrome, the palindrome thus is made exclusively of G's and Cs. In the case of such a 12-base long GC-rich palindrome, it is preferred that at least ten bases (83%) of the palindrome are G's and Cs. In some preferred embodiments, a 12-base long GC-rich palindrome is made exclusively of G's and Cs. In the case of a 14-mer GC-rich palindrome, at least twelve bases (86%) of the palindrome are G's and Cs. In some preferred embodiments, a 14-base long GC-rich palindrome is made exclusively of G's and Cs. The Cs of a GC-rich palindrome can be unmethylated or they can be methylated.

In general this domain has at least 3 Cs and Gs, more preferably 4 of each, and most preferably 5 or more of each. The number of Cs and Gs in this domain need not be identical. It is preferred that the Cs and Gs are arranged so that they are able to form a self-complementary duplex, or palindrome, such as CCGCGCGG. This may be interrupted by As or Ts, but it is preferred that the self-complementarity is at least partially preserved as for example in the motifs CGACGT-TCGTCG (SEQ ID NO: 487) or CGGCGCCGTGCCG (SEQ ID NO: 488). When complementarity is not preserved, it is preferred that the non-complementary base pairs be TG. In a preferred embodiment there are no more than 3 consecutive bases that are not part of the palindrome, preferably no more than 2, and most preferably only 1. In some embodiments, the GC-rich palindrome includes at least one CGG trimer, at least one CCG trimer, or at least one CGCG tetramer. In other embodiments, the GC-rich palindrome is not CCCCCCGGGGGG (SEQ ID NO: 489) or GGGGGGC-CCCCC (SEQ ID NO: 490), CCCCCGGGGG (SEQ ID NO: 491) or GGGGGCCCCC (SEQ ID NO: 492).

At least one of the G's of the GC rich region may be substituted with an inosine (I). In some embodiments, P includes more than one I.

In certain embodiments, the immunostimulatory oligonucleotide has one of the following formulas 5' $NX_1DCGHX_2$ 3', 5' $X_1DCGHX_2N$ 3', 5' $PX_1DCGHX_2$ 3', 5' $X_1DCGHX_2P$ 3', 5' $X_1DCGHX_2PX_3$ 3', 5' $X_1DCGHPX_3$ 3', 5' $DCGHX_2PX_3$ 3', 5' $TCGHX_2PX_3$ 3', 5' $DCGHPX_3$ 3' or 5'DCGHP 3'.

The invention provides other immune stimulatory oligonucleotides defined by a formula 5' $N_1PyGN_2P$ 3'. $N_1$ is any sequence 1 to 6 nucleotides long. Py is a pyrimidine. G is guanine. $N_2$ is any sequence 0 to 30 nucleotides long. P is a GC-rich palindrome containing a sequence at least 10 nucleotides long.

$N_1$ and $N_2$ may contain more than 50% pyrimidines, and more preferably more than 50% T. $N_1$ may include a CG, in which case there is preferably a T immediately preceding this CG. In some embodiments, N1PyG is TCG, and most preferably a $TCGN_2$, where $N_2$ is not G.

$N_1PyGN_2P$ may include one or more inosine (I) nucleotides. Either the C or the G in $N_1$ may be replaced by inosine, but the CpI is preferred to the IpG. For inosine substitutions such as IpG, the optimal activity may be achieved with the use of a "semi-soft" or chimeric backbone, where the linkage between the IG or the CI is phosphodiester. N1 may include at least one CI, TCI, IG or TIG motif.

In certain embodiments $N_1PyGN_2$ is a sequence selected from the group consisting of TTTTTCG, TCG, TTCG, TTTCG, TTTTCG, TCGT, TTCGT, TTTCGT, and TCGTCGT.

In an embodiment, the "C class" CpG oligonucleotides of the invention has the following nucleic acid sequence:

```
                                          (SEQ ID NO: 443)
5' TCGCGTCGTTCGGCGCGCGCCG 3',
or
                                          (SEQ ID NO: 444)
5' TCGTCGACGTTCGGCGCGCGCCG 3',
or
                                          (SEQ ID NO: 445)
5' TCGGACGTTCGGCGCGCGCCG 3',
or
                                          (SEQ ID NO: 446)
5' TCGGACGTTCGGCGCGCCG 3',
or
                                          (SEQ ID NO: 447)
5' TCGCGTCGTTCGGCGCGCCG 3',
or
                                          (SEQ ID NO: 448)
5' TCGACGTTCGGCGCGCGCCG 3',
or
                                          (SEQ ID NO: 449)
5' TCGACGTTCGGCGCGCCG 3',
or
                                          (SEQ ID NO: 450)
5' TCGCGTCGTTCGGCGCCG 3',
or
                                          (SEQ ID NO: 451)
5' TCGCGACGTTCGGCGCGCGCCG 3',
or
                                          (SEQ ID NO: 452)
5' TCGTCGTTTTCGGCGCGCGCCG 3',
or
                                          (SEQ ID NO: 453)
5' TCGTCGTTTTCGGCGGCCGCCG 3',
or
                                          (SEQ ID NO: 454)
5' TCGTCGTTTTACGGCGCCGTGCCG 3',
or
                                          (SEQ ID NO: 455)
5' TCGTCGTTTTCGGCGCGCGCCGT 3'.
```

In any of these sequences, all of the linkages may be all phosphorothioate bonds. In another embodiment, in any of these sequences, one or more of the linkages may be phosphodiester, preferably between the "C" and the "G" of the CpG motif making a semi-soft CpG oligonucleotide.

Some non-limiting examples of C-Class oligonucleotides include:

```
                                          (SEQ ID NO: 443)
5'T*C_G*C_G*T*C_G*T*T*C_G*G*C*G*C_G*C*G*C*C*G 3',
or
                                          (SEQ ID NO: 444)
5'T*C_G*T*C_G*A*C_G*T*T*C_G*G*C*G*C_G*C*G*C*C*G 3',
or
                                          (SEQ ID NO: 445)
5'T*C_G*G*A*C_G*T*T*C_G*G*C*G*C_G*C*G*C*C*G 3',
or
                                          (SEQ ID NO: 446)
5'T*C_G*G*A*C_G*T*T*C_G*G*C*G*C*G*C*C*G 3'
or
                                          (SEQ ID NO: 447)
5'T*C_G*C_G*T*C_G*T*T*C_G*G*C*G*C*G*C*C*G 3',
or
                                          (SEQ ID NO: 448)
5'T*C_G*A*C_G*T*T*C_G*G*C*G*C_G*C*G*C*C*G 3',
or
                                          (SEQ ID NO: 449)
5'T*C_G*A*C_G*T*T*C_G*G*C*G*C*G*C*C*G 3',
or
```

```
                                                 (SEQ ID NO: 450)
5'T*C_G*C_G*T*C_G*T*T*C_G*G*C*G*C*C*G 3',
or (SEQ ID NO: 451)
5'T*C_G*C_G*A*C_G*T*T*C_G*G*C*G*C_G*C*G*C*C*G 3',
or (SEQ ID NO: 452)
5'T*C*G*T*C*G*T*T*T*T*C*G*G*C*G*C*G*C*G*C*C*G 3',
or (SEQ ID NO: 453)
5'T*C*G*T*C*G*T*T*T*T*C*G*G*C*G*G*C*C*G*C*C*G 3',
or (SEQ ID NO: 454)
5'T*C*G*T*C_G*T*T*T*T*A*C_G*G*C*G*C*C_G*T*G*C*C*G 3',
or (SEQ ID NO: 455)
5'T*C_G*T*C*G*T*T*T*T*C*G*G*C*G*C*G*C*G*C*C*G*T 3',
wherein * refers to a phosphorothioate bond and _ refers to a
phosphodiester bond. In any of these sequences, an ethyl-
uridine or a halogen may substitute for the 5'T; examples of
halogen substitutions include but are not limited to bromo-
uridine or iodouridine substitutions.
```

The "P class" CpG immunostimulatory oligonucleotides have been described in WO2007/095316 and are characterized by the fact that they contain duplex forming regions such as, for example, perfect or imperfect palindromes at or near both the 5' and 3' ends, giving them the potential to form higher ordered structures such as concatamers. These oligonucleotides referred to as P-Class oligonucleotides have the ability in some instances to induce much high levels of IFN-α secretion than the C-Class. The P-Class oligonucleotides have the ability to spontaneously self-assemble into concatamers either in vitro and/or in vivo. Without being bound by any particular theory for the method of action of these molecules, one potential hypothesis is that this property endows the P-Class oligonucleotides with the ability to more highly crosslink TLR9 inside certain immune cells, inducing a distinct pattern of immune activation compared to the previously described classes of CpG oligonucleotides.

In an embodiment, the CpG Oligonucleotide of the present invention is a P class CpG oligonucleotide containing a 5' TLR activation domain and at least two palindromic regions, one palindromic region being a 5' palindromic region of at least 6 nucleotides in length and connected to a 3' palindromic region of at least 8 nucleotides in length either directly or through a spacer, wherein the oligonucleotide includes at least one YpR dinucleotide. In an embodiment, said oligonucleotide is not T*C_G*T*C_G*A*C_G*T*T*C_G* G*C*G*C_G*C*G*C*C*G (SEQ ID NO: 444). In one embodiment the P class CpG oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In yet another embodiment the TLR activation domain is within the 5' palindromic region. In another embodiment the TLR activation domain is immediately 5' to the 5' palindromic region. In still another embodiment the 5' palindromic region is at least 8 nucleotides in length. In another embodiment the 3' palindromic region is at least 10 nucleotides in length. In another embodiment the 5' palindromic region is at least 10 nucleotides in length. In yet another embodiment the 3' palindromic region includes an unmethylated CpG dinucleotide. In another embodiment the 3' palindromic region includes two unmethylated CpG dinucleotides. In another embodiment the 5' palindromic region includes an unmethylated CpG dinucleotide. In yet another embodiment the 5' palindromic region includes two unmethylated CpG dinucleotides. In another embodiment the 5' and 3' palindromic regions have a duplex stability value of at least 25. In another embodiment the 5' and 3' palindromic regions have a duplex stability value of at least 30. In another embodiment the 5' and 3' palindromic regions have a duplex stability value of at least 35. In another embodiment the 5' and 3' palindromic regions have a duplex stability value of at least 40. In another embodiment the 5' and 3' palindromic regions have a duplex stability value of at least 45. In another embodiment the 5' and 3' palindromic regions have a duplex stability value of at least 50. In another embodiment the 5' and 3' palindromic regions have a duplex stability value of at least 55. In another embodiment the 5' and 3' palindromic regions have a duplex stability value of at least 60. In another embodiment the 5' and 3' palindromic regions have a duplex stability value of at least 65.

In one embodiment the two palindromic regions are connected directly. In another embodiment the two palindromic regions are connected via a 3'-3' linkage. In another embodiment the two palindromic regions overlap by one nucleotide. In yet another embodiment the two palindromic regions overlap by two nucleotides. In another embodiment the two palindromic regions do not overlap. In another embodiment the two palindromic regions are connected by a spacer. In one embodiment the spacer is a nucleic acid having a length of 1-50 nucleotides. In another embodiment the spacer is a nucleic acid having a length of 1 nucleotide. In another embodiment the spacer is a non-nucleotide spacer. In one embodiment the non-nucleotide spacer is a D-spacer. In another embodiment the non-nucleotide spacer is a linker. In one embodiment the oligonucleotide has the formula 5' $XP_1SP_2T$ 3', wherein X is the TLR activation domain, $P_1$ is a palindrome, S is a spacer, $P_2$ is a palindrome, and T is a 3' tail of 0-100 nucleotides in length. In one embodiment X is TCG, TTCG, or TTTCG. In another embodiment T is 5-50 nucleotides in length. In yet another embodiment T is 5-10 nucleotides in length. In one embodiment S is a nucleic acid having a length of 1-50 nucleotides. In another embodiment S is a nucleic acid having a length of 1 nucleotide. In another embodiment S is a non-nucleotide spacer. In one embodiment the non-nucleotide spacer is a D-spacer. In another embodiment the non-nucleotide spacer is a linker. In another embodiment the oligonucleotide is not an antisense oligonucleotide or a ribozyme. In one embodiment $P_1$ is A and T rich. In another embodiment $P_1$ includes at least 4 Ts. In another embodiment $P_2$ is a perfect palindrome. In another embodiment P2 is G-C rich. In still another embodiment $P_2$ is $CGGCGCX_1GCGCCG$, where $X_1$ is T or nothing.

In one embodiment the oligonucleotide includes at least one phosphorothioate linkage. In another embodiment all internucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the CpG Oligonucleotide for use in the present invention is a P class CpG oligonucleotide with a 5' TLR activation domain and at least two complementarity-containing regions, a 5' and a 3' complementarity-containing region, each complementarity-containing region being at least 8 nucleotides in length and connected to one another either directly or through a spacer, wherein the oligonucleotide includes at least one pyrimidine-purine (YpR) dinucleotide, and wherein at least one of the complementarity-containing regions is not a perfect palindrome. In one embodiment the oligonucleotide includes at least one unmethylated CpG dinucleotide. In another embodiment the TLR activation domain is TCG, TTCG, TTTCG, TYpR, TTYpR, TTTYpR, UCG, UUCG, UUUCG, TTT, or TTTT. In another embodiment the TLR activation domain is within the 5' complementarity-containing region. In another embodiment the TLR activation domain is immediately 5' to the 5' complementarity-containing region. In another embodiment the 3' complementarity-containing region is at least 10 nucleotides in length. In yet another embodiment the 5' complementarity-containing region is at least 10 nucleotides in length. In one embodiment the 3' complementarity-containing region includes an unmethylated CpG dinucleotide. In another embodiment the 3' complementarity-containing region includes two unmethylated CpG dinucleotides. In yet another embodiment the 5' complementarity-containing region includes an unmethylated CpG dinucleotide. In another embodiment the 5' complementarity-containing region includes two unmethylated CpG dinucleotides. In another embodiment the complementarity-containing regions include at least one nucleotide analog. In another embodiment the complementarity-containing regions form an intramolecular duplex. In one embodiment the intramolecular duplex includes at least one non-Watson Crick base pair. In another embodiment the non-Watson Crick base pair is G-T, G-A, G-G, or C-A. In one embodiment the complementarity-containing regions form intermolecular duplexes. In another embodiment at least one of the intermolecular duplexes includes at least one non-Watson Crick base pair. In another embodiment the non-Watson Crick base pair is G-T, G-A, G-G, or C-A. In yet another embodiment the complementarity-containing regions contain a mismatch. In still another embodiment the complementarity-containing regions contain two mismatches. In another embodiment the complementarity-containing regions contain an intervening nucleotide. In another embodiment the complementarity-containing regions contain two intervening nucleotides.

In one embodiment the 5' and 3' complementarity-containing regions have a duplex stability value of at least 25. In another embodiment the 5' and 3' complementarity-containing regions have a duplex stability value of at least 30. In another embodiment the 5' and 3' complementarity-containing regions have a duplex stability value of at least 35. In another embodiment the complementarity-containing regions have a duplex stability value of at least 40. In another embodiment the complementarity-containing regions have a duplex stability value of at least 45. In another embodiment the complementarity-containing regions have a duplex stability value of at least 50. In another embodiment the complementarity-containing regions have a duplex stability value of at least 55. In another embodiment the complementarity-containing regions have a duplex stability value of at least 60. In another embodiment the complementarity-containing regions have a duplex stability value of at least 65.

In another embodiment the two complementarity-containing regions are connected directly. In another embodiment the two palindromic regions are connected via a 3'-3' linkage. In yet another embodiment the two complementarity-containing regions overlap by one nucleotide. In another embodiment the two complementarity-containing regions overlap by two nucleotides. In another embodiment the two complementarity-containing regions do not overlap. In another embodiment the two complementarity-containing regions are connected by a spacer. In another embodiment the spacer is a nucleic acid having a length of 1-50 nucleotides. In another embodiment the spacer is a nucleic acid having a length of 1 nucleotide. In one embodiment the spacer is a non-nucleotide spacer. In another embodiment the non-nucleotide spacer is a D-spacer. In yet another embodiment the non-nucleotide spacer is a linker.

In one embodiment the P-class oligonucleotide has the formula 5' XNSPT 3', wherein X is the TLR activation domain, N is a non-perfect palindrome, P is a palindrome, S is a spacer, and T is a 3' tail of 0-100 nucleotides in length. In another embodiment X is TCG, TTCG, or TTTCG. In another embodiment T is 5-50 nucleotides in length. In another embodiment T is 5-10 nucleotides in length. In another embodiment S is a nucleic acid having a length of 1-50 nucleotides. In another embodiment S is a nucleic acid having a length of 1 nucleotide. In another embodiment S is a non-nucleotide spacer. In another embodiment the non-nucleotide spacer is a D-spacer. In another embodiment the non-nucleotide spacer is a linker. In another embodiment the oligonucleotide is not an antisense oligonucleotide or a ribozyme. In another embodiment N is A and T rich. In another embodiment N is includes at least 4 Ts. In another embodiment P is a perfect palindrome. In another embodiment P is G-C rich. In another embodiment P is CGGCGCX$_1$GCGCCG, wherein X$_1$ is T or nothing. In another embodiment the oligonucleotide includes at least one phosphorothioate linkage. In another embodiment all interaucleotide linkages of the oligonucleotide are phosphorothioate linkages. In another embodiment the oligonucleotide includes at least one phosphodiester-like linkage. In another embodiment the phosphodiester-like linkage is a phosphodiester linkage. In another embodiment a lipophilic group is conjugated to the oligonucleotide. In one embodiment the lipophilic group is cholesterol.

In an embodiment, the "P class" CpG oligonucleotides of the invention has the following nucleic acid sequence: 5' TCGTCGACGATCGGCGCGCGCCG 3' (SEQ ID NO: 456). In said sequences, all of the linkages may be all phosphorothioate bonds. In another embodiment, one or more of the linkages may be phosphodiester, preferably between the "C" and the "G" of the CpG motif making a semi-soft CpG oligonucleotide. In any of these sequences, an ethyl-uridine or a halogen may substitute for the 5' T; examples of halogen substitutions include but are not limited to bromo-uridine or iodo-uridine substitutions.

A non-limiting example of P-Class oligonucleotides include: 5' T*C_G*T*C_G*A*C_G*A*T*C_G*G*C* G*C_G*C*G*C*C*G 3' (SEQ ID NO: 456), wherein * refers to a phosphorothioate bond and _ refers to a phosphodiester bond.

In an embodiment, all the internucleotide linkage of the CpG oligonucleotides disclosed herein are phosphodiester bonds ("soft" oligonucleotides, as described in the PCT application WO2007/026190). In another embodiment, CpG oligonucleotides of the invention are rendered resistant to degradation (e.g., are stabilized). A "stabilized oligonucleotide" refers to an oligonucleotide that is relatively resistant to in vivo degradation (e.g. via an exo- or endo-nuclease). Nucleic acid stabilization can be accomplished via backbone modifications. Oligonucleotides having phosphorothioate linkages provide maximal activity and protect the oligonucleotide from degradation by intracellular exo- and endo-nucleases.

The immunostimulatory oligonucleotides may have a chimeric backbone, which have combinations of phosphodiester and phosphorothioate linkages. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. When the phosphodiester linkage is preferentially located within the CpG motif such molecules are called "semi-soft" as described in the PCT application WO2007/026190.

Other modified oligonucleotides include combinations of phosphodiester, phosphorothioate, methylphosphonate, methylphosphorothioate, phosphorodithioate, and/or p-ethoxy linkages.

Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could, in some embodiments, includes at least one phosphodiester (phosphodiester or phosphodiester-like) linkage and at least one boranophosphonate (stabilized) linkage. In other embodiments, a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endo-nuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation, peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4, 469, 863; and alkylphosphotriesters (in which the charged oxygen moiety is alkylated as described in U.S. Pat. No. 5, 023, 243 and European Patent No. 092, 574) can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165. Methods for preparing chimeric oligonucleotides are also known. For instance patents issued to Uhlmann et al have described such techniques. Mixed backbone modified ODN may be synthesized as described in the PCT application WO2007/026190.

The oligonucleotides of the invention can also include other modifications. These include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain diol, such as tetraethyleneglycol or hexaethyleneglycol, at either or both termini have also been shown to be substantially resistant to nuclease degradation.

The size of the CpG oligonucleotide (i.e., the number of nucleotide residues along the length of the oligonucleotide) also may contribute to the stimulatory activity of the oligonucleotide. For facilitating uptake into cells, CpG oligonucleotide of the invention preferably have a minimum length of 6 nucleotide residues. Oligonucleotides of any size greater than 6 nucleotides (even many kb long) are capable of inducing an immune response if sufficient immunostimulatory motifs are present, because larger oligonucleotides are degraded inside cells. In certain embodiments, the CpG oligonucleotides are 6 to 100 nucleotides long, preferentially 8 to 30 nucleotides long. In important embodiments, nucleic acids and oligonucleotides of the invention are not plasmids or expression vectors.

In an embodiment, the CpG oligonucleotide disclosed herein comprise substitutions or modifications, such as in the bases and/or sugars as described at paragraph 134 to 147 of WO2007/026190.

In an embodiment, the CpG oligonucleotide of the present invention is chemically modified. Examples of chemical modifications are known to the skilled person and are described, for example in Uhlmann E. et al. (1990), Chem. Rev. 90:543, S. Agrawal, Ed., Humana Press, Totowa, USA 1993; Crooke, S. T. et al. (1996) Annu. Rev. Pharmacol. Toxicol. 36:107-129; and Hunziker J. et al., (1995), Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In some embodiments of the invention, CpG-containing nucleic acids might be simply mixed with immunogenic carriers according to methods known to those skilled in the art (see, e.g. WO03/024480).

In a particular embodiment of the present invention, any of the vaccine disclosed herein comprises from 2 μg to 100 mg of CpG oligonucleotide, preferably from 0.1 mg to 50 mg CpG oligonucleotide, preferably from 0.2 mg to 10 mg CpG oligonucleotide, preferably from 0.3 mg to 5 mg CpG oligonucleotide, preferably from 0.3 mg to 5 mg CpG oligonucleotide, even preferably from 0.5 to 2 mg CpG oligonucleotide, even preferably from 0.75 to 1.5 mg CpG oligonucleotide. In a preferred embodiment, any of the vaccine disclosed herein comprises approximately 1 mg CpG oligonucleotide.

In some embodiments of the invention, CpG-containing nucleic acids might be simply mixed with immunogenic carriers according to methods known to those skilled in the art (see for example WO03/024480). In other embodiments of the invention, CpG-containing nucleic acids might be enclosed within VLPs (see e.g. WO03/024481). Preferred adjuvants in the context of the present invention include alum; CpG-containing oligonucleotides, preferably CpG 7909 (SEQ ID NO: 433) and CpG24555 (SEQ ID NO: 431); and saponin-based adjuvants, preferably Iscomatrix, which could be used alone or in combination. Preferably, said CpG-containing nucleic acid comprises one or more modified linkages, preferably one or more phosphorothioate linkages, even more preferably all internucleotide linkages of the oligonucleotide are phosphorothioate linkages.

The invention therefore provides an immunogenic composition comprising an antigenic IgE peptide, preferably comprising an amino acid sequence selected from the group consisting of SEQ ID Nos: 1 to 430, more preferably an amino acid sequence selected from the group consisting of SEQ ID Nos: 1 to 153 and 220 to 430, even more preferably an amino acid sequence selected from the group consisting of SEQ ID Nos: 220 to 430 and at least one adjuvant. Said antigenic IgE peptide is preferably linked to an immunogenic carrier as disclosed herein, preferably a VLP, more preferably a HBsAg, HBcAg or Qbeta VLP. In one embodiment, said adjuvant is a saponin-based adjuvant, preferably Iscomatrix. In another embodiment, said adjuvant is Alum. In still another embodiment, said adjuvant is a CpG-containing nucleic acid. Preferably said adjuvant is CpG7909. More preferably said adjuvant is CpG24555. Preferably, said CpG-containing nucleic acid comprises one or more modified linkages, preferably one or more phosphorothioate linkages, even more preferably all internucleotide linkages of the oligonucleotide are phosphorothioate linkages.

In still another embodiment, said at least one adjuvant comprises two adjuvants, preferably selected from the group consisting of Alum, sapoinin-based adjuvants, and CpG-containing nucleic acids. In a preferred embodiment, said adjuvants are Alum and a CpG-containing nucleic acid, preferably CpG7909 or CpG24555, more preferably CpG24555. Preferably, said CpG-containing nucleic acid comprises one or more modified linkages, preferably one or more phosphorothioate linkages, even more preferably all internucleotide linkages of the oligonucleotide are phosphorothioate linkages. In another preferred embodiment, said adjuvants are a saponin-based adjuvant, preferably Iscomatrix, and a CpG-containing nucleic acid, preferably CpG7909, more preferably CpG24555. Preferably, said CpG-containing nucleic acid comprises one or more modified linkages, preferably one or more phosphorothioate linkages, even more preferably all internucleotide linkages of the oligonucleotide are phosphorothioate linkages. In another preferred embodiment, said adjuvants are Alum and a saponin-based adjuvant, preferably Iscomatrix.

In still another embodiment, said at least one adjuvant comprises three adjuvants, preferably selected from the group consisting of Alum, a saponin-based adjuvant, preferably Iscomatrix, and CpG-containing nucleic acids, more preferably CpG7909, even more preferably CpG24555. Preferably, said CpG-containing nucleic acid comprises one or more modified linkages, preferably one or more phosphorothioate linkages, even more preferably all internucleotide linkages of the oligonucleotide are phosphorothioate linkages.

Pharmaceutical Compositions of the Invention

The invention also provides pharmaceutical compositions comprising an antigenic IgE peptide of the invention or an immunogenic composition thereof, in a formulation in association with one or more pharmaceutically acceptable excipient(s) and optionally combined with one or more adjuvants (as adjuvant described described above). The term 'excipient' is used herein to describe any ingredient other than the active ingredient, i.e. the antigenic IgE peptide of the invention eventually coupled to an immunogenic carrier and optionally combined with one or more adjuvants. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the active ingredient.

Pharmaceutical compositions of the present invention and methods for their preparation will be readily apparent to those skilled in the art. Such compositions and methods for their preparation may be found, for example, in *Remington's Pharmaceutical Sciences,* 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, or proteins accepted in the art may suitably be employed for the peptides or proteins of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous, subcutaneous, intradermal and intramuscular routes, even more preferred embodiments are the intramuscular or the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-IgE peptide, preferably coupled to a an immunogenic carrier, eventually in combination with one or more adjuvants, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 0.1 mg/mL to about 20 mg/mL of a peptide of the invention, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dihydrate.

The antigenic IgE peptides of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

A suitable solution formulation for use in an atomiser using electrohydrodynamics to produce a fine mist may contain a suitable dose of the antigenic IgE peptide of the invention per actuation and the actuation volume may for example vary from 1 μL to 100 μL.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

A pharmaceutical composition comprising an antigenic IgE peptide may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compositions of the invention can be used to treat, alleviate or prevent IgE-mediated disorders or symptoms in a subject at risk or suffering from such disorder or symptom by stimulating an immune response in said subject by immunotherapy. Immunotherapy can comprise an initial immunization followed by additional, e.g. one, two, three, or more boosters.

An "immunologically effective amount" of an antigenic IgE peptide of the invention, or composition thereof, is an amount that is delivered to a mammalian subject, either in a single dose or as part of a series, which is effective for inducing an immune response against IgE in said subject. This amount varies depending upon the health and physical condition of the individual to be treated, the taxonomic group of individual to be treated, the capacity of the individual's immune system to synthesize antibodies, the formulation of the vaccine, and other relevant factors. It is expected that the amount will fall in a relatively broad range that can be determined through routine trials.

A "pharmaceutically effective dose" or "therapeutically effective dose" is that dose required to treat or prevent, or alleviate one or more IgE-related disorder or symptom in a subject. The pharmaceutically effective dose depends on inter alia the specific compound to administer, the severity of the symptoms, the susceptibility of the subject to side effects, the type of disease, the composition used, the route of administration, the type of mammal being treated, the physical characteristics of the specific mammal under consideration such as health and physical condition, concurrent medication, the capacity of the individual's immune system to synthesize antibodies, the degree of protection desired, and other factors that those skilled in the medical arts will recognize. For prophylaxis purposes, the amount of peptide in each dose is selected as an amount which induces an immunoprotective response without significant adverse side effects in typical vaccinees. Following an initial vaccination, subjects may receive one or several booster immunisations adequately spaced.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For example, antigenic IgE peptides or pharmaceutical composition of the invention can be administered to a subject at a dose of about 0.1 μg to about 200 mg, e.g., from about 0.1 μg to about 5 μg, from about 5 μg to about 10 μg, from about 10 μg to about 25 μg, from about 25 μg to about 50 μg, from about 50 μg to about 100 μg, from about 100 μg to about 500 μg, from about 500 μg to about 1 mg, from about 1 mg to about 2 mg, with optional boosters given at, for example, 1 week, 2 weeks, 3 weeks, 4 weeks, two months, three months, 6 months and/or a year later.

In some embodiments, a single dose of an antigenic IgE peptide or pharmaceutical composition according to the invention is administered. In other embodiments, multiple doses of an antigenic IgE peptide or pharmaceutical composition according to the invention are administered. The frequency of administration can vary depending on any of a variety of factors, e.g., severity of the symptoms, degree of immunoprotection desired, whether the composition is used for prophylactic or curative purposes, etc. For example, in some embodiments, an antigenic IgE peptide or pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). When the composition of the invention is used for prophylaxis purposes, they will be generally administered for both priming and boosting doses. It is expected that the boosting doses will be adequately spaced, or preferably given yearly or at such times where the levels of circulating antibody fall below a desired level. Boosting doses may consist of the antigenic IgE peptide in the absence of the original immunogenic carrier molecule. Such booster constructs may comprise an alternative immunogenic carrier or may be in the absence of any carrier. Such booster compositions may be formulated either with or without adjuvant.

The duration of administration of an antigenic IgE peptide according to the invention, e.g., the period of time over which an antigenic IgE peptide is administered, can vary, depending on any of a variety of factors, e.g., patient response, etc. For example, an antigenic IgE peptide can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

A variety of treatment methods are also contemplated by the present disclosure, which methods comprise administering an antigenic IgE peptide according to the invention. Subject treatment methods include methods of inducing an immune response in an individual to self-IgE, and methods of preventing, alleviating or treating an IgE-mediated disorder or symptom in an individual.

In one aspect, the present invention provides a method for treating, preventing or alleviating an IgE-related disorder or symptom in a subject, comprising administering a therapeutically effective amount of an antigenic IgE peptide of the invention, or immunogenic or pharmaceutical composition thereof, to said subject.

In another aspect, the present invention provides a method for inducing an immune response against self-IgE in a subject, comprising administering a therapeutically or immunogenically effective amount of an antigenic IgE peptide of the invention, or immunogenic or pharmaceutical composition thereof, to said subject.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. Said subject is preferably human, and may be either male or female, of any age.

Other aspects of the invention relate to an antigenic IgE peptide according to the invention, or of an immunogenic composition or a pharmaceutical composition thereof, for use as a medicament, preferably in treatment, alleviation or prophylaxis of IgE-related disorders.

In yet another aspect, the present invention provides the use of an antigenic IgE peptide of the invention or of an immunogenic composition or a pharmaceutical composition thereof, in the manufacture of a medicament, preferably for treating an IgE-mediated disorder In some aspects of the uses or methods of the invention, said IgE-mediated disorder is selected from the group consisting of conjunctivitis, allergic asthma, allergic rhinitis, atopic dermatitis, anaphylaxis, asthma, contact dermatitis, allergic gastroenteropathy, allergic pulmonary aspergillosis, allergic purpura, eczema, hyper IgE (Job's) syndrome, anaphylactic hypersensitivity, IgE myeloma, inflammatory bowel disease (for example, Crohn's disease, food allergies, ulcerative colitis, indeterminate colitis and infectious colitis), urticaria, psoriasis, preferably from the group consisting of asthma, allergic asthma, allergic rhinitis and food allergies.

Asthma is a chronic inflammatory disorder of the airways causing recurrent episodes of wheezing, breathlessness, chest tightness, and/or coughing in susceptible individuals. Those skilled in the art distinguish various types of asthma, including: allergic asthma, which is thought to arise in patients having developed a hypersensitivity to environmental allergens; drug-induced asthma, typically triggered by sensitivity to aspirin or other COX inhibitors; exercise-induced asthma; near-fatal and hyperacute asthma; nocturnal asthma; occupational asthma, generally caused by exposure to certain chemicals in the workplace. Thus asthma can be triggered by various stimuli, including: airborne allergens, such as dust-mites, pollens, animal dander, fungal spores, feathers . . . (extrinsic asthma); non specific irritants, such as tobacco smoke, chemical fumes, pollution, sulphur dioxide . . . (intrinsic asthma).

Allergic rhinitis generally involves a collection of symptoms, including inflammatory symptoms, predominantly in the nose, sinuses and eyes, which occur after exposure to airborne particles. Symptoms include sneezing; nasal obstruction; runny nose (and occasionally nosebleeds); coughing; headache; itching nose, mouth, eyes, throat, skin, or any area exposed to the allergen; impaired smell (and thus sensitivity to flavours); stuffy nose (nasal congestion); conjunctivitis; watering eyes; sore throat; and wheezing. Allergic rhinitis may be perennial and/or seasonal. Perennial allergic rhinitis is allergic rhinitis that lasts throughout the year. It is typically caused by continuous exposure to allergens such as animal dander, indoor mould spores, or house dust mites. Seasonal allergic rhinitis is allergic rhinitis that occurs only during certain times of the year. It is commonly caused by allergies to tree, grass, and weed pollen that are produced seasonally.

A food allergy is an exaggerated immune response triggered by eggs, peanuts, milk, or some other specific food. Any food can cause an allergic reaction, but a few foods are the main culprits. In children, the most common food allergies are to eggs, peanuts, milk, soy, tree nuts, wheat, shellfish (shrimp, crab, lobster, snails, clams). In older children and adults, the most common food allergies are: peanuts, tree nuts, shellfish, fish. The symptoms may be confined mainly to the stomach and intestines, or may involve many parts of the body after the food is digested or absorbed. Symptoms may include: scratchy throat, anaphylaxis (a severe, whole-body allergic reaction that can result in death); abdominal pain; diarrhoea; nausea; vomiting; stomach cramps; itching of the mouth, throat, eyes, skin, or any area; hives; angioedema (swelling, especially of the eyelids, face, lips, and tongue); light-headedness or fainting; nasal congestion; runny nose; shortness of breath; wheezing; difficulty swallowing; oral allergy syndrome. The oral allergy syndrome generally comprises itching lips, tongue, and throat, and sometimes swollen lips.

In other aspects of the uses or methods of the invention, said subject is a mammal, preferably a human subject.

In still other aspects of the uses or methods of the invention, said subject suffers from said IgE-mediated disorder. Alternatively, said subject is at risk of suffering from said IgE-mediated disorder.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Selection of Antigenic IgE Peptides

The structure of the constant domains CH3-CH4 from human IgE interacting with the IgE high affinity receptor FceRI alpha subunit has been solved and published (Wurzburg B A et al., (2000) Immunity, 13 (3), 375-85; Garman S C et al., (2000) Nature 20, 406 (6793), 259-66). This structural information was used together with literature suggesting that are two regions where binding occurs to identify 4 potential loops as key interaction points and to design the following 4 peptides which would correspond to areas of importance for the IgE-FceRI interaction (see FIG. 1).

| Purple: | ADSNPRGVSAYLSRPSP | (SEQ ID No: 312) |
| Blue: | LVVDLAPSKGTVN | (SEQ ID No: 165) |
| Orange: | STRKEEKQRNGTLTVTSTLP | (SEQ ID No: 1) |
| Yellow: | QCRVTHPHLPRALMRS. | (SEQ ID No: 220) |

Example 2

Preparation of Purple-VLP Conjugates

The purple peptide (SEQ ID No: 312) in which a terminal cysteine residue was added for conjugation purposes (sequence ADSNPRGVSAYLSRPSPC (SEQ ID NO: 434)) was synthesised using a standard Fmoc protocol on CLEAR amide resin. The amino acid coupling reactions were carried out using 5 fold excess of Fmoc-protected amino acid activated with 1 eq of HBTU (2-(1H-Benzotriazole-1-yl)-1, 1, 3, 3-tetramethyluronium hexafluorophosphate) in the presence of HOBt (hydroxybenzotriazole) and NMM (N-methylmorpholine). The deprotection of Fmoc group was achieved with 20% piperidine/DMF. Resin-bound peptide was then cleaved and side chain protecting groups removed simultaneously with Reagent D (TFA/H2O/DODT: 89/3/8). The peptide was made with a free N-terminus and amidated C-terminus. The crude peptide was purified to homogeneity by HPLC using a BEH 130 C18 column and a water/acetonitrile gradient in the presence of 0.1% TFA. The purified peptide was vacuum-dried using a lyophilizer. The peptide was analyzed using mass-spectrometry (LC-MS) and gave satisfactory data (see below).

TABLE 1

| Peptide | Purity | Expected Mass (Da) | Observed Mass (Da) |
|---|---|---|---|
| Purple + Cyst (SEQ ID NO: 434) | 95% | 1877.1 | 1878.1 |

The Purple+Cyst (SEQ ID NO: 434) peptide was conjugated to the Virus-Like Particles (VLP) Qβ and Hepatitis B Surface Antigen (HBsAg) in two separate conjugation experiments. The Qβ used in this study was produced by bacterial *E. Coli* fermentation in a BL21 (DE3) strain incorporating a pET28 plasmid encoding the 14 kD monomer protein: MAKLETVTLGNIGKDGKQTLVLN-PRGVNPTNGVASLSQAGAVPALEKRVTVSVSQPSR NRKNYKVQVKIQNPTACTANGSCDPS-VTRQAYADVTFSFTQYSTDEERAFVRTELAAL LAS-PLLIDAIDQLNPAY (SEQ ID NO: 435). The fermentation is induced at an OD600 of 0.8 with IPTG and allowed to proceed overnight in terrific broth (TB) with kanamycin. The VLP, which self-assembles in the host cell, was then purified from the fermentation cell pellet using the method described in the patent application EP20050105513 with the following differences: after cell disruption, the clarified homogenate was treated with ammonium sulphate at 50% saturation and the cell pellet recovered by centrifugation. Then, the pellet was redissolved in HEPES buffer and dialysed against HEPES buffer before proceeding to the first column step in the published method. After the ion-exchange column and hydroxylapatite column steps, the material was purified using a further anion-exchange column step and sterile filtered to make the final VLP bulk material, which was analysed by size-exclusion chromatography, SDS-PAGE and electron microscopy with acceptable results.

The HBsAg (subtype adw) used in this study was purchased from Aldevron (ND, USA). The HBsAg exists as spherical particles approximately 22 nm in diameter, which consist of multiple copies of a 24 kD monomeric protein embedded in a lipid bilayer vesicle. An *S. Cerevisiae* strain for production of HBsAg of this type is also available from the ATCC culture collection.

The VLPs (both Qβ and HBsAg) were activated using N-gamma-maleimido-butyryloxy-succinimide ester (GMBS) linking reagent. The GMBS reagent was dissolved in dimethyl sulphoxide (DMSO) and added to the VLP solution at a ≧10-fold molar excess. The activation reaction was allowed to proceed for ≧30 minutes and the solution was then desalted using a NAP-25 desalting column into Dulbeccos Phosphate Buffered Saline (DPBS) with 5 mM EDTA. If necessary, the protein solution was concentrated slightly using 10 kD spin microconcentrators prior to the next conjugation reaction.

Prior to the conjugation reaction, the purple peptide was dissolved in an aliquot of pH 7.4 DPBS, with 5 mM EDTA as an additive. The concentration of the peptide in solution was 10 mg/ml. The solubilised peptide was added to an aliquot of TCEP immobilised reducing agent (Pierce Chemical) which had been washed in DPBS containing 5 mM EDTA. The aliquot of peptides was incubated with mixing in the presence of the TCEP gel for approximately 1 hour, after which time the aliquot was spun down in a microfuge and the solid pellet discarded. The reduced peptide-containing supernatant was added directly to the activated VLP which had been prepared earlier.

The reaction between the VLPs and the reduced peptides was allowed to proceed for at least thirty minutes with very gentle mixing. At the end of the reaction time each sample was desalted into Dulbeccos PBS (DPBS) using NAP-10 or NAP-25 desalting columns (GE Healthcare). The desalted conjugated peptides were analysed for protein content using the Bradford (Coomassie Brilliant Blue, Pierce Chemical) assay as well as by SDS-PAGE and size-exclusion chromatography. The conjugate products were sterile filtered using a 0.22 μm filter and stored at 2-8° C. until use. Careful attention was paid to these samples during storage to prevent freezing or exposure to extremes in temperature.

The extent of the conjugation for the two VLP-peptide samples was measured using SDS-PAGE, and a molecular weight increase was observed for both samples which is consistent with the addition of the peptide to the VLP protein monomer. In addition, the QP-peptide sample was tested in the HPLC size-exclusion chromatography assay (using a Tosoh PWXL5000 HPLC column) and found to contain assembled VLP when compared to unconjugated samples of VLP. Furthermore, the Qβ-peptide sample was observed using electron microscopy using a JEOL 1230 TEM with 80 kV beam, and found to contain assembled, uniform particles. The integrity of the HBsAg-peptide conjugate particle was tested using non-reduced SDS-PAGE and since the protein did not enter the gel, the sample was deemed to contain high-molecular-mass species and to be suitable for in vivo use.

Example 3

Preparation of Orange, Purple, Yellow, and Blue-VLP Conjugates as Well as Purple-Constrained and Blue-Improved-VLP Conjugates The Yellow, Blue+Cyst, Purple+Cyst and Orange+Cyst peptides which amino acid sequences are indicated in Table 2 were synthesised according to methods known in the art and mainly according to the protocol in Example 2, as follows. The peptides were synthesized on a Symphony peptide synthesizer with a standard Fmoc protocol on CLEAR amide resin, except for peptide Yellow which was made on preloaded Fmoc-Ser(tBU)-Wang resin. See Example 2 for details about the coupling reactions and deprotection. All peptides were made with a free N-terminus and amidated C-terminus except for the peptide Yellow which was made with an acetylated N-terminus and carboxylated C-terminus. The crude peptides were purified on a HPLC system with a BEH 130 C18 column as in Example 2. The purified peptides were vacuum-dried using a lyophilizer. Finally, the peptides were analyzed with LC-MS and all peptides gave satisfactory data (see Table 3 below).

The Blue-Improved and Purple-Constrained peptides were manufactured by CEM Corporation (Matthews, N.C., USA). The peptides were manufactured using standard peptide chemistry techniques and purified using chromatography. The purified peptides were analysed using LC-MS and found to be of high purity (>95%) (see Table 3 below).

TABLE 2

Peptide Sequences

| Name | Sequence | SEQ ID No |
|---|---|---|
| Orange + Cyst | STRKEEKQRNGTLTVTSTLPC | 436 |
| Yellow | QCRVTHPHLPRALMRS | 220 |
| Blue + Cyst | LVVDLAPSKGTVNC | 437 |
| Purple + Cyst | ADSNPRGVSAYLSRPSPC | 434 |
| Blue-Improved | CLVVDLAPSKGTVNGGGGGC | 438 |
| Purple-Constrained | CADSNPRGVSAYLSRPSPC | 439 |

Underscore indicates cysteine residues assed for conjugation purposes and double underscore indicates a GC linker.

TABLE 3

LC-MS Data of Peptides.

| Peptide | Purity | Expected Mass (Da) | Observed Mass (Da) |
|---|---|---|---|
| Orange + Cyst | 97% | 2349.6 | 2352 |
| Yellow | 98.7% | 1944.3 | 1944 |
| Purple + Cyst | 95% | 1877.1 | 1878.1 |
| Blue + Cyst | 96.6% | 1415.7 | 1416 |
| Purple-Constrained | >95% | 1979.0 | 1979.4 |
| Blue-Improved | >95% | 1803.8 | 1803.2 |

Each peptide was conjugated to the Virus-Like Particle (VLP) Qβ in separate batches. The Qβ used in this study was produced by bacterial *E. Coli* fermentation and extensive purification as in Example 2.

The VLP (>1 mg/ml protein concentration by Bradford assay) was activated using N-gamma-maleimidobutyryloxy-succinimide ester (GMBS) linking reagent from Pierce Chemical as described in Example 2 above.

Prior to the conjugation reaction, each peptide was dissolved in an aliquot of pH 7.4 Dulbeccos Phosphate Buffered Saline (DPBS), with 5 mM EDTA as an additive. The concentration of each peptide in solution was in the range 8-12 mg/ml, see table 4 below for exact data. The solubilised peptide was added to an aliquot of TCEP immobilised reducing agent as described in Example 2 above. The reduced peptide-containing supernatant was added directly to the activated VLP which had been prepared earlier.

The reaction between the VLPs and the reduced peptides was allowed to proceed for at least thirty minutes with very gentle mixing. At the end of the reaction time each sample was desalted into Dulbeccos PBS (DPBS) using NAP-10 or NAP-25 desalting columns (GE Healthcare). The desalted conjugated peptides were then concentrated using 10 kD MWCO spin concentrators, and analysed for protein content using the Bradford (Coomassie Brilliant Blue, Pierce Chemical) assay as well as by SDS-PAGE and size-exclusion chromatography, see below for further details. The conjugate products were sterile filtered using a 0.22 μm filter and stored at 2-8° C. until use. Careful attention was paid to these samples during storage to prevent freezing or exposure to extremes in temperature. The VLP-peptide conjugates were analysed for extent of conjugation and particle assembly as described in Example 2 above (SDS-PAGE including densitometry, electron microscopy and size-exclusion HPLC).

TABLE 4

VLP-Peptide Conjugates

| Peptide | Amount of Peptide (mg) | Peptide Concentration in DPBS (mg/ml) | Approx amount of activated VLP added (mg) | Final Yield (mg) | Substitution* (μg peptide per mg protein) |
|---|---|---|---|---|---|
| Yellow | 4.5 | 11.3 | 5 | 3.2 | 54 |
| Orange + Cyst | 4.5 | 11.3 | 5 | 2.8 | 70 |
| Blue + Cyst | 3.5 | 8.8 | 4 | 1.9 | 47 |
| Purple + Cyst | 3.5 | 8.8 | 4 | 2.3 | 60 |
| Purple-Cons | 3 | 10 | 3 | 1.3 | 62 |
| Blue-Impr | 3 | 10 | 3 | 1.5 | 48 |

*As determined by SDS-PAGE and densitometry calculations

Example 4

Preparation of Orange, Purple, Yellow, and Blue-KLH Conjugates as Well as Purple-Constrained and Blue-Improved-KLH Conjugates The peptides of Table 2 were conjugated to KLH purchased from Pierce Chemical (Rockford, Ill., USA) and purified as follows. The peptides were made as detailed in Examples 2 and 3 above. The KLH used was Imject Malemide-activated KLH supplied by Pierce Chemical as a lyophilised solid. Vials of this KLH were reconstituted with tissue-culture-grade water prior to addition of the peptides. The peptides were treated with TCEP gel as described in Examples 2 and 3 above and the reduced-peptide-containing supernatants were added directly to aliquots of the activated KLH solution and incubated with gentle mixing. The coupling reaction was allowed to proceed for two hours, at which time the solutions were centrifuged to remove solids and desalted using gravity drip desalting columns as previous. The desalted conjugates were analysed by SDS-PAGE, Bradford protein assay, and tryptic digest followed by MS-MALDI analysis. The conjugates were sterile filtered using a 0.22 μm filter and kept at 2-8° C. until use, as freezing KLH solutions is not recommended.

Example 5

IgE Peptide Identification

This study aimed to evaluate how efficacious peptides conjugated to a Qbeta VLP (as detailed in Examples 2 and 3 above) were in inducing an antibody response that can bind to human IgE. Female Balb/c (6-8 weeks) were injected by the intramuscular route (50 microliter volume injected into each *Tibialis anterior* muscle) on days 0, 19 and 34. Necropsy took place on day 46. At necropsy 400-600 microliter blood was sampled from euthanised mice by cardiac puncture. Blood was left to coagulate overnight and the next day, serum was collected.

Antibody responses from immunized animals were investigated for some or all of the following assays: a) IgG titer determination, b) binding to serum free IgE, c) binding to FceRl bound IgE, d) degranulation assay, and e) IgE quantification assays.
a) Total IgG Titer Determination Summary: A colorimetric ELISA that generates a reciprocal titer (RT) to represent the levels of total IgG molecules which are specific to the vaccine. Serial dilutions were prepared from sera samples and tested in the assay. Serum sample prepared from pooled Ce3-vaccinated mice sera samples was used as positive control. Balb/c neg serum from Harlan Labs was used as negative control (pooled from 400 animals Harlan laboratories Code#R-0131D). Coating of assay plates: 384-well high bind assay plates (Corning International Cat#3700) were coated with 25 μL/well of Human Ce3Ce4 protein stock diluted to 1 μg/mL with 0.01 M PBS pH 7.4 and incubated on a shaker at RT for 3 hours. After washing ×2 with PBS pH 7.4, plates were blocked using 80 μL/well of 0.01 M PBS/1% BSA, incubated at RT for 1 hour before a final wash ×3 with 0.01 M PBS pH 7.4/0.05% Tween 20. Sample preparation and assay: The following day, an 8 point ½ log serial dilution of each sample was prepared starting at 1:100 dilution (PBS/1% BSA diluent), 25 μL/well of the serial dilution transferred in duplicate into the human Ce3Ce4 coated plate then incubated shaking at RT for 1.5 hours. After washing ×3 with 0.01 M PBS pH 7.4/0.05% Tween 20, added 25 μL/well of Total IgG detection antibody (Rabbit anti-mu IgG-Fc, Cat#A90-130A Bethyl Laboratories) 1:6000 with 0.01 M PBS pH 7.4/1% BSA, then incubated shaking at RT for 1 hour. After washing ×5 with 0.01 M PBS pH 7.4/0.05% Tween 20, added 25 μL/well Bio-Rad kit goat anti-rabbit horseradish peroxidase conjugate (Bio-Rad Cat#172-1019) 1:3000 with 0.01 M PBS pH 7.4/0.05% Tween 20 pH 7.4, then incubated shaking at RT for 1 hour. After washing ×4 with 0.01M PBS pH 7.4/0.05% Tween 20 then ×1 with 0.01M PBS pH 7.4 only, added 25 μL/well Mouse Typer HRP Substrate (Bio-Rad Cat#172-1064), then incubated at RT for 30 mins. Added 25 μL/well 2% oxalic acid, read at Abs 405 nm. Data analysis: A cut-off value (Abs 405 nm) was calculated by taking the mean of the duplicate reads generated by the lowest concentration of the appropriate study negative control group and multiplying this value by 2.5. Titration curves were plotted for each test sample (sample titer vs Abs 405 nm) and the sample titer (subsequently transformed into reciprocal titer) was predicted from the calculated cut-off value.

b) Free IgE Binding Titer

Summary: An electrochemiluminescence (ECL) assay that generates a reciprocal titer (RT) and max value to represent the levels of mouse IgG:human IgE complexes formed after incubation of serial dilutions of test sera overnight with a high concentration of human IgE. Serum sample prepared from pooled Ce3-vaccinated mice sera samples was used as positive control, along with a mouse antibody to a region of the human IgE Ce3 domain (AbDserotec 0100-0413 (E411 (5H2)) spiked at 50 µg/mL and 1 mg/mL into Balb/c neg serum from Harlan Labs (pooled from 400 animals Harlan laboratories Code#R-0131D), which was also used alone as a negative control. Incubation of samples with Human IgE: An 8 point ½ log serial dilution of each sample, including controls, was prepared starting at 1:3 dilution (0.01M PBS pH 7.4/1% BSA diluent). 10 µL volumes of each sample concentration was mixed with 10 µL of 100 µg/mL Human IgE (diluted from stock using 0.01 M PBS pH 7.4/1% BSA), then plates were sealed and incubated overnight at 4° C. Coating of assay plates: The following day, 384-well assay plates (Meso-Scale Diagnostics (MSD) standard bind Cat#L11XA-1, 0370PA) were coated with 12 µL/well of Sheep pAb to human IgE (Gentaur, ICL (Immunology Consultants Lab) Cat#SE-80A) diluted to 1 µg/mL with 0.01M PBS pH 7.4, then incubated on a shaker at RT for 2 hours. After washing ×3 with 0.01M PBS pH 7.4, plates were blocked using 25 µL/well of Pierce starting blocking buffer (Pierce Biotech. Cat#37538) and incubated on a shaker at RT for 40 mins, before a final wash ×3 with 0.01 M PBS pH 7.4. Sample preparation and assay: Volumes of 20 µL of the overnight incubation mix of sera with human IgE were diluted 1:5 with 80 µL/well 0.01 M PBS pH 7.4/1% BSA and then 12 µL/well transferred in duplicate into the coated MSD assay plates. After incubating on a shaker at RT for 2 hours, plates were washed ×3 with 0.01M PBS pH 7.4/0.05% Tween 20. Added 12pUwell detection antibody (Donkey pAb to mouse IgG H+L Abcam Cat#ab6707, MSD SULFO-tagged using MSD Cat#R91AN-1) 1:5000 with 0.01M PBS pH 7.4/1% BSA, then incubated shaking at RT for 1 hour. After washing ×3 with 0.01 M PBS pH 7.4/0.05% Tween 20 added 50 µL/well MSD Read buffer T (4×) with surfactant (MSD Cat#R92TC) 1:2 with MQ Water. Plates were read using an MSD Sector Imager 6000. Data Analysis: A cut-off value (Pixels) was calculated by taking the mean of the duplicate reads generated by the lowest concentration of the appropriate study negative control group and multiplying this value by 5. Titration curves were plotted for each test sample (sample titer vs Pixels) and the sample titer (subsequently transformed into reciprocal titer) was predicted from the calculated cut off value. The max peak value of the titration curves was also recorded.

c) Binding to Receptor Bound IgE

This assay measures if antibodies in serum from vaccinated mice can bind to some human IgE bound to the FceRl receptor on the surface of RBL-THE cells, those antibodies are then detected by an anti-mouse Fc specific antibody conjugated to phycoerythrin and the fluorescence is measured by flow cytometry. An anti-human IgE antibody from Biodesign diluted in non-vaccinated BALBc serum has been used as a positive control. Assay: Frozen RBL-THE cells (p12 10×10$^6$cells/ml) were thawed and washed once with assay buffer (PBS–5% goat serum). 2×10$^5$ cells/well in blocking buffer (PBS–5% goat serum–0.1 mg/ml mouse Fab (Chrom-Pure Mouse IgG, Fab fragment—Jackson Immunoresearch)) were seeded in 96-well plates and incubated on the 4° C. shaker for 1 h30. 50 µl of 4 ug/ml human IgE were added per well (diluted in assay buffer) (except the control wells Biodesign no IgE, cells only and aMo-PE) and the plates were incubated for 1 h on the 4° C. shaker. The cells were washed once with assay buffer and resuspended in 30 µl of anti-human IgE (Biodesign 10 ug/ml, 5 ug/ml, 2.5 ug/ml—positive control) diluted in 5% BALBc serum or with serum samples from vaccinated mice diluted 1:20. 1:40 and 1:80 in assay buffer. The serum samples were plated in triplicate and the controls in duplicate. Plates were incubated on the 4° C. shaker for 1 h30 then washed with assay buffer, resuspended in 100 µl of goat anti-Mouse Fc specific-PE antibody (1:200 in assay buffer, Goat Jackson Immunoresearch) and incubated for 45 min on 4° C. shaker. Cells were washed 3 times with assay buffer, resuspended in 80 µl Paraformaldehyde 2% in PBS and incubated overnight at 4° C. Fluorescence intensity was measured by flow cytometry. Data analysis: The mean fluorescence intensity of each sample was used for analysis. The negative control (aMo-PE alone) was averaged and its value subtracted from each well. The positive control was averaged and each sample was expressed as a percentage of positive control (Biodesign) at its respective serum dilution. The 1:40 serum dilution was then extracted and an ANOVA was performed.

d) Degranulation Assay

This assay measures if the serum from vaccinated mice induces degranulation of RBL-THE cells by measuring the activity of b-hexosaminidase enzyme released by RBL-THE cells in media. E25 (Xolair) diluted in non-vaccinated BALBc serum was used as a negative control (40 ug/ml) and goat polyclonal antibody from Sigma diluted in non-vaccinated BALBc serum was used as a positive control. Cell Seeding: Frozen RBL-THE p12 (10×10$^6$ cells/vial; Rat basophil leukaemia cells stably transfected with human FceRl) were thawed, washed in RBL-P media (MEM-Earles supplement with 15% FCS and 2 mM L-Glutamine) and resuspended in RBL-P media at 8×10$^5$ cells/ml with 0.25 µg/ml Human IgE. 8×10$^4$cells/well were seeded in flat bottom 96 well plate and incubated for 48 hours at 37° C./5% CO2. Samples and buffers preparation: On day 3, Tyrode's buffer 1× (NaCl 135 mM, KCl 5 mM, CaCl$_2$ 1.8 mM, MgCl2 1 mM, Glucose 5.6 mM, BSA 1 mg/ml, Hepes 20 mM, pH 7.4) was prepared. Tyrode's buffer-5% BALBc serum, Tyrode's buffer-2.5% BALBc serum and Triton 1% in Tyrode's-5% BALBc serum were also prepared. Positive control (Goat polyclonal anti-IgE antibody (82 mg/ml in PBS)—Sigma, 10632) was serially diluted in Tyrode's buffer-5% BALBc serum (1st well in Tyrode's buffer-5% BALBc serum and then in Tyrode's buffer) from 10 µg/ml to 2.5 µg/ml. The negative control (E25) was kept constant at 40 ug/ml in diluted Baibc serum (1:20, 1:40 and 1:80 serum dilution). Test serum samples from vaccinated mice were tested at 1:20, 1:40 and 1:80 serum dilution. All of the controls and test serum samples are tested in triplicate on each plate. Agonist assay: On day 3, cell plates were removed from incubator. 95 µl of media were remove from wells and cells were washed with 200 µl of Tyrode's buffer 1×, the wash buffer was removed and 70 µl of diluted antibodies (either positive control, negative control or test serum sample) were added. Cells were incubated at 37° C./5% CO2 for 1 hour. At the end of incubation, plates were removed from incubator and centrifuge at 1200 rpm for 5 minutes to sediment any detached cells. 65 µl of supernatant was removed and put into sterile 96-well plates. 25u1 of the supernatant was tested for 13-hexosaminidase activity. β-hexosaminidase activity: 25 µl of supernatant was added to a 96-well plate. 25 µl of 4 mM NAGA in citrate buffer (4 mM N-acetyl-β-D-glucosaminide (NAGA) (Sigma, N9376) in 50 mM citrate buffer pH 4.5) was added to all wells (freshly prepared), the plates were incubated for 1 h at 37° C. and 150 µl of 0.2M glycine pH 10.7 was add to stop the reaction. Plates were read at at 405 nm with Envision. Data analysis: Degranulation was expressed as a percentage of the total β-hexosaminidase activity from values for Total wells (treated with 1% Triton X-100). The % of degranulation at dilution 1:40 was then extracted for analysis and an ANOVA is performed on the serum samples.

e) Reduction of Free Human IgE Assay

Summary: An electrochemiluminescence (ECL) assay that quantifies the levels of free human IgE that remain after overnight incubation of aliquots of test sera with a serial dilution of human IgE, during which time mouse IgG:human IgE complexes form. To ensure accuracy of the human IgE quantification assay, it is essential to firstly remove any mouse IgG:human IgE complexes using protein G coated magnetic Dynabeads, which bind out any complexes via the mouse IgG Fc region. A value for the % decrease in human IgE levels from that of the appropriate negative control groups can be calculated for each sample.

As a positive control, Xolair/E25 was spiked at 40 µg/mL (standard therapy dose) into Balb/c neg serum from Harlan Labs (pooled from 400 animals Harlan laboratories Code#R-0131D), which was also used alone as a negative control. Incubation of samples with Human IgE: 2 µL volumes of each concentration of an 8 point ½ log serial dilution of human IgE (0.01M PBS pH 7.4/1% BSA diluent) were added to each of 8×10 µL volumes of test sera samples, including positive control Xolair/E25 (40 µg/mL), the IgE starting at a final concentration of 30 µg/mL. Plates were sealed and incubated overnight at 4° C. Coating of assay plates: The following day, 384-well assay plates (Meso-Scale Diagnostics (MSD) standard bind Cat#L11XA-1, 0370PA) were coated with 12 µL/well of Sheep pAb to human IgE (Gentaur, ICL (Immunology Consultants Lab) Cat#SE-80A) diluted to 5 µg/mL with 0.01M PBS pH 7.4, then incubated on a shaker at RT for 2 hours. After washing ×3 with 0.01M PBS pH 7.4, plates were blocked using 25 µL/well of Pierce starting blocking buffer (Pierce Biotech. Cat#37538) and incubated on a shaker at RT for 40 mins, before a final wash ×3 with 0.01M PBS pH 7.4. Sample and Dynabead preparation: Volumes of 5 µL of the overnight incubation mix of sera with human IgE were diluted 1:20 with 95 µL/well 0.01M PBS pH 7.4/1% BSA. [Note: Also diluted 10 µL of the 1:20 dilution a further 1:2 with 0.01 PBS pH 7.4/1% BSA to test in the Free IgE binding assay to get a measurement of mu IgG:hu IgE complexes before the Protein G bead incubation]. The required volume of 1× concentration of Protein G Dynabeads (Invitrogen Cat#10004D) was washed and prepared as in pack insert, then concentrated ×4 by resuspending in 0.25× initial bead volume. Incubation of sample with Dynabeads: Mixed 30 µL of each 1:20 sample with 15 µL/well 4× beads, incubated shaking at RT for 1 hour. Removed beads from samples using a Dynal magnetic bar plate (Invitrogen Cat#12027) and mixed 40 µL of the remaining sample with 20 µL fresh 4× bead mix, incubated shaking at RT for 1 hour. Transferred 45 µL/well remaining sample into fresh wells and centrifuge 1 min at 1000 rpm, returned plates onto the magnetic bar plate and transferred 40 µL/well into fresh wells. [Note: Used 30 µL of remaining sample to test in the Free IgE binding assay to get a measurement of mu IgG:hu IgE complexes after the Protein G bead incubation to ensure all complexes have been removed]. Quantification assay: Prepared a 12 point ½ log serial dilution standard curve of human IgE in 80% MSD mouse serum assay diluent/20% 0.01M PBS pH 7.4/1% BSA, starting at a concentration of 5 µg/mL. Diluted remaining sample from bead incubation 1:5 using MSD mouse serum assay diluent (MSD Cat#R52BB-2). Transferred serial dilutions of standard curve and samples in triplicate at 12 µL/well into coated MSD wells and incubate shaking at RT for 2 hours. After washing plates ×3 with 0.01M PBS pH 7.4/0.05% Tween 20, added 12 µL/well detection antibody (Rabbit anti-Human IgE Antibody epsilon chain specific Bethyl Cat#A80-109A, MSD SULFO-tagged using MSD Cat#R91AN-1) 1:300 with 0.01M PBS pH 7.4/1% BSA, then incubated shaking at RT for 1 hour. After washing ×3 with 0.01M PBS pH 7.4/0.05% Tween 20 added 50 µL/well MSD Read buffer T (4×) with surfactant (MSD Cat#R92TC) 1:2 with MQ Water. Plates were read using an MSD Sector Imager 6000. [Note: A Free IgE binding assay was run in tandem with this quantification assay to test samples from before and after bead incubation using the same protocol as previously described, except using the donkey detection antibody at 1:2000 with 0.01M PBS pH 7.4/1% BSA and using an anti-human detection antibody for the E25/Xolair positive control only (SULFO-tagged goat anti-human IgG MSD Cat#R32AJ-5) 1:4000 with 0.01M PBS pH 7.4/1% BSA]. Data analysis: Raw data (Pixels) was logged, standard curve plotted (Log uman IgE concentration ng/mL vs. Log Pixels) and an asymmetric 5-parameter curve fit applied. Log IgE concentrations of the test samples were predicted from the standard curve and subsequently anti-logged and multiplied by 200 to derive the actual remaining free IgE concentrations in ng/mL. For each sample and control, the % decrease in human IgE levels was calculated compared to the appropriate control group and plotted vs. human IgE (ng/mL) originally added to serum sample, both axes on Log scale, to generate a titration curve.

Results

The results are summarised in table 5 below. More specifically and surprisingly, this study showed that a combination of Yellow and Purple Qbeta conjugations when administered via the intramuscular route at a total dose of 25 microgram conjugate (i.e. 12.5 microgram individual conjugate) is the most effective, and was more effective than using either peptide conjugate as single antigen at double dose. We have shown in this study that this combination induce an antibody response with a high capacity to bind free IgE as well as that these antibodies are capable of reducing levels of IgE to up to 80% depending on the dose of IgE challenge. These antibody responses were not able to bind receptor engaged IgE and did not cause degranulation of receptor expressing target cells. Combining the Qbeta with the adjuvants Alum and CPG24555 (wherein all internucleotide linkages of the oligonucleotide are phosphorothioate linkages) were highly efficient in inducing these antibody responses. Overall it can be concluded that in terms of inducing mouse IgG antibodies with a strong ability to bind free human IgE, the Yellow peptide is the most promising peptide when administered individually or in combination with Purple or Orange peptide conjugates, or with both Purple and Orange peptide conjugates vaccinated at high dose and volume.

TABLE 5

Summary of data from Example 5

| | Reciprocal IgG titer | IgE binding titer geomean (95% confidence interval) | IgE binding max Mean (±std dev) | % Degranuation (±std dev) | % Decrease in 9186 ng/mL IgE levels (±std dev) | % Decrease in 861 ng/mL IgE levels (±std dev) | % Decrease in 81 ng/mL IgE levels (±std dev) |
|---|---|---|---|---|---|---|---|
| Yellow | 34125* | 2706 (1801-4067) | 53698 (±15329) | 10 (±0.3) | 15.4% (±7.5%) | 6.4% (±8.0%) | 34.6% (±3.8%) |
| Blue | 100* | 30* | 6361* | 15 (±0.5) | | | |
| Orange | 100* | 95* | 11427* | 9 (±0.4) | 14.7% (±6.3%) | 10.8% (±7.1%) | 7.2% (±3.2%) |
| Purple | 29920* | 405 (118-1389) | 30514 (±12365) | 9 (±0.1) | 6.2% (±4.1%) | 0.1% (±10.4%) | 12.6% (±5.5%) |
| Blue improved | 1137* | 30* | 4228* | 9 (±0.6) | | | |
| Purple constrained | 6008* | 186 (63-546) | 26194 (±10443) | 9 (±0.1) | | | |
| Yellow + Orange | 13192* | 1048 (350-3136) | 41202 (±19176) | 10 (±0.3) | 14.3% (±2.0%) | 29.7% (±4.5%) | 14.8% (±6.4%) |
| Yellow + Purple | 7793* | 6823 (400-1165) | 48357 (±11888) | 10 (±0.4) | 34.8% (±2.6%) | 60.0% (±4.5%) | 80.3% (±2.7%) |
| Blue + Orange | 4424* | 30 (30-30) | 12259 (±3685) | 10 (±0.3) | | | |
| Blue + Purple | 7146* | 500 (266-939) | 32333 (±8934) | 11 (±1.6) | | | |
| Blue improved + Purple constrained | 384* | 30* | 10490* | 12 (±0.5) | | | |
| Orange, Yellow, Blue and Purple | 8825* | 202 (91-451) | 26745 (±10920) | 11 (±1.1) | | | |
| Blue improved + Purple constrained, Orange, Yellow | 228* | 30* | 8286* | 11 (±0.3) | | | |
| VLP control | 100* | 30 (30-30) | 3650 (±606) | 10 (±0.3) | 0.3% (±4.2%) | 0% (±2.9%) | 0% (±4.4%) |
| Blue improved + Purple constrained, Orange, Yellow | 14427* | 96 (46-198) | 16712 (±4326) | 10 (±0.1) | | | |
| Blue improved + Purple constrained, Orange, Yellow (high dose) | 38128* | 316* | 24149* | 10 (±0.2) | | | |
| VLP control (high dose) | 100* | 30* | 2829* | 10 (±0.2) | | | |

N/A: Not applicable
Total conjugation dose is 25 microgram, unless high dose is administered where total dose is 50 microgram per injection Doses on days 0, 19, 34
Conjugation partner = Qbeta VLP (Viral like particle)
Adjuvant: 20 µg CPG 24555 (all internucleotide linkages phosphorothioate linkages). Alum = ALhydrogel ™ at 20% v/v
*n = 1 run on pooled samples Example 6

Hyperimmunisation Study

This study aimed to evaluate the effect of a rapid immunisation schedule for induction of high affinity antibodies against IgE. Groups of 8 female Balb/c mice (6-8 weeks old) were injected intraperitoneally and subcutaneously with the peptide KLH-conjugates (as detailed in Example 4 above) on days 0, 3, 8 and 11. A combination of CPG7909 and Alhydrogel (Alum 1.3% at 20% v/v) and Incomplete Freunds adjuvant (IFA) were used as adjuvants in this study. All peptides were conjugated to KLH. Necropsy was performed on day 22 and blood was collected as in Example 5.

Antibody responses from immunized animals were investigated for using either all or some of the following assays: a) IgG titer determination, b) binding to serum free IgE, c) binding to FceRl bound IgE, d) degranulation assay, and e) IgE quantification assays. All assays are described in detail under Example 5.

Results

Table 6 summarise the data from Example 6. Total titers in this study were approximately 10 fold less thean in VRS-IgE-008-003. The data from this study shows that Purple, Purple constrained, Yellow and Orange peptides are immunogenic. Surprisingly, the Blue peptide was a very weak antigen, and constrining the peptide and increasing solubility showed an increased immunogenicity, showing that this peptide may need to be constrained to show acceptable immunogenicity.

TABLE 6

Summary of data from Example 6

|  | Reciprocal IgG titer geomean (95% confidence interval) | IgE binding titer | IgE binding max | % Binding to IgE-FceRI (±std dev) | % Degranuation (±std dev) |
|---|---|---|---|---|---|
| Yellow | 3118 (475-20470) | 66* | 19740* | 4 (±1.3) | 7 (±0.3) |
| Blue | 100 (100-100) | 30* | 11337* | 4 (±1.1) | 7 (±0.3) |
| Blue-improved | 30 (0-6030) | 30* | 8709* | 3 (±0.6) | 5 (±0.1) |
| Orange | 719 (596-868) | 30* | 7287* | 4 (±0.7) | 4 (±0.2) |
| Purple | 1189 (673-2102) | 30* | 11103* | 3 (±0.4) | 8 (±0.1) |
| Purple constrained | 1996 (1670-2385) | 49* | 15789* | 3 (±0.7) | 8 (±0.3) |
| Orange, Yellow, Blue and Purple mix | 1665 (1606-1726) | 54* | 18349* | 5 (±0.7) | 8 (±0.2) |
| KLH control | 100 (100-100) | 30* | 6496* | 4 (±0.6) | 9 (±0.3) |

Total conjugation dose is 25 microgram per injection
Doses at days 0, 3, 8, 11
Conjugation partner = KLH
Adjuvant: 20 µg CPG 7909 (all internucleotide linkages phosphorothioate linkages), Alum = ALhydrogel ™ at 20% v/v + IFA (incomplete Freunds adjuvant)
*n = 1 run on pooled samples Example 7

Efficacy of Peptides Conjugated to KLH, HBsAg and Qbeta in Inducing Antibody Response that can Bind to Human IgE This study aimed to evaluate how efficacious peptides conjugated to KLH, HBsAg and Qbeta (as detailed in Examples 2, 3 and 4 above) were in inducing an antibody response that can bind to human IgE. Female Balb/c (6-8 weeks) were injected by the intramuscular route (50 microliter volume injected into each *Tibialis anterior* muscle) on days 0, 19 and 34. Necropsy took place on day 46. At necropsy 400-600 microliter blood was sampled from euthanised mice by cardiac puncture. Blood was left to coagulate overnight and the next day, serum was collected.

Antibody responses from immunized animals were investigated for using either all or some of the following assays: a) IgG titer determination, b) binding to serum free IgE, c) binding to FceRl bound IgE, d) degranulation assay, and e) IgE quantification assays. All assays are described in detail under Example 5.

Results

This study showed that purple and yellow peptides were highly immunogenic. Conjugation of the purple peptide to KLH, Qbeta and HBsAg allowed induction of high antibody responses that were capable of binding to free IgE to a very high degree. These antibody responses were not able to bind receptor engaged IgE and did not cause degranulation of receptor expressing target cells. Both adjuvants (AbISCO and CPG 7909 and Alum combination) were effective in inducing high levels of antibody responses.

TABLE 7

Summary of data from Example 7

|  | Reciprocal IgG titer geomean (95% confidence interval) | IgE binding titer (±std dev) | IgE binding max (±std dev) | % Binding to IgE-FceRI (±std dev) | % Degranuation (±std dev) | % Decrease in 9186 ng/mL IgE levels (±std dev) |
|---|---|---|---|---|---|---|
| Yellow-KLH (AbISCO) | 4777 (3115-7327) | 175 (71-427) | 33914 (±17977) | 9 (±4) | 7 (±1) | 0% (±3.6%) |
| Blue-KLH (AbISCO) | 100* | 30 (30-30) | 4176 (±1220) | 9 (±3) | 7 (±1) | 0% (±4.3%) |
| Blue-improved (AbISCO) | 998* | 31 (28-35) | 5338 (±3226) | 12 (±2) | 7 (±0) | 0% (±7.3%) |
| Orange-KLH (AbISCO) | 3656* | 30 (30-30) | 6896 (±2078) | 10 (±2) | 7 (±1) | 0% (±2.6%) |
| Purple-KLH (AbISCO) | 2765 (1298-5891) | 86 (34-215) | 23738 (±16509) | 10 (±2) | 7 (±0) | 0% (±5.8%) |
| Purple constrained-KLH (AbISCO) | 3011 (1518-5972) | 100 (31-325) | 15716 (±9038) | 10 (±3) | 6 (±0.4) | 0.8% (±5.4%) |
| KLH control (AbISCO) | 100 (100-100) | 30 (30-30) | 3399 (±244) | 6 (±2) | 6 (±1) | 0% (±8.3%) |
| Purple-KLH (3 doses) (AbISCO) | 25964 (6713-100415) | 335 (80-1405) | 29032 (±18281) | 7 (±0.4) | 10 (±1) | 22.6% (±2.8%) |
| KLH control (3 doses) (AbISCO) | 424 (289-623) | 34 (25-47) | 8377 (±4475) | 9 (±3) | 8 (±1) | 0% (±4.1%) |
| Purple-KLH (CPG + Alum) | 3791 (1493-9626) | 113 (40-315) | 18207 (±14530) | 11 (±1) | 9 (±1) | 0% (±6.5%) |
| Purple-Qb VLP (CPG + Alum) | 11286 (4517-28197) | 137 (61-305) | 23288 (±16580) | 9 (±4) | 6 (±2) | 0% (±3.4%) |
| Purple-Qb VLP (CPG + AbISCO) | 3792 (2149-6690) | 478 (142-1608) | 39125 (±19461) | 7 (±3) | 7 (±1) | 15.3% (±3.8%) |
| Purple-HBsAg (CPG + Alum) | 36063 (9378-138680) | 2310 (921-5792) | 42383 (±16438) | 6 (±2) | 6 (±2) | 9% (±4.1%) |
| Qbeta control (CPG + Alum) | 100* | 30 (30-30) | 4425 (±650) | 11 (±1) | 8 (±1) | 0% (±0.5%) |
| KLH control (CPG + Alum) | 100* | 30 (30-30) | 2981 (±357) | 5 (±1) | 7 (±1) | 0% (±1.6%) |

TABLE 7-continued

Summary of data from Example 7

|  | Reciprocal IgG titer geomean (95% confidence interval) | IgE binding titer (±std dev) | IgE binding max (±std dev) | % Binding to IgE-FceRI (±std dev) | % Degranuation (±std dev) | % Decrease in 9186 ng/mL IgE levels (±std dev) |
|---|---|---|---|---|---|---|
| Qbeta control (CPG + AbISCO) | 100 (100-100) | 30 (30-30) | 4234 (±278) | 13 (±3) | 7 (±2) | 0% (±12.1%) |
| CPG + AbISCO | 100 (100-100) | 30 (30-30) | 1941 (±588) | 2 (±1) | 5 (±1) | 0% (±7.8%) |

Total conjugation dose is 25 microgram per injection Doses on days 0, 21
Conjugation partner = KLH, Q beta or HBsAg VLP
Adjuvant: 20 µg CPG 24555 (all internucleotide linkages phosphorothioate linkages) + Alum = ALhydrogel™ at 20% v/v or 12 µg AbiSCO Example 8

Combination of Peptide Immunogens on KLH

This study aimed to evaluate how efficacious a combination of peptides conjugated to KLH (as detailed in Example 4 above) were in inducing an antibody response that can bind to human IgE. Female Balb/c (6-8 weeks) were injected by the intramuscular route (50 microliter volume injected into each *Tibialis anterior* muscle) on days 0, 19 and 34. Necropsy took place on day 46. At necropsy 400-600 microliter blood was sampled from euthanised mice by cardiac puncture. Blood was left to coagulate overnight and the next day, serum was collected.

Antibody responses from immunized animals were investigated for using either all or some of the following assays: a) IgG titer determination, b) binding to serum free IgE, c) binding to FceRl bound IgE, d) degranulation assay, and e) IgE quantification assays. All assays are described in detail under Example 5.
Results This study showed that a combination of Yellow and Orange, Blue and Purple, Yellow and Purple are highly immunogenic and induce antibody responses that can efficiently bind free IgE, depite the low doses used in this study due to restricted amount of peptides avaiable. These antibody responses were not able to bind receptor engaged IgE and did not cause degranulation of receptor expressing target cells.

Example 9

Efficacy of Conjugate Vaccine to Break Tolerance In Vivo (Animal Model)

The ability of IgE peptide vaccines to reduce IgE levels in vivo is evaluated in animal models, using species naturally expressing raised IgE levels (e.g. through allergies) or inducing raised IgE levels experimentally using model or real allergens to immunize animals. For example, mice are immunized with endotoxin-free ovalbumin (OVA) as a model antigen formulated with alum to induce an IgE response to OVA (example reference Lloyd C et al, J. Immunol. 2001, 166, p2033-2040). Post-induction of IgE responses, mice are vaccinated with antigenic peptides coupled to carrier and formulated with adjuvants. Peptides from homologous regions of mouse IgE can be used (in mice), homologous regions of other species in respective animal species, as well as human IgE peptides for non human primates. The efficacy of vaccinations at lowering IgE levels can then be monitored by measuring levels of IgE in sera pre- and post-vaccination. In addition, the ability of the peptides to decrease allergic inflammatory responses can be monitored by challenging mice with intra-nasal or intra-tracheal OVA (for example over 2-5 sequential days) and evaluating the allergic inflammatory response in the lungs by counting leukocyte subset infiltration in lung lavage samples and by histological assessment of eosinopphil recruitment into the lung parenchyma as well as

TABLE 8

Summary of data from Example 8

|  | Reciprocal IgG titer | IgE binding titer Geomean (95% confidence interval) | IgE binding max (±std dev) | % Binding to IgE-FceRI (±std dev) | % Degranuation (±std dev) |
|---|---|---|---|---|---|
| Yellow + Orange | 15063* | 60 (39-93) | 10793 (±6959) | 4 (±3) | 10 (±0.2) |
| Blue + Purple | 23670* | 220 (124-391) | 21928 (±11019) | 2 (±1) | 9 (±0.3) |
| Yellow + Purple | 22560* | 415 (307-561) | 35473 (±12824) | 3 (±2) | 9 (±0.7) |
| Blue + Orange | 8876* | 38 (31-46) | 6861 (±3428) | 3 (±1) | 9 (±0.2) |
| Peng peptides | 14229* | 107 (81-142) | 17931 (±5715) | 2 (±1) | 10 (±0.2) |
| Adjuvant control | 100* | 30 (30-30) | 1897 (±232) | 11 (±13) | 9 (±0.4) |

Yellow dose: 16 microgram per dose
Orange dose: 20.3 microgram per dose
Blue dose: 0.5 microgram per dose
Purple dose: 25.3 microgram per dose
Doses on days 0, 21
Conjugation partner = KLH
Adjuvant: 12 µg AbiSCO goblet cell metaplasia and mucus production (e.g. Coyle A. et al, 1996 J. Exp. Med. 183, 1303-1310.).

Example 10

Efficacy and Suitability of Linear and Chemically Constrained Peptides Conjugated to Qbeta or HBsAg at Inducing Antibodies that can Bind to Human Ige One of the challenges of using short linear peptides as immunogens for inducing anti-IgE responses is accurately representing the secondary structure of IgE, thus ensuring that antibodies generated by the vaccination efficiently recognise free, circulating IgE. Chemical constraining to introduce suitable secondary structure into the linear parental amino acid sequences can provide alternate immunogens for inducing antibody responses to IgE.

Analysis of the three dimensional structure of the Cε3Cε4 domains of IgE present in PDB 1F6A (Garman et al, 2000 Nature 406: p259-266) revealed that some of the target sequences at the interface between Cε3Cε4 and the FCεRI receptor adopt non-linear arrangements that may not be well represented by the linear sequences detailed in table 9. Sequences were therefore identified that were candidates for chemical constraining in an attempt to evaluate the ability of constrained peptides to induce anti-IgE antibodies (following in vivo administration) detectable in a free IgE binding assay.

Variants of both the Yellow (SEQ ID NO: 220) and Orange+Cyst (SEQ ID NO: 436) sequences were separately constrained by two different methods: one method involved the use of Click chemistry to introduce a triazole moiety across two adjacent atoms of the peptide sequence. The degree of constraining exerted on the peptide sequence by this method can be adjusted by the addition of methylene groups to the triazole moiety (Orange046, Orange047, Yellow043, Yellow044 were produced by this method). The second method involved cyclising via the templating effect of a heterochiral Diproline unit (D-Pro-L-Pro) which are noted in the literature to have β-turn inducing potential (Spath et al, 1998, Helvetica Chimica Acta 81, p1726-1738); (Orange044, Orange045, Yellow040, Yellow041, Yellow042 were produced by this method). Chemical structures of these constrained peptides are displayed in Table 9.

Several studies were performed to evaluate anti-human IgE immune responses induction by either linear or constrained peptides of different length conjugated to HBsAg and Qbeta (conjugations as detailed in Examples 2 and 3).

The constrained peptides Orange+Cyst (SEQ ID No: 436), Yellow (SEQ ID No: 220), Orange044, Orange045, Orange046, Orange047, Yellow040, Yellow041, Yellow042, Yellow043 and Yellow044 were conjugated to Qbeta virus-like particles using Succinimidyl-6-[β-maleimidopropionamido]hexanoate (SMPH) chemistry at 1.5× molar excess and used as immunogens in mice. Female Balb/c (6-8 weeks) were injected by the intramuscular route (50 µl injected into each Tibialis anterior muscle) with antigen and AIhydrogel plus CpG-24555 (all internucleotide linkages phosphorothioate linkages) adjuvants on days as described below in table 9. Sera prepared 1 week after the final boost were tested for anti-IgE antibody activity in the IgE binding assay as described in Example 5.

Results

The studies summarized in Table 9 showed that linear peptides derived from purple, orange and yellow peptides conjugated to Qbeta and HBsAg and delivered with the combined adjuvants AIhydrogel and CpG24555 induced antibody responses that were capable of binding to free IgE.

Additionally, most constrained peptide immunogens induced antisera capable of binding free human IgE. Blue 003, 004 and 005 surprisingly only induced weak anti-IgE responses. Orange 047 and Orange 048 did not induce anti-IgE antibodies above background levels.

TABLE 9

Summary of data from Example 10

| Sequence | Name | IgE binding max Mean (±Std Dev) |
|---|---|---|
| ADSNPRGVSAYLSRPSPc (SEQ ID NO: 493)* | PURPLE 001 | 12018 (±6900) |
| ADSNPRGVSAYLSRPSPc (SEQ ID NO: 493)* | PURPLE 001 | 17809 (±8042) |
| ADSNPRGVSAYLSRPSPggc (SEQ ID NO: 494)** | PURPLE 003 | 33548 (±19309) |
| cggADSNPRGVSAYLSRPSP (SEQ ID NO: 495)** | PURPLE 004 | 30400 (±27654) |
| ADSNPRGVggc (SEQ ID NO: 496)** | PURPLE 005 | 3707 (±286) |
| ADSNPRGVSAYLSRPSPggc (SEQ ID NO: 497) | PURPLE 014 | 5737 (±1954) |
| ADSNPRGVSAYLSRPSggc (SEQ ID NO: 498)* | PURPLE 015 | 9097 (±3135) |
| ADSNPRGVSAYLSRPSggc (SEQ ID NO: 498) | PURPLE 015 | 7602 (±3104) |
| ADSNPRGVSAYLSRPggc (SEQ ID NO: 499) | PURPLE 016 | 6087 (±1176) |
| ADSNPRGVSAYLSRggc (SEQ ID NO: 500)* | PURPLE 017 | 9453 (±2650) |
| ADSNPRGVSAYLSRggc (SEQ ID NO: 500) | PURPLE 017 | 19078 (±17703) |
| ADSNPRGVSAYLSggc (SEQ ID NO: 501) | PURPLE 018 | 5717 (±2531) |
| ADSNPRGVSAYLggc (SEQ ID NO: 502) | PURPLE 019 | 5507 (±273) |
| ADSNPRGVSAYggc (SEQ ID NO: 503) | PURPLE 020 | 4742 (±601) |

TABLE 9-continued

Summary of data from Example 10

| Sequence | Name | IgE binding max Mean (±Std Dev) |
|---|---|---|
| ADSNPRGVSAggc (SEQ ID NO: 504)* | PURPLE 021 | 13890 (±9311) |
| ADSNPRGVSAggc (SEQ ID NO: 504) | PURPLE 021 | 9028 (±10144) |
| ADSNPRGVSggc (SEQ ID NO: 505) | PURPLE 022 | 4701 (±414) |
| ADSNPRGVggc (SEQ ID NO: 506) | PURPLE 023 | 5169 (±494) |
| ADSNPRGggc (SEQ ID NO: 507) | PURPLE 024 | 4256 (±480) |
| ADSNPRggc (SEQ ID NO: 508) | PURPLE 025 | 4679 (±541) |
| ADSNPggc (SEQ ID NO: 509) | PURPLE 026 | 4969 (±393) |
| DSNPRGVSAYLSRPSPggc (SEQ ID NO: 510)* | PURPLE 027 | 10197 (±5102) |
| DSNPRGVSAYLSRPSPggc (SEQ ID NO: 510)* | PURPLE 027 | 9047 (±1509) |
| SNPRGVSAYLSRPSPggc (SEQ ID NO: 511)* | PURPLE 028 | 12685 (±5655) |
| NPRGVSAYLSRPSPggc (SEQ ID NO: 512)* | PURPLE 029 | 19549 (±10976) |
| NPRGVSAYLSRPSPggc (SEQ ID NO: 512)* | PURPLE 029 | 10323 (±7495) |
| PRGVSAYLSRPSPggc (SEQ ID NO: 513)* | PURPLE 030 | 7485 (±1494) |
| RGVSAYLSRPSPggc (SEQ ID NO: 514)* | PURPLE 031 | 29423 (±42261) |
| RGVSAYLSRPSPggc (SEQ ID NO: 514)* | PURPLE 031 | 9595 (±3569) |
| GVSAYLSRPSPggc (SEQ ID NO: 515)* | PURPLE 032 | 9102 (±3114) |
| GVSAYLSRPSPggc (SEQ ID NO: 515)* | PURPLE 032 | 9137 (±6945) |
| VSAYLSRPSPggc (SEQ ID NO: 516)* | PURPLE 033 | 8901 (±2718) |
| VSAYLSRPSPggc (SEQ ID NO: 516)* | PURPLE 033 | 8249 (±3741) |
| SAYLSRPSPggc (SEQ ID NO: 517)* | PURPLE 034 | 11229 (±11683) |
| SAYLSRPSPggc (SEQ ID NO: 517)* | PURPLE 034 | 9347 (±9239) |
| AYLSRPSPggc (SEQ ID NO: 518)* | PURPLE 035 | 8132 (±652) |
| AYLSRPSPggc (SEQ ID NO: 518)* | PURPLE 035 | 7360 (±1660) |
| YLSRPSPggc (SEQ ID NO: 519)* | PURPLE 036 | 8139 (±1924) |
| YLSRPSPggc (SEQ ID NO: 519)* | PURPLE 036 | 6872 (±1239) |
| cggDSNPRGVSAYLSRPSP (SEQ ID NO: 520)* | PURPLE 037 | 6358 (±1702) |
| cggDSNPRGVSAYLSRPSP (SEQ ID NO: 520)* | PURPLE 037 | 8767 (±3064) |
| cggSNPRGVSAYLSRPSP (SEQ ID NO: 521)* | PURPLE 038 | 6470 (±1666) |
| cggNPRGVSAYLSRPSP (SEQ ID NO: 522)* | PURPLE 039 | 7835 (±3446) |
| cggNPRGVSAYLSRPSP (SEQ ID NO: 522)* | PURPLE 039 | 8783 (±3331) |
| cggPRGVSAYLSRPSP (SEQ ID NO: 523)* | PURPLE 040 | 10233 (±7119) |
| cggRGVSAYLSRPSP (SEQ ID NO: 524)* | PURPLE 041 | 11954 (±11540) |
| cggRGVSAYLSRPSP (SEQ ID NO: 524)* | PURPLE 041 | 6544 (±1341) |
| cggGVSAYLSRPSP (SEQ ID NO: 525)* | PURPLE 042 | 4931 (±1274) |
| cggGVSAYLSRPSP (SEQ ID NO: 525)* | PURPLE 042 | 5392 (±1608) |
| cggVSAYLSRPS (SEQ ID NO: 526)* | PURPLE 043 | 6418 (±816) |
| cggVSAYLSRPSP (SEQ ID NO: 526)* | PURPLE 043 | 3447 (±970) |

TABLE 9-continued

Summary of data from Example 10

| Sequence | Name | IgE binding max Mean (±Std Dev) |
|---|---|---|
| eggSAYLSRPSP (SEQ ID NO: 527)* | PURPLE 044 | 6328 (±2224) |
| eggSAYLSRPSP (SEQ ID NO: 527)* | PURPLE 044 | 5584 (±1328) |
| eggAYLSRPSP (SEQ ID NO: 528)* | PURPLE 045 | 5870 (±1647) |
| eggAYLSRPSP (SEQ ID NO: 528)* | PURPLE 045 | 5716 (±1510) |
| eggYLSRPSP (SEQ ID NO: 529)* | PURPLE 046 | 6228 (±1102) |
| eggYLSRPSP (SEQ ID NO: 530)* | PURPLE 046 | 5947 (±1042) |
| eggADSNPRGVSAYLSRPS (SEQ ID NO: 531)* | PURPLE 047 | 9446 (±3755) |
| eggADSNPRGVSAYLSRPS (SEQ ID NO: 531)* | PURPLE 047 | 6658 (±3006) |
| eggADSNPRGVSAYLSRP (SEQ ID NO: 532)* | PURPLE 048 | 14972 (±16875) |
| eggADSNPRGVSAYLSRP (SEQ ID NO: 532)* | PURPLE 048 | 10134 (±12441) |
| eggADSNPRGVSAYLSR (SEQ ID NO: 533)* | PURPLE 049 | 4949 (±835) |
| eggADSNPRGVSAYLSR (SEQ ID NO: 533)* | PURPLE 049 | 5183 (±615) |
| eggADSNPRGVSAYLS (SEQ ID NO: 534)* | PURPLE 050 | 5903 (±1790) |
| eggADSNPRGVSAYLS (SEQ ID NO: 534)* | PURPLE 050 | 4934 (±793) |
| eggADSNPRGVSAYL (SEQ ID NO: 535)* | PURPLE 051 | 6060 (±479) |
| eggADSNPRGVSAYL (SEQ ID NO: 535)* | PURPLE 051 | 4566 (±1162) |
| eggADSNPRGVSAY (SEQ ID NO: 536)* | PURPLE 052 | 7496 (±5251) |
| eggADSNPRGVSA (SEQ ID NO: 537)* | PURPLE 053 | 5406 (±1117) |
| eggADSNPRGVSA (SEQ ID NO: 537)* | PURPLE 053 | 5534 (±527) |
| eggADSNPRGVS (SEQ ID NO: 538)* | PURPLE 054 | 5952 (±722) |
| eggADSNPRGV (SEQ ID NO: 539)* | PURPLE 055 | 6536 (±1019) |
| eggADSNPRGV (SEQ ID NO: 539)* | PURPLE 055 | 8022 (±8108) |
| eggAYLSRPSPFDLFIRKS* (SEQ ID NO: 540) | PURPLE 056 | 45475 (±18743) |
| eggAYLSRPSPFDLF (SEQ ID NO: 541)* | PURPLE 057 | 5726 (±1757) |
| eggAYLSRPSPFDLF (SEQ ID NO: 541)* | PURPLE 057 | 6185 (±1002) |
| QCRVTHPHLPRALMRS (SEQ ID NO: 542) | YELLOW 001 | 7193 (±1900) |
| QCRVTHPHLPRALMRS (SEQ ID NO: 542) | YELLOW 001 | 6482 (±1531) |
| QCRVTHPHLPRALMRS (SEQ ID NO: 542) | YELLOW 001 | 8544 (±3058) |
| QCRVTHPHLPRALMRS (SEQ ID NO: 542)^ | YELLOW 001 | 51567 (±32315) |
| QCRVTHPHLPRALMRS (SEQ ID NO: 542)* | YELLOW 001 | 6449 (±3586) |
| QCRVTHPHLPRALMRS (SEQ ID NO: 542)^^ | YELLOW 001 | 46265 (±15556) |
| RVTHPHLPRALMRSggc (SEQ ID NO: 543)** | YELLOW 002 | 60067 (±51724) |
| eggRVTHPHLPRALMRS (SEQ ID NO: 544)** | YELLOW 003 | 67569 (±22134) |
| RVTHPHLPRALMRggc (SEQ ID NO: 545) | YELLOW 009 | 8350 (±4658) |
| RVTHPHLPRALMRggc (SEQ ID NO: 545)* | YELLOW 009 | 29546 (±10133) |
| RVTHPHLPRALMggc (SEQ ID NO: 546) | YELLOW 010 | 11706 (±8804) |
| RVTHPHLPRALMggc (SEQ ID NO: 546)* | YELLOW 010 | 27517 (±13701) |

TABLE 9-continued

Summary of data from Example 10

| Sequence | Name | IgE binding max Mean (±Std Dev) |
|---|---|---|
| RVTHPHLPRALggc (SEQ ID NO: 547) | YELLOW 011 | 7570 (±1980) |
| RVTHPHLPRAggc (SEQ ID NO: 548) | YELLOW 012 | 6695 (±601) |
| cggRVTHPHLPRALMR (SEQ ID NO: 549) | YELLOW 013 | 7500 (±1440) |
| cggRVTHPHLPRALM (SEQ ID NO: 550) | YELLOW 014 | 9790 (±3374) |
| cggRVTHPHLPRALM (SEQ ID NO: 550)* | YELLOW 014 | 27898 (±8203) |
| cggRVTHPHLPRALM (SEQ ID NO: 550) | YELLOW 014 | 25321 (±21324) |
| cggRVTHPHLPRAL (SEQ ID NO: 551) | YELLOW 015 | 5312 (±890) |
| cggRVTHPHLPRA (SEQ ID NO: 552) | YELLOW 016 | 8679 (±5297) |
| cggRVTHPHLPRA (SEQ ID NO: 552)* | YELLOW 016 | 13419 (±4677) |
| RVTHPHLPRALMRSggc (SEQ ID NO: 553) | YELLOW 017 | 12415 (±7279) |
| RVTHPHLPRALMRSggc (SEQ ID NO: 553)* | YELLOW 017 | 15306 (±5774) |
| VTHPHLPRALMRSggc (SEQ ID NO: 554) | YELLOW 018 | 4842 (±824) |
| THPHLPRALMRSggc (SEQ ID NO: 555) | YELLOW 019 | 6766 (±2621) |
| cggRVTHPHLPRALMRS (SEQ ID NO: 556) | YELLOW 020 | 12381 (±5181) |
| cggRVTHPHLPRALMRS (SEQ ID NO: 556)* | YELLOW 020 | 21246 (±14412) |
| cggVTHPHLPRALMRS (SEQ ID NO: 557) | YELLOW 021 | 7082 (±2453) |
| cggTHPHLPRALMRS (SEQ ID NO: 558) | YELLOW 022 | 4941 (±536) |
| VTHPHLPRALggc (SEQ ID NO: 559) | YELLOW 024 | 4655 (±1022) |
| THPHLPRAggc (SEQ ID NO: 560) | YELLOW 025 | 7201 (±4374) |
| cggVTHPHLPRAL (SEQ ID NO: 561) | YELLOW 027 | 6952 (±2459) |
| cggVTHPHLPRA (SEQ ID NO: 562) | YELLOW 028 | 6045 (±1431) |
| QCRVTHPHLPSALMSS (SEQ ID NO: 563)* | YELLOW 029 | 5281 (±358) |
| QCRVTHPHLPRALMSS (SEQ ID NO: 564)* | YELLOW 030 | 6486 (±1954) |
| QCRVTHPHLPSALMRS (SEQ ID NO: 565)* | YELLOW 031 | 5637 (±1069) |
| QCRVTHPHLP-Cit-ALM-Cit-S (SEQ ID NO: 566)* | YELLOW 032 | 5090 (±501) |
| QCRVTHPHLPRALM-Cit-S (SEQ ID NO: 567)* | YELLOW 033 | 5641 (±801) |
| QCRVTHPHLP-Cit-ALMRS (SEQ ID NO: 568)* | YELLOW 034 | 6528 (±1437) |
| cddddRVTHPHLPRALMRS (SEQ ID NO: 569)^ | YELLOW 035 | 38979 (±20434) |
| cddddRVTHPHLPRALM (SEQ ID NO: 570)^ | YELLOW 036 | 25851 (±15732) |
| cddddVTHPHLPRALMRS (SEQ ID NO: 571)^ | YELLOW 037 | 18637 (±6978) |
| cddddVTHPHLPRALM (SEQ ID NO: 572)^ | YELLOW 038 | 15365 (±2986) |
| Cyc-QCRVTHPHLPRALMRS-DPro-LPro-Cyc | YELLOW 040 | 35761 (±6293) |

TABLE 9-continued

Summary of data from Example 10

| Sequence | Name | IgE binding max Mean (±Std Dev) |
|---|---|---|
| [structure: HS-Cys(NH₂)-NH-pyrrolidine-C(O)-S-R-V-T-H-P-H-L-P-R-A-L-M-R-dProline, cyclic] | YELLOW 041 | 55855 (±19382) |
| [structure: HS-Cys(NH₂)-NH-pyrrolidine-C(O)-V-T-H-P-H-L-P-R-A-L-M-R-dProline, cyclic] | YELLOW 042 | 31595 (±9368) |
| [structure: H₂N-Cys-R-NH-CH(CH₂-triazole)-C(O)-T-H-P-H-L-P-R-A-NH-CH(CH₂-triazole)-C(O)-M-R-NH₂] | YELLOW 043 | 19465 (±14660) |
| [structure: H₂N-Cys-R-NH-CH(CH₂CH₂-triazole)-C(O)-T-H-P-H-L-P-R-A-NH-CH(CH₂CH₂-triazole)-C(O)-M-R-NH₂] | YELLOW 044 | 11435 (±8674) |
| STRKEEKQRNGTLTVTSTLPc (SEQ ID NO: 573) | ORANGE 001 | 5295 (±645) |
| STRKEEKQRNGTLTVTSTLPc (SEQ ID NO: 573) | ORANGE 001 | 8754 (±2808) |
| STRKEEKQRNGTLTVTSTLPc (SEQ ID NO: 573) | ORANGE 002 | 5074 (±336) |
| STRKEEKQRNGTLTVTSTLPggc (SEQ ID NO: 574)^^ | ORANGE 002 | 6715 (±1063) |
| STRKEEKQRNGTLTVTSTLPggc (SEQ ID NO: 574)^ | ORANGE 002 | 8448 (±2700) |
| STRKEEKQRNGTLTVTSTLPggc (SEQ ID NO: 574)** | ORANGE 002 | 14637 (±13062) |
| cggSTRKEEKQRNGTLTVTSTLP (SEQ ID NO: 575)** | ORANGE 003 | 5747 (±3695) |
| kggCQRNGTC (SEQ ID NO: 576) | ORANGE 004 | 6121 (±2590) |
| kggCQRNGTC (SEQ ID NO: 576)** | ORANGE 004 | 3621 (±238) |
| kggCEE-Cit-QRNGTLTVC | ORANGE 005 | 6035 (±711) |
| kggcEE-Cit-QRNGTLTVC** | ORANGE 005 | 3807 (±681) |
| STRKEEKQRNGTLTVTSTggc (SEQ ID NO: 577) | ORANGE 008 | 5778 (±1059) |
| STRKEEKQRNGTLTVTSggc (SEQ ID NO: 578) | ORANGE 009 | 5822 (±953) |
| STRKEEKQRNGTLTVTggc (SEQ ID NO: 579) | ORANGE 010 | 5493 (±860) |
| STRKEEKQRNGTLTVggc (SEQ ID NO: 580) | ORANGE 011 | 5727 (±720) |
| STRKEEKQRNGTLTggc (SEQ ID NO: 581) | ORANGE 012 | 5210 (±891) |

TABLE 9-continued

Summary of data from Example 10

| Sequence | Name | IgE binding max Mean (±Std Dev) |
|---|---|---|
| STRKEEKQRNGTLggc (SEQ ID NO: 582) | ORANGE 013 | 5854 (±861) |
| cggSTRKEEKQRNGTLTVTST (SEQ ID NO: 583) | ORANGE 014 | 5661 (±770) |
| cggSTRKEEKQRNGTLTVTS (SEQ ID NO: 584) | ORANGE 015 | 5613 (±962) |
| cggSTRKEEKQRNGTLTVT (SEQ ID NO: 585) | ORANGE 016 | 5452 (±772) |
| cggSTRKEEKQRNGTLTV (SEQ ID NO: 586) | ORANGE 017 | 6362 (±1950) |
| cggSTRKEEKQRNGTLT (SEQ ID NO: 587) | ORANGE 018 | 5277 (±578) |
| cggSTRKEEKQRNGTL (SEQ ID NO: 588) | ORANGE 019 | 7611 (±4748) |
| TRKEEKQRNGTLTVTSTggc (SEQ ID NO: 589) | ORANGE 021 | 5282 (±603) |
| RKEEKQRNGTLTVTSTggc (SEQ ID NO: 590) | ORANGE 022 | 5262 (±575) |
| KEEKQRNGTLTVTSTggc (SEQ ID NO: 591) | ORANGE 023 | 6344 (±1990) |
| EEKQRNGTLTVTSTggc (SEQ ID NO: 592) | ORANGE 024 | 5005 (±773) |
| EKQRNGTLTVTSTggc (SEQ ID NO: 593) | ORANGE 025 | 5173 (±882) |
| cggTRKEEKQRNGTLTVTST (SEQ ID NO: 594)^ | ORANGE 027 | 7344 (±1926) |
| cggRKEEKQRNGTLTVTST (SEQ ID NO: 595)^ | ORANGE 028 | 7768 (±1821) |
| cggKEEKQRNGTLTVTST (SEQ ID NO: 596)^ | ORANGE 029 | 7374 (±1985) |
| cggEEKQRNGTLTVTST (SEQ ID NO: 597)^ | ORANGE 030 | 7187 (±5429) |
| cggEKQRNGTLTVTST (SEQ ID NO: 598)^ | ORANGE 031 | 8397 (±3778) |
| TRKEEKQRNGTLTVTSggc (SEQ ID NO: 599)^ | ORANGE 033 | 9604 (±4122) |
| RKEEKQRNGTLTVTggc (SEQ ID NO: 600)^ | ORANGE 034 | 9805 (±5228) |
| KEEKQRNGTLTVggc (SEQ ID NO: 601)^ | ORANGE 035 | 7339 (±2516) |
| EEKQRNGTLTggc (SEQ ID NO: 602)^ | ORANGE 036 | 9965 (±5327) |
| EKQRNGTLggc (SEQ ID NO: 603) | ORANGE 037 | 4607 (±332) |
| cggTRKEEKQRNGTLTVTS (SEQ ID NO: 604)^ | ORANGE 039 | 7214 (±1842) |
| cggRKEEKQRNGTLTVT (SEQ ID NO: 605)^ | ORANGE 040 | 6500 (±2302) |
| cggKEEKQRNGTLTV (SEQ ID NO: 606)^ | ORANGE 041 | 6973 (±2437) |
| cggEEKQRNGTLT (SEQ ID NO: 607)^ | ORANGE 042 | 8758 (±3602) |
| Cyc-STRKEEKQRNGTLTVTSTLPC-DPro-LPro | ORANGE 044 | ND |
| 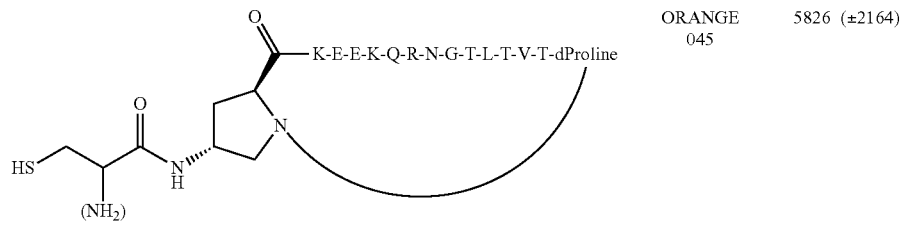 | ORANGE 045 | 5826 (±2164) |

TABLE 9-continued

Summary of data from Example 10

| Sequence | Name | IgE binding max Mean (±Std Dev) |
|---|---|---|
| [structure: HS-CH(NH₂)-C(=O)-NH-pyrrolidine ring with C(=O)-E-K-Q-R-N-G-T-L-T-dProline] | ORANGE 046 | 7991 (±4270) |
| [structure: H₂N-Cys-NH-...triazole...Q-R-N-G-T-NH-CH(-NH₂)C(=O)] | ORANGE 047 | 2528 (±656) |
| [structure: H₂N-Cys-NH-...triazole...Q-R-N-G-T-NH-CH(-NH₂)C(=O)] | ORANGE 048 | 2506 (±515) |
| LVVDLAPSKGTVNggc (SEQ ID NO: 608)** | BLUE 003 | 4684 (±796) |
| cggLVVDLAPSKGTVN (SEQ ID NO: 609)** | BLUE-004 | 8010 (±6572) |
| cggGGSDLAPSKGTVSGGggc (SEQ ID NO: 610)** | BLUE-005 | 3777 (±525) |
| N/A | NAKED Qb-VLP | 6132 (±491) |
| N/A | NAKED Qb-VLP | 3922 (±647) |
| N/A | NAKED Qb-VLP | 4830 (±323) |
| N/A | NAKED Qb-VLP | 4935 (±540) |
| N/A^ | NAKED Qb-VLP | 7550 (±1723) |
| N/A* | NAKED Qb-VLP | 6393 (±830) |
| N/A | NAKED Qb-VLP | 3779 (±403) |
| N/A** | ALUM CpG 2455 | 5098 (±2925) |
| N/A** | NAKED HBsAg | 3724 (±434) |

Total conjugate dose is 25 microgram per injection administered twice per the intramuscular route in female BALB/c mice on days 0 and 14 besides groups marked by * which were dosed with a conjugation dose of 50 microgram and groups marked with^ which were dosed 3 times on days 0, 14, and 28. Constrained peptides and groups marked with^^ were dosed 3 times on days 0, 21 and 42
Conjugation partner = Q beta or HBsAg VLP (marked with **)
Adjuvant: 20 μg CPG 24555 (all internucleotide linkages phosphorothioate linkages) + Alhydrogel ™ at 20% v/v
ND = Not Done
Note
c, cgg, gcc, cdddd and kgg are linkers added to IgE peptide sequences for conjugation purposes Example 11

Efficacy of Peptides Conjugated to Qbeta, HBsAg and DT at Inducing Antibody Response that can Bind to Human IgE This study aimed to evaluate how efficacious peptides conjugated to a variety of carriers such as DT, CRM197, Pseudomonas aeruginosa exotoxin A, HBsAg and Qbeta (as detailed in Examples above) were at inducing an antibody response that can bind to human IgE. For the generation of DT conjugates Diptheria toxoid (concentration 3 mg/ml) was derivatised with Succinimidyl-6-[β-maleimidopropionamido]hexanoate (SMPH, Thermo Fisher Scientific Inc) at a 10 fold molar excess. After this activation step, excess SMPH reagent was removed by using a NAP-25 desalting column (GE Healthcare) into Dulbeccos Phosphate Buffered Saline (DPBS) with 5 mM EDTA. Lyophilised peptide solid was then added directly to the malemide activated Diptheria toxiod and incubated with gentle mixing for 90 minutes. Where-upon the sample was applied to a NAP-25 desalting column (GE Healthcare) and eluted in Dulbeccos Phosphate Buffered Saline (DPBS) to remove free peptide. Following this, the protein solution was concentrated using 10 kD spin microconcentrators and sterilised using a 0.22 μm filter and kept at −80° C. until use. Qb-peptide and HbsAg-peptide conjugates were produced as follows: VLPs (both Qβ and HBsAg) were activated using N-gamma-maleimido-butyryloxy-succinimide ester (GMBS) linking reagent or Succinimidyl-6-[β-maleimidopropionamido]hexanoate (SMPH) both of which were obtained from Thermo Fisher Scientific Inc. The GMBS or SMPH reagent was dissolved in dimethyl sulphoxide (DMSO) and added to the VLP solution at a ≧5-fold molar excess. The activation reaction was allowed to proceed for ≧30 minutes and the solution was then desalted using a NAP-25 desalting column (GE Healthcare) into Dulbeccos Phosphate Buffered Saline (DPBS) with 5 mM EDTA. Following this, an appropriate quantity of solid lyophilised peptide was added directly to maleimide activated VLP and the reaction between the VLPs and the peptides was allowed to proceed for at least thirty minutes with very gentle mixing. At the end of the reaction time each sample was desalted into Dulbeccos PBS (DPBS) using NAP-25 desalting columns (GE Healthcare). The desalted conjugated peptides were analysed for protein content using the Bradford (Coomassie Brilliant Blue, Thermo Fisher Scientific Inc.) assay or the BCA Protein Assay (bicinchoninic acid, Thermo Fisher Scientific Inc.) as well as by SDS-PAGE and size-exclusion chromatography.

Female Balb/c (6-8 weeks) were injected by the intramuscular route (500 injected into each Tibialis anterior muscle) with peptides conjugated to Qbeta, Hepatitis B surface antigen (HBsAg) or Diphtheria toxoid (DT) with Alhydrogel plus CpG adjuvants on days 0, 19 & 34 as described below in table 10. Sera prepared 1 week after the final boost were tested for anti-IgE antibody activity in the IgE binding assay as described in Example 5. Responses are shown in Table 10.

Results

This study (Table 10) showed that PURPLE 001 and YELLOW 001 peptides (sequences shown at table 9) could induce anti-human IgE antibodies when conjugated to DT, Qbeta or HBsAg. Anti-human IgE antibodies were induced using either the GMBS linker or the SMPH linker.

TABLE 10

Summary of data from Example 11

| Peptide Ag + Carrier | Total conjugate dose (microgram) | Epitope density (peptide per monomer or equivalent) | IgE binding max Mean (StDev) |
|---|---|---|---|
| YELLOW 001 Qbeta VLP (GMBS) | 50 | ~0.5 | 5421 (±624) |
| PURPLE 001 Qbeta VLP (GMBS) | 50 | ~0.5 | 4465 (±199) |
| YELLOW 001 Qbeta VLP (SMPH) | 50 | ~0.5 | 13792 (±5544) |
| YELLOW 001 Qbeta VLP (SMPH) | 50 | ~1.0 | 37108 (±13782) |
| YELLOW 001 Qbeta VLP (SMPH) | 5 | >1.5 | 37742 (±7018) |
| YELLOW 001 Qbeta VLP (SMPH) | 50 | >1.5 | 34802 (±13636) |
| PURPLE 001 Qbeta VLP (SMPH) | 50 | ~0.5 | 10653 (±2915) |
| PURPLE 001 Qbeta VLP (SMPH) | 50 | ~1.0 | 29546 (±10133) |
| PURPLE 001 Qbeta VLP (SMPH) | 5 | >1.5 | 27517 (±13701) |
| PURPLE 001 Qbeta VLP (SMPH) | 50 | >1.5 | 27898 (±8203) |
| YELLOW 001 HBsAg (SMPH) | 5 | >1.5 | 13419 (±4677) |
| YELLOW 001 HBsAg (SMPH) | 50 | >1.5 | 15306 (±5774) |
| PURPLE 001 HBsAg (SMPH) | 5 | >1.5 | 21246 (±14412) |
| PURPLE 001 HBsAg (SMPH) | 50 | >1.5 | 11484 (±7349) |
| YELLOW 001 DT (SMPH) | 50 | >1.5 | 9038 (±2209) |
| YELLOW 001 DT (SMPH) | 50 | >1.5 | 11484 (±2097) |
| PURPLE 001 DT (SMPH) | 5 | >1.5 | 13052 (±4841) |
| PURPLE 001 DT (SMPH) | 50 | >1.5 | 17762 (±9906) |
| Qbeta control | 50 | N/A | 5646 (±105) |
| HbSAg control | 50 | N/A | 5781 (±346) |
| DT control | 50 | N/A | 5181 (±840) |

Female BALB/c mice were immunized on days 0 and 14. Sera was collected and analyzed on day 21.
Conjugation partner = Q beta, DT or HBsAg VLP (as per table above) using either SMPH and GMBS as outlined in table above.
Adjuvant: 20 μg CPG 24555 (all internucleotide linkages phosphorothioate linkages) + Alhydrogel™ at 20% v/v

TABLE 11

Summary of data from Example 12

| Peptide Ag (see sequences at table 9) | ADJUVANTS | Post 2$^{nd}$ dose IgE binding max: Mean (±std dev) | Post 3$^{rd}$ dose IgE binding max: Mean (±std dev) | Post 3$^{rd}$ dose Percentage Degranuation (±std dev) | Post 3$^{rd}$ dose Percentage decrease in IgE levels (±std dev) |
|---|---|---|---|---|---|
| PURPLE 014^ | ALUM | 25051 (±7485) | 40132 (±7125) | 9.5 (2.1) | −15.53 (13.27) |
| PURPLE 014* | ALUM | 35825 (±8690) | 39276 (±15943) | 9.7 (2) | −10.75 (12.32) |
| YELLOW 001^ | ALUM | 46380 (±15316) | 47442 (±8052) | 12.9 (5.6) | 0.619 (12.46) |
| YELLOW 001* | ALUM | 49695 (±13050) | 44900 (±13597) | 10.4 (2.5) | −8.27 (7.6) |
| YELLOW 014^ | ALUM | 22800 (±12361) | 47982 (±28244) | ND | ND |
| YELLOW 014* | ALUM | 24976 (±8424) | 28969 (±6456) | ND | ND |
| PURPLE 014^ + YELLOW 001^ | ALUM | 55655 (±20653) | 58342 (±14712) | 9.5 (1.5) | 33.23 (49.96) |
| PURPLE 014* + YELLOW 001* | ALUM | 79572 (±22961) | 71068 (±19829) | 10.1 (2.1) | 18.8 (31.9) |
| PURPLE 014^ + YELLOW 014^ | ALUM | 47695 (±10489) | 62932 (±13579) | ND | ND |
| PURPLE 014* + YELLOW 014* | ALUM | 44089 (±16271) | 45506 (±8253) | ND | ND |
| NAKED Qb-VLP** | ALUM | 2468 (±497) | 3018 (±270) | 11.4 (5.5) | −11.8 (8.03) |
| PURPLE 014^ | ALUM + CpG-24555 | 36667 (±13720) | 36947 (±15325) | 10.1 (2.7) | −0.108 (27.67) |
| PURPLE 014* | ALUM + CpG-24555 | 33429 (±9511) | 42935 (±19555) | 9.9 (2.7) | −10.42 (5.46) |
| YELLOW 001^ | ALUM + CpG-24555 | 74180 (±20978) | 80789 (±12783) | 9.3 (1.8) | 2.84 (19.68) |
| YELLOW 001* | ALUM + CpG-24555 | 75703 (±18385) | 65831 (±21843) | 9.8 (1.7) | −6.07 (10.1) |
| YELLOW 014^ | ALUM + CpG-24555 | 31477 (±13045) | 27621 (±9763) | ND | ND |
| YELLOW 014* | ALUM + CpG-24555 | 51564 (±30634) | 51346 (±22522) | ND | ND |

TABLE 11-continued

Summary of data from Example 12

| Peptide Ag (see sequences at table 9) | ADJUVANTS | Post $2^{nd}$ dose IgE binding max: Mean (±std dev) | Post $3^{rd}$ dose IgE binding max: Mean (±std dev) | Post $3^{rd}$ dose Percentage Degranulation (±std dev) | Post $3^{rd}$ dose Percentage decrease in IgE levels (±std dev) |
|---|---|---|---|---|---|
| PURPLE 014^ + YELLOW 001^ | ALUM + CpG-24555 | 78604 (±25881) | 68086 (±22146) | 10.7 (2.2) | 15.24 (34.44) |
| PURPLE 014* + YELLOW 001* | ALUM + CpG-24555 | 75617 (±26964) | 69765 (±19017) | 10 (1.5) | 23.31 (37.4) |
| PURPLE 014^ + YELLOW 014^ | ALUM + CpG-24555 | 63775 (±23432) | 42457 (±9704) | ND | ND |
| PURPLE 014* + YELLOW 014* | ALUM + CpG-24555 | 52660 (±27718) | 54023 (±26129) | ND | ND |
| NAKED Qb-VLP** | ALUM + CpG-24555 | 2932 (±336) | 3266 (±942) | 11.6 (1.9) | −17.61 (14.46) |

^ = 20 microgram dose
* = 100 microgram dose
** = 200 microgram dose
Conjugation partner = Q beta VLP.
Dosing female BALB/c mice every 4 weeks at w 0, 4, 8. Samples taken for testing 7 days post $2^{nd}$ and $3^{rd}$ dose.
The dose of Alhydrogel equals vaccine dose as above
CpG-24555 (all internucleotide linkages phosphorothioate linkages) was dosed at 100 microgram
IgE depleting activity was testing using 1000 ng/ml human IgE spiked into normal BALB/c serum (see Example 5 for details)

Example 12

Efficacy of a Combination of Peptides is Greater than Using Single Peptides Conjugated to Qbeta at Inducing Antibody Responses that can Bind to Human IgE Several studies aimed to evaluate how peptides conjugated to Qbeta (as detailed in Examples above) were at inducing an antibody response that can bind to human IgE were performed. Female Balb/c (6-8 weeks) were immunized by the intramuscular route as described in Example 5, with specific timing details as indicated in the tables. Anti-IgE responses, degranulation-inducing activity and IgE depletion activity were measured as detailed in Example 5.
Results As shown in Table 11, conjugation of the peptides (see sequences at table 9) to Qbeta induced antibody responses that were capable of binding to free IgE without causing degranulation above the control value. Using AIhydrogel as single adjuvant is effective and a combination of purple peptides and yellow peptides induced higher IgE binding antibody responses. Furthermore, the combination of peptides induced antibody responses that were more potent at binding and depleting IgE. Adding CPG 24555 to the AIhydrogel formulation increased the anti-IgE antibody responses further without inducing degranulation activity.

Example 13

Induction of Anti-Self IgE Responses by a Murine Homologue of Purple 001 and Yellow 001

The ability of IgE peptide vaccines to induce IgG anti-self IgE antibodies and reduce IgE levels in vivo was evaluated in mice with raised IgE levels (induced by preimmunization with endotoxin-free ovalbumin (OVA) as a model antigen formulated with alum—example reference Lloyd C et al, J. Immunol. 2001, 166, p2033-2040). Post-induction of IgE anti-OVA responses, mice were vaccinated with antigenic peptides coupled to Qbeta carrier and formulated with adjuvants. Peptides from homologous regions of mouse IgE were used (murine yellow 001=QCIVDHPDFPKPIVRS(SEQ ID NO: 458); murine purple001=PDHEPRGVITYLIPPSPC (SEQ ID NO: 459)). The efficacy of vaccinations at lowering IgE levels were monitored by measuring levels of IgE anti-OVA in sera pre- and post-vaccination.

a) Ovalbumin Specific IgE Quantification Assay

Summary: An electrochemiluminescence (ECL) assay which determines a concentration of OVA-specific murine IgE. An OVA specific IgE monoclonal antibody (AbD Serotec Cat#PMP68) was used as a positive control, with quantitative 12 point ½ log dilutions of this standard (spiked at a top concentration of 30 μg/mL into Balb/c neg serum from Harlan Labs (pooled from 400 animals Harlan laboratories Code#R-0131D) tested in each assay. This pooled normal serum was also used alone as a negative control. Coating of assay plates: 384-well assay plates (Meso-Scale Diagnostics (MSD) standard bind Cat#L11XA-1, 0370PA) were coated with 124/well of Rat pAb to mouse IgE—Invitrogen Cat#04700 diluted to 15 μg/mL with 0.01M PBS pH7.4, then incubated on a shaker at RT for 2 hours. After washing ×3 with 0.01M PBS pH 7.4, plates were blocked using 25 μL/well of Pierce starting blocking buffer (Pierce Biotech. Cat#37538) and incubated on a shaker at RT for 40 mins, before a final wash ×3 with 0.01M PBS pH 7.4. Sample preparation and assay: Each serum sample was diluted 1 in 200 and 1 in 500 (0.01M PBS pH 7.4/1% BSA diluent) and 124 of each dilution added, in triplicate, to the coated MSD plates, with dilutions of standard tested in parallel. After incubating on a shaker at RT for 2 hours, plates were washed ×3 with 0.01M PBS pH 7.4/ 0.05% Tween 20. Added 12 μL/well detection, SULFO tagged Ovalbumin, 1:300 with 0.01M PBS pH 7.4/1% BSA, then incubated shaking at RT for 1 hour. After washing ×3 with 0.01M PBS pH 7.4/0.05% Tween 20 added 50 μL/well MSD Read buffer T (4×) with surfactant (MSD Cat#R92TC) 1:2 with MQ Water. Plates were read using an MSD Sector Imager 6000. Data analysis: Raw data (Pixels) was logged, standard curve plotted (Log mouse IgE anti-OVA concentration ng/mL vs. Log Pixels) and an asymmetric 5-parameter curve fit applied. Log IgE concentrations of the test samples were predicted from the standard curve and subsequently anti-logged and multiplied by 200 or 500 to derive the actual IgE concentrations in ng/mL.

b) Anti Murine IgE Total IgG Titer Determination

Summary: A colorimetric ELISA that generates a reciprocal titer (RT) to represent the levels of total IgG molecules which are specific to murine IgE. Serial dilutions were prepared from sera samples and tested in the assay. Rat pAb to mouse IgE—Invitrogen Cat#04700 spiked into Balb/c neg serum from Harlan Labs at 10 μg/mL and titrated in an 8 point half log serial dilution was used as positive control. Balb/c neg serum from Harlan Labs was used as negative control (pooled from 400 animals Harlan laboratories Code#R-0131D) along with a pooled sample from the study negative group (treated same as samples). Coating of assay plates: 384-well high bind assay plates (Corning International Cat#3700) were coated with 25 µL/well of mouse IgE to OVA (AbD Serotec Cat#PMP68) stock diluted to 5 µg/mL with 0.01M PBS pH 7.4 and incubated on a shaker at RT for 2 hours. After washing ×2 with PBS pH 7.4, plates were blocked using 80 µL/well of 0.01M PBS/1% BSA, incubated at RT for 1 hour before a final wash ×3 with 0.01M PBS pH 7.4/0.05% Tween 20. Sample preparation and assay: An 8 point 1/10 serial dilution of each sample was prepared starting at 1:10 dilution (PBS/1% BSA diluent), 25 µL/well of the serial dilution transferred in duplicate into the mouse IgE coated plate then incubated shaking at RT for 1.5 hours. After washing ×3 with 0.01M PBS pH 7.4/0.05% Tween 20, 25 µL/well of Total IgG detection antibody was added (Rabbit anti-mu IgG-Fc, Cat#A90-130A Bethyl Laboratories) 1:6000 with 0.01M PBS pH 7.4/1% BSA, then incubated shaking at RT for 1 hour. After washing ×5 with 0.01M PBS pH 7.4/0.05% Tween 20, added 25 µL/well Bio-Rad kit goat anti-rabbit horseradish peroxidase conjugate (Bio-Rad Cat#172-1019) 1:3000 with 0.01M PBS pH 7.4/0.05% Tween 20 pH 7.4, then incubated shaking at RT for 1 hour. After washing ×4 with 0.01M PBS pH 7.4/0.05% Tween 20 then ×1 with 0.01M PBS pH 7.4 only, 25 µL/well Mouse Typer HRP Substrate (Bio-Rad Cat#172-1064) was added, then incubated at RT for 30 mins before adding 25 µL/well 2% oxalic acid to stop the reaction and reading Absorbance at 405 nm. Data analysis: Titration curves were plotted for each test sample (sample titer vs Abs 405 nm) and the sample titer (subsequently transformed into reciprocal titer) was predicted from a cut-off value of OD 1.

Results

Two studies (Table 12) showed that a combination of the murine homologue of Yellow 001 (mYellow-001 =QCIVDH-PDFPKPIVRS (SEQ ID NO: 458)) and the murine homologue of Purple 001 (mPurple-001 =PDHEPRGVITYL-IPPSPC (SEQ ID NO: 459)) can induce anti-self IgE antibody responses that can efficiently lower endogenous levels of IgE (compared to levels in Qbeta VLP immunized controls). Proof of mechanism was hence achieved by showing that an IgE peptide conjugate can break B-cell tolerance to the endogenous IgE molecule and that this correlates with a reduction in the endogenous IgE levels.

TABLE 12

Summary of data from Example 13

| | Anti Mouse IgE IgG reciprocal titer (95% confidence interval) Post 3 vaccinations | Total ovalbumin specific IgE (ng/ml, (Std Dev)) Post 3 vaccinations |
|---|---|---|
| mPurple-001 and mYellow-001** | 237641 (15100-3740000) | ND |
| mPurple-001 and mYellow-001 | 540947 (225419-1298000) | 4425 (±3455) |
| Qbeta VLP control | 10 (10-10) | ND |
| Qbeta VLP control | 33 (15-75) | 15735 (±8212) |

BALB/c mice were sensitzed with ovalbumin on weeks 0 and 1 to raise endogenous levels of IgE.
Mice were vaccinated with 200 microgram of the murine purple 001 and yellow 001 (i.e. 100 microgram each) combination on weeks 3, 7 and 11, and tested 1 week post 3$^{rd}$ immunization.
Conjugation partner = Q beta VLP using SMPH.
Adjuvant: 20 µg CPG 24555 (all internucleotide linkages phosphorothioate linkages) + Alhydrogel™ at 20% v/v
ND = not done Example 14

Cynomolgus Macaque Vaccination with Purple 014 and Either Yellow 001 or Yellow 014

The ability of human IgE peptide vaccines to break tolerance against self IgE in vivo was evaluated in cynomolgus macaques vaccinated with antigenic peptides coupled to carrier (Q beta VLP) and formulated with adjuvants. Peptides from human IgE were used. The efficacy of vaccinations at inducing anti-self IgE immune responses were then monitored by measuring levels of IgG anti-IgE in sera pre- and post-vaccination.

Cynomolgus Macaque Assay a) Total IgG Titer Determination for IgG Specific for the Following Antigens/VLP: Cynomolgus Macaque IgE Cε2-Cε4 Domain, Human IgE Cε3Cε4 Domain, Individual Peptides (Yellow and Purple) Conjugated to KLH, and to Qbeta.

Summary: An electrochemiluminescence (ECL) assay that generates a reciprocal titer (RT) to represent the levels of total IgG molecules which are specific to the vaccine or VLP. Serial dilutions were prepared from sera samples and tested in the assay. Cynomolgus macaque serum spiked with humanized anti-IgE monoclonal antibody (E25, Xolair) was used at 40 µg/mL as a positive control. Unspiked cynomolgus macaques serum used as a negative control. Coating of assay plates: 384-well assay plates (Meso-Scale Diagnostics (MSD) streptavidin coated Cat#L21SA-1) were coated with 12 µL/well of biotinylated cynomolgus macaque IgE Cε2-Cε4 or human IgE Cε3 Cε4 diluted to 1 µg/mL with 0.01M PBS pH 7.4/1% BSA. 384-well assay plates (Meso-Scale Diagnostics (MSD) standard bind Cat#L11XA-1, 0370PA) were coated with 12 µL/well of individual peptide (conjugated to KLH) diluted to to 1 µg/mL or Qbeta diluted to 2-5 ug/mL with 0.01M PBS pH 7.4 (no BSA). Plates were then incubated on a shaker at RT for 1 hour. After washing ×3 with 0.01M PBS pH 7.4, plates were blocked using 25 µL/well of Pierce starting blocking buffer (Pierce Biotech. Cat#37538) and incubated on a shaker at RT for 40 mins, before a final wash ×3 with 0.01M PBS pH 7.4. Sample preparation and assay: An 8 point ½ log serial dilution of each sample including controls was prepared starting at 1:20 dilution (PBS/1% BSA diluent), 12 µL/well of the serial dilution was transferred into wells of plates coated with the test antigen/VLP then incubated shaking at RT for 1 hour. After washing ×3 with 0.01M PBS pH 7.4/0.05% Tween 20, diluted SULFO-tagged Protein G to 0.02 µg/mL (PBS/1% BSA diluent) was added to the plates (12 µL/well). The plates were incubated with shaking at RT for 1 hour then washed ×3 with 0.01M PBS pH 7.4/0.05% Tween 20. 50 µL/well MSD Read buffer T (4×) with surfactant (MSD Cat#R92TC) 1:2 with MQ Water was added. Plates were read using an MSD Sector Imager 6000. Data analysis: Titration curves were plotted for each test sample (sample titer vs Pixels) and the sample titer (subsequently transformed into reciprocal titer) was predicted from a cut off value (Pixels).

b) Cynomolgus Macaques Antibody Avidity Assay

Summary: A colorimetric ELISA that generates an Avidity Index (AI) to represent the binding strength of total IgG molecules which are specific to human Cε3 Cε4. The humanized anti-IgE antibody Xolair (E25) was spiked into a pooled cynomolgus macaque serum (prepared from the Qb-VLP control group of this study) at 40 and 4 ug/mL and titrated in a 12 point half log serial dilution as positive control. Cynomolgus macaque serum from study Qb-VLP group was used as negative control along with commercial cynomolgus macaque serum. Coating of assay plates: Reacti-Bind™

Streptavidin Coated HBC Clear 384-Well Plates with Super-Block Blocking Buffer (Fisher Scientific Co Ltd P115504) were coated with 12 μL/well of biotinylated human Cε3 Cε4 at 1 μg/mL in 0.01M PBS pH 7.4 and incubated on a shaker at RT for 1 hour. After washing ×3 with PBS pH 7.4, plates were blocked using 25 μL/well of 0.01M PBS/1% BSA, incubated at RT for 40 mins before a final wash ×3 with 0.01M PBS pH 7.4/0.05% Tween 20. Sample preparation and assay: Samples were diluted with 0.01M PBS/1% BSA. Each sample had a titration curve generated and from this curve a pixel value of 180,000 was used to calculate an individual reciprocal titer (RT) dilution to use for each sample. This RT was used to dilute each sample to ensure that similar levels of antibodies from each sample were used in the avidity assay. 12 uL of each diluted sample was added to 24 wells of the coated 384 well plates and incubated shaking at RT for 1 hour. After washing ×5 with 0.01M PBS pH 7.4/0.05% Tween 20, ammonium thiocyanate was added to the plate at differing concentrations at 12 μL/well then incubated shaking for 15 minutes at RT. (12 concentrations of Ammonium thiocyanate were used: 12, 10, 8, 7, 6, 5, 4, 3, 2, 1, 0.5 and 0M were added to duplicate samples). After washing ×4 with 0.01M PBS pH 7.4/0.05% Tween 20, 12 μL/well Mouse anti-human IgG HRP-labeled (Southern Biotech 9042-05) with 0.01M PBS/1% BSA was added, then incubated shaking at RT for 1 hour. After washing ×5 with 0.01M PBS pH 7.4/0.05% Tween 20, 25 μL/well TMB Substrate (Sigma P-8665) was added, then incubated at RT in the dark for 30 mins. To stop the reaction, 25 μL/well 2% oxalic acid was added and plates read at Abs 450 nm. Data analysis: % reduction for each sample for each ammonium thiocyanate concentration was calculated using the mean Abs 405 nm for OM ammonium thiocyanate samples as 0% reduction. Titration curves were then plotted for each test sample (% reduction vs Abs 450 nm) and the AI was predicted from a cut-off value of 50% reduction.

Results:

This study (Table 13) showed that a combination of the Yellow 001 or Yellow014 with Purple 014 (see sequence at table 9) is immunogenic and induced anti-self (cynomolgus macaque) IgE and anti-human IgE antibody responses which correlated with responses to the specific peptides. Further it shows that avidity of the antibody responses can be increased by repeated dosing in the cynomolgus macaque.

TABLE 13

Summary of data from Example 14

| | Reciprocal IgG titer to cynomolgus IgE (95% confidence interval) | Reciprocal IgG titer to Yellow sequence (95% confidence interval) | Reciprocal IgG titer to Purple sequence (95% confidence interval) | Reciprocal IgG titer to human IgE (95% confidence interval) | Avidity Index (mean and Std Dev) |
|---|---|---|---|---|---|
| Yellow-001 + Purple-014 2 wks post dose 1 | 20 | 400 (203-786) | 588 (313-1106) | 20 | 1.693 (±0.05636) |
| Yellow-001 + Purple-014 2 wks post dose 2 | 840 (374-1888) | 2013 (1052-3855) | 2145 (1469-3133) | 1521 (641-3610) | 5.191 (±1.305) |
| Yellow-001 + Purple-014 2 wks post dose 3 | 1139 (170-3507) | 1716 (1213-2429) | 2125 (1706-2647) | 1802 (980-3316) | 6.757 (±0.8725) |
| Yellow-014 + Purple-014 2 wks post dose 1 | 22 (16-32) | 400 (203-786) | 588 (313-1106) | 20 | 1.693 (±0.05636) |
| Yellow-014 + Purple-014 2 wks post dose 2 | 385 (98-1505) | ND | ND | 761 (205-2819) | 5.191 (±1.305) |
| Qbeta control 2 wks post dose post dose 1 | ND | 20 (20-20) | 20 (20-20) | 20 | ND |
| Qbeta control 2 wks post dose 2 | 34 (6-194) | 20 (20-20) | 20 (20-20) | 20 | ND |
| Qbeta control 2 wks post dose 3 | 33 (7-161) | 20 (20-20) | 20 (20-20) | 20 | ND |

Cynomolgus macaques were vaccinated with 600 microgram of the purple 014 and yellow 001 or yellow 014 (i.e. 300 microgram each) combination on weeks 0, 4 and 8, and tested week 12.
Conjugation partner = Q beta VLP using SMPH.
Adjuvant: 500 μg CPG 24555 (all internucleotide linkages phosphorothioate linkages) + Alhydrogel ™ at 600 microgram.
ND = not done

The invention claimed is:

1. An antigenic IgE peptide consisting of the amino acid sequence of SEQ ID NO:312.

2. An immunogen comprising the antigenic IgE peptide according to claim 1, wherein the antigenic IgE peptide is linked to an immunogenic carrier.

3. The immunogen according to claim 2, further comprising either:
  (a) a linker joined to the C-terminus of the antigenic IgE peptide and having the formula $(G)_nC$ wherein n is an integer chosen from the group consisting of 0, 1, 2, 3, 4, 5, 6, 7, 8, 9, and 10 (where n is equal to 0, said formula represents a cysteine) or;
  (b) a linker joined to the N-terminus of the antigenic IgE peptide and having the formula $C(G)_n$ wherein n is an integer chosen from the group consisting of 0, 1, 2, 3, 4, 5, 6, 7, 8, 9, and 10 (where n is equal to 0, the formula represents a cysteine) or;
  (c) a first linker joined to the C-terminus of the antigenic IgE peptide and having the formula $(G)_nC$ wherein n is an integer chosen from the group consisting of 0, 1, 2, 3, 4, 5, 6, 7, 8, 9, and 10 (where n is equal to 0, said formula represents a cysteine) and a second linker joined to the N-terminus of the antigenic IgE peptide and having the formula $C(G)_n$ wherein n is an integer chosen from the group consisting of 0, 1, 2, 3, 4, 5, 6, 7, 8, 9, and 10 (where n is equal to 0, the formula represents a cysteine).

4. The immunogen according to claim 2, further comprising a linker joined to the C-terminus of the antigenic IgE peptide and having the formula $(G)_nC$ wherein n is an integer selected from the group consisting of 0, 1, 2, and 3 (where n is equal to 0, said formula represents a cysteine).

5. The immunogen according to claim 2, wherein the immunogenic carrier is a virus-like particle selected from the group consisting of HBcAg, HBsAg and Qbeta VLP.

6. A composition comprising the immunogen according to claim 2.

7. An immunogenic composition comprising an immunogen according to claim 2 or a composition according to claim 6 or claim, further comprising at least one adjuvant selected from the group consisting of alum, CpG-containing oligonucleotides, and saponin-based adjuvants.

8. The immunogenic composition according to claim 7, wherein said at least one adjuvant is a CpG-containing oligonucleotide selected from the group consisting CpG7909 (SEQ ID NO: 433), CpG 10103 (SEQ ID NO: 432) and CpG24555 (SEQ ID NO: 431).

9. The immunogenic composition according to claim 7, wherein said at least one adjuvant is alum.

10. The immunogenic composition according to claim 7, comprising at least two adjuvants selected from the group consisting of alum, CpG-containing oligonucleotides and saponin-based adjuvants.

11. The immunogenic composition of claim 10, wherein the at least two adjuvants are alum and CpG24555 (SEQ ID NO: 431).

12. A pharmaceutical composition comprising the immunogen according to claim 2 or the composition according to claim 6, and a pharmaceutically acceptable excipient.

13. A method for alleviating or treating an IgE-related disorder in an individual, comprising administering to the individual a therapeutically effective amount of the pharmaceutical composition of claim 12.

14. The method according to claim 13, further comprising administering at least one adjuvant selected from the group consisting of alum, CpG-containing oligonucleotides, and saponin-based adjuvants.

15. The method according to claim 14, wherein the at least one adjuvant is alum.

16. The method according to claim 14, wherein the at least one adjuvant is a CpG-containing oligonucleotide selected from the group consisting CpG7909 (SEQ ID NO:433), CpG 10103 (SEQ ID NO:432) and CpG24555 (SEQ ID NO:431).

17. The method according to claim 13, further comprising administering to the individual at least two adjuvants, wherein the at least two adjuvants are alum and CpG24555 (SEQ ID NO:431).

* * * * *